United States Patent
Petry et al.

(10) Patent No.: US 11,090,364 B2
(45) Date of Patent: Aug. 17, 2021

(54) CONJUGATES OF A PHARMACEUTICAL AGENT AND A MOIETY CAPABLE OF BINDING TO A GLUCOSE SENSING PROTEIN

(71) Applicant: SANOFI, Paris (FR)

(72) Inventors: Stefan Petry, Frankfurt am Main (DE); Oliver Plettenburg, Frankfurt am Main (DE); Norbert Tennagels, Frankfurt am Main (DE); Ulrich Werner, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 16/306,243

(22) PCT Filed: Jun. 2, 2017

(86) PCT No.: PCT/EP2017/063447
§ 371 (c)(1),
(2) Date: Nov. 30, 2018

(87) PCT Pub. No.: WO2017/207754
PCT Pub. Date: Dec. 7, 2017

(65) Prior Publication Data
US 2019/0209656 A1    Jul. 11, 2019

(30) Foreign Application Priority Data
Jun. 2, 2016  (EP) .................................... 16305640

(51) Int. Cl.
| | | |
|---|---|---|
| A61K 38/28 | (2006.01) | |
| A61K 47/54 | (2017.01) | |
| A61P 3/08 | (2006.01) | |
| C07H 13/10 | (2006.01) | |
| C07K 14/62 | (2006.01) | |
| C07H 19/04 | (2006.01) | |
| C07H 19/056 | (2006.01) | |
| C07H 15/12 | (2006.01) | |
| C07H 15/04 | (2006.01) | |
| C07H 13/08 | (2006.01) | |
| C07H 15/26 | (2006.01) | |

(52) U.S. Cl.
CPC ............ *A61K 38/28* (2013.01); *A61K 47/549* (2017.08); *A61P 3/08* (2018.01); *C07H 13/08* (2013.01); *C07H 13/10* (2013.01); *C07H 15/04* (2013.01); *C07H 15/12* (2013.01); *C07H 15/26* (2013.01); *C07H 19/04* (2013.01); *C07H 19/056* (2013.01); *C07K 14/62* (2013.01)

(58) Field of Classification Search
CPC .......... A61K 38/28; A61K 47/549; A61P 3/08
USPC ....................................................... 514/1.3
See application file for complete search history.

(56) References Cited

U.S. PATENT DOCUMENTS

| 8,722,633 B2 | 5/2014 | Bebernitz | |
| 2015/0105317 A1* | 4/2015 | Lin | ...................... A61K 47/549 |
| | | | 514/5.9 |

FOREIGN PATENT DOCUMENTS

| EP | 3463480 A1 | 4/2019 |
| WO | WO9010645 A1 | 9/1990 |
| WO | WO0192334 A1 | 12/2001 |
| WO | WO03048195 A2 | 6/2003 |
| WO | 2009121939 A2 | 10/2009 |
| WO | 2010012153 A1 | 2/2010 |
| WO | 2010031813 A1 | 3/2010 |
| WO | WO2010088294 A1 | 8/2010 |
| WO | WO2010088300 A1 | 8/2010 |
| WO | WO2010107520 A1 | 9/2010 |
| WO | WO2011000823 A1 | 1/2011 |
| WO | WO2012015681 A2 | 2/2012 |
| WO | WO2012015692 A2 | 2/2012 |
| WO | WO2012177701 A2 | 12/2012 |
| WO | WO2013121296 A1 | 8/2013 |
| WO | WO2013139906 A1 | 9/2013 |
| WO | WO 2013/182612 * | 12/2013 |
| WO | WO2014198788 A1 | 12/2014 |
| WO | WO2015051052 A2 | 4/2015 |
| WO | WO2015107115 A1 | 7/2015 |
| WO | WO2015121348 A2 | 8/2015 |
| WO | WO2017124102 A1 | 7/2017 |
| WO | 2017207754 A1 | 12/2017 |

OTHER PUBLICATIONS

Glossary of medical education terms, Institute of International Medical Education. http://www.iime.org/glossary.htm Accessed in Mar. 2013. (Year: 2013).*
Taraghdari et al. A Review on Bioengineering Approaches to Insulin Delivery: A Pharmaceutical and Engineering Perspective. Macromol. Biosci. 2019, 19, 1800458 (21 pages) (Year: 2019).*
Lehmann et al. Mono-, di- and tri-antennary D-galactose ligands as competitive inhibitors and photoaffinity labels of the hexose transporting system in erythrocytes. A model for the irreversible blocking of receptors in cell membranes. Carbohydrate Research 276 (1995) 57-74. (Year: 1995).*
Inkster et al. 2-Fluoropyridine prosthetic compounds for the 18F labeling of bombesin analogues. Bioorganic & Medicinal Chemistry Letters 23 (2013) 3920-3926. (Year: 2013).*

(Continued)

*Primary Examiner* — Yih-Horng Shiao
(74) *Attorney, Agent, or Firm* — Morrison & Foerster LLP

(57) ABSTRACT

The invention describes novel conjugates of formula (I) of a pharmaceutical agent and a moiety capable of binding to a glucose sensing protein allowing a reversible release of the pharmaceutical agent depending on the glucose concentration.

26 Claims, 3 Drawing Sheets

(56) References Cited

OTHER PUBLICATIONS

Figure 1:
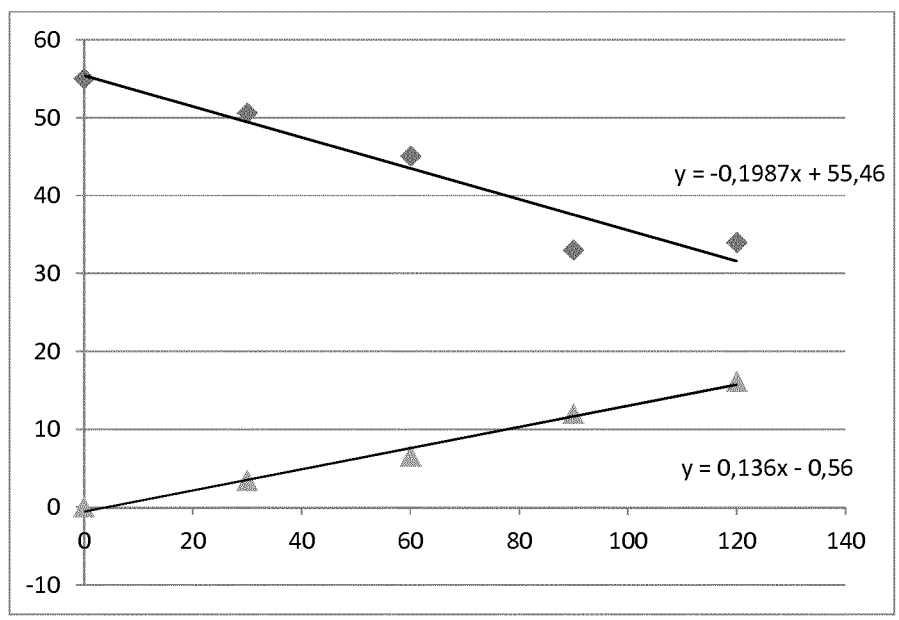

Barros, L.F. et al. (2009). "Kinetic Validation of 6-NBDG as a Probe for the Glucose Transporter GLUT1 in Astrocytes," Journal of Neurochemistry 109(Suppl. 1):94-100.

Brisco, R.D. et al. (2012; e-pub. Nov. 25, 2011). "Development of a Fluorescent Probe for the Study of the Sponge-Derived Simplexide Immunological Properties," Carbohydrate Research 348:27-32.

Carvalho, I. et al. (2010). "Click Chemistry Synthesis of a Library Of 1,2,3-Triazole-Substituted Galactose Derivatives and their Evaluation Against Trypanosoma Cruzi and its Cell Surface Trans-sialidase," Bioorganic & Medicinal Chemistry18:2412-2427.

Dergunov, S.A. et al. "Functionalization of Imprinted Nanopores in Nanometer-Thin Organic Materials," Angew. Chem. Int. Ed. 47:8264-8267.

Dutot, L. et al. (2010). "Glycosylated Cell-Penetrating Peptides and Their Conjugates to a Proapoptotic Peptide: Preparation by Click Chemistry and Cell Viability Studies," J Chem Biol 3:51-65.

European Search Report (Extended) dated Dec. 6, 2019 for EP Application No. 16305640.1, filed on Jun. 2, 2017, 12 pages.

Fernandez, S. et al. (2012; e-pub. May 24, 2012). "Preparation and Preliminary Bioevaluation of a 99m Tc(CO)3-Glucose Derivative Prepared By A Click Chemistry Route," Journal of Labelled Compounds and Radiopharmaceuticals 55(7):274-280.

International Preliminary Report on Patentability dated Dec. 4, 2018 for PCT Application No. PCT/EP2017/063447 filed on Jun. 2, 2017, 14 pages.

International Search Report and Written Opinion dated Oct. 23, 2017 for PCT Application No. PCT/EP2017/063447 filed on Jun. 2, 2017, 9 pages.

Lindsell, W.E. et al. (Feb. 25, 2000). "Synthesis of 1,3-Diynes in the Purine, Pyrimidine, 1,3,5-Triazine and Acridine Series," Tetrahedron 56(9):1233-1245.

Liu, F. et al. (1997). "Glucose-Induced Release of Glycosylpoly(ethylene glycol) Insulin Bound to a Soluble Conjugate of Concanavalin A," Bioconjugate Chem. 8:664-672.

Norberg, O. et al. (2009; e-pub. Nov. 4, 2009). "Photo-Click Immobilization of Carbohydrates on Polymerie Surfaces—A Quick Method to Functionalize Surfaces for Biomolecular Recognition Studies," Bioconjugate Chem. 20:2364-2370.

Rote Liste® (2016). 56th Edition. Medicinal product list for Germany (including EU approvals and certain medicinal products). "Antidiabetika," Chapter 12, pp. 390-406, 21 pages with Table of Contents (German Language). (English language translation of the Table of Contents of the 2016 edition of Rote Liste is provided as an English language overview of the subject matter of the above document, which is in German.).

Russo, L. et al. (2011). "Sugar-Decorated Hydroxyapatite: An Inorganic Material Bioactivated With Carbohydrates," Carbohydrate Research 346:1564-1568.

Yempalla, K.R. et al. (Aug. 31, 2015). "Nitrofuranyl Methyl Piperazines as New Anti-TB Agents: Identification, Validation, Medicinal Chemistry, and PK Studies," ACS Med. Chem. Lett. 6:1041-1046.

Burugupalli, S. et al. (2016). "Investigation Of Benzoyloximes As Benzoylating Reagents: Benzoyl-Oxyma As A Selective BenzoylatingReagent", 2016, Org. Biomol. Chem. 14(1):97-104.

Extended European Search Report dated Mar. 22, 2018, for European Patent Application No. 17306673.9, 6 pages.

Hu, G. et al. (2003). "Regioselective Benzoylation Of 6-O-Protected and 4,6-Odiprotected Hexopyranosides As Promoted By Chiral And Achiral Ditertiary 1,2-Diamines," Helvetica Chimica Acta 86(12):4369-4391.

International Preliminary Report on Patentability, dated Jun. 2, 2020, for International Application No. PCT/EP2018/083077, filed Nov. 30, 2018, 6 pages.

International Search Report and Written Opinion of the International Searching Authority, dated Mar. 14, 2019, for International Application No. PCT/EP2018/083077, filed Nov. 30, 2018, 13 pages.

Kanai, F. et al.(1993). "Direct Demonstration Of Insulininduced GLUT4 Translocation To The Surface Of Intact Cells By Insertion Of A C-Myc Epitope Into An Exofacial GLUT 4 Domain", J. Biol. Chem. 268(19):14523-14626.

Kim, S. et al. (1985). "Selective Benzoylation Of Diols With 1-(Benzoyloxy)Benzotriazole," J. Org. Chem. 50(10):1751-1752.

Muramatsu, W. et al. (Jan. 29, 2013). "Selectivity Switch In The Catalytic Functionalization Of Nonprotected Carbohydrates: Selective Synthesis In The Presence Of Anomeric And Structurally Similar Carbohydrates Under Mild Conditions," J. Org. Chem. 78(6):2336-2345.

Siebeneicher, H. et al. (2016). "Identification Of Novel GLUT Inhibitors," Bioorg. Med. Chem. Lett. 26(7):1732-1737.

Xiao, G. et al. (2017). "Catalytic Site-Selective Acylation Of Carbohydrates Directed By Cation-N Interaction," J. Am. Chem. Soc. 139(12):4346-4349.

Zhao, W. et al. (Jan. 3, 2005) "Facile Synthesis Of The Heptasaccharide Repeating Unit Of O-Deacetylated GXM Of C. Neoformans Serotype B," Bioorganic & Medicinal Chemistry 13(1):121-130.

Zhou, Y. et al. (2013). "Halide Promoted Organotinmediated Carbohydrate Benzylation: Mechanism And Application", Tetrahedron Letters 69(13):2693-2700.

Zhu, Y. et al. (2006, e-pub Dec. 15, 2005). "[13C,15N]2-Acetamido-2-Deoxy-D-Aldohexoses And Their Methyl Glycosides: Synthesis And NMR Investigations Of Jcouplings Invovling 1H, 13C, And 15N", J. Org. Chem. 71, (2):466-479.

\* cited by examiner

CONJUGATES OF A PHARMACEUTICAL AGENT AND A MOIETY CAPABLE OF BINDING TO A GLUCOSE SENSING PROTEIN

CROSS-REFERENCE TO RELATED APPLICATIONS

This application is a National Phase application under 35 U.S.C. § 371 of International Application No. PCT/EP2017/063447, filed Jun. 2, 2017, which claims priority to EP Application No. 16305640.1, filed Jun. 2, 2016, the disclosures of each of which are incorporated herein by reference in their entirety.

The invention describes novel conjugates of a pharmaceutical agent and a moiety capable of binding to a glucose sensing protein allowing a reversible release of the pharmaceutical agent depending on the glucose concentration.

Over the last decades the number of patients suffering from diseases, particularly from type 2 diabetes, has increased dramatically. Despite education and treatment the growth rate is exploding. The disease evolves slowly and in the beginning the pancreas can compensate decreasing insulin sensitivity by an increased release of insulin. At this stage oral antidiabetics like insulin sensitizers and -releasers can support this compensation mechanism, but cannot cure the disease. So after this period of time external insulin has to be injected.

Several insulins are on the market, which are classified by their duration of action. The intrinsic danger of hypoglycemia is counteracted by very flat insulin profiles (so called basal insulins), but is neither conceptionally addressed nor finally overcome by these basal insulins.

The development of a real glucose sensing insulin accomplishing a glucose dependent release from a depot simulating the natural release by the pancreas is still one of the holy grails in diabetes research. Such an insulin would generate a local (eg intraparenteral) or moving depot (blood stream) from where it is released in a glucose concentration dependent manner and finally recaptured by the system on decreasing glucose concentrations.

The blood glucose concentration is under hormonal regulation. While several hormones like glucagon, epinephrine, norepinephrine, cortisol, and hormones from the thyroid gland provoke elevated glucose levels, insulin is the only hormone which lowers glucose levels. In addition the glucose level is of course influenced by timing and composition of meals, physical stress, and infections.

In healthy persons the fasting blood glucose level is around 5 mM (900 mg/L) and can after a meal increase to 40 mM for several hours. In diabetic patients where blood glucose is out of control, the level can vary between 1-30 mM and can unpredictable fluctuate between the borders of hyperglycemia (>10 mM) and hypoglycemia (<3 mM). Despite the possibility of exact blood glucose measurement and titration of insulins, hypoglycemia is still a serious problem. This problem can be solved by glucose sensitive and -responsive delivery of pharmaceutical agents effecting the glucose level.

Non glucose-sensitive depots to protect drugs (small molecules and proteins like insulin) from degradation and elongate their half life are used frequently in medicine. For insulin for example a static subcutanous depot can be realized. Insulin is stored as insoluble hexamers. From this depot soluble monomers are released to the blood following law of mass equation.

An additional opportunity is the non-covalent binding of modified insulins to albumin. Since unmodified insulin is not binding to albumin, noncovalent hydrophobic binding is enabeled by hydrophobic modification (eg by myristic acid). Coupling of fatty acids to insulin enable protection of insulin from degradation and dramatically increases half life by hours to days.

The release of insulin from such a circulating depot can be described by the law of mass equation and is a function of the amount of insulin, the albumin depot, and the affinity of the insulin derivative to albumin. Since the depot is fixed, the amount and affinity of insulin have to be adjusted. The release of basal insulin can be controlled, but the release is glucose independent.

Within the last decade efforts have been started to establish glucose sensitive insulin depots. These efforts can be summarized and assigned to three classical principles:

Chemical recognition of glucose by boronic acids

Biochemical recognition of glucose by carbohydrate binding proteins like such as lectins (Concanavalin A, wheat germ agglutinin)

Glucose converting enzymes like glucose oxidase or hexokinase. Here binding affinity can be used as a signal. More frequently associated pH shift or change of charge is measured.

These principles can be used for glucose measurement or to translate the signals into direct or indirect glucose release. Four possibilities for realization are described below.

Direct modification of insulins

"Glucose responsive" hydrogels, these are synthetic pores, which are modified with a glucose sensing molecule (boronic acid- or glucose oxidase based). These gels are filled with insulins. In the presence of glucose they expand, get leaky, and finally release insulin on increasing glucose levels.

"Device-approaches": In this case insulin levels are only measured by a sensor.

Closed loop approaches: This describes a technical solution. A sensor measures glucose levels. The signal is transmitted to an independent insulin depot (eg a pump) which releases insulin triggered by the signal. An independent insulin reservoir is triggered and releases insulin, controlled by the sensor signal. An advantage may be a large insulin depot which is not necessarily in the body.

Several patent applications, e.g. WO 2001/92334, WO 2011/000823, or WO 2003/048195 describe the use of boronic acid modified insulin derivatives in combination with albumin for a glucose sensitive insulin release. With this approach the floating insulin/albumin depot shall be further developed to a glucose sensing floating depot.

A different approach for a glucose sensing approach has been described in WO 2010/088294, WO 2010/88300, WO 2010/107520, WO 2012/015681, WO 2012/015692, or WO 2015/051052. These documents describe the concomitant administration of concanavalin A and a glucose binding protein preferably recognizing mannose. Accordingly mannose modified insulins can be released by mannose from a depot. In addition an intrinsic mannose binding protein is described which may be responsible for the binding of mannose without the need of concanavalin.

Erythrocytes have been used as a vehicle for the transport of drugs, e.g. for tumor starvation, enzyme replacement and immunotherapy as described in WO 2015/121348, WO 2014/198788 and WO 2013/139906.

Liu et al. (Bioconjugate Chem. 1997, 8, 664-672) discloses a glucose induced release of glucosylpoly(ethylene glycol) insulin bound to a soluble conjugate of concanavalin A wherein the insulin is linked at the B1 amino group with a poly(ethylene glycol) spacer to the 1-position of the sugar.

WO2012/177701 discloses conjugates of $^{68}$Ga-DOTA labelled sugars for tissue specific disease imaging and radiotherapy.

The use of erythrocytes as a classical depot, by binding drugs to the surface of erythrocytes is described in WO 2013/121296. Here peptides are described, which bind to the surface with a very high affinity ($K_D$=6.2 nM). These peptides are used for immunomodulation e.g. in transplantation medicine.

The present invention relates to a novel conjugate comprising a pharmaceutical agent and a sugar moiety.

Further the present invention relates to a novel conjugate comprising a pharmaceutical agent and a sugar moiety for use as a pharmaceutical.

Further the present invention relates to a novel conjugate comprising a pharmaceutical agent and a sugar moiety which binds to the insulin dependent glucose transporter GluT1, which provides a release of the pharmaceutical agent dependent on the glucose concentration in blood. The insulin dependent glucose transporter GluT1 is present on erythrocytes. Binding of glucose to GluT1 is reversible based on the blood glucose concentration.

In one embodiment the conjugate of the invention is bound to GluT1 at low glucose concentrations of e.g. 1-10 mM, which are found under fasting conditions. Under these conditions, the stable floating depot of the active agent is formed. After an increase in the glucose concentration from e.g. 30 mM to 40 mM after a meal, the free glucose competes for the GluT1 binding site and the conjugate is released in a glucose concentration dependent manner and the pharmaceutical agent is available to exert its effect. As the glucose concentration decreases again, the conjugate molecules are recaptured by GluT1. Thus, the presence of undesired high amounts of free pharmaceutical agents is avoided.

The present invention relates to conjugates of formula (I):

$$P\text{-}[L_1]_m\text{-}[A_1]_o\text{-}[L_2]_p\text{-}[A_2]_r\text{-}[L_3]_q\text{-}S \qquad (I)$$

wherein P is a pharmaceutical agent, particularly a peptide, $L_1$, $L_2$, and $L_3$ are independently of each other a linker having a chain length of 1-20 atoms,
$A_1$ and $A_2$ are independently of each other a 5 to 6 membered monocyclic ring or a 9 to 12 membered bicyclic ring, or two 5 to 6 membered monocyclic and/or 9 to 12 membered bicyclic rings connected to each other, wherein each ring is independently a saturated, unsaturated, or aromatic carbocyclic or heterocyclic ring and wherein each ring may carry at least one substituent,
S is a sugar moiety which binds to the insulin independent glucose transporter GluT1, and
m, o, p, r, and q are independently of each other 0 or 1, and wherein at least one of r and o is 1,
or a pharmaceutically acceptable salt or solvate thereof.

The present invention relates also to conjugates of formula (I):

$$P\text{-}[L_1]_m\text{-}[A_1]_o\text{-}[L_2]_p\text{-}[A_2]_r\text{-}[L_3]_q\text{-}S \qquad (I)$$

wherein P is an insulin or an insulinotropic peptide,
$L_1$, $L_2$, and $L_3$ are independently of each other a linker having a chain length of 1-20 atoms,
$A_1$ and $A_2$ are independently of each other a 5 to 6 membered monocyclic ring or a 9 to 12 membered bicyclic ring, or two 5 to 6 membered monocyclic and/or 9 to 12 membered bicyclic rings connected to each other, wherein each ring is independently a saturated, unsaturated, or aromatic carbocyclic or heterocyclic ring and wherein each ring may carry at least one substituent,
S is a sugar moiety which binds to the insulin independent glucose transporter GluT1, and comprises a terminal pyranose S1 moiety which is attached via position 2, 4, or 6 to the conjugate of formula (I),
m, o, p, r, and q are independently of each other 0 or 1, and wherein at least one of r and o is 1,
or a pharmaceutically acceptable salt or solvate thereof.

Another aspect of the invention are compounds of formula (Ia) and (Ib):

$$R\text{—}(O\text{=}C)\text{-}[L_1]_m\text{-}[A_1]_o\text{-}[L_2]_p\text{-}[A_2]_r\text{-}[L_3]_q\text{-}S \qquad (Ia)$$

$$[L_1]_m\text{-}[A_1]_o\text{-}[L_2]_p\text{-}[A_2]_r\text{-}[L_3]_q\text{-}S \qquad (Ib)$$

wherein $L_1$, $L_2$, $L_3$, $A_1$, $A_2$, S, m, o, p, r, and q are defined as indicated above and R is H, halogen, OH, O-alkyl-, an anhydride forming group or another active ester forming group for coupling reactions, like 4-nitrophenylester, succinate or N-hydroxy benzotriazol.
or pharmaceutically acceptable salts or solvates thereof.

Compounds (Ia) and (Ib) are suitable as intermediates for the synthesis of the conjugates of formula (I).

Another aspect of the present invention is the conjugate of formula (I) as described above for the use in medicine, particularly in human medicine.

Another aspect of the present invention is a pharmaceutical composition comprising a conjugate of formula (I) as described above as an active agent and a pharmaceutically acceptable carrier.

Another aspect of the present invention is a method of preventing and/or treating a disorder associated with, caused by, and/or accompanied by a dysregulated glucose metabolism, comprising administering a conjugate of formula (I) or a composition as described above to a subject in need thereof, particularly a human patient.

Another aspect of the present invention is a method of preventing and/or treating diabetes type 1 or diabetes type 2.

The conjugates of formula (I) of the present invention comprise a pharmaceutical agent P, which may a biomolecule, such as a peptide. Preferably, the pharmaceutical agent has an effect of directly or indirectly lowering the glucose concentration in blood. For example, the pharmaceutical agent may be an insulin or an insulinotropic peptide.

The term "insulin" according to the present invention encompasses human insulin, porcine insulin, or analogs thereof, e.g. prandial insulins with fast action or basal insulins with long action. For example, the term "insulin" encompasses recombinant human insulin, insulin glargine, insulin detemir, insulin glulisine, insulin aspart, insulin lispro, etc. or an insulin conjugated to a polyethylene, e.g. a low molecular weight PEG having a molecular weight of 10 kDa or less. If P is an insulin, it may be attached via an amino group to form the conjugate of formula (I), e.g. via an amino side chain, particularly via the amino side chain of an insulin B29Lys residue or via the amino terminus of an insulin B1Phe residue.

Further, the pharmaceutical agent may be an insulinotropic peptide such as GLP-1, an exendin such as exendin-4, or a GLP-1 agonist such as lixisenatide, liraglutide.

The conjugate of formula (I) further comprises a sugar moiety which binds to the insulin independent glucose transporter GluT1, also known as solute carrier family 2, facilitated glucose transporter member 1 (SLC2A1). The amino acid sequence of the human protein is NP_006507, which is encoded by a nucleic acid sequence NM_006516.

GluT1 is an integral membrane protein which facilitates diffusion of glucose into the erythrocyte. The highest expression of GluT1 is found in erythrocytes.

For interaction with GluT1, the conjugate of formula (I) comprises a moiety binding to GluT1 but preventing transport through the erythrocyte membrane. A sugar moiety binding to GluT1 is preferably in an anomeric form, particularly in an anomeric 6-membered ring form such as a pyranose moiety. The sugar moiety comprises an anomeric O atom as well as a hydroxy group or a protected hydroxy group at position 3 and position 4 of a pyranose backbone. In one embodiment, the sugar moiety S of the conjugate of formula (I) comprises a terminal pyranose moiety which is attached via position 2, position 4, or position 6 of the pyranose backbone moiety.

Further, an aspect of the present invention is that introduction of at least one cyclic residue $A_1$ and/or $A_2$ adjacent to the sugar moiety causes a substantial increase in the affinity to GluT1 in comparison to glucose.

Thus, the present invention provides a pharmaceutical agent in form of a conjugate of formula (I) which forms an erythrocyte-based circulating depot that after administration releases/delivers the agent as a function of glucose concentration. Accordingly at low glucose concentrations (below 3 mM) no or only low concentration of free unbound levels of the conjugate should be detectable. On increasing blood glucose levels after a meal the conjugate is released from the circulating depot into the blood stream. The release is a consequence of a direct competition of glucose with the conjugate of formula (I). Thus, release is described by the law of mass equation und self adjusts to tiniest changes in glucose levels. The same should be true for the re-capturing process of the conjugate of formula (I) on decreasing glucose levels.

These characteristics constitute an essential advantage in comparison to the glucose sensing depots from the prior art.

By means of the present invention, the drawbacks of prior art insulins with regard to glycemia are diminished or avoided. The control of glucose recognition and associated release/retrapping will be realized within a single molecule. This minimizes delays in release/retrapping. Glucose sensitive binding and -release is controlled by interaction with endogenous transport and recognition processes. The biological recognition system based on GluT1 transport in erythrocytes is constantly regenerated by the organism.

The present conjugate of formula (I) binds to the ubiquitary glucose transporter GluT1, which has a binding affinity to glucose in the same range as glucose oxidase, a protein frequently used in glucose recognition. GluT1 is highly expressed in erythrocytes and is responsible for the basal supply of these cells. The size of the depot is large enough to accommodate the amount of pharmaceutical agent needed without affecting the erythrocyte glucose supply.

The affinity of the present conjugate of formula (I) is within an affinity window which guarantees binding at low (e.g. <3 mM) glucose levels. With increasing glucose levels (e.g. >10 mM) the conjugate of formula (I) is released accordingly. With decreasing glucose levels the unbound conjugate of formula (I) is recaptured by the transporter.

The release is following the law of mass equation and is dependent on the size of the depot, the loading, and the affinity of the conjugate of formula (I) to GluT1. Since the depot is fixed, the free conjugate fraction is defined by the affinity to GluT1.

In certain embodiments, the conjugate of formula (I) has an affinity of 10-500 nM to the insulin independent glucose transporter GluT1 as determined by affinity measurements for example by a ligand displacement assay, by MST (microscale thermophoresis) technology.

In the conjugate of formula (I) of the present invention, the individual structural moieties P, $A_1$, $A_2$, and S may be connected by linkers $L_1$, $L_2$, and $L_3$. If present, $L_1$, $L_2$, and $L_3$ are linkers having a chain length of 1-20 atoms, particularly 3 to 10, or 3 to 6 atoms.

In some embodiments, $L_1$, $L_2$, and $L_3$ are independently of each other ($C_1$-$C_{20}$) alkylene, ($C_2$-$C_{20}$) alkenylene, or ($C_2$-$C_{20}$) alkynylene, wherein one or more C-atoms may be replaced by heteroatoms or heteroatom moieties, particularly by O, NH, N($C_{1-4}$) alkyl, S, $SO_2$, O—$SO_2$, O—$SO_3$, O—$PHO_2$ or O—$PO_3$, and/or wherein one or more C-atoms may be substituted with ($C_{1-4}$) alkyl, ($C_{1-4}$) alkyloxy, oxo, carboxyl, halogen, e.g. F, Cl, Br, or I, or a phosphorus-containing group. The carboxyl group may be a free carboxylic acid group or a carboxylic acid ester, e.g. $C_1$-$C_4$ alkyl ester or a carboxamide or mono($C_1$-$C_4$) alkyl or di($C_1$-$C_4$) alkyl carboxamide group. An example of a phosphorus-containing group is a phosphoric acid or phosphoric acid ($C_{1-4}$) alkyl ester group.

In certain embodiments, the linker $L_3$ has a chain length of 1 to 15 atoms, particularly 1 to 6 or 1 to 4 atoms. For example, $L_3$ may be a ($C_1$-$C_6$) alkylene, particularly ($C_{1-4}$) alkylene group, wherein one or two C-atoms may be replaced by heteroatoms or heteroatom moieties, particularly by O, NH, N($C_{1-4}$) alkyl, S, $SO_2$, O—$SO_2$, O—$SO_3$, O—$PHO_2$ or O—$PO_3$, and/or wherein one or more C-atoms may be substituted with ($C_{1-4}$) alkyl, ($C_{1-4}$) alkyloxy, oxo, carboxyl, halogen, e.g. F, Cl, Br, or I, or a phosphorus-containing group.

In one embodiment, the linker $L_3$ is C=O.
In one embodiment, the linker $L_3$ is absent.
In one embodiment, the linker $L_2$ is —CO—$(CH_2)_3$—.
In one embodiment, the linker $L_2$ is —$(CH_2)_6$—NH—.
In one embodiment, the linker $L_2$ is —$(CH_2)_2$—CO—$(CH_2$—$CH_2$—O$)_2$—$(CH_2)_2$—NH—.
In one embodiment, the linker $L_2$ is —$CH_2$—O—$(CH_2$—$CH_2$—O$)_3$—.

The conjugate of formula (I) of the present invention comprises at least one cyclic group, particularly a cyclic group $A_2$ and optionally a further cyclic group $A_1$. An aspect of the present invention is that the presence of a cyclic group adjacent to the sugar moiety S significantly enhances the binding affinity of the sugar moiety S to the glucose transporter GluT1. The cyclic groups $A_1$ and $A_2$ may be a 5 to 6 membered monocyclic ring, a 9 to 12 membered bicyclic ring, or two 5 to 6 membered monocyclic and/or 9 to 12 membered bicyclic rings connected to each other by a bond or 1-atom bridge, e.g. such as —O— or —$CH_2$—. Each ring may be a saturated, unsaturated, or aromatic carbocyclic or heterocyclic ring. Each ring may be unsubstituted or carry at least one substituent, for example, 1 to 3 substituents selected from halogen, $NO_2$, CN, ($C_{1-4}$) alkyl, ($C_{1-4}$) alkoxy, ($C_{1-4}$)alkyl-($C_{3-7}$)cycloalkyl, ($C_{3-7}$) cycloalkyl, OH, benzyl, —O-benzyl, carboxyl, carboxyester, carboxamide, or mono ($C_{1-4}$) alkyl, or di ($C_{1-4}$) alkyl carboxamide.

In a further embodiment, $A_2$ and/or $A_1$ are a heterocyclic ring wherein 1 to 4 ring atoms, e.g. 1, 2, 3, or 4 ring atoms are selected from nitrogen, sulfur and/or oxygen and wherein the ring may be unsubstituted or may carry at least one substituent as described above. In an especially preferred embodiment, $A_2$ and $A_1$, if present, are independently of each other a 5 to 6 membered monocyclic ring, wherein the ring is a heteroalkyl ring, particularly selected from pyrrolidinyl, pyrazolidinyl, imidazolidinyl, thiazolidinyl, piperazinyl, piperidinyl, morpholinyl, wherein the ring may carry at least one substituent, or a 9 to 12 membered bicyclic ring wherein the ring is a heteroalkyl ring with 1 to 4 ring atoms being selected from N, O, and/or S, and wherein the ring may carry at least one substituent.

In an especially preferred embodiment, $A_2$ and $A_1$, if present, are selected from pyrrolidinyl, pyrazolidinyl, imidazolidinyl, triazolidinyl, piperazinyl, piperidinyl, morpholinyl.

In a further embodiment $A_2$ and/or $A_1$ are 1,2,3-triazolyl.
In a further embodiment $A_2$ is 1,2,3-triazolyl.
In a further embodiment $A_2$ is piperazinyl.

A further group of embodiments are conjugates of formula (I) wherein $A_2$ is piperazinyl, $L_2$ is absent and $A_1$ is cyclohexanyl.

A further group of embodiments are conjugates of formula (I) wherein $A_2$ is piperazinyl, $L_2$ is absent and $A_1$ is cyclohexanyl.

A further group of embodiments are conjugates of formula (I) wherein $A_2$ is piperazinyl, $L_2$ is —$CH_2$— and $A_1$ is cyclohexanyl.

A further group of embodiments are conjugates of formula (I) wherein $A_2$ is piperazinyl, $L_2$ is absent and $A_1$ is phenyl.

A further group of embodiments are conjugates of formula (I) wherein $A_2$ is 1,2,3-triazolyl, $L_2$ is absent and $A_1$ is phenyl.

A further group of embodiments are conjugates of formula (I) wherein
$L_3$ is —CO—, $A_1$ is phenyl, $L_2$ is —O— and $A_1$ is phenyl wherein each ring may be unsubstituted or carry at least one substituent, for example, 1 to 3 substituents selected from halogen, $NO_2$, CN, $(C_{1-4})$ alkyl, $(C_{1-4})$ alkoxy, $(C_{1-4})$alkyl-$(C_{3-7})$cycloalkyl, $(C_{3-7})$ cycloalkyl, OH, benzyl, —O-benzyl, carboxyl, carboxyester, carboxamide, or mono $(C_{1-4})$ alkyl, or di $(C_{1-4})$ alkyl carboxamide.

A further group of embodiments are conjugates of formula (I) wherein the group -$A_2$-$L_3$- is selected from

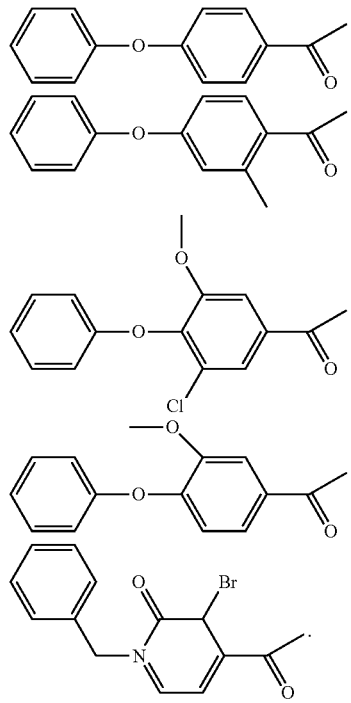

In a further embodiment of the present invention, the conjugate of formula (I) comprises a single cyclic group $A_2$ and the second cyclic group $A_1$ is absent. In such embodiments, the conjugate of formula (I) may have a structure wherein m=1, o=0, p=0, and q=0 or 1. In other embodiments, a second cyclic group $A_1$ is present. In such embodiments, the conjugates of formula (I) may have a structure wherein m=1, o=1, p=1, and q=0 or 1.

The conjugate of formula (I) comprises a sugar moiety S which binds to the insulin independent glucose transporter GluT1. This sugar moiety S may comprise a terminal pyranose moiety which is attached via position 2, 4, or 6 to the conjugate of formula (I). In one embodiment the terminal pyranose moiety is attached via position 6 to the conjugate of formula (I).

In some embodiments, the sugar moiety S may comprise a terminal pyranose moiety S1 having a backbone structure of Formula (II)

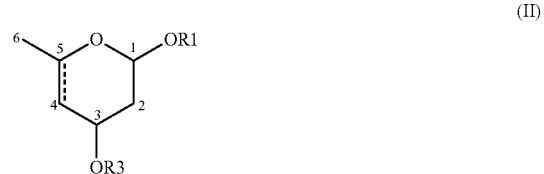

(II)

wherein 1, 2, 3, 4, 5, and 6 denote the positions of the C-atoms in the pyranose moiety,
wherein ——— is a single bond and - - - is a single or a double bond, and
R1 and R3 are H or a protecting group,
and wherein S1 is attached via position 2, 4, or 6 to the conjugate of formula (I).

The protecting group may be any suitable protecting group known in the art, e.g. an acyl group such as acetyl or benzoyl, an alkyl group such as methyl, an aralkyl group such as benzyl, or 4-methoxybenzyl (PMB) including divalent protecting groups such as isopropylidene or benzylidene.

In some embodiments, the terminal pyranose moiety may be selected from glucose, galactose, 4-deoxyglucose, and 4,5-dehydroglucose derivatives, wherein the terminal pyranose moiety is attached via position 2, 4, or 6 to the conjugate of formula (I) or is mannose attached via position 6.

In another embodiment, the terminal pyranose moiety S1 is of the Formula (IIIa) or (IIIb):

(IIIa)

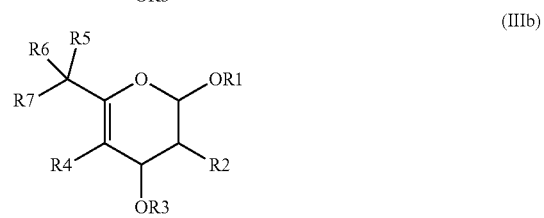

(IIIb)

wherein R1 is H or a protecting group such as methyl or acetyl,

R2 is OR8, or NHR8 or an attachment site to the conjugate of formula (I), wherein R8 is H or a protecting group such as acetyl or benzyl, R3 is H or a protecting group such as acetyl or benzyl, R4 is H, OR8, or NHR8 or an attachment site to the conjugate of formula (I), wherein R8H or a protecting group such as acetyl or benzyl, or R1 and R2 and/or R3 and R4 form together with the pyranose ring atoms to which they are bound a cyclic group, e.g. an acetal, R5 and R6 are H or together form together with the carbon atom to which they are bound a carbonyl group, R7 is OR8, or NHR8 or an attachment site to the conjugate of formula (I), wherein R8 is H or a protecting group such as acetyl or benzyl, and wherein one of R2, R4, and R7 is the attachment site to the conjugate of formula (I).

In another embodiment of the terminal pyranose moiety S1 of the formula (IIIa) and (IIIb), R1 and R3 are H. In further embodiments of the terminal pyranose moiety S1 of the formula (IIIa) and (IIIb), R2 is OR8, or an attachment site to the conjugate of formula (I), R4 is H, OR8, or an attachment site to the conjugate of formula (I), R7 is OR8 or an attachment site to the conjugate of formula (I), and wherein R8 is H or a protecting group.

In another embodiment of the terminal pyranose moiety S1 of the formula (IIIa) and (IIIb), position 6 of the pyranose moiety and particularly substituent R7 is the attachment site of the terminal pyranose moiety S1 to the conjugate of formula (I).

In specific embodiments, the pyranose moiety S1 is of formula (IVa), (IVb), (IVc), (IVd), or (IVe):

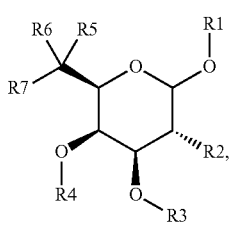
(IVa)

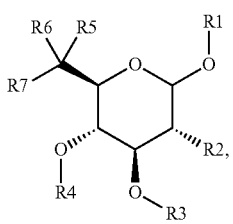
(IVb)

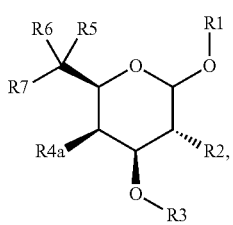
(IVc)

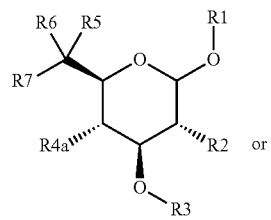
(IVd)

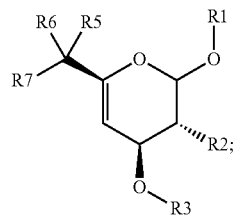
(IVe)

wherein R1, R2, R3, R5, R6, and R7 are defined as indicated above, wherein R4a is H or the attachment site to the conjugate of formula (I), and wherein R4 is H, a protecting group, or the attachment site to the conjugate of formula (I).

The sugar moiety S of the conjugate of formula (I) may comprise one or more, e.g. 2, or 3 saccharide units. For example, the sugar moiety has a structure of formula (V):

$$—[X_2—S2]_s-X_1—S1 \qquad (V)$$

wherein $X_1$ is a bond or O, particularly a bond, $X_2$ is a bond, NH or O, particularly a bond, S2 is a mono- or disaccharide moiety, particularly comprising at least one hexose or pentose moiety, S1 is a terminal pyranose moiety as defined above, and s is 0 or 1.

The saccharide moiety S2 may be a pyranose moiety, particularly selected from glucose, galactose, 4-deoxyglucose, and 4,5-dehydroglucose derivatives or a furanose moiety, particularly selected from fructose derivates.

In specific embodiments, the saccharide moiety S2 is of formula (VIa), (VIb), (VIc), (VId), or (VIe):

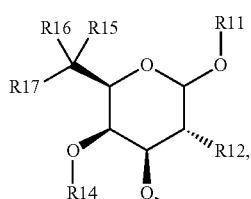
(VIa)

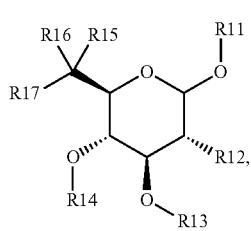
(VIb)

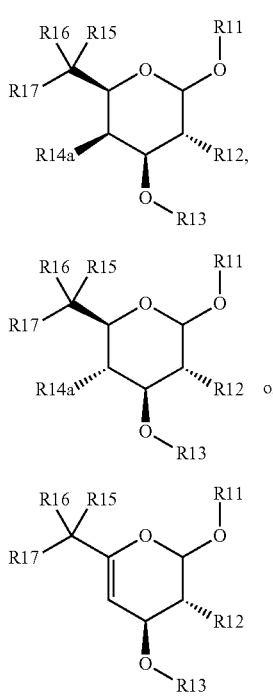

wherein R11 is a bond to $X_1$,
R12 is OR8 or NHR8 or an attachment site to $X_2$, wherein R8 is H or a protecting group such as acetyl or benzyl,
R13 is H or a protecting group such as acetyl or benzyl,
R14 is R8 or an attachment site to $X_2$, wherein R8 is H or a protecting group such as acetyl,
R14a is H or an attachment site to $X_2$,
R15 and R16 are H or together form together with the carbon atom to which they are bound a carbonyl group,
R17 is OR8 or an attachment site to $X_2$, wherein R8 is H or a protecting group such as acetyl or benzyl,
or R11 and R12 and/or R13 and R14 form together with the ring atoms to which they are bound a cyclic group such as an acetal,
and wherein one of R12, R14, R14a and R17 is an attachment site to $X_2$.

In further embodiments, the conjugate of formula (I) reversibly binds to the insulin independent glucose transporter GluT1, dependent from the glucose concentration in the surrounding medium, which is blood after administration. In a further embodiment the conjugate of formula (I) of the present invention is not transported through the cell membrane upon binding to GluT1. In a further embodiment the sugar moiety S comprises a single terminal saccharide moiety. In still further embodiments, the sugar moiety S does not comprise a mannose unit, particularly a terminal mannose unit.

Definitions

"Alkyl" means a straight-chain or branched carbon chain. Alkyl groups may be unsubstituted or substituted, wherein one or more hydrogens of an alkyl carbon may be replaced by a substituent such as halogen. Examples of alkyl include methyl, trifluoromethyl, ethyl, n-propyl, isopropyl, n-butyl, isobutyl, sec-butyl, tert-butyl, n-pentyl, and n-hexyl.

"Alkylene" means a straight-chain or branched carbon chain bonded to each side. Alkylene groups may be unsubstituted or substituted.

"Aryl" refers to any substituent derived from a monocyclic or polycyclic or fused aromatic ring, including heterocyclic rings, e.g. phenyl, thiophene, indolyl, naphthyl, pyridyl, which may optionally be further substituted.

"Acyl" means a chemical functional group of the structure R—(C=O)—, wherein R is an alkyl, aryl, or aralkyl.

"Halogen" means fluoro, chloro, bromo, or iodo. Preferably, halogen is fluoro or chloro.

A "5 to 7 membered monocyclic ring" means a ring with 5 or 7 ring atoms that may contain up to the maximum number of double bonds (aromatic or non-aromatic ring which is fully, partially or un-saturated) wherein at least one ring atom up to 4 ring atoms may be replaced by a heteroatom selected from the group consisting of sulfur (including —S(O)—, —S(O)$_2$—), oxygen and nitrogen (including =N(O)—). Examples for 5 to 7 membered rings include carbocycles such as cyclopentane, cyclohexane, and benzene, or heterocycles such as furan, thiophene, pyrrole, pyrroline, imidazole, imidazoline, pyrazole, triazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepame, azepine, or homopiperazine.

"9 to 12 membered bicyclic ring" means a system of two rings with 9 to 12 ring atoms, where at least one ring atom is shared by both rings and that may contain up to the maximum number of double bonds (aromatic or non-aromatic ring which is fully, partially or un-saturated) wherein at least one ring atom up to 6 ring atoms may be replaced by a heteroatom selected from the group consisting of sulfur (including —S(O)—, —S(O)$_2$—), oxygen, and nitrogen (including =N(O)—) and wherein the ring is linked to the rest of the molecule via a carbon or nitrogen atom. Examples for 9 to 12 membered rings include carbocycles such as naphthalene and heterocycles such as indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine, or pteridine. The term 9 to 12 membered heterobicycle also includes spiro structures of two rings like 1,4-dioxa-8-azaspiro[4.5]decane or bridged heterocycles like 8-aza-bicyclo[3.2.1]octane.

The term "protecting group" means a chemical protecting group for protecting OH— groups, known in the art of sugar chemistry as described in Theodora W. Greene, Peter G. M. Wuts, Protective Groups in Organic Synthesis, 3rd Edition, John Wiley & Sonc, Inc. 1999. Examples of a protecting group are: acetyl, benzyl, or p-methoxybenzyl; or isopropylidene groups for protecting two hydroxy groups.

The term "anhydride forming group" means a chemical group which forms with the carbonyl group to which it is attached an anhydride. An example is acetic anhydride which acetylates said carbonyl group.

The term "active ester forming group" means a chemical group which forms with the carbonyl group to which it is attached an ester which activates said carbonyl group for a coupling reaction with an amino group containing conpound forming an amide group.

Examples of active ester forming groups are 4-Nitrophenylester, N-Hydroxybenzotriazol (HOBt), 1-Hydroxy-7-azabenzotriazol oder N-Hydroxysuccinimid (HOSu).

The term "pharmaceutically acceptable" means approved by a regulatory agency such as the EMEA (Europe) and/or the FDA (US) and/or any other national regulatory agency for use in animals, and/or in humans.

The conjugate of formula (I) of the present invention is suitable for use in medicine, e.g. in veterinary medicine or in human medicine. Particularly, the conjugate of formula (I) is suitable for human medicine. Due to the glucose dependent release/recapture mechanism, the conjugate of formula (I) is particularly suitable for use in the prevention and/or treatment of disorders associated with, caused by, and/or accompanied by a dysregulated glucose mechanism, for example for use in the prevention and/or treatment of diabetes mellitus, particularly of diabetes type 2 or type 1.

The invention also provides a pharmaceutical composition comprising a conjugate of formula (I) as described above as an active agent and a pharmaceutically acceptable carrier.

The term "pharmaceutical composition" indicates a mixture containing ingredients that are compatible when mixed and which may be administered. A pharmaceutical composition includes one or more medicinal drugs. Additionally, the pharmaceutical composition may include one or more pharmaceutically acceptable carriers such as solvents, adjuvants, emollients, expanders, stabilizers, and other components, whether these are considered active or inactive ingredients.

The conjugates of formula (I) of the present invention, or salts thereof, are administered in conjunction with an acceptable pharmaceutical carrier as part of a pharmaceutical composition. A "pharmaceutically acceptable carrier" is a compound or mixture of compounds which is physiologically acceptable while retaining the therapeutic properties of the substance with which it is administered. Standard acceptable pharmaceutical carriers and their formulations are known to one skilled in the art and described, for example, in Remington: The Science and Practice of Pharmacy, (20th ed.) ed. A. R. Gennaro A. R., 2000, Lippencott Williams & Wilkins. One exemplary pharmaceutically acceptable carrier is physiological saline solution.

Acceptable pharmaceutical carriers include those used in formulations suitable for oral, rectal, nasal, or parenteral (including subcutaneous, intramuscular, intravenous, intradermal, and transdermal) administration. The compounds of the present invention will typically be administered parenterally.

The term "pharmaceutically acceptable salt" means salts of the conjugates of formula (I) of the invention which are safe and effective for use in mammals. Pharmaceutically acceptable salts may include, but are not limited to, acid addition salts and basic salts. Examples of acid addition salts include chloride, sulfate, hydrogen sulfate, (hydrogen) phosphate, acetate, citrate, tosylate, or mesylate salts. Examples of basic salts include salts with inorganic cations, e.g. alkaline or alkaline earth metal salts such as sodium, potassium, magnesium, or calcium salts and salts with organic cations such as amine salts. Further examples of pharmaceutically acceptable salts are described in Remington: The Science and Practice of Pharmacy, (20th ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimica Acta, Zurich, Switzerland, and Wiley-VCH, Weinheim, Germany.

The term "solvate" means complexes of the conjugates of formula (I) of the invention or salts thereof with solvent molecules, e.g. organic solvent molecules and/or water.

The compounds of the present invention will be administered in a "therapeutically effective amount". This term refers to a nontoxic but sufficient amount of the conjugate of formula (I) to provide the desired effect. The amount of a conjugate of formula (I) of the formula (I) necessary to achieve the desired biological effect depends on a number of factors, for example the specific conjugate of formula (I) chosen, the intended use, the mode of administration, and the clinical condition of the patient. An appropriate "effective" amount in any individual case may be determined by one of ordinary skill in the art using routine experimentation.

Pharmaceutical compositions of the invention are those suitable for parenteral (for example subcutaneous, intramuscular, intradermal, or intravenous), oral, rectal, topical, and peroral (for example sublingual) administration, although the most suitable mode of administration depends in each individual case on the nature and severity of the condition to be treated and on the nature of the conjugate of formula (I)) used in each case.

Suitable pharmaceutical compositions may be in the form of separate units, for example capsules, tablets, and powders in vials or ampoules, each of which contains a defined amount of the conjugate of formula (I); as powders or granules; as solution or suspension in an aqueous or non-aqueous liquid; or as an oil-in-water or water-in-oil emulsion. It may be provided in single dose injectable form, for example in the form of a pen. The compositions may, as already mentioned, be prepared by any suitable pharmaceutical method which includes a step in which the active ingredient and the carrier (which may consist of one or more additional ingredients) are brought into contact.

The conjugates of formula (I) of the present invention can be widely combined with other pharmacologically active compounds, such as all drugs mentioned in the Rote Liste 2016 e.g. with all antidiabetics mentioned in the Rote Liste 2016, chapter 12.

The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

General methods for the synthesis of conjugates of formula (I) and intermediates thereof are described in the following schemes:

Scheme 1:

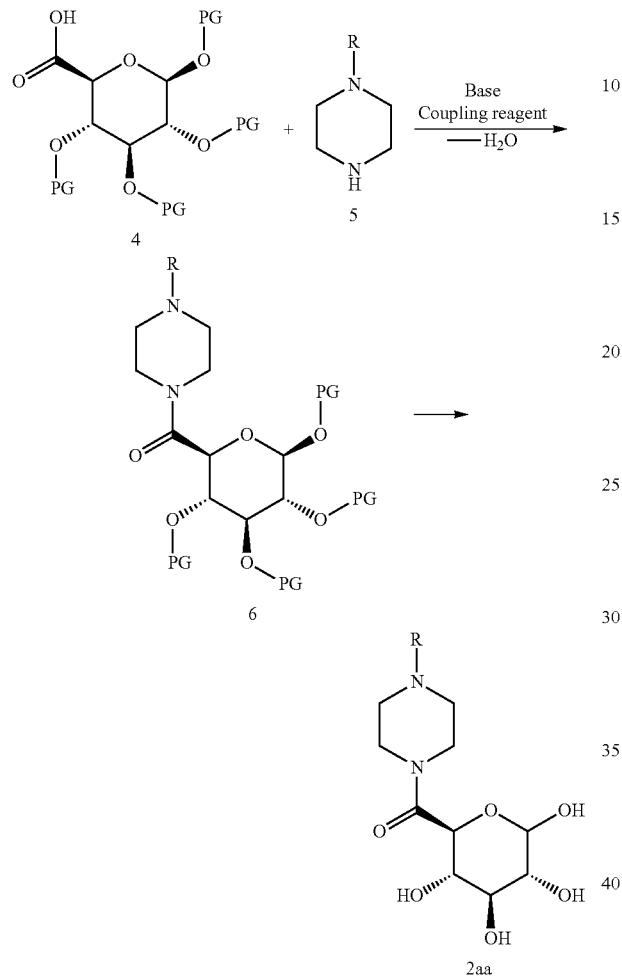

Unsaturated compounds of formula 2ba can be synthesized like shown in scheme 2:

Scheme 2:

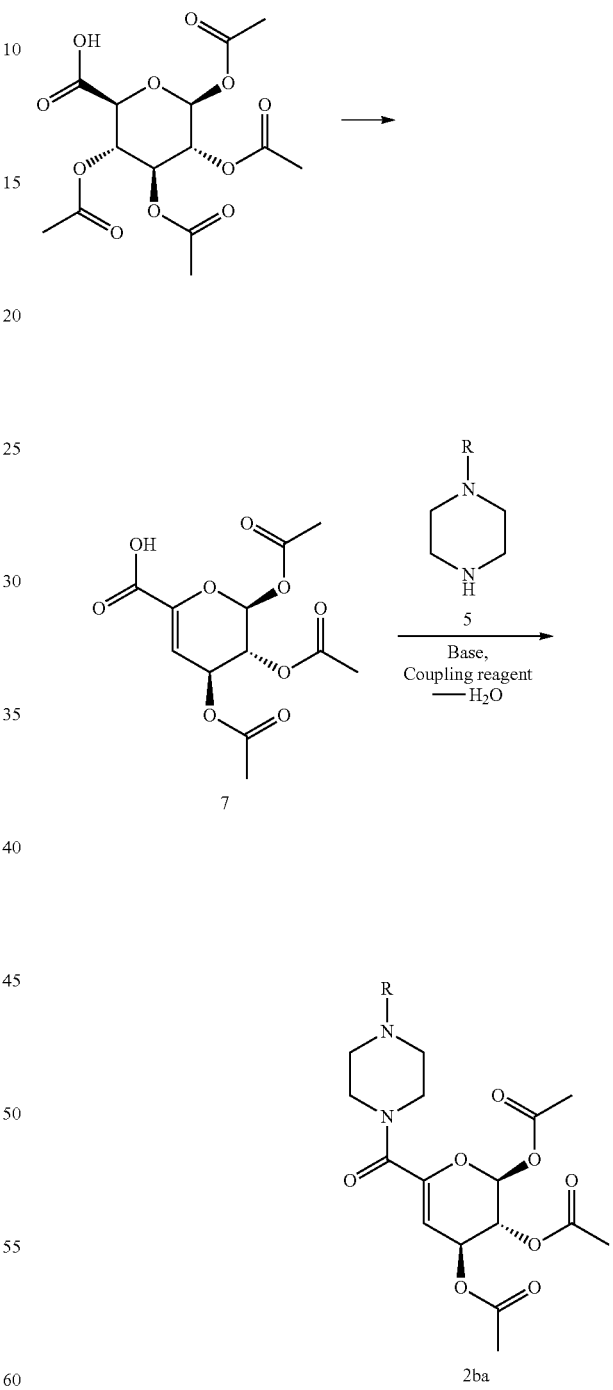

OH-protected glucuronic acid compounds 4, where the protecting groups (PG) are e.g. acetyl, benzyl, or p-methoxybenzyl, or isopropylidene groups for protecting two hydroxy groups at the same time, or the like, can be coupled with amines 5 using well known amide coupling procedures e.g. using HATU, TBTU, BEP, TOTU, or other activating methods for carboxylic acids in common known solvents like dimethylformamide, tetrahydrofuran, dichloromethane, acetonitrile, or the like. Dependent on the protecting group, the deprotection to compounds 2aa takes place under different conditions such as basic, acidic, hydrogenating or oxidative conditions. For example, acetyl groups are cleaved under basic conditions using sodium or lithium hydroxide in solvents like methanol, water, tetrahydrofuran, or combinations thereof. Isopropylidene groups are cleaved under acidic conditions, e.g. using trifluoroacetic acid in water, hydrogenating conditions using e.g. palladium on charcoal or other hydrogenating catalysts under hydrogen atmosphere in solvents like methanol, ethanol, toluene, acetic acid, tetrahydrofuran or the like, or oxidative conditions like cerium ammonium nitrate or DDQ, like for p-methoxybenzyl.

Starting from acetyl protected glucuronic acid, deacetylation using acetic acid anhydride and triethylamine generates compound 7, which can be coupled with compounds 5 using coupling reagents for amide bond syntheses, like described above, to give compounds 2ba.

A further method to synthesize compounds 2ba is shown in scheme 3:

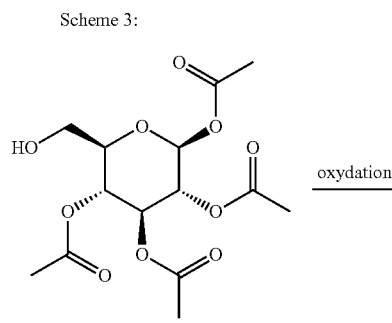

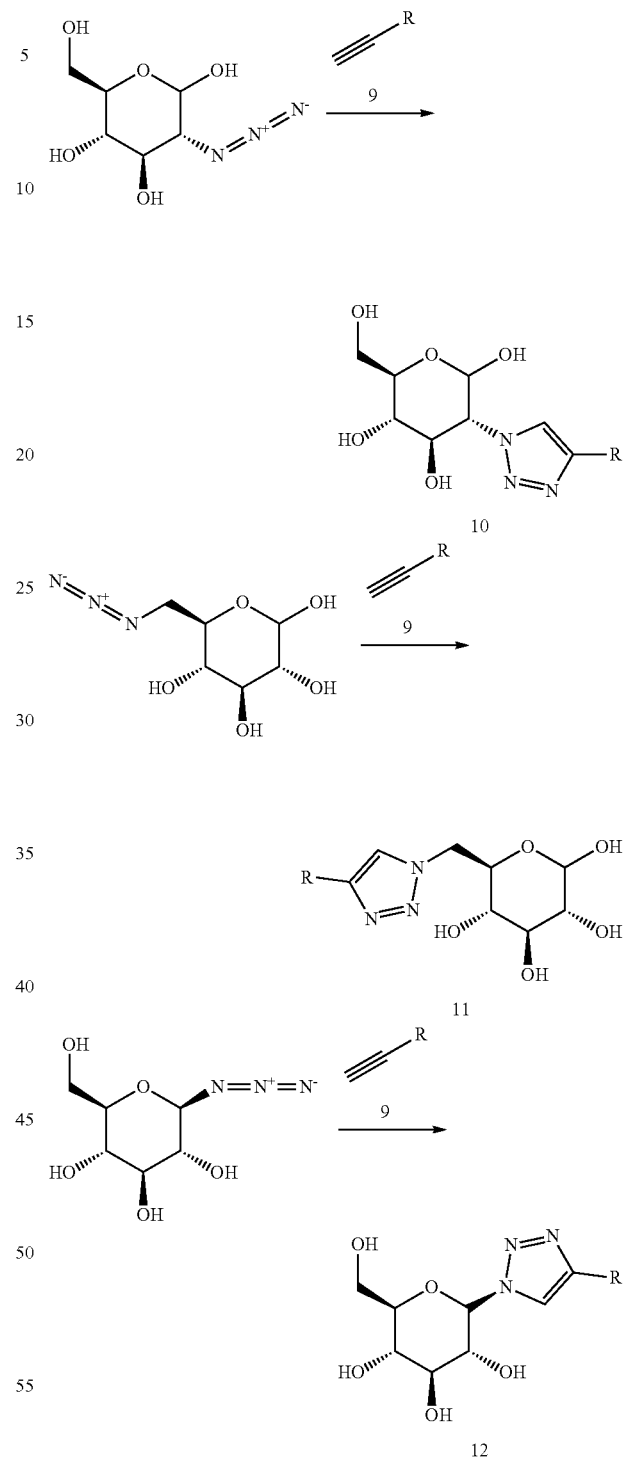

Starting from 1,2,3,4-tetra acetyl protected glucose, oxidation using Swern conditions leads to aldehyde 8. Reductive amination of aldehyde 8 and amines 5 using reductive amination conditions like sodium cyanoborohydride, sodium triacetoxyborohydride or the like, in solvents like dichloroethane, dichloromethane, methanol, and/or acetic acid leads to compounds 2ba.

Compounds 10, 11, and 12 can be synthesized as described in scheme 4.

Compounds of formula 10, 11, and 12 can be synthesized using copper catalysed [3+2]-cycloaddition conditions, also known as azide-alkyne or click cycloaddition. 1-, 2- or 6-azido-deoxyglucose and alkynes 9, are reacted with $CuSO_4*5H_2O$, tris(3-hydroxypropyltriazolylmethyl)amine (THPTA) and sodium ascorbate.

Alkynes 9 can be synthesized as shown in scheme 5.

Scheme 5:
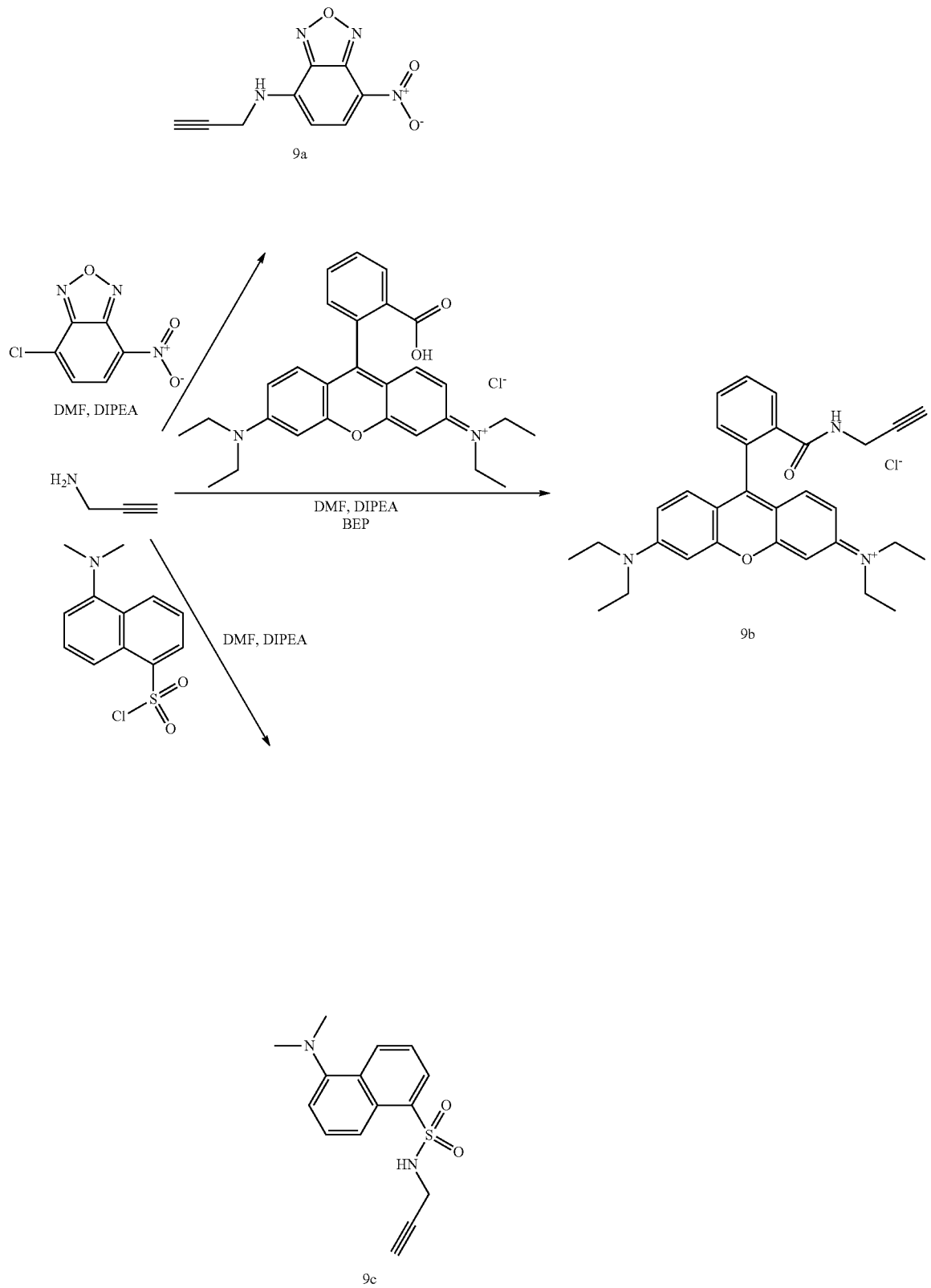

Alkynes 9 can be synthesized using propargylamine under different reaction conditions: alkylation conditions using bases like diisopropylamine, triethylamine or the like, in presence of different chlorides or halides like for 9a and 9c, or peptide coupling conditions like for 9b.

Compounds 14, 17, and 18 can be synthesized as described in scheme 6.

Scheme 6:

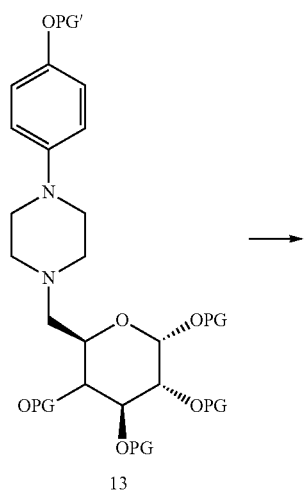
13

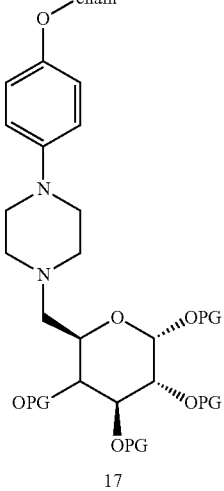
17

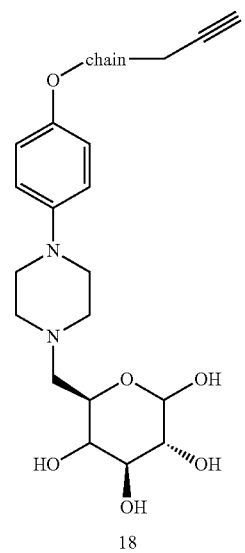
18

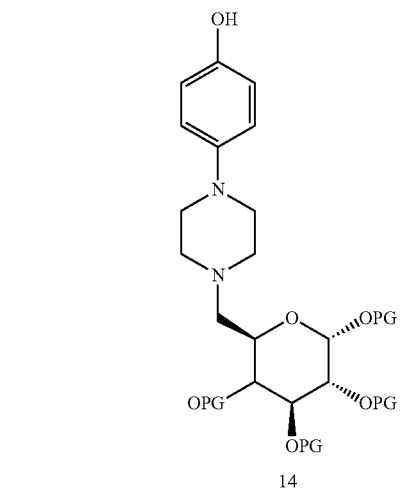
14

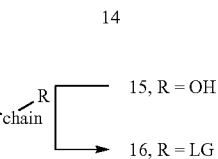
15, R = OH
16, R = LG

Compounds 14 can be synthesized using known deprotection methods. When protecting group PG is, for example, a benzyl group, it can be deprotected under hydrogenation conditions as described above. Alkynes 15 can be converted into alkylating reagents 16 with R describing a leaving group like O-tosyl, O-mesyl, halogen or the like. Compounds 14 and compounds 16 can be reacted to obtain compounds 17 under alkylating conditions, e.g. using bases like triethylamine, diisopropylamine, sodium hydride or the like in aprotic solvents like dimethylformamide, tetrahydrofuran, toluene or the like. Deprotection of compounds 17 to compounds 18 is dependent of the used protecting groups, the conditions are as described above.

Galactosyl derivatives 20 can be synthesized like described in scheme 7.

Scheme 7:

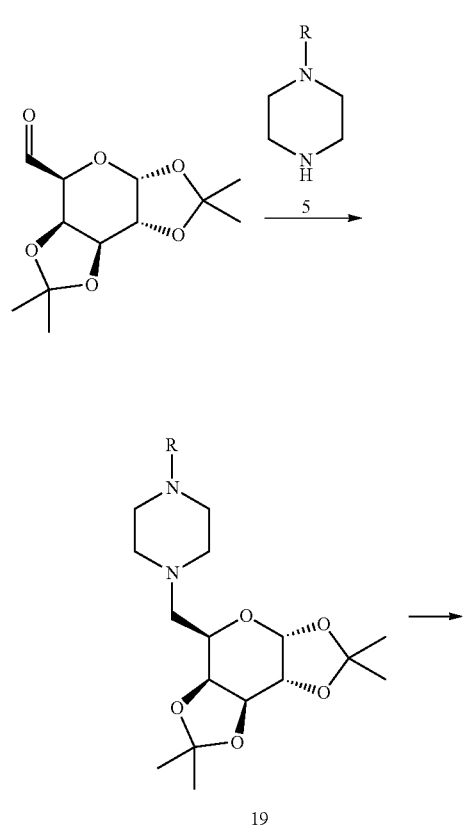

Reductive amination of isopropylidene protected galactosyl-aldehyde and amines 5 using known reductive amination conditions as described in scheme 3 lead to compounds 19. Deprotection of the isopropylidene groups can be done as described in scheme 1.

The synthesis of compounds 1 is described in scheme 8.

Scheme 8:

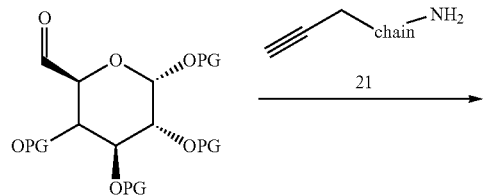

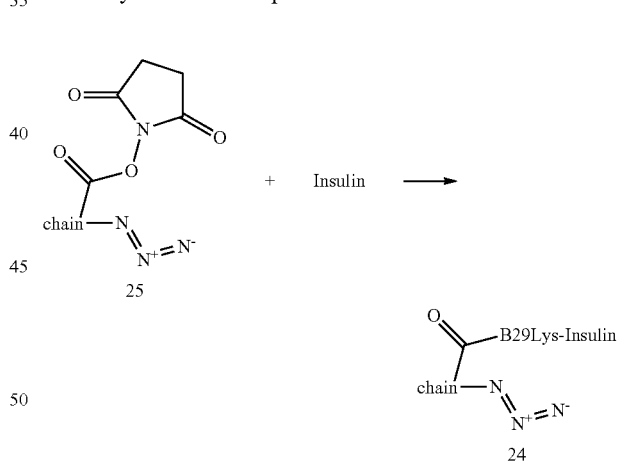

The synthesis of compounds 22 can be done under reductive amination conditions for compounds 21 and protected carbohydrate aldehydes as described in scheme 3. Deprotection of compounds 22 to compounds 23 can be done as described in scheme 1. Compounds 23 can be coupled using copper-catalyzed azide-alkyne cycloaddition conditions as described in scheme 4 to yield compounds 1.

The synthesis of compounds 24 is described in scheme 9.

The synthesis of compounds 24 can be carried out by reaction of compounds 25 with insulin under basic conditions, e.g. pH 10. Therefore the insulin is dissolved in a dimethylformamide-water mixture and brought to pH 10 by an organic base like triethylamine. At low temperatures (e.g. 0° C.) the activated azido-dioxopyrrolidines 25 are added to yield compounds of formula 24.

Abbreviations

BEP 2-bromo-1-ethyl pyridinium tetrafluoroborate
d Dublet
dd Double dublet ddd Double double dublet
DDQ 2,3-dichloro-5,6-dicyano-1,4-benzochinone
DMSO dimethylsulfoxide
ELSD Evaporative Light Scattering Detector
Eq. Equivalent/s
ES-API Electro spray atmospheric pressure ionisation
FCS Fetal calf serum
HATU 1-[bis(dimethylamino)methylene]-1H-1,2,3-triazolo[4,5-b]pyridinium 3-oxide hexafluorophosphate
HOBt 1-hydroxybenzotriazole
HPLC High pressure liquid chromatography
Hz Hertz
J coupling constant
KRB Krebs-Ringer bicarbonate buffer
LG leaving group
LC/MS Liquid chromatography/mass spectra
m multiplet
MEM Minimum-Essential-Medium
MHz Megahertz
MPLC Medium pressure liquid chromatography
NEAA Non-essential amino acids
NMR Nuclear magnetic resonance
PG Protecting group
q quadruplet
s singulet
t triplet
td dublet of triplets
TBTU N,N,N',N'-Tetramethyl-O-(benzotriazol-1-yl)uronium tetrafluoroborate
TLC Thin layer chromatography
THPTA tris(3-hydroxypropyltriazolylmethyl)amine
TOTU O-[(ethoxycarbonyl)cyanomethylenamino]-N,N,N',N'-tetramethyluronium tetrafluoroborate
$t_R$ Retention time
$R_f$ Relative to front value
UV Ultra violet
v/v Volume by volume

EXPERIMENTAL PART

Chromatographic and Spectroscopic Methods
TLC/UV-Lamp
Thin layer chromatography (TLC) was done on glass plates from Merck coated with silica gel 60 F254. Detection was done with an UV-Lamp from Lamag at wavelengths of 254 nm and 366 nm.
Compounds which could not be detected by UV were stained by different methods: (a) 10% $H_2SO_4$ in ethanol, b) 1% $KMnO_4$-solution, c) molybdatophosphoric acid-cerium(IV)sulfate solution in sulfuric acid (6 mL concentrated sulfuric acid and 94 mL water, 2.5 g molybdatophosphoric acid, 1 g cerium(IV)sulfate).
MPLC
Chromatography on normal phase was done on a CombiFlash® Rf (Teledyne ISCO). The used gradients were given in the description of the examples.
HPLC
Preparative reversed phase HPLC was done using acetonitrile/water on an Agilent 1200 preparative HPLC machine and an Agilent Prep-$C_{18}$ column (10 μm, 21.5×150 mm).
$^1$H-NMR
For $^1$H-NMR-spectra a Bruker ARX, 400 MHz device was used.
$^{13}$C-NMR
For $^{13}$C-NMR-spectra a Bruker Avance, 600 MHz device was used.
LC/MS
For retention time and mass detection a LC/MS-system from Waters Acquity SDS with a Waters Acquity BEH $C_{18}$ (1.7 μm, 2.1×50 mm) column was used. The injection volume was 0.5 μl. Molecular weights are given in gramm per mol [g/mol], detected masses in mass per charge [m/e].
LC/MS—Method 1
95% $H_2O$ (0.05% formic acid) to 95% acetonitrile (0.035% formic acid) in 2 min, 95% acetonitrile till 2.60 min, 0.9 mL/min, 10×2 mm Phenomenex Luna$C_{18}$ 3 μm.
LC/MS—Method 2
93% $H_2O$ (0.05% trifluoroacetic acid) to 95% acetonitrile (0.05% trifluoroacetic acid) in 1 min, 95% acetonitrile till 1.45 min, 1.1 mL/min, 10×2.0 mm Luna$C_{18}$ 3 μm
LC/MS—Method 3
99% $H_2O$ (0.05% trifluoroacetic acid) to 93% $H_2O$ (0.05%) in 0.4 min, 95% acetonitrile (0.05% trifluoroacetic acid) in 0.8 min, 95% acetonitrile till 1.8 min, 1.1 mL/min, 10×2.0 mm Luna$C_{18}$ 3 μm
LC/MS—Method 4
10% acetonitrile (0.1% formic acid) till 90% acetonitrile (0.1% formic acid) in 10 min, 90% acetonitrile till 10.67 min, 10% acetonitrile from 11 to 12 min, 0.5 mL/min, Aeris Widepore 3, 3 μm, 100×2.1 mm, 40° C.
Syntheses
Method A Amide coupling with
1,2,3,4-tetra-O-acetyl-β-D-glucuronic acid To a solution of 0.55 mmol 1,2,3,4-tetra-O-acetyl-β-D-glucuronic acid in 5 mL dimethylformamide were added 1.4 eq. (0.77 mmol) 1-[bis(dimethylamino)methylene]-1H-1,2,3-triazolo[4,5-b]pyridinium 3-oxide hexafluorophosphate (HATU) and 1.4 eq. (0.77 mmol) amine. The reaction mixture was stirred for 2-6 hours at room temperature. Reaction control was done by TLC. As work up 5-10 mL dichloromethane were added and the organic phase was washed with 1M HCl, water, saturated aqueous $NaHCO_3$ solution, and water. The organic phases were dried with $Na_2SO_4$, filtered, and evaporated. If needed the crude mixture was purified by MPLC.

Example 1

[(2S,3R,4S,5S,6S)-2,3,5-Triacetoxy-6-(4-methylpiperazine-1-carbonyl)tetrahydropyran-4-yl] acetate

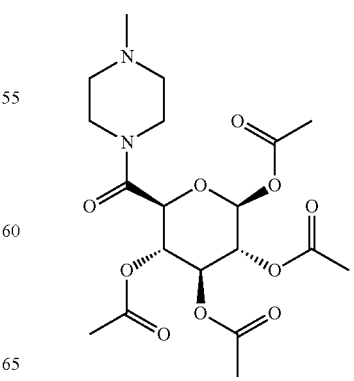

Example 1 was synthesized from 1,2,3,4-tetra-O-acetyl-β-D-glucuronic acid and 1-methylpiperazine following the procedure described in synthesis method A.

Purification: MPLC CombiFlash Rf (Teledyne ISCO): column: RediSep Silica 12 g; flow rate: 30 mL/min; wavelength for detection: 254 nm; eluent: (A) dichloromethane, (B) ethanol.

Mplc Gradient:

| start % B | end % B | duration [min] |
|---|---|---|
| 0 | 0 | 2.2 |
| 0 | 4.8 | 2.8 |
| 4.8 | 4.8 | 6.0 |
| 4.8 | 10.1 | 6.0 |
| 10.1 | 10.1 | 9.1 |

Yield: 137 mg (0.308 mmol, 55.8%), white solid.
TLC: $R_f$=0.250 (dichloromethane/ethanol, 19:1).
LC/MS (ES-API): m/z=445.13 [M+H]$^+$; calculated: 445.44; $t_R$ (λ=220 nm): 0.93 min (LC/MS—method 1).
$^1$H-NMR (400 MHz, DMSO-d$_6$): δ=5.96 (d, J=8.3 Hz, 1H, CH), 5.37 (t, J=9.5 Hz, 1H, CH), 5.25 (t, J=9.5 Hz, 1H, CH), 4.97 (m, 2H, 2×CH), 3.63 (m, 1H, NCH$_2$), 3.55 (m, 1H, CH$_2$), 3.39 (m, 1H, NCH$_2$), 3.23 (m, 1H, NCH$_2$), 2.36 (m, 2H, NCH$_2$), 2.16 (s, 3H, CH$_3$), 2.11 (m, 2H, NCH$_2$), 2.08 (s, 3H, CH$_3$), 2.02 (s, 3H, CH$_3$), 1.93 (s, 3H, CH$_3$), 1.90 (s, 3H, CH$_3$) ppm.

Example 2

[(2S,3R,4S,5S,6S)-2,3,5-Triacetoxy-6-(4-ethylpiperazine-1-carbonyl)tetrahydropyran-4-yl] acetate

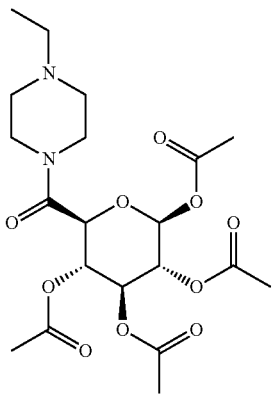 [SMILES: CCN1CCN(C(=O)[C@H]2O[C@@H](OC(C)=O)[C@H](OC(C)=O)[C@@H](OC(C)=O)[C@@H]2OC(C)=O)CC1]

Example 2 was synthesized from 1,2,3,4-tetra-O-acetyl-β-D-glucuronic acid and 1-ethylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 2.2 |
| 0 | 4.8 | 2.8 |
| 4.8 | 4.8 | 6.0 |
| 4.8 | 10.1 | 6.0 |
| 10.1 | 10.1 | 9.1 |

Yield: 201 mg (0.438 mmol, 79.4%), white solid.
TLC: $R_f$=0.492 (dichloromethane/ethanol, 19:1).
LC/MS (ES-API): m/z=459.12 [M+H]$^+$; calculated: 459.46; $t_R$ (λ=220 nm): 0.98 min (LC/MS—Method 1).
$^1$H-NMR (400 MHz, DMSO-d$_6$): δ=5.97 (d, J=8.3 Hz, 1H, CH), 5.38 (t, J=9.5 Hz, 1H, CH), 5.25 (t, J=9.5 Hz, 1H, CH), 4.97 (m, 2H, 2×CH), 3.58 (m, 2H, NCH$_2$), 3.40 (m, 1H, NCH$_2$), =3.24 (m, 1H, NCH$_2$), 2.41 (m, 2H, NCH$_2$), 2.32 (m, 2H, CH$_2$), 2.16 (m, 2H, NCH$_2$), 2.08 (s, 3H, CH$_3$), 2.02 (s, 3H, CH$_3$), 1.93 (s, 3H, CH$_3$), 1.89 (s, 3H, CH$_3$), 0.99 (t, J=7.1 Hz, 3H, CH$_3$) ppm.

Example 3

[(2S,3R,4S,5S,6S)-2,3,5-Triacetoxy-6-(4-n-propylpiperazine-1-carbonyl)tetrahydropyran-4-yl] acetate (8)

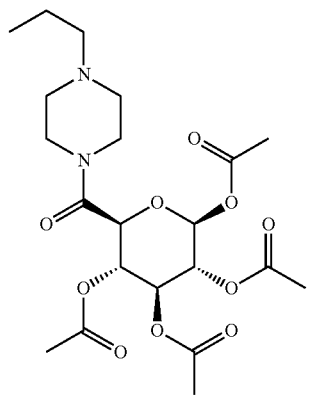 [SMILES: CCCN1CCN(C(=O)[C@H]2O[C@@H](OC(C)=O)[C@H](OC(C)=O)[C@@H](OC(C)=O)[C@@H]2OC(C)=O)CC1]

Example 3 was synthesized from 1,2,3,4-tetra-O-acetyl-β-D-glucuronic acid and 1-n-propylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | Duration [min] |
|---|---|---|
| 0 | 0 | 1.5 |
| 0 | 5.0 | 5.0 |
| 5.0 | 5.0 | 8.0 |

Yield: 144 mg (0.305 mmol, 55.2%), white solid.
TLC: $R_f$=0.417 (dichloromethane/ethanol, 19:1).
LC/MS (ES-API): m/z=473.14 [M+H]$^+$; calculated: 473.89; $t_R$ (λ=220 nm): 1.06 min (LC/MS—Method 1).
$^1$H-NMR (400 MHz, DMSO-d$_6$): δ=5.96 (d, J=8.3 Hz, 1H, CH), 5.38 (t, J=9.5 Hz, 1H, CH), 5.25 (t, J=9.5 Hz, 1H, CH), 4.98 (m, 2H, 2×CH), 3.58 (m, 2H, NCH$_2$), 3.40 (m, 1H, NCH$_2$), 3.24 (m, 1H, NCH$_2$), 2.39 (m, 2H, NCH$_2$), 2.22

(m, 2H, NCH$_2$), 2.15 (m, 2H, NCH$_2$), 2.07 (s, 3H, CH$_3$), 2.02 (s, 3H, CH$_3$), 1.93 (s, 3H, CH$_3$), 1.89 (s, 3H, CH$_3$), 1.43 (m, 2H, CH$_2$), 0.85 (t, J=7.3 Hz, 3H, CH$_3$) ppm.

Example 4

[(2S,3R,4S,5S,6S)-2,3,5-Triacetoxy-6-(4-n-butylpiperazine-1-carbonyl)tetrahydropyran-4-yl] acetate

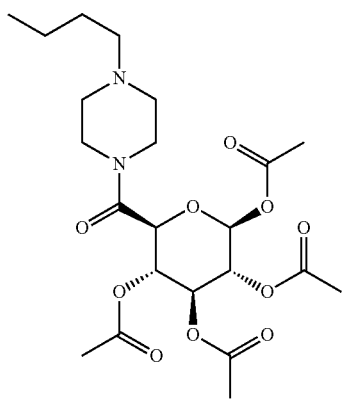 [SMILES: CCCCN1CCN(C(=O)[C@H]2O[C@@H](OC(C)=O)[C@H](OC(C)=O)[C@@H](OC(C)=O)[C@@H]2OC(C)=O)CC1]

Example 4 was synthesized from 1,2,3,4-tetra-O-acetyl-β-D-glucuronic acid and 1-n-butylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 10.1 | 20.0 |
| 10.1 | 10.1 | 3 |
| 10.1 | 0.0 | 0.0 |
| 0.0 | 0.0 | 1.0 |

Yield: 191 mg (0.393 mmol, 71.1%), white solid.

TLC: R$_f$=0.458 (dichloromethane/ethanol, 19:1).

LC/MS (ES-API): m/z=487.19 [M+H]$^+$; calculated: 487.51; t$_R$ (λ=220 nm): 1.14 min (LC/MS—Method 1).

$^1$H-NMR (400 MHz, DMSO-d$_6$): δ=5.96 (d, J=8.4 Hz, 1H, CH), 5.38 (t, J=9.4 Hz, 1H, CH), 5.25 (t, J=9.4 Hz, 1H, CH), 4.97 (m, 2H, 2×CH), 3.57 (m, 2H, NCH$_2$), 3.40 (m, 1H, NCH$_2$), 3.24 (m, 1H, NCH$_2$), 2.40 (m, 2H, NCH$_2$), 2.26 (m, 2H, NCH$_2$), 2.15 (m, 2H, NCH$_2$), 2.07 (s, 3H, CH$_3$), 2.02 (s, 3H, CH$_3$), 1.93 (s, 3H, CH$_3$), 1.90 (s, 3H, CH$_3$), 1.39 (m, 2H, CH$_2$), 1.28 (m, 2H, CH$_2$), 0.87 (t, J=7.4 Hz, 3H, CH$_3$) ppm.

Example 5

[(2S,3R,4S,5S,6S)-2,3,5-Triacetoxy-6-(4-n-hexylpiperazine-1-carbonyl)tetrahydropyran-4-yl] acetate

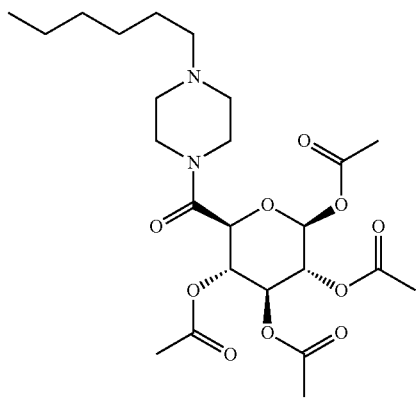 [SMILES: CCCCCCN1CCN(C(=O)[C@H]2O[C@@H](OC(C)=O)[C@H](OC(C)=O)[C@@H](OC(C)=O)[C@@H]2OC(C)=O)CC1]

Example 5 was synthesized from 1,2,3,4-tetra-O-acetyl-β-D-glucuronic acid and 1-n-hexylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 20.2 | 20.0 |
| 20.2 | 20.2 | 2.9 |
| 20.2 | 0.0 | 0.0 |
| 0.0 | 0.0 | 1.0 |

Yield: 226 mg (0.439 mmol, 79.6%), white solid.

TLC: R$_f$=0.489 (dichloromethane/ethanol, 19:1).

LC/MS (ES-API): m/z=515.24 [M+H]$^+$; calculated: 515.57; t$_R$ (λ=220 nm): 1.34 min (LC/MS—Method 1).

$^1$H-NMR (400 MHz, 26.9° C., DMSO-d$_6$): δ=5.96 (d, J=8.3 Hz, 1H, CH), 5.37 (t, J=9.5 Hz, 1H, CH), 5.25 (t, J=9.5 Hz, 1H, CH), 4.97 (m, 2H, CH), 3.57 (m, 2H, NCH$_2$), 3.40 (m, 1H, CH$_2$), 3.23 (m, 1H, NCH$_2$), 2.39 (m, 2H, NCH$_2$), 2.25 (t, J=7.1 Hz, 2H, NCH$_2$), 2.15 (m, 2H, NCH$_2$), 2.16 (s, 3H, CH$_3$), 2.07 (s, 3H, CH$_3$), 2.02 (s, 3H, CH$_3$), 1.93 (s, 3H, CH$_3$), 1.89 (s, 3H, CH$_3$), 1.40 (m, 2H, CH$_2$), 1.26 (m, 6H, 3×CH$_2$), 0.86 (t, J=6.9 Hz, 2H, CH$_3$) ppm.

Example 6

[(2S,3R,4S,5S,6S)-2,3,5-Triacetoxy-6-(4-isopropylpiperazine-1-carbonyl)tetrahydropyran-4-yl] acetate

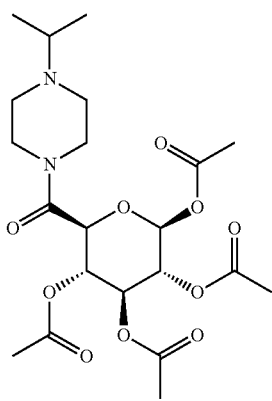 [SMILES: CC(=O)O[C@@H]1O[C@H](C(=O)N2CCN(C(C)C)CC2)[C@@H](OC(C)=O)[C@H](OC(C)=O)[C@H]1OC(C)=O]

Example 6 was synthesized from 1,2,3,4-tetra-O-acetyl-β-D-glucuronic acid and 1-isopropylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 20.2 | 20.0 |
| 20.2 | 20.2 | 2.9 |
| 20.2 | 0.0 | 0.0 |
| 0.0 | 0.0 | 1.0 |

Yield: 129 mg (0.273 mmol, 49.5%), white solid.

TLC: $R_f$=0.412 (dichloromethane/ethanol, 19:1).

LC/MS (ES-API): m/z=473.18 [M+H]$^+$; calculated: 473.47; $t_R$ (λ=220 nm): 1.02 min (LC/MS—Method 1).

$^1$H-NMR (400 MHz, 26.9° C., DMSO-d$_6$): δ=5.97 (d, J=8.3 Hz, 1H, CH), 5.38 (t, J=9.4 Hz, 1H, CH), 5.25 (t, J=9.4 Hz, 1H, CH), 4.97 (m, 2H, 2×CH), 3.56 (m, 2H, NCH$_2$), 3.39 (m, 1H, CH$_2$), 3.24 (m, 1H, NCH$_2$), 2.66 (m, 1H, CH), 2.43 (m, 2H, NCH$_2$), 2.27 (m, 2H, NCH$_2$), 2.08 (s, 3H, CH$_3$), 2.02 (s, 3H, CH$_3$), 1.93 (s, 3H, CH$_3$), 1.90 (s, 3H, CH$_3$), 0.95 (dd, 6H, CH$_3$) ppm.

Example 7

[(2S,3R,4S,5S,6S)-2,3,5-Triacetoxy-6-(4-tert-butylpiperazine-1-carbonyl)tetrahydropyran-4-yl] acetate

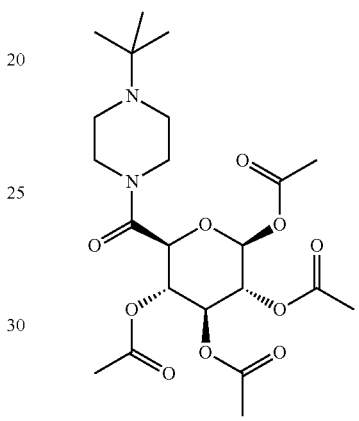

Example 7 was synthesized from 1,2,3,4-tetra-O-acetyl-β-D-glucuronic acid and 1-tert-butylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 20.2 | 20.0 |
| 20.2 | 20.2 | 2.9 |
| 20.2 | 0.0 | 0.0 |
| 0.0 | 0.0 | 1.0 |

Yield: 139 mg (0.286 mmol, 51.8%), white solid.

TLC: $R_f$=0.464 (dichloromethane/ethanol, 19:1).

LC/MS (ES-API): m/z=487.20 [M+H]$^+$; calculated: 487.51; $t_R$: 1.06 min (LC/MS—Method 1).

$^1$H-NMR (400 MHz, DMSO-d$_6$): δ=5.97 (d, J=8.3 Hz, 1H, CH), 5.38 (t, J=9.5 Hz, 1H, CH), 5.25 (t, J=9.5 Hz, 1H, CH), 4.97 (m, 2H, CH), 3.53 (m, 2H, NCH$_2$), 3.39 (m, 1H, CH$_2$), 3.26 (m, 1H, NCH$_2$), 2.67 (m, 2H, NCH$_2$), 2.32 (m, 2H, NCH$_2$), 2.07 (s, 3H, CH$_3$), 2.02 (s, 3H, CH$_3$), 1.93 (s, 3H, CH$_3$), 1.90 (s, 3H, CH$_3$), 0.99 (s, 9H, 3×CH$_3$) ppm.

Example 8

[(2S,3R,4S,5S,6S)-2,3,5-Triacetoxy-6-(4-allylpiperazine-1-carbonyl)tetrahydropyran-4-yl] acetate

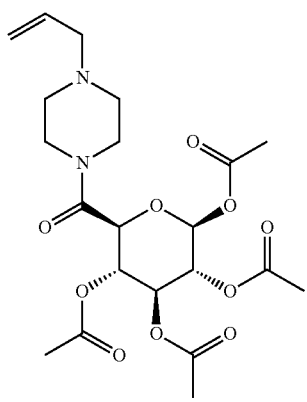 [SMILES: C=CCN1CCN(C(=O)[C@H]2O[C@@H](OC(C)=O)[C@H](OC(C)=O)[C@@H](OC(C)=O)[C@@H]2OC(C)=O)CC1]

Example 8 was synthesized from 1,2,3,4-tetra-O-acetyl-β-D-glucuronic acid and 1-allylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 9.9 | 9.9 |

Yield: 184 mg (0.260 mmol, 70.8%), white solid.

TLC: $R_f$=0.479 (dichloromethane/ethanol, 19:1).

LC/MS (ES-API): m/z=471.26 [M+H]$^+$; calculated: 471.19; $t_R$: 1.02 min (LC/MS—Method 1).

$^1$H-NMR (400 MHz, DMSO-$d_6$): δ=5.97 (d, J=8.1 Hz, 1H, CH), 5.81 (m, 1H, H$_2$C=CH), 5.36 (t, J=9.4 Hz, 1H, CH), 5.24 (t, J=9.4 Hz, 1H, CH), 5.17 (m, 2H, HC=CH$_2$), 4.98 (m, 2H, CH), 3.61 (m, 2H, NCH$_2$), 3.42 (m, 1H, NCH$_2$), 3.23 (m, 1H, NCH$_2$), 2.96 (m, 2H, NCH$_2$), 2.41 (m, 2H, NCH$_2$), 2.17 (m, 2H, NCH$_2$), 2.08 (s, 3H, CH$_3$), 2.02 (s, 3H, CH$_3$), 1.94 (s, 3H, CH$_3$), 1.90 (s, 3H, CH$_3$) ppm.

Example 9

[(2S,3R,4S,5S,6S)-2,3,5-Triacetoxy-6-(4-cyclohexylpiperazine-1-carbonyl)tetrahydropyran-4-yl] acetate

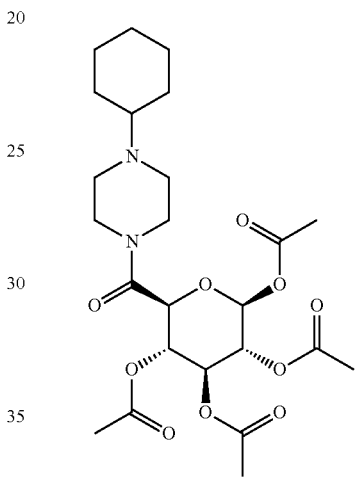

Example 9 was synthesized from 1,2,3,4-tetra-O-acetyl-β-D-glucuronic acid and 1-cyclohexylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 9.9 | 9.9 |

Yield: 227 mg (0.443 mmol, 80.2%), white solid.

TLC: $R_f$=0.610 (dichloromethane/ethanol, 19:1).

LC/MS (ES-API): m/z=513.15 [M+H]$^+$; calculated: 513.24; $t_R$: 1.22 min (LC/MS—Method 1).

$^1$H-NMR (400 MHz, 116.9° C., DMSO-$d_6$): 5.93 (d, J=7.8 Hz, 1H, CH), 5.33 (m, 2H, 2×CH), 4.99 (m, 1H, CH), 4.88 (m, 1H, CH), 3.71 (m, 4H, NCH$_2$), 3.04 (m, 6H, NCH$_2$), 3.23 (m, 2H, NCH$_2$), 2.36 (m, 2H, NCH$_2$), 2.06 (s, 3H, CH$_3$), 1.99 (s, 3H, CH$_3$), 1.93 (s, 3H, CH$_3$), 1.90 (s, 3H, CH$_3$), 1.82 (m, 2H, CH$_2$), 1.63 (m, 1H, CH), 1.30 (m, 8H, CH$_2$) ppm.

Example 10

[(2S,3R,4S,5S,6S)-2,3,5-Triacetoxy-6-[4-(cyclohexylmethyl)piperazine-1-carbonyl]tetrahydropyran-4-yl] acetate

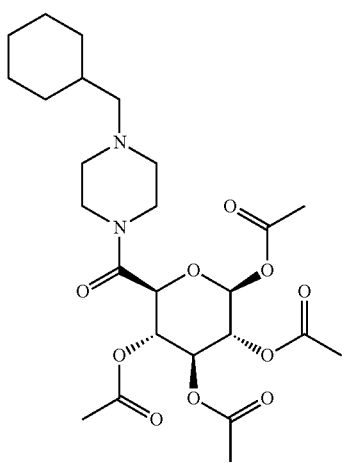 [SMILES: CC(=O)O[C@@H]1O[C@H](C(=O)N2CCN(CC3CCCCC3)CC2)[C@@H](OC(C)=O)[C@H](OC(C)=O)[C@H]1OC(C)=O]

Example 10 was synthesized from 1,2,3,4-tetra-O-acetyl-β-D-glucuronic acid and 1-cyclohexylmethylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 20.0 | 20.0 |
| 20.0 | 20.0 | 3 |
| 20.0 | 0.0 | 0.0 |
| 0.0 | 0.0 | 1.0 |

Yield: 178 mg (0.338 mmol, 61.2%), white solid.

TLC: $R_f$=0.346 (ethylacetate/n-heptan, 2:1).

LC/MS (ES-API): m/z=527.22 [M+H]$^+$; calculated: 527.25; $t_R$: 1.31 min (LC/MS—Method 1).

$^1$H-NMR (400 MHz, DMSO-$d_6$): δ=5.97 (d, J=8.3 Hz, 1H, CH), 5.39 (t, J=9.4 Hz, 1H, CH), 5.27 (t, J=9.4 Hz, 1H, CH), 4.96 (m, 2H, CH), 3.58 (m, 2H, NCH$_2$), 3.40 (m, 1H, CH$_2$), 3.25 (m, 1H, NCH$_2$), 2.37 (m, 2H, NCH$_2$), 2.13 (m, 2H, NCH$_2$), 2.19 (m, 2H, NCH$_2$), 2.08 (s, 3H, CH$_3$), 2.02 (s, 3H, CH$_3$), 1.94 (s, 3H, CH$_3$), 1.89 (s, 3H, CH$_3$), 1.69 (m, 4H, 2×CH$_2$), 1.47 (m, 1H, CH), 1.18 (m, 2H, 2×CH$_2$), 0.82 (m, 2H, CH$_2$) ppm.

Example 11

[(2S,3R,4S,5S,6S)-2,3,5-Triacetoxy-6-[4-(2-cyclohexylethyl)piperazine-1-carbonyl]tetrahydropyran-4-yl] acetate

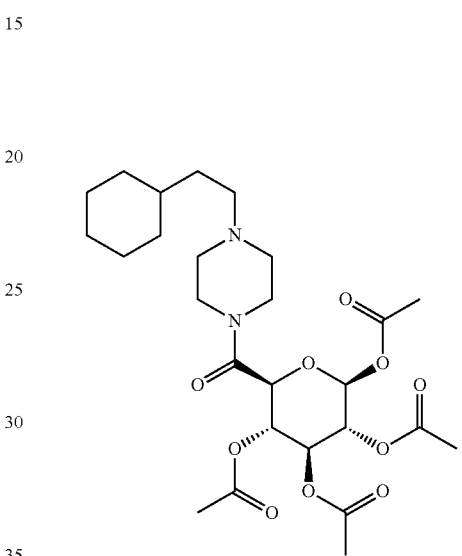

Example 11 was synthesized from 1,2,3,4-tetra-O-acetyl-β-D-glucuronic acid and 1-cyclohexylethylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 18.7 | 18.7 |

Yield: 183 mg (0.339 mmol, 61.3%), white solid.

TLC: $R_f$=0.511 (dichloromethane/ethanol, 19:1).

LC/MS (ES-API): m/z=541.24 [M+H]$^+$; calculated: 541.27; $t_R$: 1.41 min (LC/MS—Method 1).

$^1$H-NMR (400 MHz, 116.9° C., DMSO-$d_6$): δ=5.93 (d, J=7.8 Hz, 1H, CH), 5.33 (m, 2H, 2×CH), 4.99 (m, 1H, CH), 4.88 (m, 1H, CH), 3.71 (m, 4H, NCH$_2$), 3.04 (m, 6H, NCH$_2$), 3.23 (m, 2H, NCH$_2$), 2.36 (m, 2H, NCH$_2$), 2.06 (s, 3H, CH$_3$), 1.99 (s, 3H, CH$_3$), 1.93 (s, 3H, CH$_3$), 1.90 (s, 3H, CH$_3$), 1.71 (m, 1H, CH), 1.61 (m, 6H, CH$_2$), 1.24 (m, 4H, CH$_2$), 1.02 (m, 2H, CH$_2$) ppm.

Example 12

[(2S,3R,4S,5S,6S)-2,3,5-Triacetoxy-6-(4-phenylpiperazine-1-carbonyl)tetrahydropyran-4-yl] acetate

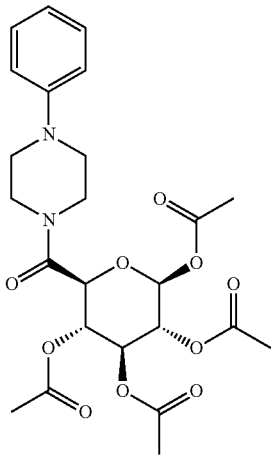 [SMILES: CC(=O)O[C@@H]1O[C@H](C(=O)N2CCN(c3ccccc3)CC2)[C@@H](OC(C)=O)[C@H](OC(C)=O)[C@H]1OC(C)=O]

Example 12 was synthesized from 1,2,3,4-tetra-O-acetyl-β-D-glucuronic acid and 1-phenylpiperazine following the procedure described in synthesis method A.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

Yield: 260 mg (0.514 mmol, 62.0%), white solid.

TLC: $R_f$=0.695 (dichloromethane/ethanol, 19:1).

LC/MS (ES-API): m/z=507.14 [M+H]$^+$; calculated: 507.19; $t_R$: 1.70 min (LC/MS—Method 1).

MPLC Gradient

| start % B | end % B | duration [min] |
|---|---|---|
| 0 | 0 | 1.3 |
| 0 | 100.0 | 13.7 |
| 100.0 | 100.0 | 3.7 |
| 100.0 | 0.0 | 0.0 |
| 0.0 | 0.0 | 1.3 |

$^1$H-NMR (400 MHz, DMSO-$d_6$): δ=7.24 (t, J=8.2 Hz, 2H, ArH), 6.95 (d, J=8.2 Hz, 2H, ArH), 6.81 (t, J=7.4 Hz, 1H, ArH), 6.00 (d, J=8.4 Hz, 1H, CH), 5.40 (t, J=9.9 Hz, 1H, CH), 5.29 (t, J=9.9 Hz, 1H, CH), 5.05 (d, J=9.6 Hz, 1H, CH), 5.00 (m, 1H, CH), 3.81 (m, 1H, NCH$_2$), 3.75 (m, 1H, NCH$_2$), 3.57 (m, 1H, CH$_2$), 3.39 (m, 1H, NCH$_2$), 3.24 (m, 2H, NCH$_2$), 2.82 (m, 2H, NCH$_2$), 2.07 (s, 3H, CH$_3$), 2.03 (s, 3H, CH$_3$), 1.94 (s, 3H, CH$_3$), 1.91 (s, 3H, CH$_3$) ppm.

$^{13}$C-NMR (150 MHz, DMSO-$d_6$): δ=169.64 (s, C), 169.04 (s, C), 169.02 (s, C), 168.43 (s, C), 163.04 (s, C), 150.69 (s, C), 128.99 (s, CH), 119.47 (s, CH), 115.97 (s, CH), 90.94 (s, CH), 72.02 (s, CH), 69.37 (s, CH), 69.15 (s, CH), 68.55 (s, CH), 49.14 (s, CH$_2$), 48.07 (s, CH$_2$), 44.78 (s, CH$_2$), 41.41 (s, CH$_2$), 20.44 (s, 2 CH$_3$), 20.30 (s, 2 CH$_3$) ppm.

Example 13

[(2S,3R,4S,5S,6S)-2,3,5-Triacetoxy-6-[4-[(E)-cinnamyl]piperazine-1-carbonyl]tetrahydropyran-4-yl] acetate

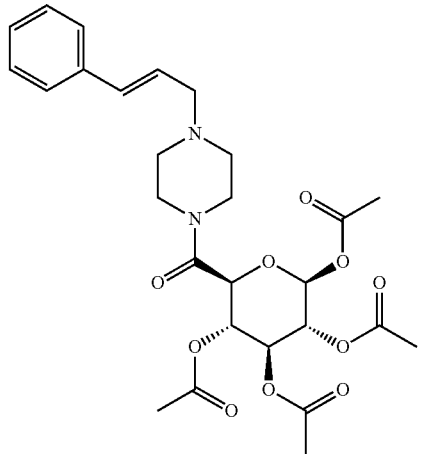 [SMILES: CC(=O)O[C@@H]1O[C@H](C(=O)N2CCN(C/C=C/c3ccccc3)CC2)[C@@H](OC(C)=O)[C@H](OC(C)=O)[C@H]1OC(C)=O]

Example 13 was synthesized from 1,2,3,4-tetra-O-acetyl-β-D-glucuronic acid and trans-1-cinnamylpiperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 9.9 | 9.9 |

Yield: 253 mg (0.463 mmol, 83.8%), white solid.

TLC: $R_f$=0.644 (dichloromethane/ethanol, 19:1).

LC/MS (ES-API): m/z=547.27 [M+H]$^+$; calculated: 547.22; $t_R$: 1.34 min (LC/MS—Method 1).

$^1$H-NMR (400 MHz, DMSO-$d_6$): δ=7.44 (d, J=7.2 Hz, 2H, ArH), 7.32 (t, J=7.2 Hz, 2H, ArH), 7.23 (t, J=7.2 Hz, 2H, ArH), 6.54 (d, J=15.9 Hz, 1H, CH), 6.29 (m, 1H, CH), 5.96 (d, J=8.4 Hz, 1H, CH), 5.37 (t, J=9.5 Hz, 1H, CH), 5.25 (t, J=9.5 Hz, 1H, CH), 4.97 (m, 2H, CH), 3.61 (m, 2H, NCH$_2$), 3.42 (m, 1H, CH$_2$), 3.26 (m, 1H, NCH$_2$), 3.12 (m, 2H, NCH$_2$), 2.47 (m, 2H, NCH$_2$), 2.22 (m, 2H, NCH$_2$), 2.06 (s, 3H, CH$_3$), 2.02 (s, 3H, CH$_3$), 1.93 (s, 3H, CH$_3$), 1.89 (s, 3H, CH$_3$) ppm.

Example 14

[(2S,3R,4S,5S,6S)-2,3,5-Triacetoxy-6-[4-(4-chlorophenyl)piperazine-1-carbonyl]tetrahydropyran-4-yl] acetate

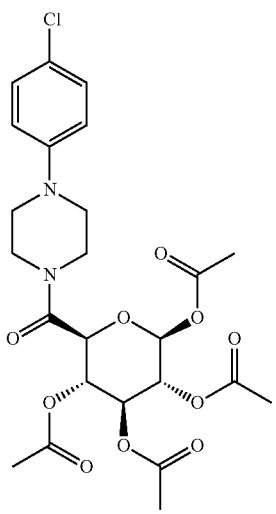 [SMILES: CC(=O)O[C@@H]1O[C@H](C(=O)N2CCN(c3ccc(Cl)cc3)CC2)[C@@H](OC(C)=O)[C@H](OC(C)=O)[C@H]1OC(C)=O]

Example 14 was synthesized from 1,2,3,4-tetra-O-acetyl-β-D-glucuronic acid and 1-(4-chlorophenyl)-piperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 2.4 |
| 0 | 5.0 | 7.9 |
| 5.0 | 5.0 | 3.7 |

Yield: 153 mg (0.282 mmol, 51.3%), white solid.

TLC: $R_f$=0.619 (ethylacetate/n-heptane, 2:1).

LC/MS (ES-API): m/z=541.19 [M+H]$^+$; calculated: 541.15; $t_R$: 1.80 min (LC/MS—Method 1).

$^1$H-NMR (400 MHz, DMSO-$d_6$): δ=7.25 (d, J=9.0 Hz, 2H, ArH), 6.96 (d, J=9.0 Hz, 2H, ArH), 6.00 (d, J=8.3 Hz, 1H, CH), 5.40 (t, J=9.5 Hz, 1H, CH), 5.28 (t, J=9.5 Hz, 1H, CH), 5.01 (m, 2H, 2×CH), 3.76 (m, 2H, NCH$_2$), 3.56 (m, 1H, NCH$_2$), 3.37 (m, 1H, NCH$_2$), 3.25 (m, 2H, NCH$_2$), 2.92 (m, 2H, NCH$_2$), 2.07 (s, 3H, CH$_3$), 2.03 (s, 3H, CH$_3$), 1.94 (s, 3H, CH$_3$), 1.90 (s, 3H, CH$_3$) ppm.

Example 15

[(2S,3R,4S,5S,6S)-2,3,5-Triacetoxy-6-[4-(2-chlorophenyl)piperazine-1-carbonyl]tetrahydropyran-4-yl] acetate

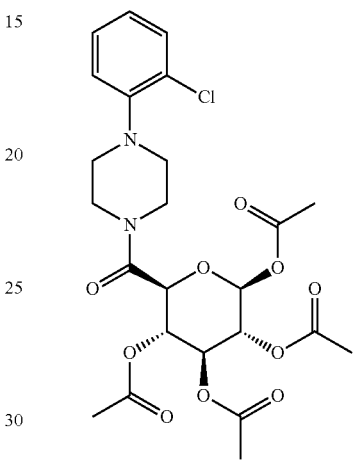

Example 15 was synthesized from 1,2,3,4-tetra-O-acetyl-β-D-glucuronic acid and 1-(2-chlorophenyl)-piperazine following the procedure described in synthesis method A.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

MPLC Gradient

| start % B | end % B | duration [min] |
|---|---|---|
| 0 | 0 | 1.3 |
| 0 | 100.0 | 13.7 |
| 100.0 | 100.0 | 3.7 |
| 100.0 | 0.0 | 0.0 |
| 0.0 | 0.0 | 1.3 |

Yield: 148 mg (0.274 mmol, 49.6%), white solid.

TLC: $R_f$=0.589 (dichloromethane/ethanol, 19:1).

LC/MS (ES-API): m/z=541.10 [M+H]$^+$; calculated: 541.15; $t_R$: 1.80 min (LC/MS—Method 1).

$^1$H-NMR (400 MHz, DMSO-$d_6$): δ=7.44 (dd, J=1.4 Hz, 2H, ArH), 7.33 (m, 2H, ArH), 7.14 (dd, J=1.4 Hz, 2H, ArH), 7.07 (m, 2H, ArH), 5.98 (d, J=8.3 Hz, 1H, CH), 5.39 (t, J=9.4 Hz, 1H, CH), 5.29 (t, J=9.4 Hz, 1H, CH), 5.01 (m, 2H, 2×CH), 3.84 (m, 1H, NCH$_2$), 3.76 (m, 1H, NCH$_2$), 3.57 (m, 1H, CH$_2$), 3.38 (m, 1H, NCH$_2$), 3.02 (m, 2H, NCH$_2$), 2.80 (m, 2H, NCH$_2$), 2.08 (s, 3H, CH$_3$), 2.03 (s, 3H, CH$_3$), 1.94 (s, 3H, CH$_3$), 1.92 (s, 3H, CH$_3$) ppm.

Example 16

[(2S,3R,4S,5S,6S)-2,3,5-Triacetoxy-6-[4-(4-bromophenyl)piperazine-1-carbonyl]tetrahydropyran-4-yl] acetate

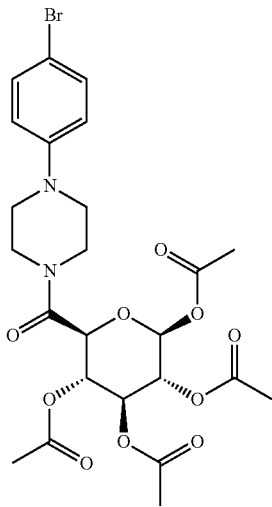 [SMILES: CC(=O)O[C@@H]1O[C@H](C(=O)N2CCN(c3ccc(Br)cc3)CC2)[C@@H](OC(C)=O)[C@H](OC(C)=O)[C@H]1OC(C)=O]

Example 16 was synthesized from 1,2,3,4-tetra-O-acetyl-β-D-glucuronic acid and 1-(4-bromophenyl)-piperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 1.0 |
| 0 | 20.2 | 20.0 |
| 20.2 | 20.2 | 2.9 |
| 20.2 | 0.0 | 0.0 |
| 0.0 | 0.0 | 1.0 |

Yield: 168 mg (0.287 mmol, 52.0%), white solid.

TLC: $R_f$=0.635 (ethylacetate/n-heptane, 2:1).

LC/MS (ES-API): m/z=585.14 [M+H]$^+$; calculated: 585.10; $t_R$: 1.82 min (LC/MS—Method 1).

$^1$H-NMR (400 MHz, DMSO-d$_6$): δ=7.37 (d, J=9.0 Hz, 2H, ArH), 6.92 (d, J=9.0 Hz, 2H, ArH), 6.00 (d, J=8.3 Hz, 1H, CH), 5.40 (t, J=9.4 Hz, 1H, CH), 5.28 (t, J=9.4 Hz, 1H, CH), 5.01 (m, 2H, 2×CH), 3.76 (m, 2H, NCH$_2$), 3.56 (m, 1H, NCH$_2$), 3.37 (m, 1H, NCH$_2$), 3.25 (m, 2H, NCH$_2$), 2.93 (m, 2H, NCH$_2$), 2.07 (s, 3H, CH$_3$), 2.03 (s, 3H, CH$_3$), 1.94 (s, 3H, CH$_3$), 1.90 (s, 3H, CH$_3$) ppm.

Example 17

[(2S,3R,4S,5S,6S)-2,3,5-Triacetoxy-6-[4-(4-methoxyphenyl)piperazine-1-carbonyl]tetrahydropyran-4-yl] acetate

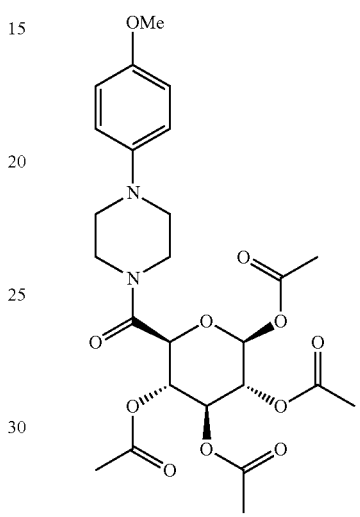

Example 17 was synthesized from 1,2,3,4-tetra-O-acetyl-β-D-glucuronic acid and 1-(4-methoxyphenyl)-piperazine following the procedure described in synthesis method A.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

MPLC Gradient

| start % B | end % B | duration [min] |
|---|---|---|
| 0 | 0 | 1.0 |
| 0 | 10.0 | 20.0 |
| 10.0 | 10.0 | 3.0 |
| 10.0 | 0.0 | 0.0 |
| 0.0 | 0.0 | 1.0 |

Yield: 192 mg (0.320 mmol, 58.0%), white solid.

TLC: $R_f$=0.508 (ethylacetate/n-heptane, 2:1).

LC/MS (ES-API): m/z=537.14 [M+H]$^+$; calculated: 537.20; $t_R$: 1.64 min (LC/MS—Method 1).

$^1$H-NMR (400 MHz, DMSO-d$_6$): δ=6.91 (d, J=9.1 Hz, 2H, ArH), 6.83 (d, J=9.1 Hz, 2H, ArH), 5.99 (d, J=8.0 Hz, 1H, CH), 5.40 (t, J=9.9 Hz, 1H, CH), 5.28 (t, J=9.9 Hz, 1H, CH), 5.00 (m, 2H, 2×CH), 3.77 (m, 2H, NCH$_2$), 3.69 (s, 3H, OCH$_3$), 3.56 (m, 1H, CH$_2$), 3.37 (m, 1H, NCH$_2$), 3.08 (m, 2H, NCH$_2$), 2.80 (m, 2H, NCH$_2$), 2.07 (s, 3H, CH$_3$), 2.03 (s, 3H, CH$_3$), 1.94 (s, 3H, CH$_3$), 1.90 (s, 3H, CH$_3$) ppm.

Example 18

[(2S,3R,4S,5S,6S)-2,3,5-Triacetoxy-6-[4-(3-methoxyphenyl)piperazine-1-carbonyl]tetrahydropyran-4-yl] acetate

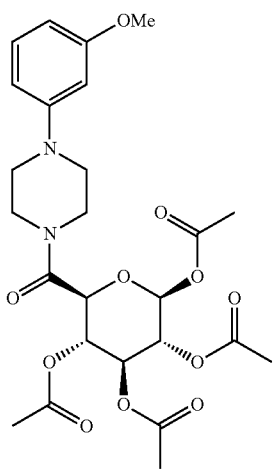 [SMILES: COc1cccc(N2CCN(C(=O)[C@H]3O[C@@H](OC(C)=O)[C@H](OC(C)=O)[C@@H](OC(C)=O)[C@@H]3OC(C)=O)CC2)c1]

Example 18 was synthesized from 1,2,3,4-tetra-O-acetyl-β-D-glucuronic acid and 1-(3-methoxyphenyl)-piperazine following the procedure described in synthesis method A.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

MPLC Gradient

| start % B | end % B | duration [min] |
|---|---|---|
| 0 | 0 | 1.0 |
| 0 | 10.0 | 20.0 |
| 10.0 | 10.0 | 3.0 |
| 10.0 | 0.0 | 0.0 |
| 0.0 | 0.0 | 1.0 |

Yield: 120 mg (0.224 mmol, 40.6%), white solid.

TLC: $R_f$=0.571 (ethylacetate/n-heptane, 2:1).

LC/MS (ES-API): m/z=537.12 [M+H]$^+$; calculated: 537.20; $t_R$: 1.70 min (LC/MS—Method 1).

$^1$H-NMR (400 MHz, DMSO-d$_6$): δ=7.12 (d, J=8.2 Hz, 1H, ArH), 6.83 (d, J=8.2 Hz, 1H, ArH), 6.47 (s, 1H, ArH), 6.41 (d, J=8.2 Hz, 1H, ArH), 6.00 (d, J=8.0 Hz, 1H, CH), 5.39 (t, J=9.9 Hz, 1H, CH), 5.28 (t, J=9.9 Hz, 1H, CH), 5.00 (m, 2H, 2×CH), 3.78 (m, 2H, NCH$_2$), 3.72 (s, 3H, OCH$_3$), 3.56 (m, 1H, CH$_2$), 3.37 (m, 1H, NCH$_2$), 3.24 (m, 2H, NCH$_2$), 2.92 (m, 2H, NCH$_2$), 2.08 (s, 3H, CH$_3$), 2.02 (s, 3H, CH$_3$), 1.96 (s, 3H, CH$_3$), 1.90 (s, 3H, CH$_3$) ppm.

Example 19

[(2S,3R,4S,5S,6S)-2,3,5-Triacetoxy-6-[4-(2-methoxyphenyl)piperazine-1-carbonyl]tetrahydropyran-4-yl] acetate

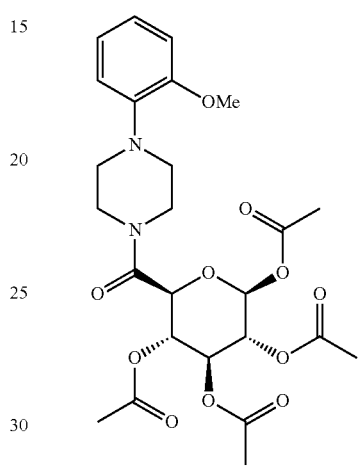

Example 19 was synthesized from 1,2,3,4-tetra-O-acetyl-β-D-glucuronic acid and 1-(2-methoxyphenyl)-piperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 2.5 |
| 0 | 5.0 | 8.5 |
| 5.0 | 5.0 | 3.9 |

Yield: 150 mg (0.280 mmol, 50.6%), white solid.

TLC: $R_f$=0.492 (ethylacetate/n-heptane, 2:1).

LC/MS (ES-API): m/z=537.14 [M+H]$^+$; calculated: 537.20; $t_R$: 1.67 min (LC/MS—Method 1).

$^1$H-NMR (400 MHz, DMSO-d$_6$): δ=6.98 (t, J=4.1 Hz, 1H, ArH), 6.96 (t, J=4.1 Hz, 1H, ArH), 6.89 (d, J=2.2 Hz, 2H, ArH), 6.86 (d, J=2.2 Hz, 2H, ArH), 5.98 (d, J=8.4 Hz, 1H, CH), 5.40 (t, J=9.5 Hz, 1H, CH), 5.29 (t, J=9.5 Hz, 1H, CH), 5.00 (m, 2H, 2×CH), 3.83 (m, 1H, NCH$_2$), 3.79 (s, 3H, OCH$_3$), 3.74 (m, 1H, NCH$_2$), 3.70 (m, 1H, CH$_2$), 3.54 (m, 1H, NCH$_2$), 3.03 (m, 2H, NCH$_2$), 2.74 (m, 2H, NCH$_2$), 2.07 (s, 3H, CH$_3$), 2.03 (s, 3H, CH$_3$), 1.94 (s, 3H, CH$_3$), 1.91 (s, 3H, CH$_3$) ppm.

Example 20

[(2S,3R,4S,5S,6S)-2,3,5-Triacetoxy-6-[4-(1,3-benzodioxol-5-ylmethyl)piperazine-1-carbonyl]tetrahydropyran-4-yl] acetate

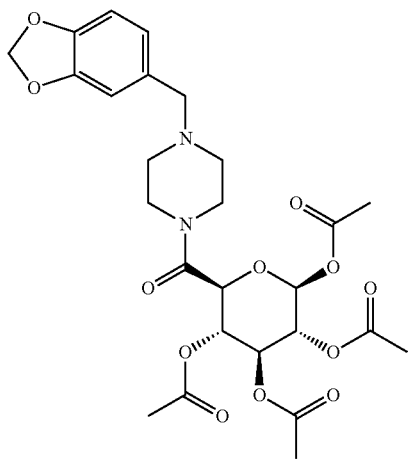 [SMILES: CC(=O)O[C@@H]1O[C@H](C(=O)N2CCN(Cc3ccc4c(c3)OCO4)CC2)[C@@H](OC(C)=O)[C@H](OC(C)=O)[C@H]1OC(C)=O]

Example 20 was synthesized from 1,2,3,4-tetra-O-acetyl-β-D-glucuronic acid and 1-(1,3-benzodioxol-5-ylmethyl)piperazine following the procedure described in synthesis method A.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.
MPLC Gradient

| start % B | end % B | duration [min] |
|---|---|---|
| 0 | 0 | 1.0 |
| 0 | 10.0 | 20.0 |
| 10.0 | 10.0 | 3.0 |
| 10.0 | 0.0 | 0.0 |
| 0.0 | 0.0 | 1.0 |

Yield: 221 mg (0.391 mmol, 70.9%), white solid.
TLC: $R_f$=0.478 (dichloromethane/ethanol, 19:1).
LC/MS (ES-API): m/z=565.14 [M+H]$^+$; calculated: 565.19; $t_R$: 1.24 min (LC/MS—Method 1).
$^1$H-NMR (400 MHz, DMSO-d$_6$): δ=6.84 (m, 2H, ArH), 6.73 (dd, J=1.4 Hz, 1H, ArH), 5.99 (s, 2H, O—CH$_2$—O), 5.95 (d, J=8.4 Hz, 1H, CH), 5.36 (t, J=9.5 Hz, 1H, CH), 5.24 (t, J=9.5 Hz, 1H, CH), 4.96 (m, 2H, 2×CH), 3.62 (m, 2H, NCH$_2$), 3.55 (m, 1H, CH$_2$), 3.39 (m, 1H, NCH$_2$), 3.23 (m, 1H, NCH$_2$), 2.39 (m, 2H, NCH$_2$), 2.21 (m, 2H, NCH$_2$), 2.07 (s, 3H, CH$_3$), 2.02 (s, 3H, CH$_3$), 1.93 (s, 3H, CH$_3$), 1.88 (s, 3H, CH$_3$) ppm.

Method B
Deacetylation of Glucuronic Acid Amides 20 mg of [(2,3,5-triacetoxy-6-piperazine-1-carbonyl]tetrahydropyran-4-yl] acetates were dissolved in 2 mL methanol/H$_2$O/tetrahydrofuran (5:4:1) and cooled to 0° C. 20 μl of a 2 M lithium hydroxide solution in water were added and stirred for 2-12 hours at 0° C. The reaction control was done by TLC and LC/MS. As work-up procedure the reaction mixture was neutralized with 1M HCl, and the organic solvents were evaporated. The residue was diluted with water and lyophilized. The enantiomers were not separated. NMR signals were listed for only one enantiomer.

Example 21

(4-Methylpiperazin-1-yl)-[(2S,3S,4S,5R)-3,4,5,6-tetrahydroxytetrahydropyran-2-yl]methanone

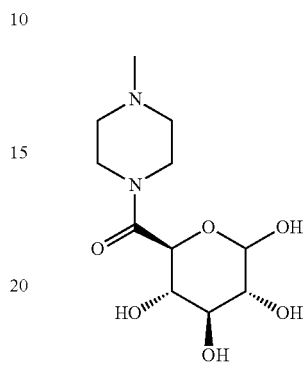

Example 21 was synthesized from example 1 following the deacetylation procedure described in synthesis method B.
Yield: 11.9 mg (43.07 μmol, 95.7%), colorless oil.
LC/MS (ES-API): m/z=277.15 [M+H]$^+$; calculated: 277.13; $t_R$ (ELSD): 0.21 min (LC/MS—Method 1).
$^1$H-NMR (400 MHz, DMSO-d$_6$): δ=6.51 (d, J=4.5 Hz, 1H, CH), 5.0-4.3 (m, 4H, 4×OH), 3.5-3.0 (m, 12H, 4×CH$_2$, 4×CH), 2.21 (m, 3H, CH$_3$) ppm.

Example 22

(4-Ethylpiperazin-1-yl)-[(2S,3S,4S,5R)-3,4,5,6-tetrahydroxytetrahydropyran-2-yl]methanone

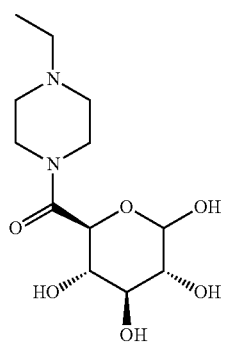 [SMILES: CCN1CCN(C(=O)[C@H]2OC(O)[C@H](O)[C@@H](O)[C@@H]2O)CC1]

Example 22 was synthesized from example 2 following the deacetylation procedure described in synthesis method B.
Yield: 11.8 mg (40.65 μmol, 93.2%), colorless oil.
LC/MS (ES-API): m/z=291.23 [M+H]$^+$; calculated: 291.15; $t_R$ (ELSD): 0.20 min (LC/MS—Method 1).
$^1$H-NMR (400 MHz, DMSO-d$_6$): δ=6.48 (d, J=4.6 Hz, 1H, CH), 4.8-4.3 (m, 4H, 4×OH), 3.5-3.0 (m, 12H, 4×CH$_2$, 4×CH), 2.20 (m, 5H, CH$_2$CH$_3$) ppm.

Example 23

(4-n-Propylpiperazin-1-yl)-[(2S,3S,4S,5R)-3,4,5,6-tetrahydroxytetrahydropyran-2-yl]methanone

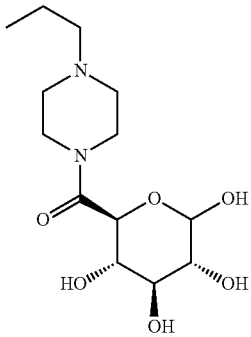 [SMILES: CCCN1CCN(C(=O)[C@H]2OC(O)[C@H](O)[C@@H](O)[C@@H]2O)CC1]

Example 23 was synthesized from example 3 following the deacetylation procedure described in synthesis method B.

Yield: 12.4 mg (40.74 μmol, 96.3%), colorless oil.

LC/MS (ES-API): m/z=305.21 [M+H]$^+$; calculated: 305.16; $t_R$ (ELSD): 0.19 min (LC/MS—Method 1).

$^1$H-NMR (400 MHz, DMSO-d$_6$): δ=6.51 (d, J=4.4 Hz, 1H, CH), 4.9-4.1 (m, 4H, 4×OH), 3.6-3.0 (m, 12H, 4×CH$_2$, 4×CH), 2.32 (m, 2H, NCH$_2$), 1.49 (m, 2H, CH$_2$), 0.89 (t, J=7.3 Hz, 3H, CH$_3$) ppm.

Example 24

(4-n-Butylpiperazin-1-yl)-[(2S,3S,4S,5R)-3,4,5,6-tetrahydroxytetrahydropyran-2-yl]methanone

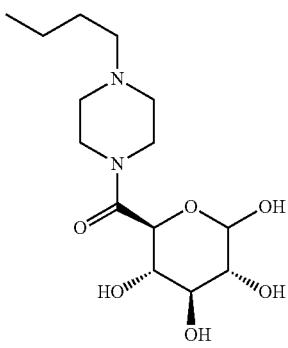 [SMILES: CCCCN1CCN(C(=O)[C@H]2OC(O)[C@H](O)[C@@H](O)[C@@H]2O)CC1]

Example 24 was synthesized from example 4 following the deacetylation procedure described in synthesis method B.

Yield: 12.7 mg (39.89 μmol, 97.0%), colorless oil.

LC/MS (ES-API): m/z=319.21 [M+H]$^+$; calculated: 319.18; $t_R$ (ELSD): 0.23 min (LC/MS—Method 1).

$^1$H-NMR (400 MHz, DMSO-d$_6$): δ=6.52 (d, J=4.5 Hz, 1H, CH), 4.87 (dd, J=4.2 Hz, 1H, OH), 4.75 (dd, J=4.9 Hz, 1H, OH), 4.29 (d, J=8.9 Hz, 1H, OH), 4.02 (d, J=9.4 Hz, 1H, OH), 3.6-3.15 (m, 12H, 4×CH$_2$, 4×CH), 2.32 (m, 2H, NCH$_2$), 1.46 (m, 2H, CH$_2$), 1.29 (m, 2H, CH$_2$), 0.89 (t, J=7.1 Hz, 3H, CH$_3$) ppm.

Example 25

(4-n-Hexylpiperazin-1-yl)-[(2S,3S,4S,5R)-3,4,5,6-tetrahydroxytetrahydropyran-2-yl]methanone

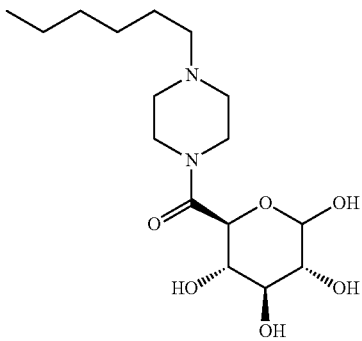 [SMILES: CCCCCCN1CCN(C(=O)[C@H]2OC(O)[C@H](O)[C@@H](O)[C@@H]2O)CC1]

Example 25 was synthesized from example 5 following the deacetylation procedure described in synthesis method B.

Yield: 12.6 mg (36.37 μmol, 93.6%), white solid.

LC/MS (ES-API): m/z=347.17 [M+H]$^+$; calculated: 347.21; $t_R1$ (λ=220 nm): 0.50 min; $t_R2$ (λ=220 nm): 0.53 min (LC/MS—Method 1).

$^1$H-NMR (400 MHz, DMSO-d$_6$): δ=6.50 (d, J=4.4 Hz, 1H, CH), 4.85 (dd, J=4.4 Hz, 1H, OH), 4.76 (dd, J=4.8 Hz, 1H, OH), 4.27 (d, J=8.8 Hz, 1H, OH), 4.12 (d, J=9.3 Hz, 1H, OH), 3.6-3.1 (m, 12H, 4×CH$_2$, 4×CH), 2.32 (m, 2H, NCH$_2$), 1.43 (m, 8H, 4×CH$_2$), 0.90 (t, J=7.2 Hz, 3H, CH$_3$) ppm.

Example 26

(4-Isopropylpiperazin-1-yl)-[(2S,3S,4S,5R)-3,4,5,6-tetrahydroxytetrahydropyran-2-yl]methanone

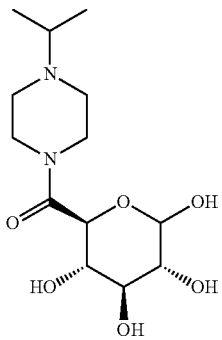 [SMILES: CC(C)N1CCN(C(=O)[C@H]2OC(O)[C@H](O)[C@@H](O)[C@@H]2O)CC1]

Example 26 was synthesized from example 6 following the deacetylation procedure described in synthesis method B.

Yield: 12.2 mg (40.09 μmol, 94.7%), colorless oil.

LC/MS (ES-API): m/z=305.23 [M+H]$^+$; calculated: 305.16; $t_R$ (ELSD): 0.21 min (LC/MS—Method 1).

$^1$H-NMR (400 MHz, DMSO-d$_6$): δ=6.48 (d, J=4.6 Hz, 1H, CH), 4.8-4.1 (m, 4H, 4×OH), 3.5-3.1 (m, 12H, 4×CH$_2$, 4×CH), 2.43 (m, 2H, NCH), 1.01 (m, 6H, 2×CH$_3$) ppm.

Example 27

(4-tert-Butylpiperazin-1-yl)-[(2S,3S,4S,5R)-3,4,5,6-tetrahydroxytetrahydropyran-2-yl]methanone

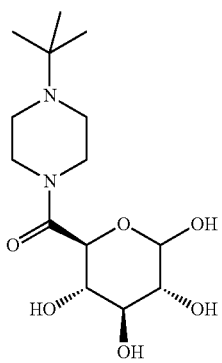 [SMILES: CC(C)(C)N1CCN(C(=O)[C@H]2OC(O)[C@H](O)[C@@H](O)[C@@H]2O)CC1]

Example 27 was synthesized from example 7 following the deacetylation procedure described in synthesis method B.

Yield: 12.5 mg (39.26 μmol, 95.5%), white solid.

LC/MS (ES-API): m/z=319.25 [M+H]$^+$; calculated: 319.18; $t_R$ (ELSD): 0.22 min (LC/MS—Method 1).

$^1$H-NMR (400 MHz, DMSO-d$_6$): δ=6.49 (d, J=4.9 Hz, 1H, CH), 4.9-4.0 (m, 4H, 4×OH), 3.5-3.1 (m, 12H, 4×CH$_2$, 4×CH), 1.04 (m, 9H, 3×CH$_3$) ppm.

Example 28

(4-Allylpiperazin-1-yl)-[(2S,3S,4S,5R)-3,4,5,6-tetrahydroxytetrahydropyran-2-yl]methanone

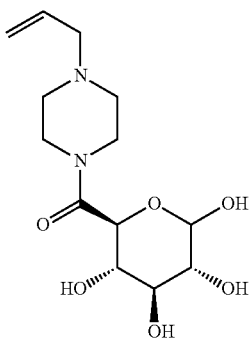 [SMILES: C=CCN1CCN(C(=O)[C@H]2OC(O)[C@H](O)[C@@H](O)[C@@H]2O)CC1]

Example 28 was synthesized from example 8 following the deacetylation procedure described in synthesis method B.

Yield: 12.4 mg (41.02 μmol, 96.5%), colorless oil.

LC/MS (ES-API): m/z=303.22 [M+H]$^+$; calculated: 303.15; $t_R$ (ELSD): 0.21 min (LC/MS—Method 1).

$^1$H-NMR (400 MHz, DMSO-d$_6$): δ=6.29 (d, J=4.5 Hz, 1H, CH), 4.7-4.0 (m, 4H, 4×OH), 3.4-3.1 (m, 12H, 4×CH$_2$, 4×CH), 2.41 (m, 5H, 2×CH$_2$, CH) ppm.

Example 29

(4-Cyclohexylpiperazin-1-yl)-[(2S,3S,4S,5R)-3,4,5,6-tetrahydroxytetrahydropyran-2-yl]methanone

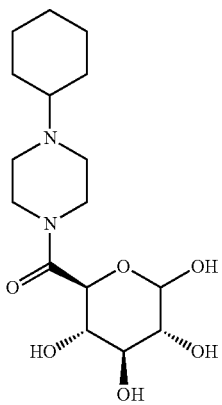 [SMILES: O=C([C@H]1OC(O)[C@H](O)[C@@H](O)[C@@H]1O)N1CCN(C2CCCCC2)CC1]

Example 29 was synthesized from example 9 following the deacetylation procedure described in synthesis method B.

Yield: 12.9 mg (37.46 μmol, 96.0%), white solid.

LC/MS (ES-API): m/z=345.25 [M+H]$^+$; calculated: 345.19; $t_R$1 (ELSD): 0.28 min (LC/MS—Method 1).

$^1$H-NMR (400 MHz, DMSO-d$_6$): δ=6.51 (d, J=4.8 Hz, 1H, CH), 4.6-4.0 (m, 4H, 4×OH), 3.4-2.9 (m, 12H, 4×CH$_2$, 4×CH), 1.71 (m, 4H, 2×CH$_2$), 1.54 (m, 1H, CH), 1.19 (m, 6H, 3×CH$_2$) ppm.

Example 30

(4-Cyclohexylmethylpiperazin-1-yl)-[(2S,3S,4S,5R)-3,4,5,6-tetrahydroxytetrahydropyran-2-yl]methanone

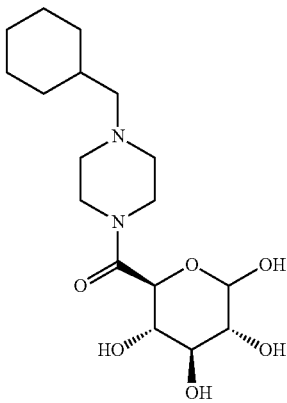 [SMILES: O=C([C@H]1OC(O)[C@H](O)[C@@H](O)[C@@H]1O)N1CCN(CC2CCCCC2)CC1]

Example 30 was synthesized from example 10 following the deacetylation procedure described in synthesis method B.

Yield: 13.1 mg (36.55 μmol, 96.2%), white solid.

LC/MS (ES-API): m/z=359.16 [M+H]$^+$; calculated: 359.21; $t_R$1 (λ=220 nm): 0.46 min; $t_R$2 (λ=220 nm): 0.48 min (LC/MS—Method 1).

$^1$H-NMR (400 MHz, DMSO-d$_6$): δ=6.47 (d, J=4.5 Hz, 1H, CH), 4.9-4.3 (m, 4H, 4×OH), 3.5-2.9 (m, 12H, 4×CH$_2$,

4×CH), 2.07 (m, 2H, NCH$_2$), 1.74 (m, 4H, 2×CH$_2$), 1.52 (m, 1H, CH), 1.21 (m, 4H, 2×CH$_2$), 0.87 (m, 2H, CH$_2$) ppm.

Example 31

(4-Cyclohexylethylpiperazin-1-yl)-[(2S,3S,4S,5R)-3,4,5,6-tetrahydroxytetrahydropyran-2-yl]methanone

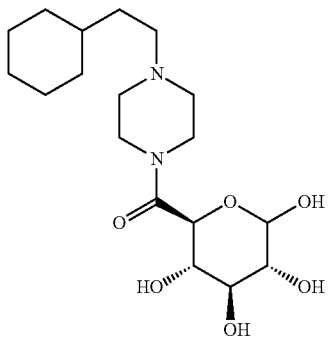 [SMILES: O=C([C@H]1OC(O)[C@H](O)[C@@H](O)[C@@H]1O)N1CCN(CCC2CCCCC2)CC1]

Example 31 was synthesized from example 11 following the deacetylation procedure described in synthesis method B.

Yield: 12.2 mg (32.76 μmol, 88.5%), white solid.

LC/MS (ES-API): m/z=373.17 [M+H]$^+$; calculated: 373.23; t$_R$1 (λ=220 nm): 0.81 min; t$_R$2 (λ=220 nm): 0.84 min (LC/MS—Method 1).

$^1$H-NMR (400 MHz, DMSO-d$_6$): δ=6.42 (d, J=4.8 Hz, 1H, CH), 4.6-4.1 (m, 4H, 4×OH), 3.6-3.0 (m, 12H, 4×CH$_2$, 4×CH), 2.05 (m, 2H, NCH$_2$), 1.72 (m, 4H, 2×CH$_2$), 1.50 (m, 1H, CH), 1.23 (m, 4H, 2×CH$_2$), 0.90 (m, 2H, CH$_2$), 0.87 (m, 2H, CH$_2$) ppm.

Example 32

(4-Phenylpiperazin-1-yl)-[(2S,3S,4S,5R)-3,4,5,6-tetrahydroxytetrahydropyran-2-yl]methanone

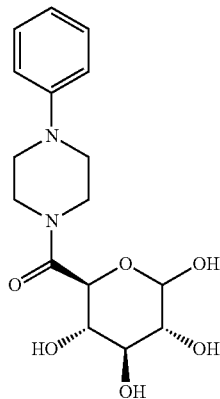 [SMILES: O=C([C@H]1OC(O)[C@H](O)[C@@H](O)[C@@H]1O)N1CCN(c2ccccc2)CC1]

Example 32 was synthesized from example 12 following the deacetylation procedure described in synthesis method B.

Yield: 11.8 mg (34.87 μmol, 88.3%), white solid.

LC/MS (ES-API): m/z=339.13 [M+H]$^+$; calculated: 339.15; t$_R$1 (λ=220 nm): 0.90 min; t$_R$2 (λ=220 nm): 0.95 min (LC/MS—Method 1).

$^1$H-NMR (400 MHz, DMSO-d$_6$): δ=7.23 (t, J=7.9 Hz, 2H, ArH), 6.95 (d, J=7.8 Hz, 2H, ArH), 6.81 (t, J=7.3 Hz, 1H, ArH), 6.66 (d, J=7.0 Hz, 1H, OH), 4.81 (d, J=4.7 Hz, 1H, OH), 4.74 (d, J=5.3 Hz, 1H, OH), 4.62 (d, J=6.4 Hz, 1H, OH), 4.43 (t, J=7.3 Hz, 1H, CH), 4.09 (d, J=9.3 Hz, 1H, CH), 3.70-3.45 (m, 8H, 4×NCH$_2$), 3.25-3.00 (m, 3H, 3×CH) ppm.

$^{13}$C-NMR (150 MHz, DMSO-d$_6$): δ=166.48 (s, CO), 150.76 (s, C), 129.06 (s, CH), 119.28 (s, CH), 115.78 (s, CH), 93.06 (s, CH), 74.52 (s, CH), 72.71 (s, CH), 71.33 (s, CH), 70.98 (s, CH), 48.93 (s, CH$_2$), 48.22 (s, CH$_2$), 44.59 (s, CH$_2$), 41.15 (s, CH$_2$) ppm.

Example 33

[4-[(E)-Cinnamyl]piperazin-1-yl]-[(2S,3S,4S,5R)-3,4,5,6-tetrahydroxytetrahydropyran-2-yl]methanone

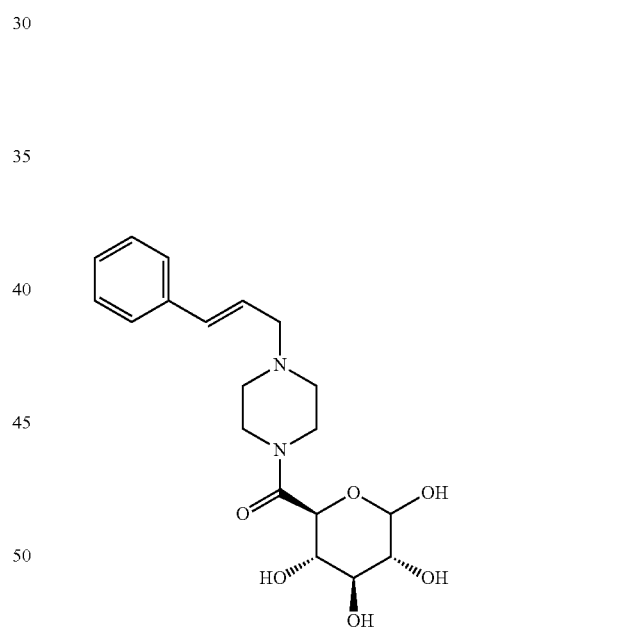

Example 33 was synthesized from example 13 following the deacetylation procedure described in synthesis method B.

Yield: 12.7 mg (33.56 μmol, 91.7%), white solid.

LC/MS (ES-API): m/z=379.25 [M+H]$^+$; calculated: 379.19; t$_R$1 (λ=220 nm): 0.56 min; t$_R$2 (λ=220 nm): 0.60 min (LC/MS—Method 1).

$^1$H-NMR (400 MHz, DMSO-d$_6$): δ=7.40 (d, J=7.0 Hz, 2H, ArH), 7.33 (t, J=7.0 Hz, 2H, ArH), 7.21 (t, J=7.0 Hz, 2H, ArH), 6.44 (d, J=4.6 Hz, 1H, CH), 4.6-4.1 (m, 4H, 4×OH), 3.65 (m, 2H, NCH$_2$), 3.51 (m, 2H, 2×CH), 3.4-2.9 (m, 12H, 4×NCH$_2$, 4×CH) ppm.

Example 34

[4-(4-Chlorophenyl)piperazin-1-yl]-[(2S,3S,4S,5R)-3,4,5,6-tetrahydroxytetrahydropyran-2-yl]methanone

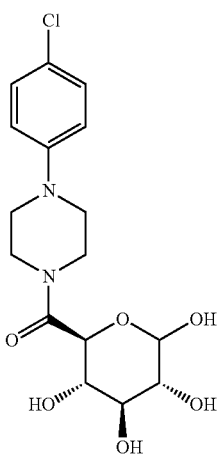 [SMILES: O=C([C@H]1OC(O)[C@H](O)[C@@H](O)[C@@H]1O)N1CCN(c2ccc(Cl)cc2)CC1]

Example 34 was synthesized from example 14 following the deacetylation procedure described in synthesis method B.

Yield: 13.6 mg (36.48 μmol, 98.7%), white solid.

LC/MS (ES-API): m/z=373.16 [M+H]$^+$; calculated: 373.11; $t_R$1 (λ=220 nm): 1.20 min; $t_R$2 (λ=220 nm): 1.24 min (LC/MS—Method 1).

$^1$H-NMR (400 MHz, DMSO-$d_6$): δ=7.40 (d, J=7.8 Hz, 4H, ArH), 6.49 (d, J=4.7 Hz, 1H, CH), 4.9-4.3 (m, 4H, 4×OH), 3.7-3.0 (m, 12H, 4×NCH$_2$, 4×CH) ppm.

Example 35

[4-(2-Chlorophenyl)piperazin-1-yl]-[(2S,3S,4S,5R)-3,4,5,6-tetrahydroxytetrahydropyran-2-yl]methanone

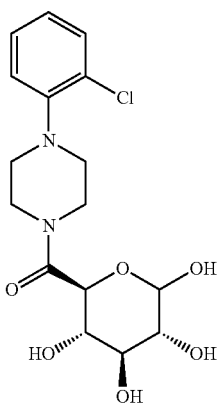 [SMILES: O=C([C@H]1OC(O)[C@H](O)[C@@H](O)[C@@H]1O)N1CCN(c2ccccc2Cl)CC1]

Example 35 was synthesized from example 15 following the deacetylation procedure described in synthesis method B.

Yield: 13.3 mg (35.68 μmol, 96.5%), white solid.

LC/MS (ES-API): m/z=373.06 [M+H]$^+$; calculated: 373.11; $t_R$1 (λ=220 nm): 1.23 min; $t_R$2 (λ=220 nm): 1.26 min (LC/MS—Method 1).

$^1$H-NMR (400 MHz, DMSO-$d_6$): δ=7.45 (d, J=7.8 Hz, 1H, ArH), 7.31 (t, J=7.8 Hz, 1H, ArH), 7.14 (d, J=7.8 Hz, 1H, ArH), 7.03 (t, J=7.8 Hz, 1H, ArH), 6.52 (d, J=4.7 Hz, 1H, CH), 4.9-4.3 (m, 4H, 4×OH), 3.7-3.0 (m, 12H, 4×NCH$_2$, 4×CH) ppm.

Example 36

[4-(4-Bromophenyl)piperazin-1-yl]-[(2S,3S,4S,5R)-3,4,5,6-tetrahydroxytetrahydropyran-2-yl]methanone

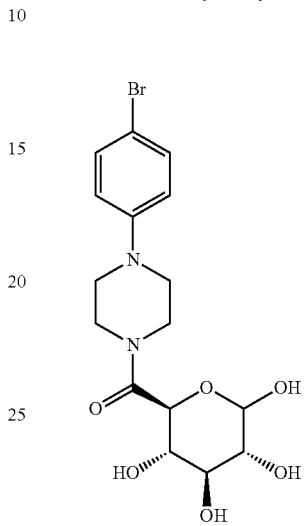

Example 36 was synthesized from example 16 following the deacetylation procedure described in synthesis method B.

Yield: 12.9 mg (30.92 μmol, 90.5%), white solid.

LC/MS (ES-API): m/z=416.11 [M+H]$^+$; calculated: 416.06; $t_R$1 (λ=220 nm): 1.25 min; $t_R$2 (λ=220 nm): 1.28 min (LC/MS—Method 1).

$^1$H-NMR (400 MHz, DMSO-$d_6$): δ=7.69 (d, J=8.0 Hz, 4H, ArH), 6.52 (d, J=4.9 Hz, 1H, CH), 4.8-4.1 (m, 4H, 4×OH), 3.6-3.1 (m, 12H, 4×NCH$_2$, 4×CH) ppm.

Example 37

[4-(4-Methoxyphenyl)piperazin-1-yl]-[(2S,3S,4S,5R)-3,4,5,6-tetrahydroxytetrahydropyran-2-yl]methanone

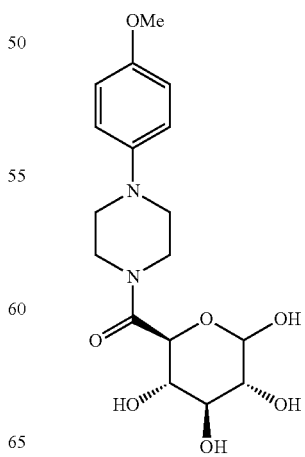

Example 37 was synthesized from example 17 following the deacetylation procedure described in synthesis method B.

Yield: 13.4 mg (36.38 μmol, 97.6%), white solid.

LC/MS (ES-API): m/z=369.11 [M+H]$^+$; calculated: 369.16; $t_R$1 (λ=220 nm): 0.74 min; $t_R$2 (λ=220 nm): 0.80 min (LC/MS—Method 1).

$^1$H-NMR (400 MHz, DMSO-d$_6$): δ=6.91 (d, J=8.2 Hz, 2H, ArH), 6.83 (d, J=8.2 Hz, 2H, ArH), 6.53 (d, J=4.4 Hz, 1H, CH), 4.8-4.1 (m, 4H, 4×OH), 3.69 (s, 3H, OCH$_3$), 3.6-2.9 (m, 12H, 4×NCH$_2$, 4×CH) ppm.

Example 38

[4-(3-Methoxyphenyl)piperazin-1-yl]-[(2S,3S,4S,5R)-3,4,5,6-tetrahydroxytetrahydropyran-2-yl]methanone

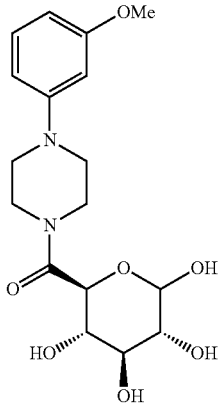 [SMILES: COc1cccc(N2CCN(C(=O)[C@H]3OC(O)[C@H](O)[C@@H](O)[C@@H]3O)CC2)c1]

Example 38 was synthesized from example 18 following the deacetylation procedure described in synthesis method B.

Yield: 13.1 mg (35.56 μmol, 95.4%), white solid.

LC/MS (ES-API): m/z=369.10 [M+H]$^+$; calculated: 369.16; $t_R$1 (λ=220 nm): 1.01 min; $t_R$2 (λ=220 nm): 1.04 min (LC/MS—Method 1).

$^1$H-NMR (400 MHz, DMSO-d$_6$): δ=7.14 (d, J=8.2 Hz, 1H, ArH), 6.84 (d, J=8.2 Hz, 1H, ArH), 6.57 (s, 1H, ArH), 6.51 (d, J=8.2 Hz, 1H, ArH), 6.43 (d, J=4.4 Hz, 1H, CH), 4.8-4.1 (m, 4H, 4×OH), 3.72 (s, 3H, OCH$_3$), 3.60-3.45 (m, 4H, 4×CH), 3.25-3.00 (m, 8H, 4×NCH$_2$) ppm.

Example 39

[4-(2-Methoxyphenyl)piperazin-1-yl]-[(2S,3S,4S,5R)-3,4,5,6-tetrahydroxytetrahydropyran-2-yl]methanone

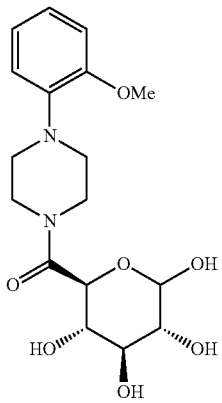 [SMILES: COc1ccccc1N1CCN(C(=O)[C@H]2OC(O)[C@H](O)[C@@H](O)[C@@H]2O)CC1]

Example 39 was synthesized from example 19 following the deacetylation procedure described in synthesis method B.

Yield: 12.8 mg (34.75 μmol, 93.2%), white solid.

LC/MS (ES-API): m/z=369.19 [M+H]$^+$; calculated: 369.16; $t_R$1 (λ=220 nm): 0.85 min; $t_R$2 (λ=220 nm): 0.90 min (LC/MS—Method 1).

$^1$H-NMR (400 MHz, DMSO-d$_6$): δ=6.98 (m, 2H, ArH), 6.87 (d, J=7.2 Hz, 2H, ArH), 6.49 (d, J=4.4 Hz, 1H, CH), 4.8-4.1 (m, 4H, 4×OH), 3.70 (s, 3H, OCH$_3$), 3.6-3.2 (m, 4H, 4×CH), 3.0-2.8 (m, 8H, 4×NCH$_2$) ppm.

Example 40

[4-(1,3-Benzodioxol-5-ylmethyl)piperazin-1-yl]-[(2S,3S,4S,5R)-3,4,5,6-tetrahydroxytetrahydropyran-2-yl]methanone

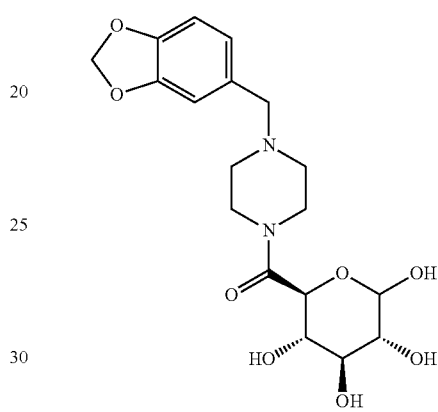

Example 40 was synthesized from example 20 following the deacetylation procedure described in synthesis method B.

Yield: 12.6 mg (31.79 μmol, 89.7%), white solid.

LC/MS (ES-API): m/z=397.11 [M+H]$^+$; calculated: 397.15; $t_R$1 (λ=220 nm): 0.95 min; $t_R$2 (λ=220 nm): 0.99 min (LC/MS—Method 1).

$^1$H-NMR (400 MHz, DMSO-d$_6$): δ=6.82 (m, 2H, ArH), 6.75 (dd, J=1.4 Hz, 1H, ArH), 6.00 (s, 2H, O—CH$_2$—O), 6.49 (d, J=4.4 Hz, 1H, CH), 4.8-4.1 (m, 4H, 4×OH), 3.6-3.2 (m, 4H, 4×CH), 3.0-2.8 (m, 8H, 4×NCH$_2$), 2.41 (m, 2H, NCH$_2$) ppm.

Example 41

[(2S,3R,4S)-2,3-Diacetoxy-6-(4-butylpiperazine-1-carbonyl)-3,4-dihydro-2H-pyran-4-yl] acetate

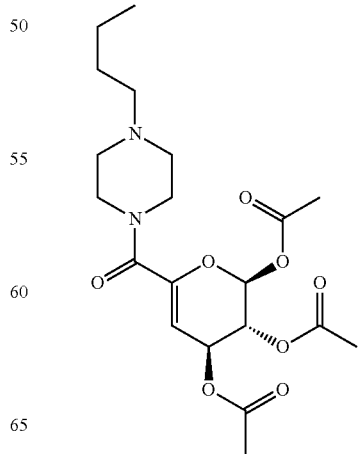

Step 1: (2S,3R,4S)-2,3,4-triacetoxy-3,4-dihydro-2H-pyran-6-carboxylic acid

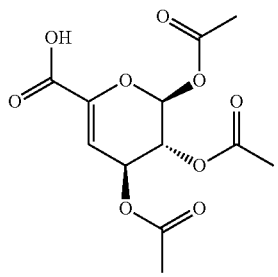

A solution of 2 g (5.52 mmol) 1,2,3,4-tetra-O-acetyl-β-D-glucuronic acid in 6 mL (63.59 mmol) acetic acid anhydride and 3 mL (22.08 mmol; 4 eq.) triethylamine was stirred at room temperature for 8 hours. The reaction mixture was diluted with water and lyophillized.
Yield: 1.6 g (5.38 mmol, 95.8%), colorless oil.
LC/MS (ES-API): not detectable.
$^1$H-NMR (400 MHz, CDCl$_3$): δ=7.99 (s, 1H, COOH), 6.33 (s, 1H, CH), 6.27 (m, 1H, CH), 5.19 (m, 1H, CH), 5.10 (m, 1H, CH), 2.05 (s, 3H, CH$_3$), 2.04 (s, 3H, CH$_3$), 2.03 (s, 3H, CH$_3$) ppm.
Method C Amide coupling with (2S,3R,4S)-2,3,4-triacetoxy-3,4-dihydro-2H-pyran-6-carboxylic acid (example 41, step 1)

To a solution of 0.66 mmol (2S,3R,4S)-2,3,4-triacetoxy-3,4-dihydro-2H-pyran-6-carboxylic acid (example 41, step 1) in 2 mL dimethylformamide were added 1.2 eq. (0.79 mmol) HATU and 1.4 eq. (0.93 mmol) amine. The reaction mixture was stirred at room temperature for 2 hours. The reaction was controlled by TLC and LC/MS. After completion the reaction mixture was extracted with 5-10 mL dichloromethane. The organic phase was washed with 1 M aqueous HCl, water, saturated aqueous NaHCO$_3$ solution, and water. The organic phase was dried with Na$_2$SO$_4$, filtered, and evaporated. The crude material was purified by MPLC.

Step 2: [(2S,3R,4S)-2,3-diacetoxy-6-(4-butylpiperazine-1-carbonyl)-3,4-dihydro-2H-pyran-4-yl] acetate Example 41 was synthesized from example 41, step 1 and 1-n-butylpiperazine following the amide coupling procedure described in synthesis method C.
Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.
MPLC Gradient

| start % B | end % B | duration [min] |
|---|---|---|
| 0 | 0 | 2.2 |
| 0 | 4.8 | 2.8 |
| 4.8 | 4.8 | 6.0 |
| 4.8 | 10.0 | 10.1 | 6.0 |
| 10.1 | 10.1 | 9.1 |

Yield: 141 mg (0.331 mmol, 50.8%), orange oil.
LC/MS (ES-API): m/z=427.20 [M+H]$^+$; calculated: 427.20; t$_R$ (λ=220 nm): 0.57 min (LC/MS—Method 1).
$^1$H-NMR (400 MHz, CDCl$_3$): δ=6.28 (d, J=3.6 Hz, 1H, C═CH), 5.67 (d, J=3.8 Hz, 1H, CH), 5.25 (m, 1H, CH), 5.19 (m, 1H, CH), 3.73 (m, 4H, 2×NCH$_2$), 2.60 (m, 4H, 2×NCH$_2$), 2.15 (s, 3H, CH$_3$), 2.13 (s, 3H, CH$_3$), 2.10 (s, 3H, CH$_3$) ppm.

Example 42

[(2S,3R,4S)-2,3-Diacetoxy-6-(4-tert-butylpiperazine-1-carbonyl)-3,4-dihydro-2H-pyran-4-yl] acetate

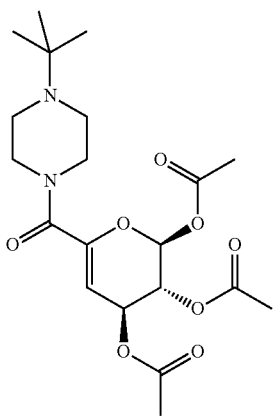 [SMILES: CC(=O)O[C@@H]1OC(C(=O)N2CCN(C(C)(C)C)CC2)=C[C@H](OC(C)=O)[C@H]1OC(C)=O]

Example 42 was synthesized from example 41, step 1 and 1-tert-butylpiperazine following the amide coupling procedure described in synthesis method C.
Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.
MPLC Gradient

| start % B | end % B | duration [min] |
|---|---|---|
| 0 | 0 | 2.2 |
| 0 | 4.8 | 2.8 |
| 4.8 | 4.8 | 6.0 |
| 4.8 | 10.0 | 10.1 | 6.0 |
| 10.1 | 10.1 | 9.1 |

Yield: 81 mg (0.190 mmol, 28.7%), orange oil.
LC/MS (ES-API): m/z=427.15 [M+H]$^+$; calculated: 427.20; t$_R$ (λ=220 nm): 0.53 min (LC/MS—Method 1).
$^1$H-NMR (400 MHz, CDCl$_3$): δ=6.29 (d, J=3.6 Hz, 1H, C═CH), 5.69 (d, J=3.8 Hz, 1H, CH), 5.24 (m, 1H, CH), 5.20 (m, 1H, CH), 3.75 (m, 4H, 2×NCH$_2$), 2.62 (m, 4H, 2×NCH$_2$), 2.16 (s, 3H, CH$_3$), 2.13 (s, 3H, CH$_3$), 2.10 (s, 3H, CH$_3$), 1.27 (s, 9H, 3×CH$_3$) ppm.

Example 43

[(2S,3R,4S)-2,3-Diacetoxy-6-[4-(cyclohexylmethyl)piperazine-1-carbonyl]-3,4-dihydro-2H-pyran-4-yl] acetate

Example 44

[(2S,3R,4S)-2,3-Diacetoxy-6-(4-phenylpiperazine-1-carbonyl)-3,4-dihydro-2H-pyran-4-yl] acetate

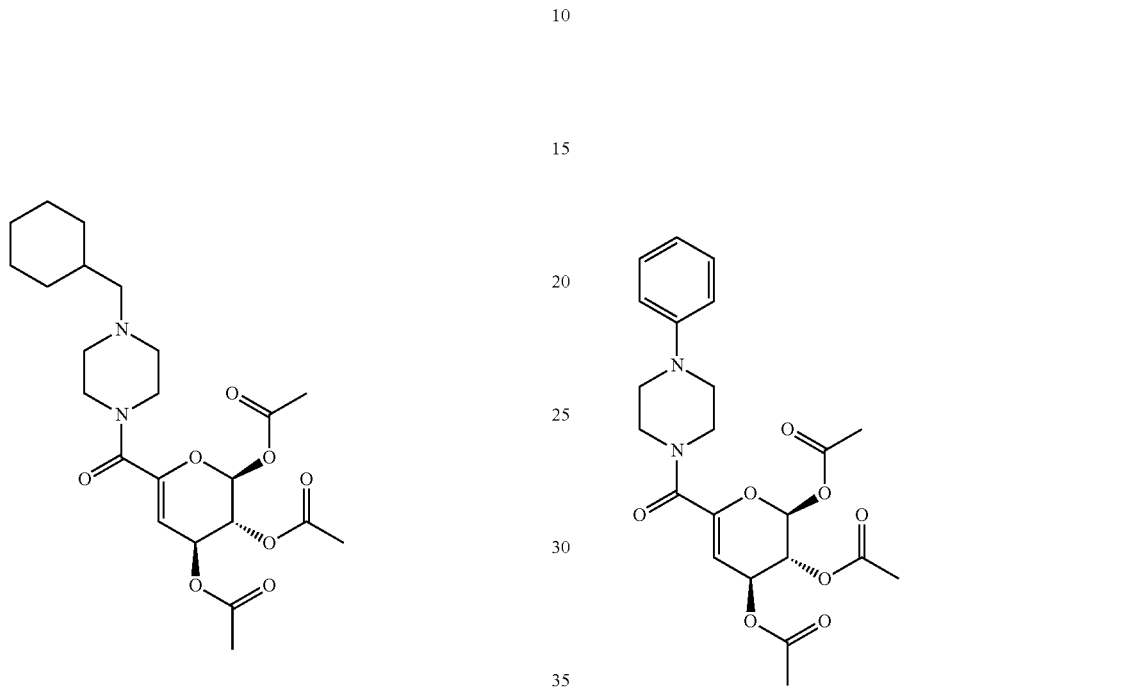

Example 43 was synthesized from example 41, step 1 and 1-cyclohexylmethylpiperazine following the amide coupling procedure described in synthesis method C.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 2.2 |
| 0 | 4.8 | 2.8 |
| 4.8 | 4.8 | 6.0 |
| 4.8 | 10.0 | 6.0 |
| 10.1 | 10.1 | 9.1 |

Yield: 145 mg (0.311 mmol, 47.0%), orange oil.

LC/MS (ES-API): m/z=467.20 [M+H]$^+$; calculated: 467.23; $t_R$ (λ=220 nm): 0.64 min (LC/MS—Method 1).

$^1$H-NMR (400 MHz, CDCl$_3$): δ=6.29 (d, J=3.2 Hz, 1H, C=CH), 5.63 (d, J=3.2 Hz, 1H, CH), 5.24 (m, 1H, CH), 5.19 (m, 1H, CH), 3.75 (m, 4H, 2×NCH$_2$), 2.62 (m, 4H, 2×NCH$_2$), 2.16 (s, 3H, CH$_3$), 2.13 (s, 3H, CH$_3$), 2.11 (s, 3H, CH$_3$), 1.73 (m, 1H, CH), 1.62 (m, 4H, 2×CH$_2$), 1.13 (m, 4H, 2×CH$_2$), 0.92 (m, 2H, CH$_2$) ppm.

Example 44 was synthesized from example 41, step 1 and 1-phenylpiperazine following the amide coupling procedure described in synthesis method C.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

MPLC Gradient

| start % B | end % B | duration [min] |
|---|---|---|
| 0 | 0 | 2.2 |
| 0 | 4.8 | 2.8 |
| 4.8 | 4.8 | 6.0 |
| 4.8 | 10.0 | 6.0 |
| 10.1 | 10.1 | 9.1 |

Yield: 135 mg (0.303 mmol, 45.5%), orange oil.

LC/MS (ES-API): m/z=447.13 [M+H]$^+$; calculated: 447.17; $t_R$ (λ=220 nm): 0.81 min (LC/MS—Method 1).

$^1$H-NMR (400 MHz, CDCl$_3$): δ=7.31 (t, J=7.9 Hz, 2H, ArH), 7.00 (m, 3H, ArH), 6.32 (dd, J=0.9 Hz, 1H, C=CH), 5.67 (dd, J=0.8 Hz, 1H, CH), 5.27 (m, 1H, CH), 5.21 (m, 1H, CH), 3.76 (m, 4H, 2×NCH$_2$), 3.22 (m, 4H, 2×NCH$_2$), 2.15 (s, 3H, CH$_3$), 2.13 (s, 3H, CH$_3$), 2.10 (s, 3H, CH$_3$) ppm.

Example 45

[(2S,3R,4S)-2,3-Diacetoxy-6-[(4-phenylpiperazin-1-yl)methyl]-3,4-dihydro-2H-pyran-4-yl] acetate

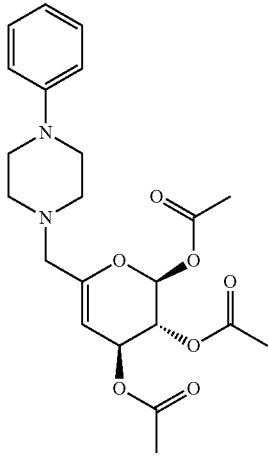 [SMILES: CC(=O)O[C@@H]1OC(CN2CCN(c3ccccc3)CC2)=C[C@H](OC(C)=O)[C@H]1OC(C)=O]

Step 1: [(2S,3R,4S)-2,3-diacetoxy-6-formyl-3,4-dihydro-2H-pyran-4-yl] acetate

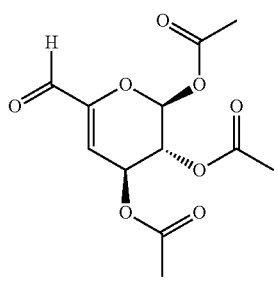 [SMILES: CC(=O)O[C@@H]1OC(C=O)=C[C@H](OC(C)=O)[C@H]1OC(C)=O]

A solution of 2.87 mL dry DMSO (40.31 mmol; 2.6 eq.) in 3 mL dry dichloromethane was dropped slowly to a solution of 1.61 mL oxalylchloride (18.60 mmol; 1.2 eq.) in 4 mL dry dichloromethane at −70° C. After stirring the reaction mixture at −70° C. for 30 minutes, a solution of 5.4 g 1,2,3,4-tetra-O-acetyl-β-D-glucopyranose in 20 mL dry dichloromethane was added. After stirring the reaction mixture at −70° C. for 30 minutes, 11 mL triethylamine were added slowly. The reaction mixture was warmed to room temperature and diluted with 20 mL water. After stirring for 10 minutes at room temperature, the aqueous phase was separated and extracted with dichloromethane. The combined organic phases were dried with $Na_2SO_4$, filtered, and evaporated.

Yield: 3.13 g (10.94 mmol, 70.5%), colorless oil.

TLC: $R_f$=0.509 (ethylacetate/n-heptane, 2:1).

LC/MS (ES-API): m/z=304.05 $[M+H_2O]^+$; calculated: 287.07; $t_R$ (λ=254 nm): 0.63 min (LC/MS—Method 1).

$^1$H-NMR (400 MHz, DMSO-$d_6$): δ=9.28 (s, 1H, CHO), 5.19 (d, J=4.2 Hz, 1H, CH), 5.10 (m, 2H, 2×CH), 2.08 (s, 3H, $CH_3$), 2.07 (s, 3H, $CH_3$), 2.04 (s, 3H, $CH_3$) ppm.

Method D

Reductive amination with [(2S,3R,4S)-2,3-diacetoxy-6-formyl-3,4-dihydro-2H-pyran-4-yl] acetate (example 45, step 1)

To a solution of 0.52 mmol [(2S,3R,4S)-2,3-diacetoxy-6-formyl-3,4-dihydro-2H-pyran-4-yl] acetate (example 45, step 1) in 10 mL dichloroethane were added 0.57 mmol (1.1 eq.) amine and 0.74 mmol (1.41 eq.) sodiumtriacetoxyborohydride. The reaction mixture was stirred at room temperature over night. The reaction was controlled by TLC and LC/MS. The reaction mixture was filtered and evaporated. The crude material was purified by MPLC.

Step 2: [(2S,3R,4S)-2,3-diacetoxy-6-[(4-phenylpiperazin-1-yl)methyl]-3,4-dihydro-2H-pyran-4-yl] acetate Example 45 was synthesized from example 45, step 1 and 1-phenylpiperazine following the reductive amidation procedure described in synthesis method D.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

Yield: 154 mg (0.356 mmol, 68.0%), yellow oil.

TLC: $R_f$=0.639 (ethylacetate/n-heptane, 2:1).

LC/MS (ES-API): m/z=433.20 $[M+H]^+$; calculated: 433.19; $t_R$ (λ=220 nm): 1.26 min (LC/MS—Method 1).

MPLC Gradient

| start % B | end % B | duration [min] |
| --- | --- | --- |
| 0.0 | 0.0 | 1.6 |
| 0.0 | 70.2 | 28.0 |

$^1$H-NMR (400 MHz, DMSO-$d_6$): δ=7.20 (t, J=8.0 Hz, 2H, ArH), 6.92 (d, J=8.0 Hz, 2H, ArH), 6.76 (d, J=7.2 Hz, 1H, ArH), 5.96 (dd, J=3.6 Hz, J=1.0 Hz 1H, CH), 5.12 (d, J=4.2 Hz, 1H, CH), 5.04 (m, 2H, 2×CH), 3.12 (m, 4H, 2×$NCH_2$), 3.02 (AB-system, q, J=14.3 Hz, 2H, $CH_2$), 2.50 (m, 4H, 2×$NCH_2$), 2.08 (s, 3H, $CH_3$), 2.07 (s, 3H, $CH_3$), 2.04 (s, 3H, $CH_3$) ppm.

$^{13}$C-NMR (150 MHz, DMSO-$d_6$): δ=169.83 (s, C), 168.62 (s, C), 168.40 (s, C), 151.31 (s, 2×C), 129.16 (s, CH), 118.98 (s, CH), 115.23 (s, CH), 97.54 (s, CH), 93.66 (s, C), 88.92 (s, CH), 66.82 (s, CH), 64.19 (s, CH), 52.04 (s, 2×CH), 47.96 (s, 2×CH), 21.13 (s, $CH_3$), 20.85 (s, $CH_3$), 20.74 (s, $CH_3$) ppm.

Example 46

[(2S,3R,4S)-2,3-Diacetoxy-6-[[4-[(E)-cinnamyl]piperazin-1-yl]methyl]-3,4-dihydro-2H-pyran-4-yl] acetate

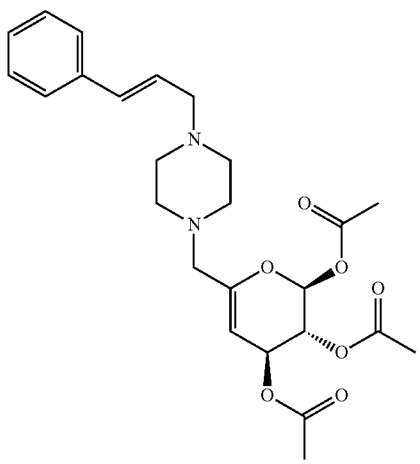 [SMILES: CC(=O)O[C@@H]1OC(CN2CCN(C/C=C/c3ccccc3)CC2)=C[C@H](OC(C)=O)[C@H]1OC(C)=O]

Example 46 was synthesized from example 45, step 1 and trans-1-cinnamylpiperazine following the reductive amidation procedure described in synthesis method D.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

Yield: 194 mg (0.411 mmol, 78.3%), yellow oil.

TLC: $R_f$=0.136 (ethylacetate/n-heptane, 2:1).

LC/MS (ES-API): m/z=473.23 [M+H]$^+$; calculated: 473.22; $t_R$ ($\lambda$=220 nm): 1.32 min (LC/MS—Method 1).

MPLC Gradient

| start % B | end % B | duration [min] |
|---|---|---|
| 0.0 | 0.0 | 1.3 |
| 0.0 | 13.3 | 15.1 |

$^1$H-NMR (400 MHz, DMSO-d$_6$): δ=7.42 (d, J=7.3 Hz, 2H, ArH), 7.31 (t, J=7.3 Hz, 2H, ArH), 7.23 (t, J=7.3 Hz, 1H, ArH), 6.52 (d, J=15.9 Hz, 1H, CH), 6.27 (m, 1H, CH), 6.18 (dd, J=1.2 Hz, 1H, CH), 5.08 (d, J=4.1 Hz, 1H, CH), 5.03 (m, 2H, 2×CH), 3.33 (m, 6H, 3×NCH$_2$), 2.96 (q, J=14.2 Hz, 2H, CH$_2$), 2.41 (m, 4H, 2×NCH$_2$), 2.08 (s, 3H, CH$_3$), 2.07 (s, 3H, CH$_3$), 2.04 (s, 3H, CH$_3$) ppm.

Example 47

[(2S,3R,4S)-2,3-Diacetoxy-6-[[4-(1,3-benzodioxol-5-ylmethyl)piperazin-1-yl]methyl]-3,4-dihydro-2H-pyran-4-yl] acetate

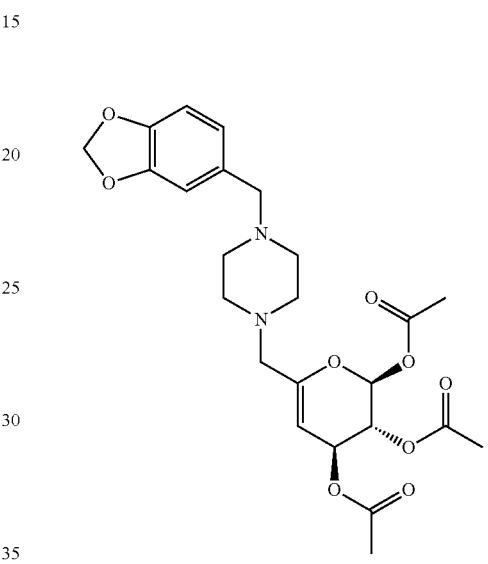

Example 47 was synthesized from example 45, step 1 and 1-(1,3-benzodioxol-5-ylmethyl)piperazine following the reductive amidation procedure described in synthesis method D.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

Yield: 249 mg (0.508 mmol, 96.9%), yellow oil.

TLC: $R_f$=0.242 (ethylacetate/n-heptane, 2:1).

LC/MS (ES-API): m/z=491.24 [M+H]$^+$; calculated: 491.19; $t_R$ ($\lambda$=220 nm): 1.19 min (LC/MS—Method 1).

MPLC Gradient

| start % B | end % B | duration [min] |
|---|---|---|
| 0.0 | 0.0 | 1.9 |
| 0.0 | 10.1 | 13.1 |

$^1$H-NMR (400 MHz, DMSO-d$_6$): δ=6.84 (m, 2H, ArH), 6.73 (dd, J=1.4 Hz, 1H, ArH), 6.28 (dd, J=1.0 Hz, 1H, CH), 5.97 (s, 2H, O—CH$_2$—O), 5.08 (d, J=4.2 Hz, 1H, CH), 5.04 (m, 2H, 2×CH), 3.31 (m, 4H, 2×NCH$_2$), 2.94 (q, J=14.4 Hz, 2H, CH$_2$), 2.38 (m, 4H, 2×NCH$_2$), 2.08 (s, 3H, CH$_3$), 2.07 (s, 3H, CH$_3$), 2.03 (s, 3H, CH$_3$) ppm.

Example 48

[(2S,3R,4S)-2,3-Diacetoxy-6-[[4-(4-chlorophenyl)piperazin-1-yl]methyl]-3,4-dihydro-2H-pyran-4-yl] acetate

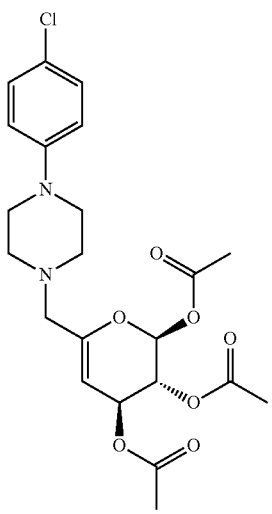 [SMILES: CC(=O)O[C@@H]1OC(CN2CCN(c3ccc(Cl)cc3)CC2)=C[C@H](OC(C)=O)[C@H]1OC(C)=O]

Example 48 was synthesized from example 45, step 1 and 1-(4-chlorophenyl)piperazine following the reductive amidation procedure described in synthesis method D.

Purification: MPLC CombiFlash Rf (Teledyne ISCO); column: RediSep Silica 12 g; flow rate: 30 mL/min; wavelength for detection: 220 nm; eluent: (A) dichloromethane, (B) ethanol.

Yield: 131 mg (0.281 mmol, 53.5%), yellow oil.

TLC: $R_f$=0.636 (ethylacetate/n-heptane, 2:1).

LC/MS (ES-API): m/z=467.16 [M+H]$^+$; calculated: 467.91; $t_R$ ($\lambda$=220 nm): 1.40 min (LC/MS—Method 1).

MPLC Gradient

| start % B | end % B | duration [min] |
|---|---|---|
| 0.0 | 0.0 | 2.0 |
| 0.0 | 10.1 | 23.0 |

$^1$H-NMR (400 MHz, DMSO-d$_6$): δ=7.21 (d, J=9.1 Hz, 2H, ArH), 6.93 (d, J=9.1 Hz, 2H, ArH), 6.20 (dd, J=1.1 Hz, 1H, CH), 5.12 (d, J=4.4 Hz, 1H, CH), 5.04 (m, 2H, 2×CH), 3.12 (m, 4H, 2×NCH$_2$), 3.02 (q, J=14.1 Hz, 2H, CH$_2$), 2.51 (m, 4H, 2×NCH$_2$), 2.07 (s, 3H, CH$_3$), 2.06 (s, 3H, CH$_3$), 2.04 (s, 3H, CH$_3$) ppm.

Example 49

[(2S,3R,4S)-2,3-Diacetoxy-6-[[4-(2-chlorophenyl)piperazin-1-yl]methyl]-3,4-dihydro-2H-pyran-4-yl] acetate

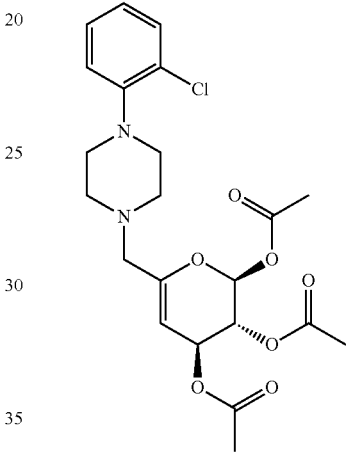

Example 49 was synthesized from example 45, step 1 and 1-(2-chlorophenyl)piperazine following the reductive amidation procedure described in synthesis method D.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

Yield: 144 mg (0.308 mmol, 58.9%), yellow oil.

TLC: $R_f$=0.621 (ethylacetate/n-heptane, 2:1).

LC/MS (ES-API): m/z=467.16 [M+H]$^+$; calculated: 467.91; $t_R$ ($\lambda$=220 nm): 1.38 min (LC/MS—Method 1).

MPLC Gradient

| start % B | end % B | duration [min] |
|---|---|---|
| 0.0 | 0.0 | 1.6 |
| 0.0 | 70.2 | 23.0 |

$^1$H-NMR (400 MHz, DMSO-d$_6$): δ=7.39 (d, J=7.9 Hz, 1H, ArH), 7.28 (t, J=7.7 Hz, 1H, ArH), 7.17 (d, J=8.1 Hz, 1H, ArH), 7.03 (t, J=7.6 Hz, 1H, ArH), 6.21 (dd, J=1.2 Hz, 1H, CH), 5.13 (d, J=4.1 Hz, 1H, CH), 5.04 (m, 2H, 2×CH), 3.07 (q, J=14.4 Hz, 2H, CH$_2$), 2.98 (m, 4H, 2×NCH$_2$), 2.59 (m, 4H, 2×NCH$_2$), 2.08 (s, 3H, CH$_3$), 2.07 (s, 3H, CH$_3$), 2.03 (s, 3H, CH$_3$) ppm.

Example 50

[(2S,3R,4S)-2,3-Diacetoxy-6-[[4-(4-methoxyphenyl)piperazin-1-yl]methyl]-3,4-dihydro-2H-pyran-4-yl] acetate

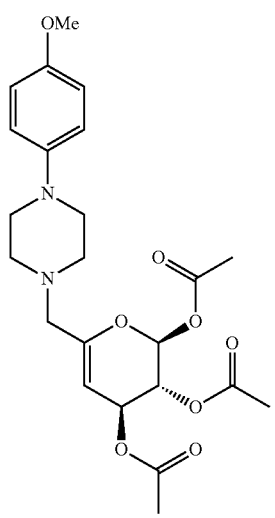 [SMILES: COc1ccc(N2CCN(CC3=C[C@H](OC(C)=O)[C@@H](OC(C)=O)[C@H](OC(C)=O)O3)CC2)cc1]

Example 50 was synthesized from example 45, step 1 and 1-(4-methoxyphenyl)piperazine following the reductive amidation procedure described in synthesis method D.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

Yield: 151 mg (0.326 mmol, 62.3%), yellow oil.

TLC: $R_f$=0.530 (ethylacetate/n-heptane, 2:1).

LC/MS (ES-API): m/z=463.19 [M+H]$^+$; calculated: 463.20; $t_R$ ($\lambda$=220 nm): 1.25 min (LC/MS—Method 1).

MPLC Gradient

| start % B | end % B | duration [min] |
|---|---|---|
| 0.0 | 0.0 | 1.3 |
| 0.0 | 100.0 | 13.7 |
| 100.0 | 100.0 | 3.6 |

$^1$H-NMR (400 MHz, DMSO-d$_6$): δ=6.88 (d, J=9.1 Hz, 2H, ArH), 6.80 (d, J=9.1 Hz, 2H, ArH), 6.20 (dd, J=1.0 Hz, 1H, CH), 5.12 (d, J=4.1 Hz, 1H, CH), 5.04 (m, 2H, 2×CH), 3.69 (s, 3H, OCH$_3$), 3.00 (m, 6H, CH$_2$+NCH$_2$), 2.52 (m, 4H, NCH$_2$), 2.08 (s, 3H, CH$_3$), 2.07 (s, 3H, CH$_3$), 2.04 (s, 3H, CH$_3$) ppm.

Example 51

[(2S,3R,4S)-2,3-Diacetoxy-6-[[4-(3-methoxyphenyl)piperazin-1-yl]methyl]-3,4-dihydro-2H-pyran-4-yl] acetate

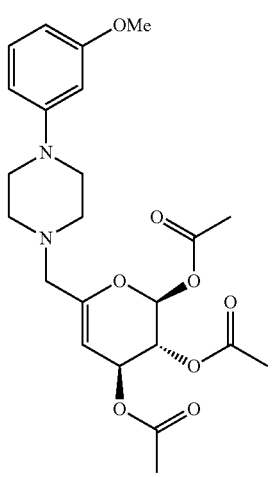 [SMILES: COc1cccc(N2CCN(CC3=C[C@H](OC(C)=O)[C@@H](OC(C)=O)[C@H](OC(C)=O)O3)CC2)c1]

Example 51 was synthesized from example 45, step 1 and 1-(3-methoxyphenyl)piperazine following the reductive amidation procedure described in synthesis method D.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

Yield: 135 mg (0.292 mmol, 55.7%), yellow oil.

TLC: $R_f$=0.591 (ethylacetate/n-heptane, 2:1).

LC/MS (ES-API): m/z=463.24 [M+H]$^+$; calculated: 463.20; $t_R$ ($\lambda$=220 nm): 1.28 min (LC/MS—Method 1).

MPLC Gradient

| start % B | end % B | duration [min] |
|---|---|---|
| 0.0 | 0.0 | 1.3 |
| 0.0 | 100.0 | 13.7 |
| 100.0 | 100.0 | 3.6 |

$^1$H-NMR (400 MHz, DMSO-d$_6$): δ=7.09 (t, J=8.2 Hz, 1H, ArH), 6.51 (d, J=8.2 Hz, 1H, ArH), 6.43 (s, 1H, ArH), 6.35 (dd, J=1.1 Hz, 1H, CH), 5.12 (d, J=4.3 Hz, 1H, CH), 5.04 (m, 1H, CH), 3.71 (s, 3H, OCH$_3$), 3.11 (m, 4H, 2×NCH$_2$), 3.01 (q, J=14.3 Hz, 2H, CH$_2$), 2.52 (m, 4H, 2×NCH$_2$), 2.08 (s, 3H, CH$_3$), 2.07 (s, 3H, CH$_3$), 2.04 (s, 3H, CH$_3$) ppm.

Example 52

[(2S,3R,4S)-2,3-Diacetoxy-6-[[4-(2-methoxyphenyl)piperazin-1-yl]methyl]-3,4-dihydro-2H-pyran-4-yl] acetate

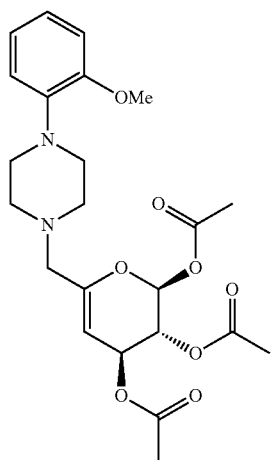 [SMILES: COc1ccccc1N1CCN(CC2=C[C@H](OC(C)=O)[C@@H](OC(C)=O)[C@H](OC(C)=O)O2)CC1]

Example 52 was synthesized from example 45, step 1 and 1-(2-methoxyphenyl)piperazine following the reductive amidation procedure described in synthesis method D.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

Yield: 167 mg (0.361 mmol, 68.9%), yellow oil.

TLC: $R_f$=0.533 (ethylacetate/n-heptane, 2:1).

LC/MS (ES-API): m/z=463.24 [M+H]$^+$; calculated: 463.20; $t_R$ ($\lambda$=220 nm): 1.26 min (LC/MS—Method 1).

MPLC Gradient

| start % B | end % B | duration [min] |
|---|---|---|
| 0.0 | 0.0 | 1.3 |
| 0.0 | 100.0 | 13.7 |
| 100.0 | 100.0 | 3.6 |

$^1$H-NMR (400 MHz, DMSO-d$_6$): δ=6.90 (m, 4H, ArH), 6.21 (dd, J=1.0 Hz, 1H, CH), 5.12 (d, J=4.4 Hz, 1H, CH), 5.03 (m, 1H, CH), 3.68 (s, 3H, OCH$_3$), 3.04 (q, J=14.3 Hz, 2H, CH$_2$), 2.96 (m, 4H, 2×NCH$_2$), 2.54 (m, 4H, 2×NCH$_2$), 2.10 (s, 3H, CH$_3$), 2.09 (s, 3H, CH$_3$), 2.05 (s, 3H, CH$_3$) ppm.

Example 53

[(2S,3R,4S)-2,3-Diacetoxy-6-[[4-(4-bromophenyl)piperazin-1-yl]methyl]-3,4-dihydro-2H-pyran-4-yl] acetate

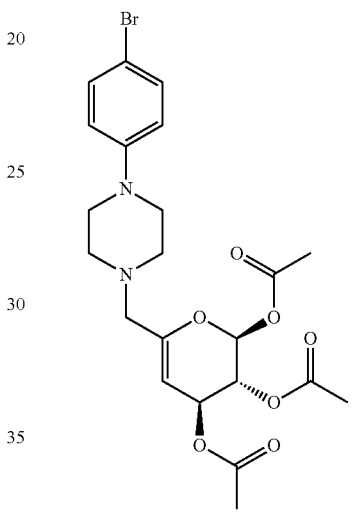

Example 53 was synthesized from example 45, step 1 and 1-(4-bromophenyl)piperazine following the reductive amidation procedure described in synthesis method D.

Purification: MPLC CombiFlash Rf (Teledyne ISCO); column: RediSep Silica 12 g; flow rate: 30 mL/min; wavelength for detection: 254 nm; eluent: (A) n-heptane, (B) ethylacetate.

Yield: 248 mg (0.485 mmol, 92.5%), yellow oil.

TLC: $R_f$=0.644 (ethylacetate/n-heptane, 2:1).

LC/MS (ES-API): m/z=511.14 [M+H]$^+$; calculated: 511.10; $t_R$ ($\lambda$=220 nm): 1.42 min (LC/MS—Method 1).

MPLC Gradient

| start % B | end % B | duration [min] |
|---|---|---|
| 0.0 | 0.0 | 1.3 |
| 0.0 | 100.0 | 13.7 |
| 100.0 | 100.0 | 3.6 |

$^1$H-NMR (400 MHz, DMSO-d$_6$): δ=7.33 (d, J=9.0 Hz, 2H, ArH), 6.88 (d, J=9.0 Hz, 2H, ArH), 6.20 (dd, J=1.2 Hz, 1H, CH), 5.12 (d, J=4.3 Hz, 1H, CH), 5.04 (m, 2H, 2×CH), 3.12 (m, 4H, 2×NCH$_2$), 3.03 (q, J=14.2 Hz, 2H, CH$_2$), 2.52 (m, 4H, 2×NCH$_2$), 2.09 (s, 3H, CH$_3$), 2.08 (s, 3H, CH$_3$), 2.05 (s, 3H, CH$_3$) ppm.

Example 54

5-(Dimethylamino)-N-[[1-[(3R,4R,5S,6R)-2,4,5-trihydroxy-6-(hydroxymethyl)tetrahydropyran-3-yl]triazol-4-yl]methyl]naphthalene-1-sulfonamide

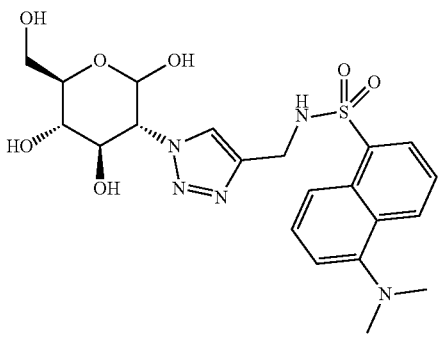 [SMILES: CN(C)c1cccc2c(S(=O)(=O)NCc3cn([C@H]4C(O)O[C@H](CO)[C@@H](O)[C@@H]4O)nn3)cccc12]

Step 1: 5-(dimethylamino)-N-prop-2-ynyl-naphthalene-1-sulfonamide

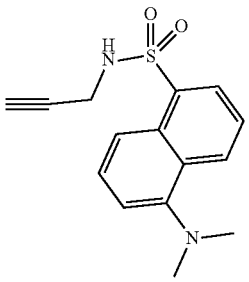 [SMILES: C#CCNS(=O)(=O)c1cccc2c(N(C)C)cccc12]

To a solution of 405 mg (1.5 mmol) dansylchloride in 4 mL dimethylformamide were added 91 mg (1.65 mmol) propargylamine and 530 µl (3 mmol, 2 eq.) N,N-diisopropylethylamine. The reaction mixture was stirred at 100° C. in the microwave for 45 minutes. The reaction mixture was filtered and evaporated.

Purification: MPLC CombiFlash Rf (Teledyne ISCO); column: RediSep Silica 24 g Gold; flow rate: 40 mL/min; wavelength for detection: 254 nm; eluent: (A) dichloromethane, (B) ethanol.
MPLC Gradient

| start % B | end % B | duration [min] |
|---|---|---|
| 0.0 | 0.0 | 2.0 |
| 0.0 | 50.0 | 33.0 |

Yield: 92 mg (0.319 mmol, 21.5%), yellow oil.
TLC: $R_f$=0.510 (dichloromethane/ethanol, 19:1).
LC/MS (ES-API): m/z=289.13 [M+H]$^+$; calculated: 289.09; $t_R$ (λ=220 nm): 1.62 min (LC/MS—Method 1).
$^1$H-NMR (400 MHz, DMSO-d$_6$): δ=8.48 (d, J=8.6 Hz, 1H, ArH), 8.40 (s, 1H, SO$_2$NH), 8.25 (d, J=8.6 Hz, 1H, ArH), 8.13 (dd, J=1.1 Hz, 1H, ArH), 7.60 (m, 2H, ArH), 7.26 (d, J=7.4 Hz, 1H, ArH), 3.71 (s, 2H, NCH$_2$), 2.91 (s, 1H, CH), 2.84 (s, 6H, 2×NCH$_3$) ppm.

Method E
Copper-Catalyzed A$_2$ ide-Alkyne-Cycloaddition (CuAAC) with A$_2$ idodeoxyglucose To a solution of 146 µmol azidodeoxyglucose (1-azido-1-deoxyglucose, 2-azido-2-deoxyglucose, or 6-azido-6-deoxyglucose) in 0.5 mL water 1.1 eq. alkyne were added. If needed dimethylformamide was added until the reaction mixture was a clear solution. A mixture of 0.1 eq. CuSO$_4$*5 H$_2$O (0.1 M in water), 0.25 eq. sodium ascorbate (1 M in water), and 0.4 eq. THPTA (0.5 M in water) was added. The reaction mixture was stirred at room temperature for 2-6 hours. The reaction was controlled by TLC and LC/MS. The reaction mixture was evaporated and purified by HPLC. Alpha/beta isomers were not separated, NMR data belong to only one isomer.

Purification: Agilent 1200 preparative HPLC; column: Agilent Prep-C$_{18}$ column (10 µm, 21.5×150 mm); flow rate: 40 mL/min; wavelength for detection: 220 nm; 254 nm; 324 nm; eluent: (A) water, (B) acetonitrile.
HPLC-Gradient

| start % B | end % B | duration [min] |
|---|---|---|
| 3.0 | 3.0 | 5.0 |
| 3.0 | 90.0 | 7.5 |
| 90.0 | 90.0 | 2.5 |
| 90.0 | 10.0 | 0.5 |
| 10.0 | 10.0 | 2.0 |

Step 2: 5-(dimethylamino)-N-[[1-[(3R,4R,5S,6R)-2,4,5-trihydroxy-6-(hydroxymethyl)-tetrahydropyran-3-yl]triazol-4-yl]methyl]naphthalene-1-sulfonamide Example 54 was synthesized from 2-azido-2-deoxyglucose and example 45, step 1 following the CuAAC procedure described in synthesis method E.

Yield: 33 mg (67 µmol, 46.7%), yellow oil.
TLC: $R_f$=0.032 (dichloromethane/ethanol, 4:1).
LC/MS (ES-API): m/z=494.19 [M+H]$^+$; calculated: 494.16; $t_R$1 (λ=220 nm): 1.17 min; $t_R$2 (λ=220 nm): 1.20 min (LC/MS—Method 1).
$^1$H-NMR (400 MHz, DMSO-d$_6$): δ=8.47 (d, J=8.6 Hz, 2H, ArH), 8.40 (s, 1H, SNH), 8.13 (d, J=7.3 Hz, 1H, ArH), 7.84 (s, 1H, NCH), 7.61 (m, 2H, ArH), 7.27 (d, J=7.4 Hz, 1H, ArH), 6.95 (d, J=6.4 Hz, 1H, OH), 5.17 (d, J=6.2 Hz, 1H, OH), 5.09 (d, J=6.2 Hz, 1H, OH), 4.89 (dd, J=6.4 Hz, 1H, CH), 4.61 (dd, J=6.4 Hz, 1H, OH), 4.07 (s, 2H, NCH$_2$), 4.01 (m, 1H, CH), 3.85 (m, 1H, CH), 3.74 (m, 1H, CH), 3.53 (m, 2H, CH$_2$), 3.22 (m, 1H, CH$_2$), 2.84 (s, 6H, 2×NCH$_3$) ppm.

Example 55

(3R,4R,5S,6R)-6-(Hydroxymethyl)-3-(4-phenyltriazol-1-yl)tetrahydropyran-2,4,5-triol

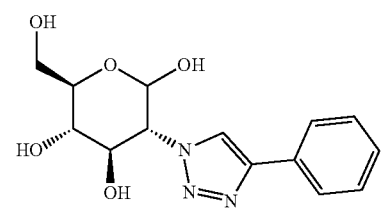 [SMILES: OC[C@H]1OC(O)[C@H](n2cc(-c3ccccc3)nn2)[C@@H](O)[C@@H]1O]

Example 55 was synthesized from 2-azido-2-deoxyglucose and ethynylbenzene following the CuAAC procedure described in synthesis method E.

Yield: 15 mg (49 μmol, 33.4%), white solid.

TLC: $R_f$=0.333 (dichloromethane/ethanol, 4:1).

LC/MS (ES-API): m/z=308.10 [M+H]$^+$; calculated: 308.12; $t_R$1 (λ=220 nm): 0.81 min; $t_R$2 (λ=220 nm): 0.85 min (LC/MS—Method 1).

$^1$H-NMR (400 MHz, DMSO-d$_6$): δ=8.61 (s, 1H, NCH), 7.86 (dd, J=1.3 Hz, 2H, ArH), 7.45 (m, 2H, ArH), 7.40 (m, 1H, ArH), 7.10 (d, J=6.2 Hz, 1H, OH), 5.48 (d, J=6.2 Hz, 1H, OH), 5.25 (d, J=6.6 Hz, 1H, OH), 5.25 (t, J=4.2 Hz, 1H, CH), 4.65 (t, J=6.1 Hz, 1H, OH), 4.65 (dd, J=10.8 Hz, J=3.1 Hz, 1H, CH), 4.08 (m, 1H, CH), 3.96 (m, 1H, OH), 3.76 (m, 1H, CH$_2$), 3.52 (m, 1H, CH$_2$), 3.36 (m, 1H, CH), 3.29 (m, 1H, CH) ppm.

$^{13}$C-NMR (150 MHz, DMSO-d$_6$): δ=145.70 (s, C), 131.00 (s, C), 128.90 (s, CH), 127.64 (s, CH), 125.05 (s, CH), 120.64 (s, CH), 90.80 (s, CH), 72.42 (s, CH), 70.93 (s, CH), 69.72 (s, CH), 65.24 (s, CH), 60.86 (s, CH$_2$) ppm.

Example 56

(3R,4R,5S,6R)-6-(Hydroxymethyl)-3-[4-(p-tolyl)triazol-1-yl]tetrahydropyran-2,4,5-triol

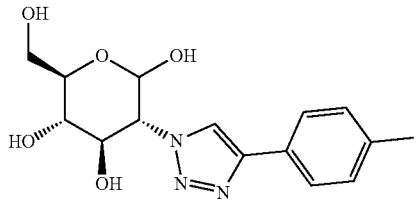 [SMILES: Cc1ccc(-c2cn([C@H]3C(O)O[C@H](CO)[C@@H](O)[C@@H]3O)nn2)cc1]

Example 56 was synthesized from 2-azido-2-deoxyglucose and 1-ethynyl-4-methylbenzene following the CuAAC procedure described in synthesis method E.

Yield: 34 mg (106 μmol, 72.4%), white solid.

TLC: $R_f$=0.349 (dichloromethane/ethanol, 4:1).

LC/MS (ES-API): m/z=322.19 [M+H]$^+$; calculated: 322.13; $t_R$1 (λ=220 nm): 1.07 min; $t_R$2 (λ=220 nm): 1.11 min (LC/MS—Method 1).

$^1$H-NMR (400 MHz, DMSO-d$_6$): δ=8.47 (s, 1H, NCH), 7.76 (d, J=8.1 Hz, 2H, ArH), 7.24 (d, J=8.1 Hz, 2H, ArH), 6.93 (d, J=4.4 Hz, 1H, OH), 5.29 (d, J=5.4 Hz, 1H, OH), 5.20 (d, J=5.4 Hz, 1H, OH), 5.00 (dd, J=8.0 Hz, 1H, CH), 4.56 (dd, J=3.2 Hz, 1H, OH), δ=4.09 (m, 1H, CH), 3.96 (m, 1H, CH), 3.76 (m, 1H, CH$_2$), 3.53 (m, 1H, CH$_2$), 3.36 (m, 1H, CH), 3.28 (m, 1H, CH), 2.35 (s, 3H, CH$_3$) ppm.

Example 57

(3R,4R,5S,6R)-6-(Hydroxymethyl)-3-[4-(3-phenylpropyl)triazol-1-yl]tetrahydropyran-2,4,5-triol

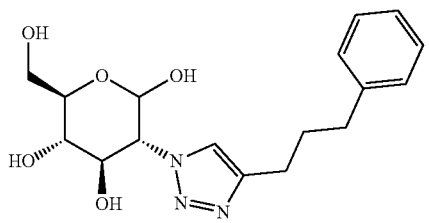 [SMILES: OC[C@H]1OC(O)[C@H](n2cc(CCCc3ccccc3)nn2)[C@@H](O)[C@@H]1O]

Example 57 was synthesized from 2-azido-2-deoxyglucose and pent-4-yn-1-ylbenzene following the CuAAC procedure described in synthesis method E.

Yield: 40 mg (114 μmol, 78.3%), white solid.

TLC: $R_f$=0.406 (dichloromethane/ethanol, 4:1).

LC/MS (ES-API): m/z=350.19 [M+H]$^+$; calculated: 350.16; $t_R$1 (λ=220 nm): 1.24 min; $t_R$2 (λ=220 nm): 1.26 min (LC/MS—Method 1).

$^1$H-NMR (400 MHz, DMSO-d$_6$): δ=8.78 (s, 1H, NCH), 7.75 (m, 5H, ArH), 6.81 (d, J=5.0 Hz, 1H, OH), 5.22 (d, J=5.7 Hz, 1H, OH), 5.12 (d, J=5.7 Hz, 1H, OH), 4.92 (dd, J=6.7 Hz, 1H, CH), 4.52 (dd, J=5.5 Hz, 1H, OH), 4.09 (m, 1H, CH), 3.95 (m, 1H, CH), 3.76 (m, 1H, CH$_2$), 3.53 (m, 1H, CH$_2$), 3.36 (m, 1H, CH), 3.28 (m, 1H, CH), 2.61 (m, 4H, CH$_2$), 1.90 (m, 2H, CH$_2$) ppm.

Example 58

Methyl 4-[1-[(3R,4R,5S,6R)-2,4,5-trihydroxy-6-(hydroxymethyl)tetrahydropyran-3-yl]triazol-4-yl]benzoate

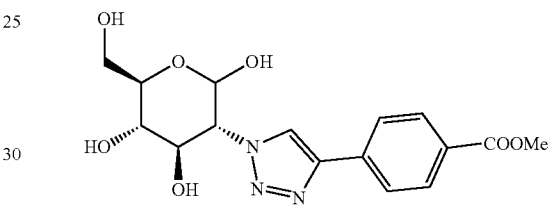

Example 58 was synthesized from 2-azido-2-deoxyglucose and 4-ethynylmethylbenzoate following the CuAAC procedure described in synthesis method E.

Yield: 31 mg (85 μmol, 58.0%), white solid.

TLC: $R_f$=0.429 (dichloromethane/ethanol, 4:1).

LC/MS (ES-API): m/z=366.12 [M+H]$^+$; calculated: 366.12; $t_R$1 (λ=220 nm): 0.97 min; $t_R$2 (λ=220 nm): 1.00 min (LC/MS—Method 1).

$^1$H-NMR (400 MHz, DMSO-d$_6$): δ=8.80 (s, 1H, NCH), 8.05 (d, J=8.2 Hz, 2H, ArH), 8.00 (d, J=8.2 Hz, 2H, ArH), 7.09 (d, J=6.4 Hz, 1H, OH), 5.49 (d, J=6.3 Hz, 1H, OH), 5.25 (d, J=5.7 Hz, 1H, OH), 5.00 (dd, J=8.0 Hz, 1H, CH), 4.65 (dd, J=5.2 Hz, 1H, OH), 4.09 (m, 1H, CH), 3.95 (m, 1H, CH), 3.87 (s, 3H, OCH$_3$), 3.76 (m, 1H, CH$_2$), 3.53 (m, 1H, CH$_2$), 3.36 (m, 1H, CH), 3.28 (m, 1H, CH) ppm.

Example 59

(3R,4R,5S,6R)-3-[4-[[Benzyl(methyl)amino]methyl]triazol-1-yl]-6-(hydroxymethyl)tetrahydropyran-2,4,5-triol

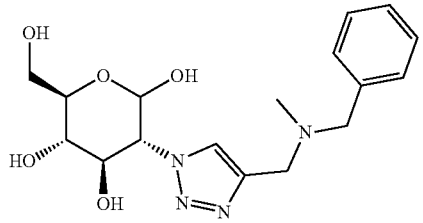 [SMILES: CN(Cc1ccccc1)Cc1cn([C@H]2C(O)O[C@H](CO)[C@@H](O)[C@@H]2O)nn1]

Example 59 was synthesized from 2-azido-2-deoxyglucose and N-benzyl-N-methylprop-2-yn-1-amine following the CuAAC procedure described in synthesis method E.

Yield: 32 mg (88 µmol, 60.1%), white solid.

TLC: R$_f$=0.064 (dichloromethane/ethanol, 4:1).

LC/MS (ES-API): m/z=365.20 [M+H]$^+$; calculated: 365.17; t$_R$ (ELSD): 0.34 min (LC/MS—Method 1).

$^1$H-NMR (400 MHz, DMSO-d$_6$): δ=8.00 (s, 1H, NCH), 7.71 (m, 5H, ArH), 6.82 (d, J=6.0 Hz, 1H, OH), 5.25 (d, J=5.8 Hz, 1H, OH), 5.14 (d, J=5.8 Hz, 1H, OH), 4.93 (dd, J=5.7 Hz, 1H, CH), 4.49 (dd, J=5.2 Hz, 1H, OH), 4.08 (m, 1H, CH), 3.95 (m, 1H, CH), 3.76 (m, 2H, CH$_2$), 3.62 (s, 3H, NCH$_3$), 3.36 (m, 1H, CH), 3.28 (m, 1H, CH), 2.13 (m, 4H, 2×NCH$_2$) ppm.

Example 60

(3R,4R,5S,6R)-6-(Hydroxymethyl)-3-[4-(6-methoxy-2-naphthyl)triazol-1-yl]tetrahydropyran-2,4,5-triol

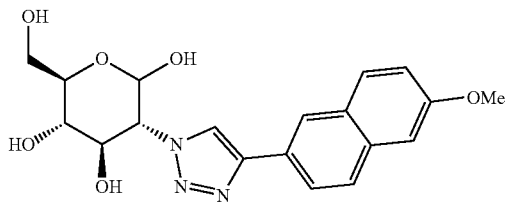 [SMILES: COc1ccc2cc(-c3cn([C@H]4C(O)O[C@H](CO)[C@@H](O)[C@@H]4O)nn3)ccc2c1]

Example 60 was synthesized from 2-azido-2-deoxyglucose and 2-ethynyl-6-methoxynaphthalene following the CuAAC procedure described in synthesis method E.

Yield: 28 mg (72 µmol, 49.4%), white solid.

TLC: R$_f$=0.461 (dichloromethane/ethanol, 4:1).

LC/MS (ES-API): m/z=388.16 [M+H]$^+$; calculated: 388.14; t$_R$1 (λ=220 nm): 1.27 min; t$_R$2 (λ=220 nm): 1.29 min (LC/MS—Method 1).

$^1$H-NMR (400 MHz, DMSO-d$_6$): δ=8.64 (s, 1H, NCH), 7.88 (m, 4H, ArH), 7.34 (s, 1H, ArH), 7.07 (d, J=6.5 Hz, 1H, OH), 5.47 (d, J=6.4 Hz, 1H, OH), 5.23 (d, J=6.4 Hz, 1H, OH), 5.00 (dd, J=6.6 Hz, 1H, CH), 4.49 (dd, J=5.2 Hz, 1H, OH), 4.11 (m, 1H, CH), 3.98 (m, 1H, CH), 3.89 (s, 3H, OCH$_3$), 3.77 (m, 1H, CH$_2$), 3.53 (m, 1H, CH$_2$), 3.46 (m, 1H, CH), 3.38 (m, 1H, CH) ppm.

Example 61

(3R,4R,5S,6R)-3-[4-[4-Chloro-6-methyl-2-(p-tolyl)pyrimidin-5-yl]triazol-1-yl]-6-(hydroxymethyl)tetrahydropyran-2,4,5-triol

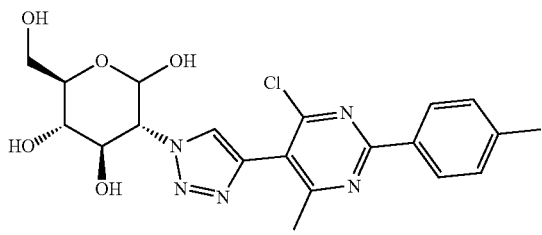 [SMILES: Cc1ccc(-c2nc(C)c(-c3cn([C@H]4C(O)O[C@H](CO)[C@@H](O)[C@@H]4O)nn3)c(Cl)n2)cc1]

Example 61 was synthesized from 2-azido-2-deoxyglucose and 4-chloro-5-ethynyl-6-methyl-2-(p-tolyl)pyrimidine following the CuAAC procedure described in synthesis method E.

Yield: 51 mg (110 µmol, 75.5%), white solid.

TLC: R$_f$=0.556 (dichloromethane/ethanol, 4:1).

LC/MS (ES-API): m/z=462.22 [M+H]$^+$; calculated: 462.15; t$_R$1 (λ=220 nm): 1.51 min; t$_R$2 (λ=220 nm): 1.52 min (LC/MS—Method 1).

$^1$H-NMR (400 MHz, DMSO-d$_6$): δ=8.19 (d, J=8.2 Hz, 2H, ArH), 7.89 (s, 1H, NCH), 7.71 (d, J=8.2 Hz, 2H, ArH), 6.93 (d, J=6.6 Hz, 1H, OH), 5.21 (d, J=6.1 Hz, 1H, OH), 5.14 (d, J=6.1 Hz, 1H, OH), 4.91 (dd, J=6.7 Hz, 1H, CH), 4.50 (dd, J=5.5 Hz, 1H, OH), 4.21 (s, 3H, CH$_3$), 4.05 (m, 1H, CH), 3.97 (m, 1H, CH), 3.85 (m, 2H, CH$_2$), 3.71 (m, 1H, CH), 3.50 (m, 1H, CH), 2.62 (s, 3H, CH$_3$) ppm.

Example 62

Ethyl-2-diethoxyphosphoryl-3-[1-[(3R,4R,5S,6R)-2,4,5-trihydroxy-6-(hydroxymethyl)-tetrahydropyran-3-yl]triazol-4-yl]propanoate

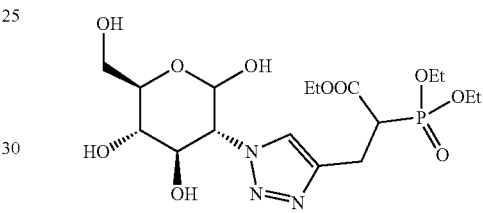

Example 62 was synthesized from 2-azido-2-deoxyglucose and ethyl 2-diethoxyphosphorylpent-4-ynoate following the CuAAC procedure described in synthesis method E.

Yield: 30 mg (64 µmol, 43.9%), white solid.

TLC: R$_f$=0.389 (dichloromethane/ethanol, 4:1).

LC/MS (ES-API): m/z=468.17 [M+H]$^+$; calculated: 468.17; t$_R$1 (λ=220 nm): 0.99 min; t$_R$2 (λ=220 nm): 1.01 min (LC/MS—Method 1).

$^1$H-NMR (400 MHz, DMSO-d$_6$): δ=7.89 (s, 1H, NCH), 6.90 (d, J=6.6 Hz, 1H, OH), 5.17 (d, J=6.0 Hz, 1H, OH), 5.10 (d, J=6.0 Hz, 1H, OH), 4.86 (dd, J=6.5 Hz, 1H, CH), 4.61 (dd, J=5.5 Hz, 1H, OH), 4.01 (m, 1H, CH), 3.88 (m, 1H, CH), 3.61 (m, 1H, CH), 3.50 (m, 1H, CH$_2$), 3.22 (m, 1H, CH$_2$), 3.01 (m, 1H, CH), 1.29 (m, 9H, CH$_3$), 1.14 (m, 6H, CH$_2$) ppm.

Example 63

(3R,4R,5S,6R)-6-(Hydroxymethyl)-3-[4-[[(4-nitro-2,1,3-benzoxadiazol-7-yl)amino]methyl]triazol-1-yl]tetrahydropyran-2,4,5-triol

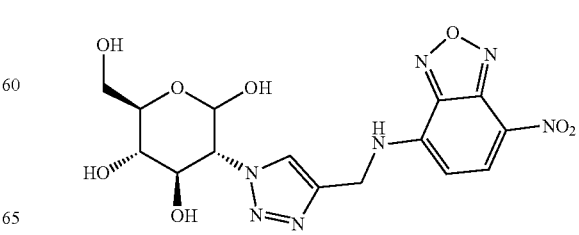

Step 1: 4-nitro-N-prop-2-ynyl-2,1,3-benzoxadiazol-7-amine

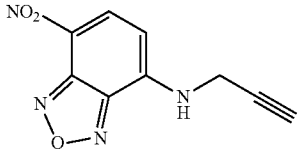 [SMILES: C#CCNc1ccc([N+](=O)[O-])c2nonc12]

To a solution of 450 mg (2.23 mmol) 4-chloro-7-nitro-2,1,3-benzoxadiazole in 4 mL dry dimethylformamide were added 135 mg (2.46 mmol) propargylamine and 395 µl (2.23 mmol) N,N-diisopropylethylamine. The reaction mixture was stirred at 100° C. in the microwave for 45 minutes and evaporated.

Purification: MPLC CombiFlash Rf (Teledyne ISCO); column: RediSep Silica 40 g; flow rate: 40 mL/min; wavelength for detection: 254 nm; eluent: (A) n-heptane, (B) ethylacetate.

MPLC Gradient

| start % B | end % B | duration [min] |
|---|---|---|
| 0.0 | 0.0 | 1.6 |
| 0.0 | 27.7 | 16.6 |
| 27.7 | 79.8 | 19.9 |
| 79.8 | 0.0 | 0.0 |
| 0.0 | 0.0 | 2.9 |

Yield: 98 mg (0.449 mmol, 20.1%), orange solid.

TLC: $R_f$=0.664 (dichloromethane/ethanol, 19:1).

LC/MS (ES-API): m/z=219.01 [M+H]$^+$; calculated: 219.04; $t_R$ (λ=220 nm): 1.32 min (LC/MS—Method 1).

$^1$H-NMR (400 MHz, DMSO-d$_6$): δ=9.62 (s, 1H, NH), 8.62 (d, J=8.7 Hz, 1H, ArH), 6.48 (d, J=8.7 Hz, 1H, ArH), 4.34 (s, 2H, NCH$_2$), 3.37 (s, 1H, CH) ppm.

Step 2: (3R,4R,5S,6R)-6-(hydroxymethyl)-3-[4-[[(4-nitro-2,1,3-benzoxadiazol-7-yl)amino]methyl]triazol-1-yl]tetrahydropyran-2,4,5-triol Example 63 was synthesized from 2-azido-2-deoxyglucose and example 63, step 1 following the CuAAC procedure described in synthesis method E.

Yield: 43 mg (101 µmol, 69.5%), orange solid.

TLC: $R_f$=0.294 (dichloromethane/ethanol, 4:1).

LC/MS (ES-API): m/z=424.10 [M+H]$^+$; calculated: 424.16; $t_R$1 (λ=220 nm): 0.77 min; $t_R$2 (λ=220 nm): 0.81 min (LC/MS—Method 1).

$^1$H-NMR (400 MHz, DMSO-d$_6$): δ=9.83 (s, 1H, NH) 8.62 (d, J=8.7 Hz, 1H, ArH), 8.04 (s, 1H, NCH), 6.93 (d, J=6.4 Hz, 1H, OH), 6.51 (d, J=8.7 Hz, 1H, ArH), 5.21 (d, J=6.2 Hz, 1H, OH), 5.14 (d, J=6.2 Hz, 1H, OH), 4.92 (dd, J=6.4 Hz, 1H, CH), 4.67 (s, 2H, NCH$_2$), 4.61 (dd, J=6.4 Hz, 1H, OH), 4.06 (m, 1H, CH), 3.90 (m, 1H, CH), 3.64 (m, 1H, CH), 3.52 (m, 2H, CH$_2$), 3.22 (m, 1H, CH$_2$), 3.01 (m, 1H, CH) ppm.

Example 64

(3R,4R,5S,6R)-3-[4-(Cyclohexylmethyl)triazol-1-yl]-6-(hydroxymethyl)tetrahydropyran-2,4,5-triol

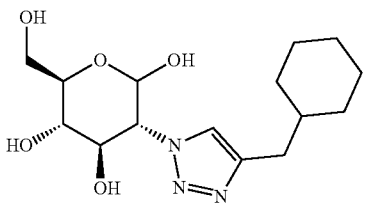 [SMILES: OC[C@H]1OC(O)[C@H](n2cc(CC3CCCCC3)nn2)[C@@H](O)[C@@H]1O]

Example 64 was synthesized from 2-azido-2-deoxyglucose and prop-2-yn-1-ylcyclohexane following the CuAAC procedure described in synthesis method E.

Yield: 23 mg (70 µmol, 48.0%), white solid.

TLC: $R_f$=0.437 (dichloromethane/ethanol, 4:1).

LC/MS (ES-API): m/z=328.24 [M+H]$^+$; calculated: 328.18; $t_R$1 (λ=220 nm): 1.23 min; $t_R$2 (λ=220 nm): 1.26 min (LC/MS—Method 1).

$^1$H-NMR (400 MHz, DMSO-d$_6$): δ=7.67 (s, 1H, NCH), 6.78 (d, J=6.5 Hz, 1H, OH), 5.19 (d, J=6.3 Hz, 1H, OH), 5.14 (d, J=5.7 Hz, 1H, OH), 4.90 (dd, J=8.0 Hz, 1H, CH), 4.52 (dd, J=6.2 Hz, 1H, OH), 4.41 (dd, J=4.2 Hz, 1H, OH), 4.07 (m, 1H, CH), 3.76 (m, 2H, CH$_2$), 3.56 (m, 2H, 2×CH), 3.20 (m, 1H, CH), 1.60 (m, 6H, CH$_2$), 1.55 (m, 1H, CH), 1.21 (m, 4H, CH$_2$), 0.93 (m, 2H, CH$_2$) ppm.

Example 65

(3R,4R,5S,6R)-6-(Hydroxymethyl)-3-(4-pentyltriazol-1-yl)tetrahydropyran-2,4,5-triol

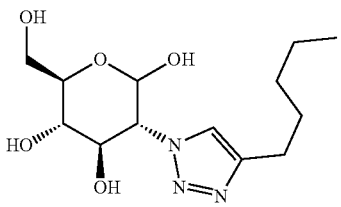 [SMILES: CCCCCc1cn([C@H]2C(O)O[C@H](CO)[C@@H](O)[C@@H]2O)nn1]

Example 65 was synthesized from 2-azido-2-deoxyglucose and hept-1-yne following the CuAAC procedure described in synthesis method E.

Yield: 19 mg (63 µmol, 43.1%), white solid.

TLC: $R_f$=0.405 (dichloromethane/ethanol, 4:1).

LC/MS (ES-API): m/z=302.22 [M+H]$^+$; calculated: 302.16; $t_R$1 (λ=220 nm): 1.08 min; $t_R$2 (λ=220 nm): 1.12 min (LC/MS—Method 1).

$^1$H-NMR (400 MHz, DMSO-d$_6$): δ=7.73 (s, 1H, NCH), 6.81 (d, J=4.5 Hz, 1H, OH), 5.21 (d, J=5.7 Hz, 1H, OH), 5.16 (d, J=5.6 Hz, 1H, OH), 4.91 (dd, J=6.7 Hz, 1H, CH), 4.52 (dd, J=5.9 Hz, 1H, OH), 4.39 (dd, J=3.2 Hz, 1H, OH), 4.04 (m, 1H, CH), 3.71 (m, 2H, CH$_2$), 3.52 (m, 2H, 2×CH), 3.20 (m, 1H, CH), 2.59 (m, 2H, CH$_2$), 1.59 (m, 2H, CH$_2$), 1.31 (m, 4H, CH$_2$), 0.93 (m, 3H, CH$_3$) ppm.

Example 66

(3R,4R,5S,6R)-3-[4-(3-Chloropropyl)triazol-1-yl]-6-(hydroxymethyl)tetrahydropyran-2,4,5-triol

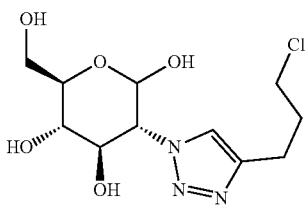

Example 66 was synthesized from 2-azido-2-deoxyglucose and 5-chloro-pent-1-yne following the CuAAC procedure described in synthesis method E.

Yield: 36 mg (117 µmol, 80.0%), white solid.
TLC: $R_f$=0.286 (dichloromethane/ethanol, 4:1).
LC/MS (ES-API): m/z=308.21 [M+H]$^+$; calculated: 308.09; $t_R$1 (λ=220 nm): 0.72 min; $t_R$2 (λ=220 nm): 0.74 min (LC/MS—Method 1).
$^1$H-NMR (400 MHz, DMSO-d$_6$): δ=7.75 (s, 1H, NCH), 6.32 (d, J=4.4 Hz, 1H, OH), 5.24 (d, J=5.6 Hz, 1H, OH), 4.91 (dd, J=4.1 Hz, 1H, CH), 4.79 (d, J=5.0 Hz, 1H, OH), 4.63 (dd, J=5.9 Hz, 1H, OH), 4.32 (dd, J=8.2 Hz, 1H, OH), 3.92 (m, 1H, CH), 3.68 (t, J=6.5 Hz, 2H, CH$_2$), 3.43 (m, 3H, 3×CH), 3.10 (m, 1H, CH$_2$), 2.91 (m, 1H, CH$_2$), 2.00 (m, 4H, 2×CH$_2$) ppm.

Example 67

(3R,4R,5S,6R)-6-(Hydroxymethyl)-3-[4-[7-(4-nitro-2,1,3-benzoxadiazol-7-yl)heptyl]triazol-1-yl]tetrahydropyran-2,4,5-triol

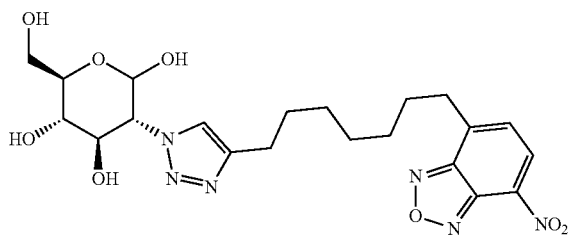 [SMILES: O=[N+]([O-])c1ccc(CCCCCCCc2cn([C@H]3C(O)O[C@H](CO)[C@@H](O)[C@@H]3O)nn2)c2nonc12]

Step 1:
4-nitro-N-oct-7-ynyl-2,1,3-benzoxadiazol-7-amine

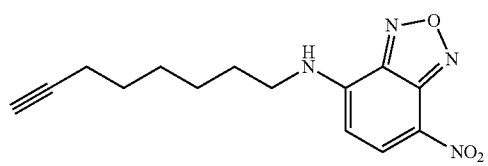 [SMILES: C#CCCCCCCNc1ccc([N+](=O)[O-])c2nonc12]

To a solution of 300 mg (1.49 mmol) 4-chloro-7-nitrobenzofurazane in 4 mL dry dimethylformamide was added 216 mg (1.64 mmol) 7-octyn-1-amine and 527 µl (2.98 mmol) N,N-diisopropylethylamine. The reaction mixture was stirred at room temperature for 2 days and evaporated.

Purification: MPLC CombiFlash Rf (Teledyne ISCO); column: RediSep Silica 40 g; flow rate: 40 mL/min; wavelength for detection: 254 nm; eluent: (A) n-heptane, (B) ethylacetate.
MPLC Gradient

| start % B | end % B | duration [min] |
|---|---|---|
| 0.0 | 0.0 | 1.6 |
| 0.0 | 27.7 | 16.6 |
| 27.7 | 79.8 | 19.9 |
| 79.8 | 0.0 | 0.0 |
| 0.0 | 0.0 | 2.9 |

Yield: 96 mg (0.333 mmol, 22.4%), orange solid.
TLC: $R_f$=0.689 (dichloromethane/ethanol, 19:1).
LC/MS (ES-API): m/z=289.10 [M+H]$^+$; calculated: 289.30; $t_R$ (λ=220 nm): 1.25 min (LC/MS—Method 1).
$^1$H-NMR (400 MHz, DMSO-d$_6$): δ=9.53 (s, 1H, NH), 8.51 (d, J=8.8 Hz, 2H, ArH), 6.41 (d, J=8.9 Hz, 1H, OH), 5.23 (d, J=5.7 Hz, 1H, OH), 4.87 (dd, J=4.2 Hz, 1H, CH), 4.56 (d, J=6.7 Hz, 1H, OH), 4.63 (dd, J=5.9 Hz, 1H, OH), 4.32 (dd, J=8.2 Hz, 1H, OH), 3.71 (m, 2H, 2×CH), 3.45 (m, 3H, 3×CH), 3.31 (m, 1H, CH$_2$), 3.20 (m, 1H, CH$_2$), 2.59 (m, 2H, CH$_2$), 1.65 (m, 6H, 3×CH$_2$), 1.36 (m, 4H, 2×CH$_2$) ppm.

Step 2: (3R,4R,5S,6R)-6-(hydroxymethyl)-3-[4-[7-(4-nitro-2,1,3-benzoxadiazol-7-yl)heptyl]triazol-1-yl]tetrahydropyran-2,4,5-triol Example 67 was synthesized from 2-azido-2-deoxyglucose and example 67, step 1 following the CuAAC procedure described in synthesis method E.

Yield: 32 mg (64 µmol, 44.3%), orange solid.
TLC: $R_f$=0.833 (dichloromethane/ethanol, 4:1).
LC/MS (ES-API): m/z=494.24 [M+H]$^+$; calculated: 494.19; $t_R$1 (λ=220 nm): 1.33 min; $t_R$2 (λ=220 nm): 1.35 min (LC/MS—Method 1).
$^1$H-NMR (400 MHz, DMSO-d$_6$): δ=9.53 (s, 1H, NH), 8.51 (d, J=8.8 Hz, 2H, ArH), 8.00 (s, 1H, NCH), 6.41 (d, J=8.9 Hz, 1H, OH), 5.23 (d, J=5.7 Hz, 1H, OH), 4.87 (dd, J=4.2 Hz, 1H, CH), 4.56 (d, J=6.7 Hz, 1H, OH), 4.63 (dd, J=5.9 Hz, 1H, OH), 4.32 (dd, J=8.2 Hz, 1H, OH), 3.71 (m, 2H, 2×CH), 3.45 (m, 3H, 3×CH), 3.31 (m, 1H, CH$_2$), 3.20 (m, 1H, CH$_2$), 2.59 (m, 2H, CH$_2$), 1.65 (m, 6H, 3×CH$_2$), 1.36 (m, 4H, 2×CH$_2$) ppm.

Example 68

5-(Dimethylamino)-N-[[1-[[(2R,3S,4S,5R)-3,4,5,6-tetrahydroxytetrahydropyran-2-yl]methyl]triazol-4-yl]methyl]naphthalene-1-sulfonamide

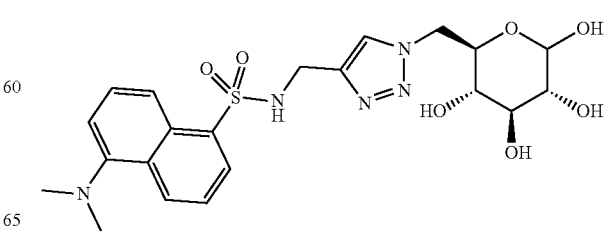

Example 68 was synthesized from 6-azido-6-deoxyglucose and example 54, step 1 following the CuAAC procedure described in synthesis method E.

Yield: 18 mg (36.47 µmol, 49.9%), white-yellow solid.
TLC: R$_f$=0.045 (dichloromethane/ethanol, 4:1).
LC/MS (ES-API): m/z=494.25 [M+H]$^+$; calculated: 494.16; t$_R$1 (λ=220 nm): 1.18 min; t$_R$2 (λ=220 nm): 1.20 min (LC/MS—Method 1).
$^1$H-NMR (400 MHz, DMSO-d$_6$): δ=8.46 (d, J=8.4 Hz, 2H, ArH), 8.13 (d, J=7.0 Hz, 1H, ArH), 7.84 (s, 1H, NCH), 7.67 (s, 1H, SNH), 7.57 (m, 2H, ArH), 7.25 (d, J=7.2 Hz, 1H, ArH), 6.31 (d, J=6.4 Hz, 1H, OH), 5.23 (d, J=6.3 Hz, 1H, OH), 4.92 (d, J=6.2 Hz, 1H, OH), 4.85 (dd, J=6.4 Hz, 1H, CH), 4.58 (d, J=6.0 Hz, 1H, OH), 6=4.21 (m, 1H, CH$_2$), 4.07 (s, 2H, NCH$_2$), 3.89 (m, 1H, CH$_2$), 3.47 (m, 1H, CH), 3.14 (m, 1H, CH), 2.96 (m, 1H, CH), 2.81 (s, 6H, 2×NCH$_3$) ppm.

Example 69

(3R,4S,5S,6R)-6-[(4-Phenyltriazol-1-yl)methyl]tetrahydropyran-2,3,4,5-tetrol

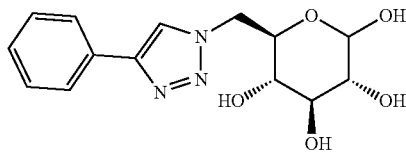 [SMILES: OC1O[C@H](Cn2cc(-c3ccccc3)nn2)[C@@H](O)[C@H](O)[C@H]1O]

Example 69 was synthesized from 6-azido-6-deoxyglucose and ethynylbenzene following the CuAAC procedure described in synthesis method E.

Yield: 36 mg (117 µmol, 80.1%), white solid.
TLC: R$_f$=0.242 (dichloromethane/ethanol, 4:1).
LC/MS (ES-API): m/z=308.16 [M+H]$^+$; calculated: 308.12; t$_R$1 (λ=220 nm): 0.90 min; t$_R$2 (λ=220 nm): 0.97 min (LC/MS—Method 1).
$^1$H-NMR (400 MHz, DMSO-d$_6$): δ=8.49 (s, 1H, NCH), 7.86 (dd, J=1.3 Hz, 2H, ArH), 7.46 (m, 2H, ArH), 7.42 (m, 1H, ArH), 6.36 (d, J=6.0 Hz, 1H, OH), 5.31 (d, J=5.8 Hz, 1H, OH), 4.96 (t, J=5.7 Hz, 1H, CH), 4.90 (d, J=4.2 Hz, 1H, OH), 4.65 (d, J=6.1 Hz, 1H, OH), 4.41 (m, 2H, CH$_2$), 3.99 (m, 1H, CH), 3.49 (m, 1H, CH), 3.22 (m, 1H, CH), 3.00 (m, 1H, CH) ppm.
$^{13}$C-NMR (150 MHz, DMSO-d$_6$): δ=146.03 (s, C), 130.84 (s, C), 128.85 (s, CH), 127.75 (s, CH), 125.09 (s, CH), 122.25 (s, CH), 92.35 (s, CH), 72.69 (s, CH), 72.07 (s, CH), 71.89 (s, CH), 69.97 (s, CH), 61.26 (s, CH$_2$) ppm.

Example 70

(3R,4S,5S,6R)-6-[[4-(p-Tolyl)triazol-1-yl]methyl]tetrahydropyran-2,3,4,5-tetrol

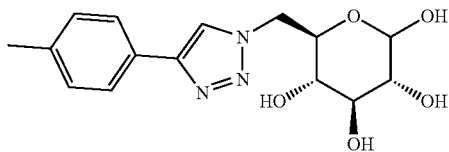 [SMILES: Cc1ccc(-c2cn(C[C@H]3OC(O)[C@H](O)[C@@H](O)[C@@H]3O)nn2)cc1]

Example 70 was synthesized from 6-azido-6-deoxyglucose and 1-ethynyl-4-methylbenzene following the CuAAC procedure described in synthesis method E.

Yield: 32 mg (100 µmol, 68.1%), white solid.
TLC: R$_f$=0.250 (dichloromethane/ethanol, 4:1).
LC/MS (ES-API): m/z=322.19 [M+H]$^+$; calculated: 322.13; t$_R$1 (λ=220 nm): 1.12 min; t$_R$2 (λ=220 nm): 1.16 min (LC/MS—Method 1).
$^1$H-NMR (400 MHz, DMSO-d$_6$): δ=8.49 (s, 1H, NCH), 7.72 (d, J=8.0 Hz, 2H, ArH), 7.21 (d, J=8.0 Hz, 2H, ArH), 6.43 (d, J=4.4 Hz, 1H, OH), 5.30 (d, J=5.4 Hz, 1H, OH), 4.94 (d, J=5.4 Hz, 1H, OH), 4.90 (dd, J=4.2 Hz, 1H, CH), 4.58 (d, J=5.3 Hz, 1H, OH), 4.40 (m, 1H, CH$_2$), 4.00 (m, 1H, CH$_2$), 3.49 (m, 1H, CH), 3.17 (m, 1H, CH), 3.06 (m, 1H, CH), 2.94 (m, 1H, CH), 2.36 (s, 3H, CH$_3$) ppm.

Example 71

(3R,4S,5S,6R)-6-[[4-(3-Phenylpropyl)triazol-1-yl]methyl]tetrahydropyran-2,3,4,5-tetrol

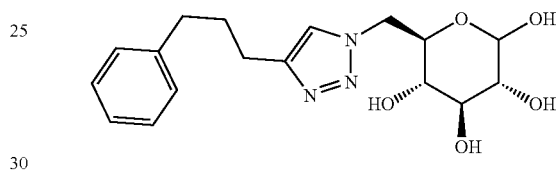

Example 71 was synthesized from 6-azido-6-deoxyglucose and pent-4-yn-1-ylbenzene following the CuAAC procedure described in synthesis method E.

Yield: 43 mg (123 µmol, 84.2%), white solid.
TLC: R$_f$=0.273 (dichloromethane/ethanol, 4:1).
LC/MS (ES-API): m/z=350.18 [M+H]$^+$; calculated: 350.16; t$_R$1 (λ=220 nm): 1.29 min; t$_R$2 (λ=220 nm): 1.35 min (LC/MS—Method 1).
$^1$H-NMR (400 MHz, DMSO-d$_6$): δ=7.72 (s, 1H, NCH), 7.25 (m, 2H, ArH), 7.20 (m, 3H, ArH), 6.31 (d, J=5.0 Hz, 1H, OH), 5.23 (d, J=5.6 Hz, 1H, OH), 4.89 (d, J=6.5 Hz, 1H, CH), 4.80 (d, J=5.0 Hz, 1H, OH), 4.55 (dd, J=5.5 Hz, 1H, OH), 4.31 (m, 1H, CH$_2$), 3.93 (m, 1H, CH$_2$), 3.49 (m, 2H, 2×CH), 3.11 (m, 1H, CH), 2.97 (m, 1H, CH), 2.63 (m, 4H, CH$_2$), 1.90 (m, 2H, CH$_2$) ppm.

Example 72

Methyl-4-[1-[[(2R,3S,4S,5R)-3,4,5,6-tetrahydroxytetrahydropyran-2-yl]methyl]triazol-4-yl]-benzoate

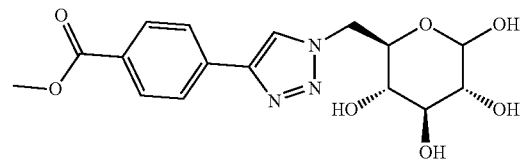 [SMILES: COC(=O)c1ccc(-c2cn(C[C@H]3OC(O)[C@H](O)[C@@H](O)[C@@H]3O)nn2)cc1]

Example 72 was synthesized from 6-azido-6-deoxyglucose and 4-ethynylmethylbenzoate following the CuAAC procedure described in synthesis method E.

Yield: 34 mg (93 µmol, 63.6%), white solid.
TLC: R$_f$=0.258 (dichloromethane/ethanol, 4:1).

LC/MS (ES-API): m/z=366.23 [M+H]$^+$; calculated: 366.12; $t_R$1 ($\lambda$=220 nm): 1.05 min; $t_R$2 ($\lambda$=220 nm): 1.08 min (LC/MS—Method 1).

$^1$H-NMR (400 MHz, DMSO-d$_6$): $\delta$=8.59 (s, 1H, NCH), 8.01 (m, 4H, ArH), 6.37 (d, J=5.0 Hz, 1H, OH), 5.31 (d, J=5.6 Hz, 1H, OH), 4.94 (d, J=4.8 Hz, 1H, OH), 4.89 (dd, J=4.3 Hz, 1H, CH), 4.61 (d, J=5.1 Hz, 1H, OH), 4.44 (m, 1H, CH$_2$), 4.02 (m, 1H, CH$_2$), 3.90 (s, 3H, OCH$_3$), 3.51 (m, 1H, CH), 3.19 (m, 1H, CH), 3.08 (m, 1H, CH), 2.91 (m, 1H, CH) ppm.

Example 73

(3R,4S,5S,6R)-6-[[4-[[Benzyl(methyl)amino]methyl]triazol-1-yl]methyl]tetrahydropyran-2,3,4,5-tetrol

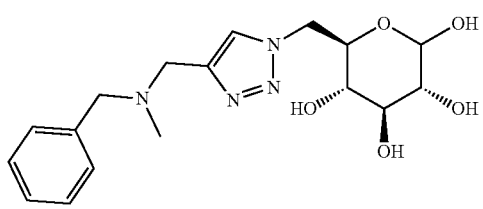 [SMILES: CN(Cc1ccccc1)Cc1cn(C[C@H]2OC(O)[C@H](O)[C@@H](O)[C@@H]2O)nn1]

Example 73 was synthesized from 6-azido-6-deoxyglucose and N-benzyl-N-methylprop-2-yn-1-amine following the CuAAC procedure described in synthesis method E.

Yield: 36 mg (99 μmol, 67.6%), white solid.

TLC: R$_f$=0.053 (dichloromethane/ethanol, 4:1).

LC/MS (ES-API): m/z=365.20 [M+H]$^+$; calculated: 365.18; $t_R$ (ELSD): 0.37 min (LC/MS—Method 1).

$^1$H-NMR (400 MHz, DMSO-d$_6$): $\delta$=7.85 (s, 1H, NCH), 7.31 (m, 5H, ArH), 6.33 (d, J=6.1 Hz, 1H, OH), 5.24 (d, J=5.8 Hz, 1H, OH), 4.90 (d, J=5.6 Hz, 1H, OH), 4.87 (dd, J=6.0 Hz, 1H, CH), 4.58 (d, J=5.0 Hz, 1H, OH), 4.41 (m, 1H, CH$_2$), 3.97 (m, 1H, CH$_2$), 3.62 (s, 3H, NCH$_3$), 3.50 (m, 2H, 2×CH), 3.15 (m, 1H, CH), 2.96 (m, 1H, CH), 2.10 (m, 4H, 2×NCH$_2$) ppm.

Example 74

(3R,4S,5S,6R)-6-[[4-(6-Methoxy-2-naphthyl)triazol-1-yl]methyl]tetrahydropyran-2,3,4,5-tetrol

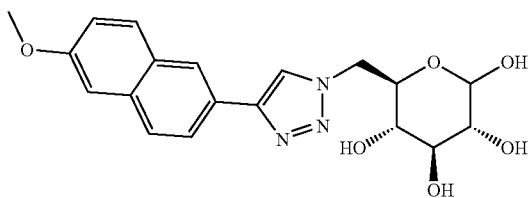 [SMILES: COc1ccc2cc(-c3cn(C[C@H]4OC(O)[C@H](O)[C@@H](O)[C@@H]4O)nn3)ccc2c1]

Example 74 was synthesized from 6-azido-6-deoxyglucose and 2-ethynyl-6-methoxynaphthalene following the CuAAC procedure described in synthesis method E.

Yield: 43 mg (111 μmol, 75.9%), white solid.

TLC: R$_f$=0.288 (dichloromethane/ethanol, 4:1).

LC/MS (ES-API): m/z=388.20 [M+H]$^+$; calculated: 388.14; $t_R$1 ($\lambda$=220 nm): 1.30 min; $t_R$2 ($\lambda$=220 nm): 1.33 min (LC/MS—Method 1).

$^1$H-NMR (400 MHz, DMSO-d$_6$): $\delta$=8.51 (s, 1H, NCH), 7.86 (m, 4H, ArH), 7.34 (s, 2H, ArH), 6.39 (d, J=5.8 Hz, 1H, OH), 5.41 (d, J=6.1 Hz, 1H, OH), 4.94 (d, J=6.0 Hz, 1H, OH), 4.90 (dd, J=6.3 Hz, 1H, CH), 4.58 (d, J=5.2 Hz, 1H, OH), 4.42 (m, 1H, CH$_2$), 4.01 (m, 1H, CH$_2$), 3.90 (s, 3H, OCH$_3$), 3.51 (m, 1H, CH), 3.19 (m, 1H, CH), 3.06 (m, 1H, CH), 2.97 (m, 1H, CH) ppm.

Example 75

(3R,4S,5S,6R)-6-[[4-[[(4-Nitro-2,1,3-benzoxadiazol-7-yl)amino]methyl]triazol-1-yl]methyl]tetrahydropyran-2,3,4,5-tetrol

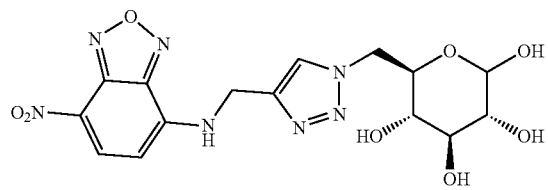 [SMILES: O=[N+]([O-])c1ccc(NCc2cn(C[C@H]3OC(O)[C@H](O)[C@@H](O)[C@@H]3O)nn2)c2nonc12]

Example 75 was synthesized from 6-azido-6-deoxyglucose and example 63, step 1 following the CuAAC procedure described in synthesis method E.

Yield: 56 mg (132 μmol, 90.5%), orange solid.

TLC: R$_f$=0.121 (dichloromethane/ethanol, 4:1).

LC/MS (ES-API): m/z=424.16 [M+H]$^+$; calculated: 424.11; $t_R$1 ($\lambda$=220 nm): 0.83 min; $t_R$2 ($\lambda$=220 nm): 0.87 min (LC/MS—Method 1).

$^1$H-NMR (400 MHz, DMSO-d$_6$): $\delta$=9.85 (s, 1H, NH) 8.53 (d, J=8.4 Hz, 1H, ArH), 8.01 (s, 1H, NCH), 6.51 (d, J=8.4 Hz, 1H, ArH), 6.33 (d, J=6.0 Hz, 1H, OH), 5.24 (d, J=6.1 Hz, 1H, OH), 4.94 (d, J=6.2 Hz, 1H, OH), 4.86 (dd, J=5.8 Hz, 1H, CH), 4.65 (s, 2H, NCH$_2$), 4.57 (dd, J=6.0 Hz, 1H, OH), 4.37 (m, 1H, CH$_2$), 3.91 (m, 1H, CH$_2$), 3.49 (m, 1H, CH), 3.14 (m, 1H, CH), 2.95 (m, 1H, CH) ppm.

Example 76

(3R,4S,5S,6R)-6-[[4-(Cyclohexylmethyl)triazol-1-yl]methyl]tetrahydropyran-2,3,4,5-tetrol

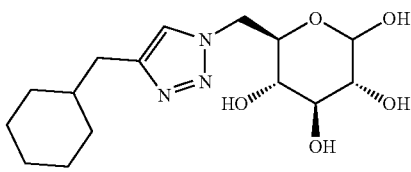 [SMILES: OC1O[C@H](Cn2cc(CC3CCCCC3)nn2)[C@@H](O)[C@H](O)[C@H]1O]

Example 76 was synthesized from 6-azido-6-deoxyglucose and prop-2-yn-1-ylcyclohexane following the CuAAC procedure described in synthesis method E.

Yield: 33 mg (101 μmol, 68.9%), white-yellow solid.

TLC: R$_f$=0.220 (dichloromethane/ethanol, 4:1).

LC/MS (ES-API): m/z=328.24 [M+H]$^+$; calculated: 328.18; $t_R$1 ($\lambda$=220 nm): 1.23 min; $t_R$2 ($\lambda$=220 nm): 1.29 min (LC/MS—Method 1).

$^1$H-NMR (400 MHz, DMSO-d$_6$): $\delta$=7.68 (s, 1H, NCH), 6.33 (d, J=5.0 Hz, 1H, OH), 5.22 (d, J=5.5 Hz, 1H, OH), 4.87 (dd, J=4.3 Hz, 1H, CH), 4.78 (d, J=5.0 Hz, 1H, OH), 4.59 (dd, J=2.3 Hz, 1H, OH), 4.55 (d, J=6.7 Hz, 1H, OH), 4.36 (m, 1H, CH$_2$), 3.92 (m, 1H, CH$_2$), 3.44 (m, 1H, CH), 3.12 (m, 1H, CH), 2.90 (m, 1H, CH), 2.49 (m, 2H, CH$_2$), 1.64 (m, 6H, 3×CH$_2$), 1.53 (m, 1H, CH), 1.17 (m, 4H, 2×CH$_2$), 0.95 (m, 2H, CH$_2$) ppm.

Example 77

(3R,4S,5S,6R)-6-[(4-Pentyltriazol-1-yl)methyl]tetrahydropyran-2,3,4,5-tetrol

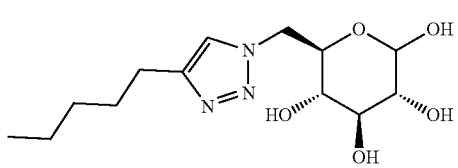 [SMILES: CCCCCc1cn(C[C@H]2OC(O)[C@H](O)[C@@H](O)[C@@H]2O)nn1]

Example 77 was synthesized from 6-azido-6-deoxyglucose and hept-1-yne following the CuAAC procedure described in synthesis method E.

Yield: 7 mg (23 µmol, 15.9%), white-yellow solid.

TLC: R$_f$=0.235 (dichloromethane/ethanol, 4:1).

LC/MS (ES-API): m/z=302.25 [M+H]$^+$; calculated: 302.16; t$_R$1 (λ=220 nm): 1.12 min; t$_R$2 (λ=220 nm): 1.17 min (LC/MS—Method 1).

$^1$H-NMR (400 MHz, DMSO-d$_6$): δ=7.70 (s, 1H, NCH), 6.33 (d, J=4.8 Hz, 1H, OH), 5.23 (d, J=5.7 Hz, 1H, OH), 4.87 (dd, J=4.0 Hz, 1H, CH), 4.78 (d, J=4.9 Hz, 1H, OH), 4.60 (dd, J=2.3 Hz, 1H, OH), 4.55 (d, J=6.6 Hz, 1H, OH), 4.31 (m, 1H, CH$_2$), 3.92 (m, 1H, CH$_2$), 3.52 (m, 1H, CH), 3.12 (m, 1H, CH), 2.94 (m, 1H, CH), 2.58 (t, J=7.5 Hz, 2H, CH$_2$), 1.58 (m, 2H, CH$_2$), 1.30 (m, 4H, CH$_2$), 0.87 (m, 3H, CH$_3$) ppm.

Example 78

(3R,4S,5S,6R)-6-[[4-(3-Chloropropyl)triazol-1-yl]methyl]tetrahydropyran-2,3,4,5-tetrol

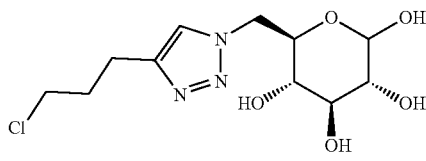 [SMILES: OC1O[C@H](Cn2cc(CCCCl)nn2)[C@@H](O)[C@H](O)[C@H]1O]

Example 78 was synthesized from 6-azido-6-deoxyglucose and 5-chloro-pent-1-yne following the CuAAC procedure described in synthesis method E.

Yield: 24 mg (78 µmol, 53.3%), white-yellow solid.

TLC: R$_f$=0.182 (dichloromethane/ethanol, 4:1).

LC/MS (ES-API): m/z=308.17 [M+H]$^+$; calculated: 308.09; t$_R$1 (λ=220 nm): 0.70 min; t$_R$2 (λ=220 nm): 0.72 min (LC/MS—Method 1).

$^1$H-NMR (400 MHz, DMSO-d$_6$): δ=7.78 (s, 1H, NCH), 6.33 (d, J=5.0 Hz, 1H, OH), 5.24 (d, J=5.7 Hz, 1H, OH), 4.89 (dd, J=4.9 Hz, 1H, CH), 4.79 (d, J=5.3 Hz, 1H, OH), 4.61 (dd, J=2.2 Hz, 1H, OH), 4.55 (d, J=6.6 Hz, 1H, OH), 4.34 (m, 1H, CH$_2$), 3.93 (m, 1H, CH$_2$), 3.68 (t, J=6.6 Hz, 2H, CH$_2$), 3.44 (m, 2H, 2×CH), 3.15 (m, 1H, CH), 2.91 (m, 1H, CH), 2.07 (m, 4H, 2×CH$_2$) ppm.

Example 79

(3R,4S,5S,6R)-6-[[4-[6-[(4-Nitro-2,1,3-benzoxadiazol-7-yl)amino]hexyl]triazol-1-yl]methyl]tetrahydropyran-2,3,4,5-tetrol

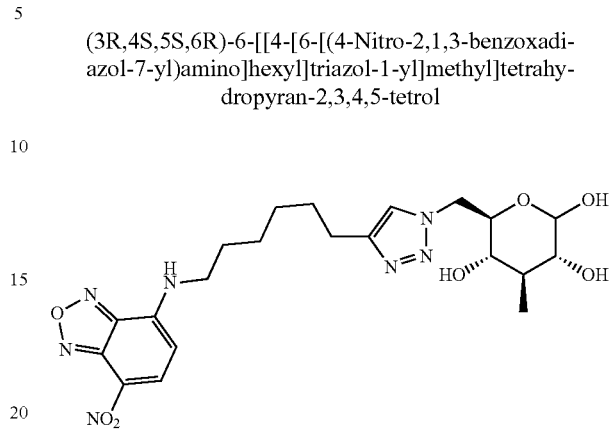

Example 79 was synthesized from 6-azido-6-deoxyglucose and example 67, step 1 following the CuAAC procedure described in synthesis method E.

Yield: 20 mg (40.53 µmol, 55.4%), orange oil.

TLC: R$_f$=0.222 (dichloromethane/ethanol, 4:1).

LC/MS (ES-API): m/z=494.23 [M+H]$^+$; calculated: 494.19; t$_R$1 (λ=220 nm): 1.33 min; t$_R$2 (λ=220 nm): 1.35 min (LC/MS—Method 1).

$^1$H-NMR (400 MHz, DMSO-d$_6$): δ=9.50 (s, 1H, NH), 8.49 (d, J=8.8 Hz, 2H, ArH), 769 (s, 1H, NCH), 6.41 (d, J=5.9 Hz, 1H, OH), 5.23 (d, J=5.7 Hz, 1H, OH), 4.91 (d, J=6.7 Hz, 1H, OH), 4.87 (dd, J=4.0 Hz, 1H, CH), 4.63 (dd, J=5.9 Hz, 1H, OH), 4.56 (d, J=6.2 Hz, 1H, OH), 4.30 (m, 1H, CH$_2$), 3.91 (m, 1H, CH$_2$), 3.49 (m, 2H, 2×CH), 3.17 (m, 1H, CH), 2.94 (m, 1H, CH), 2.58 (m, 2H, CH$_2$), 1.65 (m, 4H, 2×CH$_2$), 1.40 (m, 6H, 3×CH$_2$) ppm.

Example 80

5-(Dimethylamino)-N-[[1-[(2R,3R,4S,5S,6R)-3,4,5-trihydroxy-6-(hydroxymethyl)tetrahydropyran-2-yl]triazol-4-yl]methyl]naphthalene-1-sulfonamide

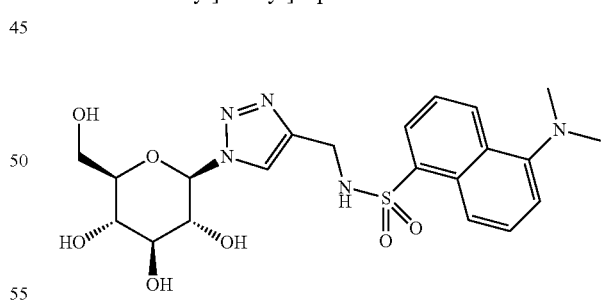

Example 80 was synthesized from 1-azido-1-deoxyglucose and example 54, step 1 following the CuAAC procedure described in synthesis method E.

Yield: 46 mg (94 µmol, 63.7%), white-yellow solid.

TLC: R$_f$=0.129 (dichloromethane/ethanol, 4:1).

LC/MS (ES-API): m/z=494.26 [M+H]$^+$; calculated: 494.16; t$_R$ (λ=220 nm): 1.20 min (LC/MS—Method 1).

$^1$H-NMR (400 MHz, DMSO-d$_6$): δ=8.48 (d, J=8.4 Hz, 1H, ArH), 8.32 (d, J=8.6 Hz, 1H, ArH), 8.14 (dd, J=1.1 Hz, 1H, ArH), 8.02 (s, 1H, NCH), 7.62 (m, 2H, ArH), 7.27 (d, J=7.6 Hz, 1H, ArH), 5.49 (d, J=9.2 Hz, 1H, OH), 5.31 (d,

J=6.2 Hz, 1H, OH), 5.23 (d, J=4.9 Hz, 1H, OH), 5.13 (d, J=5.4 Hz, 1H, CH), 4.62 (dd, J=5.4 Hz, 1H, OH), 4.08 (d, J=5.1 Hz, 1H, NCH$_2$), 3.68 (m, 2H, CH$_2$), 3.43 (m, 2H, 2×CH), 3.19 (m, 1H, CH), 2.84 (s, 6H, 2×NCH$_3$) ppm.

Example 81

(2R,3S,4S,5R,6R)-2-(Hydroxymethyl)-6-(4-phenyl-triazol-1-yl)tetrahydropyran-3,4,5-triol

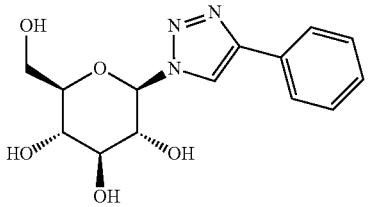 [SMILES: OC[C@H]1O[C@@H](n2cc(-c3ccccc3)nn2)[C@H](O)[C@@H](O)[C@@H]1O]

Example 81 was synthesized from 1-azido-1-deoxyglucose and ethynylbenzene following the CuAAC procedure described in synthesis method E.

Yield: 40 mg (130 μmol, 89.0%), white solid.

TLC: R$_f$=0.295 (dichloromethane/ethanol, 4:1).

LC/MS (ES-API): m/z=308.14 [M+H]$^+$; calculated: 308.12; t$_R$ (λ=220 nm): 0.92 min (LC/MS—Method 1).

$^1$H-NMR (400 MHz, DMSO-d$_6$): δ=8.81 (s, 1H, NCH), 7.88 (d, J=8.0 Hz, 2H, ArH), 7.46 (t, J=7.5 Hz, 2H, ArH), 7.34 (d, J=7.5 Hz, 1H, ArH), 5.57 (d, J=9.2 Hz, 1H, CH), 5.42 (d, J=5.8 Hz, 1H, OH), 5.31 (d, J=4.9 Hz, 1H, OH), 5.16 (d, J=5.5 Hz, 1H, OH), 4.62 (dd, J=5.6 Hz, 1H, OH), 3.81 (m, 1H, CH$_2$), 3.73 (m, 1H, CH$_2$), 3.49 (m, 2H, 2×CH), 3.17 (m, 1H, CH$_2$) ppm.

$^{13}$C-NMR (150 MHz, DMSO-d$_6$): δ=146.31 (s, C), 130.62 (s, C), 128.91 (s, CH), 127.92 (s, CH), 125.15 (s, CH), 120.47 (s, CH), 87.68 (s, CH), 79.95 (s, CH), 76.85 (s, CH), 72.19 (s, CH), 69.60 (s, CH), 60.76 (s, CH$_2$) ppm.

Example 82

(2R,3S,4S,5R,6R)-2-(Hydroxymethyl)-6-[4-(p-tolyl)triazol-1-yl]tetrahydropyran-3,4,5-triol

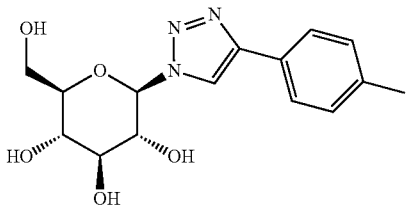 [SMILES: Cc1ccc(-c2cn([C@@H]3O[C@H](CO)[C@@H](O)[C@H](O)[C@H]3O)nn2)cc1]

Example 82 was synthesized from 1-azido-1-deoxyglucose and 1-ethynyl-4-methylbenzene following the CuAAC procedure described in synthesis method E.

Yield: 39 mg (121 μmol, 83.0%), white solid.

TLC: R$_f$=0.326 (dichloromethane/ethanol, 4:1).

LC/MS (ES-API): m/z=322.20 [M+H]$^+$; calculated: 322.13; t$_R$ (λ=220 nm): 1.14 min (LC/MS—Method 1).

$^1$H-NMR (400 MHz, DMSO-d$_6$): δ=8.76 (s, 1H, NCH), 7.77 (d, J=8.3 Hz, 2H, ArH), 7.27 (d, J=8.3 Hz, 2H, ArH), 5.55 (d, J=9.1 Hz, 1H, OH), 5.41 (d, J=5.9 Hz, 1H, OH), 5.30 (d, J=5.1 Hz, 1H, OH), 5.15 (d, J=5.5 Hz, 1H, CH), 4.61 (dd, J=5.5 Hz, 1H, OH), 3.80 (m, 1H, CH$_2$), 3.72 (m, 1H, CH$_2$), 3.45 (m, 2H, 2×CH), 3.26 (m, 1H, CH), 2.34 (s, 3H, CH$_3$) ppm.

Example 83

(2R,3S,4S,5R,6R)-2-(Hydroxymethyl)-6-[4-(3-phenylpropyl)triazol-1-yl]tetrahydropyran-3,4,5-triol

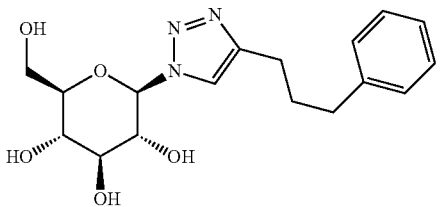 [SMILES: OC[C@H]1O[C@@H](n2cc(CCCc3ccccc3)nn2)[C@H](O)[C@@H](O)[C@@H]1O]

Example 83 was synthesized from 1-azido-1-deoxyglucose and pent-4yn-1ylbenzene following the CuAAC procedure described in synthesis method E.

Yield: 50 mg (143 μmol, 97.9%), white solid.

TLC: R$_f$=0.356 (dichloromethane/ethanol, 4:1).

LC/MS (ES-API): m/z=350.21 [M+H]$^+$; calculated: 350.16; t$_R$ (λ=220 nm): 1.27 min (LC/MS—Method 1).

$^1$H-NMR (400 MHz, DMSO-d$_6$): δ=8.07 (s, 1H, NCH), 7.25 (m, 5H, ArH), 5.46 (d, J=9.2 Hz, 1H, OH), 5.31 (d, J=5.9 Hz, 1H, OH), 5.24 (d, J=5.0 Hz, 1H, OH), 5.12 (d, J=5.5 Hz, 1H, CH), 4.59 (dd, J=5.0 Hz, 1H, OH), 3.72 (m, 2H, CH$_2$), 3.42 (m, 2H, 2×CH), 3.21 (m, 1H, CH), 2.63 (m, 4H, 2×CH$_2$), 1.90 (m, 2H, CH$_2$) ppm.

Example 84

Methyl-4-[1-[(2R,3R,4S,5S,6R)-3,4,5-trihydroxy-6-(hydroxymethyl)tetrahydropyran-2-yl]triazol-4-yl]benzoate

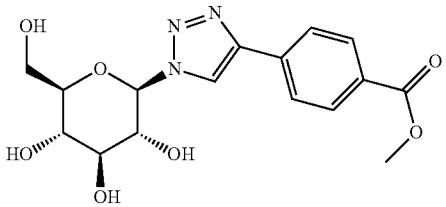 [SMILES: COC(=O)c1ccc(-c2cn([C@@H]3O[C@H](CO)[C@@H](O)[C@H](O)[C@H]3O)nn2)cc1]

Example 84 was synthesized from 1-azido-1-deoxyglucose and 4-ethynylmethylbenzoate following the CuAAC procedure described in synthesis method E.

Yield: 44 mg (120 μmol, 82.4%), white solid.

TLC: R$_f$=0.062 (dichloromethane/ethanol, 4:1).

LC/MS (ES-API): m/z=366.12 [M+H]$^+$; calculated: 366.12; t$_R$1 (λ=220 nm): 0.97 min (LC/MS—Method 1).

$^1$H-NMR (400 MHz, DMSO-d$_6$): δ=9.00 (s, 1H, NCH), 8.05 (s, 4H, ArH), 5.60 (d, J=9.3 Hz, 1H, OH), 5.44 (d, J=5.9 Hz, 1H, OH), 5.32 (d, J=4.8 Hz, 1H, OH), 5.17 (d, J=5.5 Hz, 1H, CH), 4.62 (dd, J=5.8 Hz, 1H, OH), 3.87 (s, 3H, OCH$_3$), 3.87 (m, 1H, CH$_2$), 3.80 (m, 1H, CH$_2$), 3.49 (m, 1H, CH), 3.43 (m, 1H, CH), 3.27 (m, 1H, CH) ppm.

Example 85

(2R,3R,4S,5S,6R)-2-[4-[[Benzyl(methyl)amino]methyl]triazol-1-yl]-6-(hydroxymethyl)tetrahydropyran-3,4,5-triol

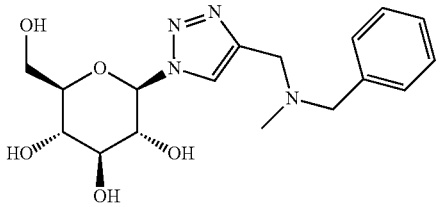

Example 85 was synthesized from 1-azido-1-deoxyglucose and N-benzyl-N-methylprop-2-yn-1-amine following the CuAAC procedure described in synthesis method E.

Yield: 51 mg (140 μmol, 95.7%), white solid.

TLC: R$_f$=0.091 (dichloromethane/ethanol, 4:1).

LC/MS (ES-API): m/z=365.20 [M+H]$^+$; calculated: 365.17; t$_R$ (ELSD): 0.34 min (LC/MS—Method 1).

$^1$H-NMR (400 MHz, DMSO-d$_6$): δ=8.19 (s, 1H, NCH), 7.33 (m, 4H, ArH), 7.25 (m, 1H, ArH), 5.50 (d, J=9.4 Hz, 1H, OH), 5.34 (d, J=6.1 Hz, 1H, OH), 5.24 (d, J=5.0 Hz, 1H, OH), 5.12 (d, J=5.7 Hz, 1H, CH), 4.60 (dd, J=5.6 Hz, 1H, OH), 3.77 (m, 1H, CH$_2$), 3.70 (m, 1H, CH$_2$), 3.62 (s, 2H, NCH$_2$), 3.52 (s, 2H, NCH$_2$), 3.43 (m, 1H, CH), 3.38 (m, 1H, CH), 3.24 (m, 1H, CH) 2.11 (s, 3H, NCH$_3$) ppm.

Example 86

(2R,3S,4S,5R,6R)-2-(Hydroxymethyl)-6-[4-(6-methoxy-2-naphthyl)triazol-1-yl]tetrahydropyran-3,4,5-triol

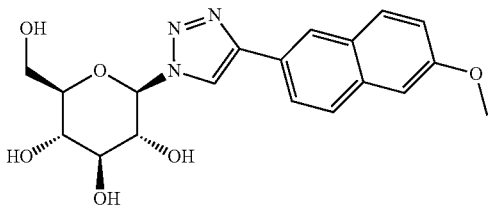 [SMILES: COc1ccc2cc(-c3cn([C@@H]4O[C@H](CO)[C@@H](O)[C@H](O)[C@H]4O)nn3)ccc2c1]

Example 86 was synthesized from 1-azido-1-deoxyglucose and 2-ethynyl-6-methoxynaphthalene following the CuAAC procedure described in synthesis method E.

Yield: 42 mg (108 μmol, 74.1%), white solid.

TLC: R$_f$=0.318 (dichloromethane/ethanol, 4:1).

LC/MS (ES-API): m/z=388.10 [M+H]$^+$; calculated: 388.14; t$_R$ (λ=220 nm): 0.95 min (LC/MS—Method 1).

$^1$H-NMR (400 MHz, DMSO-d$_6$): δ=8.51 (s, 1H, NCH), 7.86 (m, 4H, ArH), 7.34 (s, 2H, ArH), 6.39 (d, J=5.8 Hz, 1H, OH), 5.41 (d, J=6.1 Hz, 1H, OH), 4.94 (d, J=6.0 Hz, 1H, OH), 4.90 (dd, J=6.3 Hz, 1H, OH), 4.58 (d, J=5.2 Hz, 1H, OH), 4.42 (m, 1H, CH$_2$), 4.01 (m, 1H, CH$_2$), 3.90 (s, 3H, OCH$_3$), 3.51 (m, 1H, CH), 3.19 (m, 1H, CH), 3.06 (m, 1H, CH), 2.97 (m, 1H, CH) ppm.

Example 87

Ethyl-2-diethoxyphosphoryl-3-[1-[(2R,3R,4S,5S,6R)-3,4,5-trihydroxy-6-(hydroxymethyl)tetrahydropyran-2-yl]triazol-4-yl]propanoate

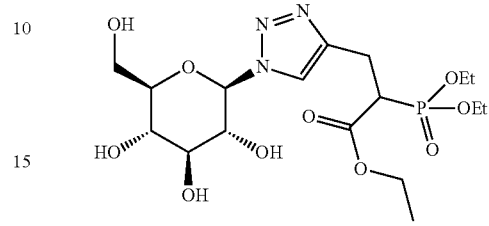

Example 87 was synthesized from 1-azido-1-deoxyglucose and 2-(diethoxyphosphoryl)ethylpent-4-ynoate following the CuAAC procedure described in synthesis method E.

Yield: 48 mg (103 μmol, 70.2%), white solid.

TLC: R$_f$=0.258 (dichloromethane/ethanol, 4:1).

LC/MS (ES-API): m/z=468.26 [M+H]$^+$; calculated: 468.17; t$_R$ (λ=220 nm): 1.04 min (LC/MS—Method 1).

$^1$H-NMR (400 MHz, DMSO-d$_6$): δ=8.05 (s, 1H, NCH), 5.46 (d, J=9.1 Hz, 1H, OH), 5.30 (d, J=6.3 Hz, 1H, OH), 5.24 (d, J=4.7 Hz, 1H, OH), 5.12 (d, J=5.5 Hz, 1H, CH), 4.59 (dd, J=5.3 Hz, 1H, OH), 4.08 (m, 2H, CH$_2$), 3.70 (m, 2H, CH$_2$), 3.43 (m, 4H, 4×CH), 3.00 (m, 1H, CH), 1.25 (m, 6H, 3×CH$_2$), 1.13 (s, 9H, 3×CH$_3$) ppm.

Example 88

(2R,3S,4S,5R,6R)-2-(Hydroxymethyl)-6-[4-[[(4-nitro-2,1,3-benzoxadiazol-7-yl)amino]methyl]triazol-1-yl]tetrahydropyran-3,4,5-triol

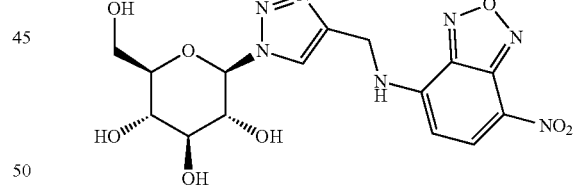

Example 88 was synthesized from 1-azido-1-deoxyglucose and example 63, step 1 following the CuAAC procedure described in synthesis method E.

Yield: 58 mg (138 μmol, 93.7%).

TLC: R$_f$=0.152 (dichloromethane/ethanol, 4:1).

LC/MS (ES-API): m/z=424.13 [M+H]$^+$; calculated: 424.16; t$_R$1 (λ=220 nm): 0.84 min (LC/MS—Method 1).

$^1$H-NMR (400 MHz, DMSO-d$_6$): δ=9.87 (s, 1H, NH), 8.51 (d, J=8.9 Hz, 1H, ArH), 8.35 (s, 1H, NCH), 6.55 (d, J=8.9 Hz, 1H, ArH), 5.50 (d, J=9.3 Hz, 1H, OH), 5.32 (d, J=6.0 Hz, 1H, OH), 5.25 (d, J=4.9 Hz, 1H, OH), 5.12 (d, J=5.5 Hz, 1H, CH), 4.80 (s, 2H, NCH$_2$), 4.60 (dd, J=5.5 Hz, 1H, OH), 3.70 (m, 2H, CH$_2$), 3.43 (m, 2H, 2×CH), 3.19 (m, 1H, CH) ppm.

Example 89

(2R,3R,4S,5S,6R)-2-[4-(Cyclohexylmethyl)triazol-1-yl]-6-(hydroxymethyl)tetrahydropyran-3,4,5-triol

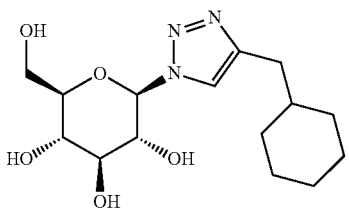 [SMILES: OC[C@H]1O[C@@H](n2cc(CC3CCCCC3)nn2)[C@H](O)[C@@H](O)[C@@H]1O]

Example 89 was synthesized from 1-azido-1-deoxyglucose and prop-2-yn-1-ylcyclohexane following the CuAAC procedure described in synthesis method E.

Yield: 35 mg (107 µmol, 73.1%), white solid.

TLC: $R_f$=0.258 (dichloromethane/ethanol, 4:1).

LC/MS (ES-API): m/z=328.26 [M+H]$^+$; calculated: 328.18; $t_R$ (λ=220 nm): 1.27 min (LC/MS—Method 1).

$^1$H-NMR (400 MHz, DMSO-d$_6$): δ=7.99 (s, 1H, NCH), 5.45 (d, J=9.3 Hz, 1H, OH), 5.30 (d, J=6.0 Hz, 1H, OH), 5.23 (d, J=5.0 Hz, 1H, OH), 5.11 (d, J=5.3 Hz, 1H, CH), 4.59 (dd, J=5.5 Hz, 1H, OH), 3.71 (m, 2H, CH$_2$), 3.42 (m, 2H, 2×CH), 3.22 (m, 2H, 2×CH), 1.66 (m, 6H, 3×CH$_2$), 1.54 (m, 1H, CH), 1.17 (m, 4H, 2×CH$_2$), 0.95 (m, 2H, CH$_2$) ppm.

Example 90

(2R,3R,4S,5S,6R)-2-[4-(3-Chloropropyl)triazol-1-yl]-6-(hydroxymethyl)tetrahydropyran-3,4,5-triol

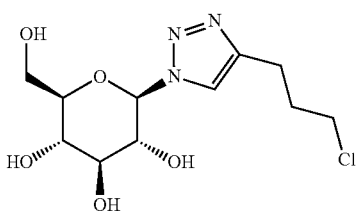 [SMILES: OC[C@H]1O[C@@H](n2cc(CCCCl)nn2)[C@H](O)[C@@H](O)[C@@H]1O]

Example 90 was synthesized from 1-azido-1-deoxyglucose and 5-chloro-pent-1-yne following the CuAAC procedure described in synthesis method E.

Yield: 17 mg (55 µmol, 37.8%), white solid.

TLC: $R_f$=0.288 (dichloromethane/ethanol, 4:1).

LC/MS (ES-API): m/z=308.12 [M+H]$^+$; calculated: 308.09; $t_R$1 (λ=220 nm): 0.62 min (LC/MS—Method 1).

$^1$H-NMR (400 MHz, DMSO-d$_6$): δ=8.09 (s, 1H, NCH), 5.46 (d, J=9.1 Hz, 1H, OH), 5.31 (d, J=6.0 Hz, 1H, OH), 5.25 (d, J=4.7 Hz, 1H, OH), 5.12 (d, J=5.8 Hz, 1H, CH), 4.60 (dd, J=5.2 Hz, 1H, OH), 3.74 (m, 2H, CH$_2$), 3.70 (m, 2H, CH$_2$), 3.39 (m, 2H, 2×CH), 3.22 (m, 2H, 2×CH), 2.77 (m, 2H, CH$_2$), 2.06 (m, 2H, CH$_2$) ppm.

Example 91

[6-(Diethylamino)-9-[2-[[1-[(2R,3R,4S,5S,6R)-3,4,5-trihydroxy-6-(hydroxymethyl)tetrahydropyran-2-yl]triazol-4-yl]methylcarbamoyl]phenyl]xanthen-3-ylidene]-diethyl-ammonium chloride

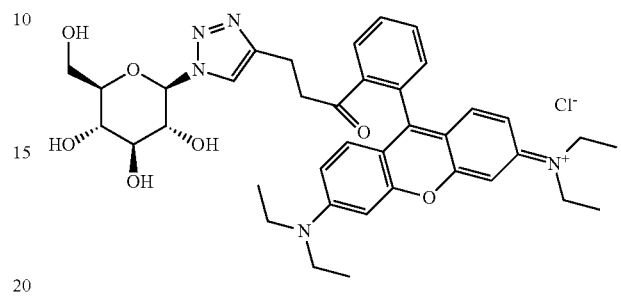

Step 1: [6-(diethylamino)-9-[2-(prop-2-ynylcarbamoyl)phenyl]xanthen-3-ylidene]-diethyl-ammonium chloride

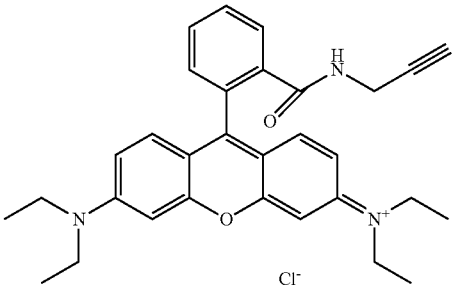 [SMILES: C#CCNC(=O)c1ccccc1-c1c2ccc(=[N+](CC)CC)cc-2oc2cc(N(CC)CC)ccc12 ; [Cl-]]

To a solution of 500 mg (244 µmol) Rhodamin B in 5 mL dimethylformamide were added 78 mg (1.39 mmol; 1.4 eq.) propargylamine, 554 mg (1.98 mmol; 2 eq.) 2-bromo-1-ethylpyridinium tetrafluoroborate, and 348 µl (1.98 mmol; 2 eq.) N,N-diisopropylethylamine. The reaction mixture was stirred at room temperature for 4 hours and evaporated.

Purification: MPLC CombiFlash Rf (Teledyne ISCO); column: RediSep Silica 24 g Gold; flow rate: 40 mL/min; wavelength for detection: 254 nm; eluent: (A) dichloromethane, (B) ethanol.

MPLC Gradient

| start % B | end % B | duration [min] |
| --- | --- | --- |
| 0.0 | 0.0 | 5.0 |
| 0.0 | 100.0 | 45.0 |

Yield: 223 mg (0.432 mmol, 43.6%), light pink solid.

TLC: $R_f$=0.622 (dichloromethane/ethanol, 19:1).

LC/MS (ES-API): m/z=480.28 [M+H]$^+$; calculated: 480.27; $t_R$ (λ=220 nm): 2.08 min (LC/MS—Method 1).

$^1$H-NMR (400 MHz, DMSO-d$_6$): δ=7.80 (m, 1H, ArH), 7.51 (m, 1H, ArH), 7.03 (m, 1H, ArH), 6.35 (m, 6H, ArH), 3.79 (d, J=6.9 Hz, 2H, NCH$_2$), 3.31 (m, 8H, H), 2.65 (m, 8H, CH$_2$), 1.08 (t, J=6.9 Hz, 12H, CH$_3$) ppm.

Step 2: [6-(diethylamino)-9-[2-[[1-[(2R,3R,4S,5S,6R)-3,4,5-trihydroxy-6-(hydroxymethyl)tetrahydropyran-2-yl]triazol-4-yl]methylcarbamoyl]phenyl]xanthen-3-ylidene]-diethyl-ammonium chloride Example 91 was synthesized from 1-azido-1-deoxyglucose and example 91, step 1 following the CuAAC procedure described in synthesis method E.

Yield: 33 mg (67 µmol, 46.7%), white-yellow solid.

TLC: $R_f$=0.485 (dichloromethane/ethanol, 4:1).

LC/MS (ES-API): m/z=686.38 [M+H]$^+$; calculated: 686.33; $t_R$ ($\lambda$=220 nm): 1.67 min (LC/MS—Method 1).

$^1$H-NMR (400 MHz, DMSO-d$_6$): δ=8.09 (s, 1H, NCH), 7.82 (m, 1H, ArH), 7.51 (m, 1H, ArH), 7.08 (m, 1H, ArH), 6.33 (m, 6H, ArH), 5.40 (d, J=9.1 Hz, 1H, OH), 5.24 (d, J=6.0 Hz, 1H, OH), 5.19 (d, J=4.7 Hz, 1H, OH), 5.08 (d, J=5.6 Hz, 1H, CH), 4.63 (dd, J=5.0 Hz, 1H, OH), 3.82 (d, J=6.9 Hz, 2H, NCH$_2$), 3.77 (m, 2H, CH$_2$), 3.69 (m, 2H, CH$_2$), 3.42 (m, 2H, 2×CH), 3.29 (m, 8H, H), 3.18 (m, 2H, 2×CH), 2.73 (m, 2H, CH$_2$), 2.60 (m, 8H, CH$_2$), 2.03 (m, 2H, CH$_2$), 1.05 (t, J=6.9 Hz, 12H, CH$_3$) ppm.

Example 92

(2R,3S,4S,5R,6R)-2-(Hydroxymethyl)-6-[4-[6-[(4-nitro-2,1,3-benzoxadiazol-7-yl)amino]hexyl]triazol-1-yl]tetrahydropyran-3,4,5-triol

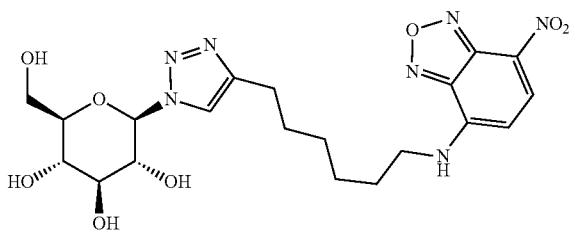 [SMILES: O=[N+]([O-])c1ccc(NCCCCCCc2cn([C@@H]3O[C@H](CO)[C@@H](O)[C@H](O)[C@H]3O)nn2)c2nonc12]

Example 92 was synthesized from 1-azido-1-deoxyglucose and example 67, step 1 following the CuAAC procedure described in synthesis method E.

Yield: 24 mg (48 µmol, 66.6%), orange solid.

TLC: $R_f$=0.310 (dichloromethane/ethanol, 4:1).

LC/MS (ES-API): m/z=494.25 [M+H]$^+$; calculated: 494.19; $t_R$ ($\lambda$=220 nm): 1.34 min (LC/MS—Method 1).

$^1$H-NMR (400 MHz, DMSO-d$_6$): δ=8.48 (d, J=8.6 Hz, 1H, ArH), 8.00 (s, 1H, NCH), 8.14 (d, J=8.6 Hz, 1H, ArH), 5.45 (d, J=9.3 Hz, 1H, OH), 5.29 (d, J=6.1 Hz, 1H, OH), 5.24 (d, J=4.9 Hz, 1H, OH), 5.11 (d, J=5.6 Hz, 1H, CH), 4.58 (dd, J=5.5 Hz, 1H, OH), 3.93 (s, 1H, NCH$_2$), 3.72 (m, 2H, CH$_2$), 3.41 (m, 3H, 3×CH), 3.20 (m, 1H, CH), 1.66 (m, 6H, 3×CH$_2$), 1.41 (m, 4H, 2×CH$_2$) ppm.

Example 93

[(2S,3R,4S,6S)-2,3-Diacetoxy-6-(4-phenylpiperazine-1-carbonyl)tetrahydropyran-4-yl] acetate

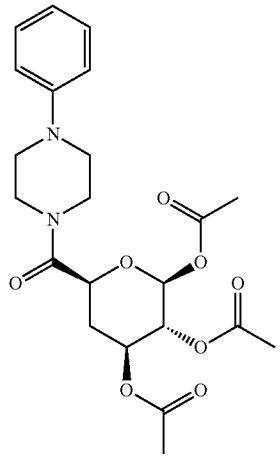 [SMILES: CC(=O)O[C@@H]1O[C@H](C(=O)N2CCN(c3ccccc3)CC2)C[C@H](OC(C)=O)[C@H]1OC(C)=O]

A suspension of 7 mg (0.1 eq.) Pd/C (10%) in 3 mL dry methanol (argon atmosphere) was overlayed with hydrogen and stirred at room temperature for 30 minutes. A solution of 30 mg example 41, step 1 in 2 mL dry methanol was added. The reaction mixture was stirred at room temperature for 3 hours and filtered over celite.

Purification: MPLC CombiFlash Rf (Teledyne ISCO); column: RediSep Silica 4 g; flow rate: 12 mL/min; wavelength for detection: 220 nm; eluent: (A) dichloromethane, (B) ethanol.

MPLC Gradient

| start % B | end % B | duration [min] |
| --- | --- | --- |
| 0 | 0 | 4.0 |
| 0 | 5.0 | 3.0 |
| 5.0 | 5.0 | 10.0 |

Yield: 19 mg (42.37 µmol, 63.0%), orange oil.

LC/MS (ES-API): m/z=449.10 [M+H]$^+$; calculated: 449.18; $t_R$ ($\lambda$=220 nm): 0.79 min (LC/MS—Method 1).

$^1$H-NMR (400 MHz, CDCl$_3$): δ=7.28 (m, 2H, ArH), 6.92 (m, 3H, ArH), 5.55 (d, J=7.9 Hz, 1H, CH), 5.13 (d, J=5.2 Hz, 1H, CH), 5.08 (d, J=7.7 Hz, 1H, CH), 4.36 (dd, J=1.7 Hz, J=11.6 Hz 1H, CH), 3.99 (m, 1H, NCH$_2$), 3.82 (m, 1H, NCH$_2$), 3.54 (m, 2H, NCH$_2$), 3.28 (m, 2H, NCH$_2$), 3.03 (m, 2H, NCH$_2$), 2.32 (ddd, J=2.4 Hz, 1H, CH$_2$), 2.17 (pseudo-q, J=11.6 Hz, 1H, CH$_2$), 2.11 (s, 3H, CH$_3$), 2.06 (s, 6H, 2×CH$_3$) ppm.

Example 94 (4-Phenylpiperazin-1-yl)-[(2S,4S,5R)-4,5,6-trihydroxytetrahydropyran-2-yl]methanone

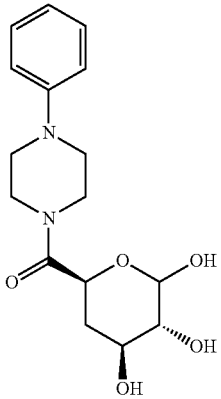 [SMILES: O=C([C@@H]1C[C@H](O)[C@@H](O)C(O)O1)N1CCN(c2ccccc2)CC1]

To a solution of 10 mg example 93 in 1 mL methanol 4 µl of a 5.4 M aqueous sodium methoxide solution were added. The reaction mixture was agitated at room temperature for 10 minutes and controlled by TLC and LC/MS. The reaction mixture was quenched and evaporated Yield: 4 mg (12.41 µmol, 55.6%), orange oil.
LC/MS (ES-API): m/z=323.05 [M+H]$^+$; calculated: 323.15; $t_R$ (ELSD): 0.11 min (LC/MS—Method 1).
$^1$H-NMR (400 MHz, MeOD): δ=7.14 (t, J=8.0 Hz, 2H, ArH), 6.88 (d, J=8.0 Hz, 2H, ArH), 6.76 (t, J=7.0 Hz, 1H, ArH), 5.12 (d, J=3.6 Hz, 1H, OH), 4.78 (dd, J=2.0 Hz, 1H, OH), 4.42 (d, J=7.6 Hz, 1H, OH), 4.33 (dd, J=2.0 Hz, 1H, OH), 3.6-4.0 (m, 4H, 4×CH), 3.4-3.0 (m, 8H, 4×NCH$_2$), 1.94 (dd, J=4.7 Hz, 1H, CH$_2$), 1.91 (qi, J=12.2 Hz, 1H, CH$_2$) ppm.

Example 95

1-[[(3aR,5R,5aS,8aS,8bR)-2,2,7,7-Tetramethyl-5,5a,8a,8b-tetrahydro-3aH-di[1,3]dioxolo[4,5-a:4',5'-c]pyran-5-yl]methyl]-4-(4-benzyloxyphenyl)piperazine

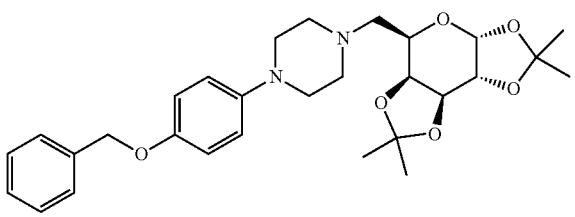 [SMILES: CC1(C)O[C@H]2[C@@H](O1)[C@@H](CN1CCN(c3ccc(OCc4ccccc4)cc3)CC1)O[C@@H]1OC(C)(C)O[C@@H]12]

To a solution of (3aR,5S,5aR,8aS,8bR)-2,2,7,7-tetramethyl-5,5a,8a,8b-tetrahydro-3aH-di[1,3]dioxolo[4,5-a:4',5'-c]pyran-5-carbaldehyde (300 mg, 1.16 mmol, 1 eq.), 1-(4-(benzyloxy)phenyl)piperazine (374 mg, 1.39 mmol, 1.2 eq.), and acetic acid (132 µl, 2.32 mmol, 2 eq.) in methanol was added sodium borohydride (147 mg, 2.32 mmol, 2 eq.). The reaction mixture was agitated overnight at room temperature and evaporated. The residue was separated between ethylacetate and a saturated solution of NaHCO$_3$. The aqueous phase was extracted twice with ethylacetate. The organic phase was dried with MgSO$_4$, evaporated in vacuo, and purified by flash chromatography on silica gel (100% heptane till 100% ethylacetate in 40 minutes).

Yield: 394 mg (771 µmol, 66%), oil.
LC/MS (ES-API): m/z=511.2 [M+H]+; calculated: 511.6; $t_R$ (λ=220 nm): 0.77 min (LC/MS—Method 2).
$^1$H-NMR (400 MHz, DMSO-d$_6$): δ=7.44-7.28 (m, 5H), 6.86 (s, 4H), 5.45 (d, 1H, J=5.1 Hz), 5.01 (s, 2H), 4.57 (dd, 1H, J=7.9, 2.2 Hz), 4.31 (dd, 1H, J=5.1, 2.34 Hz), 4.21 (dd, 1H, J=7.9, 1.6 Hz), 2.98 (t, 4H, J=4.9 Hz), 2.65-2.57 (m, 3H), 2.42 (dd, 1H, J=12.7, 7.0 Hz), 1.45 (m, 3H), 1.35 (m, 1H), 1.28 (m, 1H) ppm.

Example 96

(3R,4S,5R,6R)-6-[[4-(4-Benzyloxyphenyl)piperazin-1-yl]methyl]tetrahydropyran-2,3,4,5-tetrol

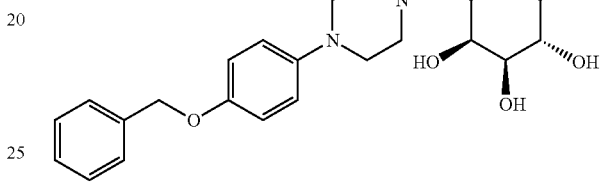

Method F
A solution of isopropylidene compounds (1 eq.) in trifluoroacetic acid/water (4/1, v/v) was agitated at room temperature for 2 hours, evaporated under vacuo, and lyophilised.

Example 96 was obtained from example 95 following the isopropylidene deprotection described in synthesis method F.

Yield: 21 mg (38.4 µmol, quant.).
LC/MS (ES-API): m/z=431.1 [M+H]$^+$; calculated: 431.2; $t_R$ (λ=220 nm): 0.620 min (LC/MS—Method 2).
$^1$H-NMR (400 MHz, MeOD): δ=7.33 (s, 1H), 7.31 (s, 1H), 7.26 (t, 2H, J=7.1 Hz), 7.22-7.17 (m, 1H), 6.87 (q, 4H, J=6.87 Hz), 5.13 (d, 0.9H), 4.93 (s, 3H), 4.43 (d, 0.5H, J=6.6 Hz), 4.37 (d, 0.5H, J=9.6 Hz), 3.95 (d, 0.7H, J=8.4 Hz), 3.76 (s, 1H), 3.74-3.66 (m, 2H), 3.56-3.38 (m, 4H), 3.31 (s, 1H), 3.28 (s, 1H), 3.26 (s, 1H), 3.22 (s, 2H) ppm. Mixture of diastereoisomers.

Example 97

4-[4-[[(3aR,5R,5aS,8aS,8bR)-2,2,7,7-Tetramethyl-5,5a,8a,8b-tetrahydro-3aH-di[1,3]dioxolo[4,5-a:4',5'-c]pyran-5-yl]methyl]piperazin-1-yl]phenol

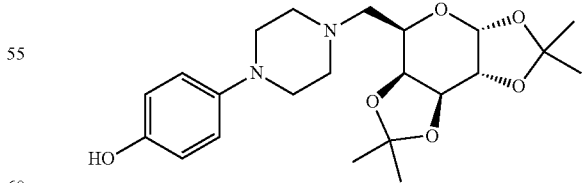

To a solution of example 95 (395 mg, 77 µmol, 1 eq.) in methanol (3 mL) under argon was added Pd/C (8.3 mg, 77 µmol, 0.1 eq.). The reaction mixture was purged with a flux of hydrogen. The reaction mixture was agitated at room temperature for 1 hour. The reaction mixture was filtrated on celite, rinse with methanol, and evaporated in vacuo.

Yield: 366 mg (870 μmol, quant.).

LC/MS (ES-API): m/z=421.1 [M+H]+; calculated: 421.5; $t_R$ (λ=220 nm): 0.60 min (LC/MS—Method 2).

$^1$H-NMR (400 MHz, DMSO-$d_6$): δ=6.72 (d, 2H, J=8.7 Hz), 6.62 (d, 2H, J=8.7 Hz), 5.42 (d, 1H, J=5.1 Hz), 4.53 (dd, 1H, J=7.8, 2.3 Hz), 4.26-4.18 (m, 2H), 3.93-3.86 (m, 1H), 2.94 (t, 4H, J=5.0 Hz), 2.69-2.49 (m, 4H), 1.50 (s, 3H), 1.35 (s, 3H), 1.28 (s, 6H) ppm.

Example 98

(2S,3R,4S,5R,6R)-6-[[4-(4-Hydroxyphenyl)piperazin-1-yl]methyl]tetrahydropyran-2,3,4,5-tetrol

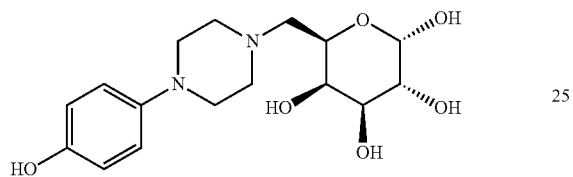

Example 98 was obtained from example 97 following the isopropylidene deprotection described in synthesis method F.

Yield: 31 mg (55 μmol, 93%), oil.

LC/MS (ES-API): m/z=341.2 [M+H]$^+$; calculated: 341.2; $t_R$=0.07 min (LC/MS—Method 2).

$^1$H-NMR (400 MHz, MeOD): δ=6.8 (d, 2H, J=9.0 Hz), 6.64 (d, 2H, J=9.0 Hz), 5.12 (d, 1H, J=3.6 Hz), 4.40 (dd, 1H, J=5.8, 1.3 Hz), 4.35 (dd, 1H, J=10.0, 2.5 Hz), 3.95-3.90 (m, 1H), 3.77-3.69 (m, 4H), 3.56-3.46 (m, 4H), 3.43-3.40 (m, 2H), 3.31-3.23 (m, 3H) ppm. Mixture of diastereoisomers.

Example 99

1-[[(3aR,5R,5aS,8aS,8bR)-2,2,7,7-Tetramethyl-5,5a,8a,8b-tetrahydro-3aH-di[1,3]dioxolo[4,5-a:4',5'-c]pyran-5-yl]methyl]-4-[4-[2-[2-(2-prop-2-ynoxyethoxy)ethoxy]ethoxy]phenyl]piperazine

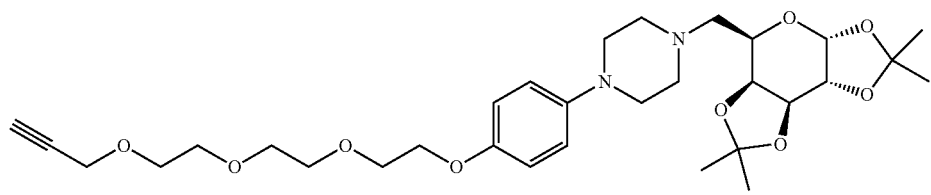 [SMILES: C#CCOCCOCCOCCOc1ccc(N2CCN(C[C@H]3O[C@@H]4OC(C)(C)O[C@@H]4[C@H]4OC(C)(C)O[C@H]43)CC2)cc1]

Step 1: 2-[2-(2-prop-2-ynoxyethoxy)ethoxy]ethyl 4-methylbenzenesulfonate

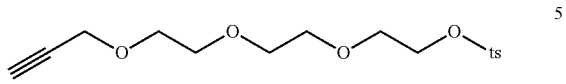

To a solution of 2-(2-(2-(prop-2-yn-1-yloxy)ethoxy)ethoxy)ethanol (50 mg, 266 μmol, 1 eq.) in pyridine (2 mL) were added N,N,N',N'-tetramethyl-1,6-diaminohexane (5.8 μl, 27 μmol, 0.1 eq.) and 4-methylbenzene-1-sulfonyl chloride (76 mg, 398 μmol, 1.5 eq.). The reaction mixture was agitated at room temperature for 2 hours. The reaction mixture was evaporated in vacuo.

Purification: flash chromatography on silica gel (100% heptane till 100% ethylacetate in 30 minutes).

Yield: 62 mg (181 μmol, 68%).

LC/MS (ES-API): m/z=343.1 [M+H]$^+$; calculated: 343.4; t$_R$ (λ=220 nm): 0.804 min (LC/MS—Method 2).

$^1$H-NMR (400 MHz, DMSO-d$_6$): δ=7.78 (d, 2H, J=8.5 Hz), 7.48 (d, 2H, J=8.5 Hz), 4.15-4.08 (m, 4H), 3.61-3.47 (m, 10H), 3.41 (t, 1H, J=2.5 Hz), 2.42 (s, 3H) ppm.

Step 2: 1-[[(3aR,5R,5aS,8aS,8bR)-2,2,7,7-Tetramethyl-5,5a,8a,8b-tetrahydro-3aH-di[1,3]dioxolo[4,5-a:4',5'-c]pyran-5-yl]methyl]-4-[4-[2-[2-(2-prop-2-ynoxyethoxy)ethoxy]ethoxy]phenyl]piperazine A solution of example 99, step 1 (41 mg, 120 μmol, 1.2 eq.), example 97 (42 mg, 100 μmol, 1 eq.), and Cs$_2$CO$_3$ (130 mg, 400 μmol, 4 eq.) in dimethylformamide (1 mL) under argon was irradiated in the microwave for 10 minutes at 70° C. and 40 minutes at 80° C. The crude mixture was diluted with ethylacetate. The organic phase was washed with a saturated solution of NaHCO$_3$, water, dried with MgSO$_4$, and evaporated in vacuo.

Purification: flash chromatography on silica gel (dichloromethane till dichloromethane/methanol 9/1 in 30 minutes).

Yield: 16 mg (27 μmol, 27%).

LC/MS (ES-API): m/z=591.3 [M+H]$^+$; calculated: 591.3; t$_R$ (λ=220 nm): 0.70 min (LC/MS—Method 2).

$^1$H-NMR (400 MHz, DMSO-d$_6$): δ=6.89-6.81 (m, 4H), 5.57 (d, 1H, J=5.1 Hz), 4.60 (dd, 1H, J=7.8, 2.3 Hz), 4.31 (dd, 1H, J=5.1, 2.3 Hz), 4.25-4.19 (m, 4H), 4.07 (t, 2H, J=5.1 Hz), 4.02-3.96 (m, 1H), 3.82 (t, 2H, J=5.1 Hz), 3.75-3.66 (m, 10H), 3.11 (t, 4H, J=4.5 Hz), 2.80-2.58 (m, 6H), 2.43-2.40 (m, 1H), 2.08 (s, 1H), 1.73 (s, 1H), 1.54 (s, 3H), 1.46 (s, 3H), 1.34 (s, 3H), 1.33 (s, 3H) ppm.

Example 100

(3R,4S,5R,6R)-6-[[4-[4-[2-[2-(2-Prop-2-ynoxyethoxy)ethoxy]ethoxy]phenyl]piperazin-1-yl]methyl]tetrahydropyran-2,3,4,5-tetrol

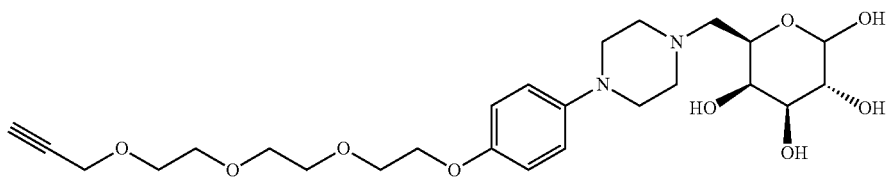 [SMILES: C#CCOCCOCCOCCOc1ccc(N2CCN(C[C@H]3OC(O)[C@H](O)[C@@H](O)[C@H]3O)CC2)cc1]

Example 100 was obtained from example 99 following the isopropylidene deprotection described in synthesis method F.

Yield: 18 mg (28 µmol, quant).

LC/MS (ES-API): m/z=511.2 [M+H]$^+$; calculated: 511.3; $t_R$ (λ=220 nm): 0.552 min (LC/MS—Method 2).

$^1$H-NMR (400 MHz, MeOD): δ=6.99 (d, 2H, J=8.9 Hz), 6.91 (d, 2H, J=8.78 Hz), 5.23 (d, 0.6H, J=3.5 Hz), 4.52 (d, 0.5H, J=6.0 Hz), 4.47 (d, 0.6H, J=10.0 Hz), 4.23-4.16 (m, 3.2H), 4.11-4.02 (m, 2H), 3.88-3.75 (m, 5H), 3.73-3.59 (m, 15H), 3.57-3.49 (m, 1.4H), 3.08 (sl, 2H), 2.84 (s, 1.2H) ppm. Mixture of diastereoisomers.

Example 101

1-[[(3aR,5R,5aS,8aS,8bR)-2,2,7,7-Tetramethyl-5,5a, 8a,8b-tetrahydro-3aH-di[1,3]dioxolo[4,5-a:4',5'-c] pyran-5-yl]methyl]-4-(4-chlorophenyl)piperazine

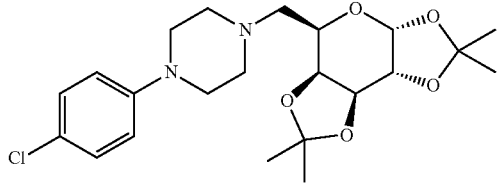 [SMILES: CC1(C)O[C@H]2[C@@H](O1)[C@@H](CN1CCN(c3ccc(Cl)cc3)CC1)O[C@@H]1OC(C)(C)O[C@@H]12]

To a solution of (3aR,5S,5aR,8aS,8bR)-2,2,7,7-tetramethyl-5,5a,8a,8b-tetrahydro-3aH-di[1,3]dioxolo[4,5-a:4',5'-c]pyran-5-carbaldehyde (50 mg, 194 µmol, 1 eq.), 1-(4-chlorophenyl)piperazine (114 mg, 581 µmol, 3 eq.), and acetic acid (22 µl, 387 µmol, 2 eq.) in methanol was added sodium cyanoboronhydride (25 mg, 387 µmol, 2 eq.). The reaction mixture was agitated overnight at room temperature and evaporated in vacuo. The crude mixture was separated between ethylacetate and a saturated solution of NaHCO$_3$. The aqueous phase was extracted twice with ethylacetate. The organic phase was dried with MgSO$_4$ and evaporated.

Purification: flash chromatography on silica gel (100% heptane till 100% ethylacetate in 40 minutes).

Yield: 63 mg (144 µmol, 74%), oil.

LC/MS (ES-API): m/z=439.2 [M+H]$^+$; calculated: 439.9; $t_R$ (λ=220 nm): 0.713 min (LC/MS—Method 2).

$^1$H-NMR (400 MHz, DMSO-d$_6$): δ=7.21 (d, 2H, J=8.9 Hz), 6.93 (d, 2H, J=8.9 Hz), 5.45 (d, 1H, J=5.1 Hz), 4.58 (dd, 1H, J=7.9, 2.4 Hz), 4.32 (dd, 1H, J=5.2, 2.3 Hz), 4.21 (dd, 1H, J=7.9, 1.7 Hz), 3.90-3.85 (m, 1H), 3.10 (t, 4H, J=4.9 Hz), 2.65-2.57 (m, 4H), 2.43 (dd, 2H, J=13.0, 7.1 Hz), 1.45 (s, 3H), 1.35 (s, 3H), 1.28 (s, 6H) ppm.

Example 102

(3R,4S,5R,6R)-6-[[4-(4-Chlorophenyl)piperazin-1-yl]methyl]tetrahydropyran-2,3,4,5-tetrol

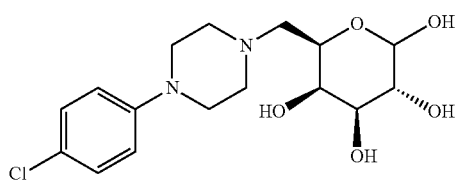 [SMILES: OC1O[C@H](CN2CCN(c3ccc(Cl)cc3)CC2)[C@H](O)[C@H](O)[C@H]1O]

Example 102 was obtained from example 101 following the isopropylidene deprotection described in synthesis method F.

Yield: 78 mg (133 µmol, 95%).

LC/MS (ES-API): m/z=359.1 [M+H]$^+$; calculated: 359.1; $t_R$ (λ=220 nm): 0.493 min (LC/MS—Method 2).

$^1$H-NMR (400 MHz, MeOD): δ=7.27 (d, 2H, J=8.5 Hz), 7.01 (d, 2H, J=8.5 Hz). 5.24 (d, 0.5H, J=3.0 Hz), 4.55 (d, 0.5H, J=6.7 Hz), 4.48 (d, 0.5H, J=9.8 Hz), 4.07 (d, 0.5H, J=9.2 Hz), 3.90-3.76 (m, 2H), 3.66-3.30 (m, 9H) ppm. Mixture of diastereoisomers.

Example 103

N-[2-[2-[2-[[(3aR,5R,5aS,8aS,8bR)-2,2,7,7-Tetramethyl-5,5a,8a,8b-tetrahydro-3aH-di[1,3]dioxolo[4,5-a:4',5'-c]pyran-5-yl]methylamino]ethoxy]ethoxy]ethyl]pent-4-ynamide

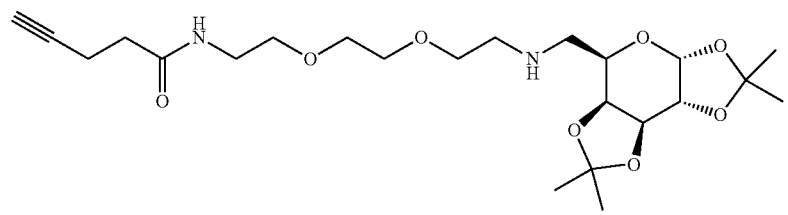 [SMILES: C#CCCC(=O)NCCOCCOCCNC[C@H]1O[C@@H]2OC(C)(C)O[C@@H]2[C@H]2OC(C)(C)O[C@H]21]

Step 1: tert-butyl N-[2-[2-[2-(pent-4-ynoylamino)ethoxy]ethoxy]ethyl]carbamate

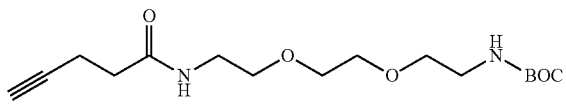 [SMILES: C#CCCC(=O)NCCOCCOCCNC(=O)OC(C)(C)C]

To a solution of pent-4-ynoic acid (43.5 mg, 442 µmol, 1.1 eq.) and tert-butyl (2-(2-(2-aminoethoxy)ethoxy)ethyl)carbamate (100 mg, 402 µmol, 1 eq.) in dimethylformamide (3 mL) was added N,N-diisopropylethylamine (77 µl, 443 µmol, 1.1 eq.), HOBt (67.8 mg, 443 µmol, 1.1 eq.) and N-(3-dimethylaminopropyl)-N'-ethylcarbodiimide (84.9 mg, 443 µmol, 1.1 eq.). The reaction mixture was agitated overnight at room temperature. The crude mixture was diluted with ethylacetate, washed with 0.5 N aqueous HCl, a saturated solution of NaHCO$_3$, and brine, dried with MgSO$_4$, and concentrated in vacuo.

Purification: flash chromatography on silica gel (100% heptane till 100% ethylacetate in 20 minutes, 100% ethylacetate for 10 minutes)

Yield: 99 mg (301 µmol, 75%).

LC/MS (ES-API): m/z=351.2 [M+Na]$^+$; calculated: 351.4; t$_R$: 0.675 min (LC/MS—Method 2).

$^1$H-NMR (400 MHz, DMSO-d$_6$): δ=3.49 (s, 4H), 3.41-3.34 (m, 4H), 3.19 (q, 2H, J=5.8 Hz), 3.05 (q, 2H, J=5.8 Hz), 2.89 (s, 2H), 2.73 (s, 2H), 2.37-2.31 (m, 2H), 2.28-2.24 (m, 2H), 1.90 (s, 1H), 1.37 (s, 9H) ppm.

Step 2: N-[2-[2-(2-aminoethoxy)ethoxy]ethyl]pent-4-ynamide

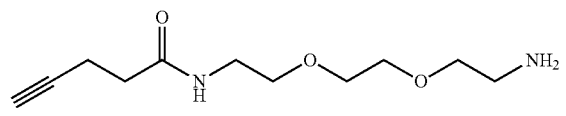 [SMILES: C#CCCC(=O)NCCOCCOCCN]

A solution of example 103, step 1 (98 mg, 298 µmol, 1 eq.) in trifluoroacetic acid/dichloromethane (1/1, v/v, 1 mL) was agitated at room temperature for 30 minutes. The reaction mixture was evaporated under vacuo and lyophilised.

Yield: 108 mg (315 µmol, quant).

LC/MS (ES-API): m/z=229.2 [M+H]$^+$; calculated: 229.1; t$_R$: 0.123 min (LC/MS—Method 2).

$^1$H-NMR (400 MHz, MeOD): δ=3.72 (t, 2H, J=4.9 Hz), 3.67 (s, 4H), 3.58 (t, 2H, J=5.5 Hz), 3.40 (t, 2H, J=5.5 Hz), 3.15 (t, 2H, J=4.8 Hz), 2.51-2.45 (m, 2H), 4.44-2.39 (m, 2H), 2.28 (s, 1H) ppm.

Step 3: N-[2-[2-[2-[[(3aR,5R,5aS,8aS,8bR)-2,2,7,7-tetramethyl-5,5a,8a,8b-tetrahydro-3aH-di[1,3]dioxolo[4,5-a:4',5'-c]pyran-5-yl]methylamino]ethoxy]ethoxy]ethyl]pent-4-ynamide A solution of (3aR,5S,5aR,8aS,8bR)-2,2,7,7-tetramethyl-5,5a,8a,8b-tetrahydro-3aH-di[1,3]dioxolo[4,5-a:4',5'-c]pyran-5-carbaldehyde (41.5 mg, 160 µmol, 1 eq.), example 103, step 2 (55 mg, 160 µmol, 1 eq.), and triethylamine (44.8 µl, 321 µmol, 2 eq.) in methanol (3 mL) containing 4 Å molecular sieves was agitated overnight at room temperature. Sodium borohydride (12 mg, 321 µmol, 2 eq.) was added to the reaction mixture. The reaction mixture was agitated at room temperature for 2 hours. A 1 N aqueous solution of sodium hydride was added. The reaction mixture was extracted with ether (three times). The organic phase was dried with MgSO$_4$ and evaporated in vacuo.

Purification: flash chromatography on silica gel (dichloromethane till dichloromethane/methanol 9/1 in 30 minutes).

Yield: 21.4 mg (45.5 µmol, 28%), oil.

LC/MS (ES-API): m/z=471.2 [M+H]$^+$; calculated: 471.5; t$_R$ (λ=220 nm): 0.615 min (LC/MS—Method 2).

$^1$H-NMR (400 MHz, MeOD): δ=6.70 (t, 1H, J=5.2 Hz), 6.21 (s, 1H), 5.72 (d, 1H, J=7.9 Hz), 5.31 (t, 1H, J=9.3 Hz), 5.20 (t, 1H, J=9.3 Hz), 5.11 (t, 1H, J=8.5 Hz), 4.07 (d, 1H, J=9.8 Hz), 3.62 (s, 5H), 3.59-3.53 (m, 5H), 3.52-3.46 (m, 4H), 3.40-3.31 (m, 1H) ppm.

Example 104

N-[2-[2-[2-[[(3R,4S,5R)-3,4,5,6-Tetrahydroxytetrahydropyran-2-yl]methylamino]ethoxy]ethoxy]ethyl]pent-4-ynamide

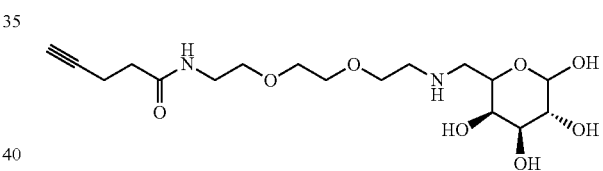

Example 104 was obtained from example 103 following the isopropylidene deprotection described in synthesis method F.

Yield: 17.3 mg (44 µmol, quant).

LC/MS (ES-API): m/z=391.1 [M/5+H]$^+$; calculated: 391.4; t$_R$ (λ=220 nm): 0.07 min (LC/MS—Method 2).

Example 105

[(2S,3R,4S,5S)-2,3,5-Triacetoxy-6-[2-[2-[2-(pent-4-ynoylamino)ethoxy]ethoxy]ethylcarbamoyl]tetrahydropyran-4-yl] acetate

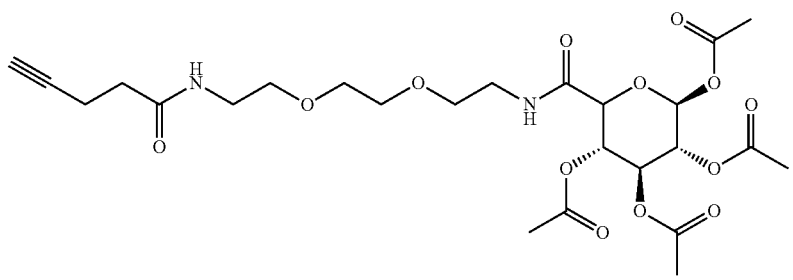 [SMILES: C#CCCC(=O)NCCOCCOCCNC(=O)C1O[C@@H](OC(C)=O)[C@H](OC(C)=O)[C@@H](OC(C)=O)[C@@H]1OC(C)=O]

To a solution of (2R,3S,4S,5R)-2,3,4,5-tetraacetoxycyclohexanecarboxylic acid (101 mg, 280 μmol, 1.2 eq.) in dimethylformamide (3 mL) was added HATU (106.7 mg, 280 μmol, 1.2 eq.) and 4 Å molecular sieves. After 5 minutes example 103, step 2 (80 mg, 233 μmol, 1 eq.) was added. The reaction mixture was agitated at room temperature for 72 hours. The reaction mixture was diluted with ethylacetate. The organic phase was washed with 1N aqueous HCl, saturated NaHCO$_3$, and brine, dried with MgSO$_4$, filtered, and evaporated in vacuo.

Purification: flash chromatography on silica gel (dichloromethane till dichloromethane/methanol 9/1 in 30 minutes)

Yield: 74.45 mg (130 μmol, 56%), oil.

LC/MS (ES-API): m/z=513.2 [M-OAc]$^+$; calculated: 513.6; t$_R$ (λ=220 nm): 0.652 min (LC/MS—Method 2).

$^1$H-NMR (400 MHz, DMSO-d$_6$): δ=8.15 (t, 1H, J=5.6 Hz), 7.93 (t, 1H, J=5.6 Hz), 5.96 (d, 1H, J=8.3 Hz), 5.43 (t, 1H, J=9.8 Hz), 5.08 (t, 1H, J=9.8 hz), 4.98 (dd, 1H, J=9.8, 8.4 Hz), 4.30 (s, 1H, J=9.8 Hz), 3.49 (s, 4H), 3.38 (q, 4H, J=6.0 Hz), 3.24-3.13 (m, 4H), 2.73 (t, 1H, J=2.6 Hz), 2.37-2.31 (m, 2H), 2.30-2.24 (m, 2H), 2.07 (s, 3H), 2.00 (s, 3H), 1.95 (s, 3H), 1.93 (s, 3H) ppm.

Example 106

(3S,4S,5R)-3,4,5,6-Tetrahydroxy-N-[2-[2-[2-(pent-4-ynoylamino)ethoxy]ethoxy]ethyl]tetrahydropyran-2-carboxamide

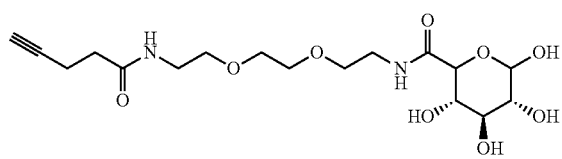 [SMILES: C#CCCC(=O)NCCOCCOCCNC(=O)C1OC(O)[C@H](O)[C@@H](O)[C@@H]1O]

Method G

To a solution of the tetraacetate derivative (1 eq.) in methanol/water/THF (5/4/1, v/v/v) at 0° C. was added a solution of an aqueous 1 N lithium hydroxide solution (1 eq.). The reaction mixture was agitated 15 minutes at 0° C., quenched with a 1 N aqueous solution of HCl, evaporated, and lyophilised.

Example 106 was obtained from example 105 using acetyl deprotection method G.

Yield: 62.2 mg (153 μmol, quant).

LC/MS (ES-API): m/z=405.2 [M+H]$^+$; calculated: 404.4; t$_R$ (λ=324 nm): 0.087 min (LC/MS—Method 2).

$^1$H-NMR (400 MHz, DMSO-d$_6$): δ=6.77 (d, 0.5H, J=6.7 Hz), 6.47 (d, 0.5H, J=4.6 Hz), 4.98-4.92 (m, 2H), 4.90 (d, 0.5H, J=4.3 Hz), 4.77 (d, 0.5H, J=4.9 Hz), 4.57 (d, 0.5H, J=6.3 Hz), 4.32 (t, 0.5H, J=7.4 Hz), 3.95 (t, 0.5H, J=10 Hz), 3.50 (d, 4H, J=2.7 Hz), 3.49-3.37 (m, 4H), 3.26-3.09 (m, 6H), 2.98-2.91 (m, 0.5H), 2.74 (t, 1H, J=2.6 Hz), 2.37-2.32 (m, 2H), 2.99-2.45 (m, 2H) ppm. Mixture of diastereoisomers.

Example 107

N-[[(3aR,5aS,8aS,8bR)-2,2,7,7-Tetramethyl-5,5a,8a,8b-tetrahydro-3aH-di[1,3]dioxolo[4,5-a:4',5'-c]pyran-5-yl]methyl]oct-7-yn-1-amine

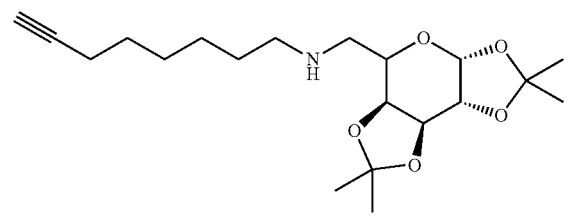 [SMILES: C#CCCCCCCNCC1O[C@@H]2OC(C)(C)O[C@@H]2[C@H]2OC(C)(C)O[C@@H]12]

A solution of (3aR,5S,5aR,8aS,8bR)-2,2,7,7-tetramethyl-5,5a,8a,8b-tetrahydro-3aH-di[1,3]dioxolo[4,5-a:4',5'-c]pyran-5-carbaldehyde (50 mg, 174 μmol, 1 eq.), oct-7-yn-1-amine hydrochloride (31 mg, 192 μmol, 1.1 eq.), and triethylamine (27 μl, 192 μmol, 1.1 eq.) in methanol (1 mL) was agitated at room temperature for 3 hours. The reaction mixture was cooled to 0° C. and sodium boronhydride (13 mg, 348 μmol, 2 eq.) was added. The reaction mixture was agitated at 0° C. for one hour. A 1 N aqueous solution of sodium hydroxide was added. The aqueous phase was extracted with ether (three times), dried over MgSO$_4$, filtered, and evaporated in vacuo.

Purification: flash chromatography on silica gel (dichloromethane till dichloromethane/methanol 9/1 in 30 min).

Yield: 29 mg (79 μmol, 45%), oil.

LC/MS (ES-API): m/z=368.4 [M+H]$^+$; calculated: 368.5; t$_R$: 0.684 min (LC/MS—Method 2).

$^1$H-NMR (400 MHz, DMSO-d$_6$): δ=5.43 (d, 1H, J=5.2 Hz), 4.55 (dd, 1H, J=7.7, 2.3 Hz), 4.44-4.39 (m, 0.3H), 4.30 (dd, 1H, J=5.1, 2.3 Hz), 4.20 (dd, 1H, J=7, 7, 1.7 Hz), 3.74 (td, 1H, J=6.5, 1.5 Hz), 3.40-3.37 (m, 0.7H), 2.72 (t, 0.6H, J=2.8 Hz), 2.68-2.65 (m, 0.3H), 2.63-2.58 (m, 0.9H), 1.7 (t, 0.8H, J=2.5 Hz), 1.48-1.22 (m, 20.6H) ppm.

Example 108

(3R,4S,5R)-6-[(Oct-7-ynylamino)methyl]tetrahydropyran-2,3,4,5-tetrol

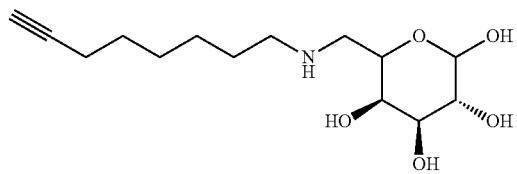 [SMILES: C#CCCCCCCNCC1OC(O)[C@H](O)[C@@H](O)[C@H]1O]

Example 108 was obtained from example 107 following the isopropylidene deprotection described in synthesis method F.

Yield: 32 mg (80 μmol, quant).

LC/MS (ES-API): m/z=288.2 [M+H]$^+$; calculated: 288.2; t$_R$=0.648 min (LC/MS—Method 3).

$^1$H-NMR (400 MHz, DMSO-d$_6$): δ=6.71 (d, 0.5H, J=7.5 Hz), 6.38 (d, 0.5H, J=4.6 Hz), 5.00 (t, 0.5H, J=4.0 Hz), 4.91-4.79 (m, 2H), 4.71 (s, 0.5H), 4.51 (s, 0.5H), 4.29 (t, 0.5H, J=6.8 Hz), 4.12-4.07 (m, 0.5H), 3.70-3.65 (m, 1H), 3.63-3.51 (m, 1.5H), 3.19-3.00 (m, 2H), 2.95-2.83 (m, 2H), 2.75 (t, 0.5H, J=2.6 Hz), 2.19-2.07 (m, 2H), 1.72 (t, 1H, J=2.6 Hz), 1.64-1.52 (m, 2H), 1.48-1.52 (m, 6H) ppm. Mixture of diastereoisomers.

Example 109

[(2S,3R,4S,5S)-2,3,5-Triacetoxy-6-(oct-7-ynylcarbamoyl)tetrahydropyran-4-yl]acetate

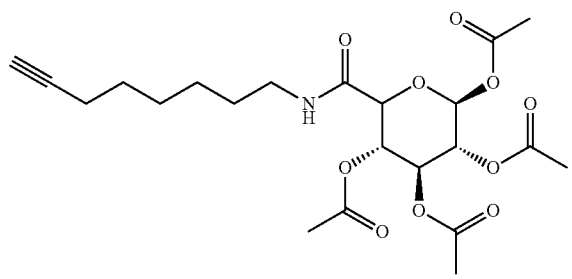 [SMILES: C#CCCCCCCNC(=O)C1O[C@@H](OC(C)=O)[C@H](OC(C)=O)[C@@H](OC(C)=O)[C@@H]1OC(C)=O]

To a solution of (2R,3S,4S,5R)-2,3,4,5-tetraacetoxycyclohexanecarboxylic acid (20 mg, 55 µmol, 1 eq.) in dimethylformamide (2 mL) with 4 Å molecular sieves was added HATU (29.4 mg, 77 µmol, 1.4 eq.) followed by oct-7-yn-1-amine hydrochloride (26.8 mg, 166 µmol, 3 eq.) in 0.5 mL dimethylformamide. The reaction mixture was agitated overnight at room temperature and evaporated in vacuo.

Purification: flash chromatography on silica gel, (heptane till ethyl acetate in 20 min, 100% ethyl acetate for 20 min).

Yield: 25.5 mg (54 µmol, 98%), white solid.

LC/MS (ES-API): m/z=492.1 [M+H]$^+$; calculated: 492.5; $t_R$=0.851 min (LC/MS—Method 2).

$^1$H-NMR (400 MHz, CDCl$_3$): δ=6.29 (t, 1H, J=4.9 Hz), 5.76 (d, 1H, J=8.0 Hz), 5.30 (t, 1H, J=9.4 Hz), 5.19 (t, 1H J=9.4 Hz), 5.11 (td, 1H, J=8.0, 1.5 Hz), 4.05 (d, 1H, J=9.4 Hz), 3.30-3.13 (m, 2H), 2.28 (td, 1H, J=7.0, 2.6 Hz), 2.14 (s, 3H), 2.07 (s, 3H), 2.04 (s, 3H), 2.03 (s, 3H), 1.95 (t, 1H, J=2.6 Hz), 1.78 (t, 1H, J=2.3 Hz), 1.58-1.22 (m, 8H) ppm.

Example 110

(3S,4S,5R)-3,4,5,6-Tetrahydroxy-N-oct-7-ynyl-tetrahydropyran-2-carboxamide

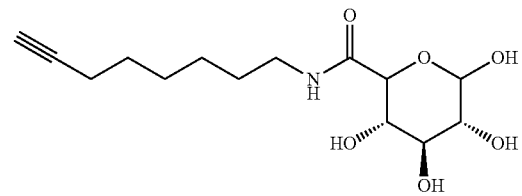 [SMILES: C#CCCCCCCNC(=O)C1OC(O)[C@H](O)[C@@H](O)[C@@H]1O]

Example 110 was obtained from example 109 using acetyl deprotection method G.

Yield: 17 mg (49 µmol, 91%), orange oil.

LC/MS (ES-API): m/z=302.1 [M+H]$^+$; calculated: 302.1; $t_R$ (λ=220 nm): 0.831 min (LC/MS—Method 3).

$^1$H-NMR (400 MHz, MeOD): δ=5.19 (s, 0.5H), 4.55 (d, 0.5H, J=7.5 Hz), 4.17 (d, 0.7H, J=9.9 Hz), 3.71 (t, 1H, J=9.0H), 3.58 (s, 0.3H), 3.51-3.39 (m, 1.7H), 3.27-3.18 (m, 3H), 2.18 (s, 3H), 2.12 (s, 1.1H), 1.92 (s, 0.9H), 1.74 (s, 1.4H), 1.59-1.29 (m, 6H) ppm. Mixture of diastereoisomers.

Example 111

N-[6-[1-(4-(Human Insulin-B29Lys-amino)-4-oxobutyl)triazol-4-yl]hexyl]-(3S,4S,5R)-3,4,5,6-tetrahydroxy-tetrahydropyran-2-carboxamide

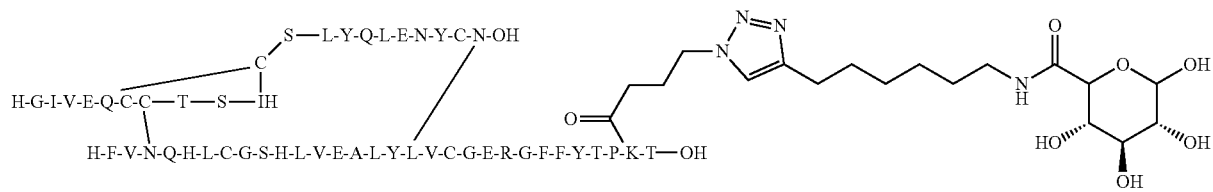

Step 1: 4-azido-butan-(human Insulin-B29Lys)-amide

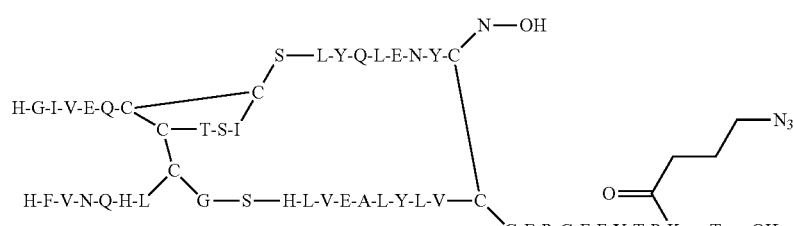

To a solution of human insulin (300 mg, 51 µmol, 1 eq.) in dimethylformamide/water (½, v/v, 9 mL) was added triethylamine (144 µl, 1.03 mmol, 20 eq.) to get to pH=10.

The reaction mixture was cooled to 0° C. A solution of 2,5-dioxopyrrolidin-1-yl 4-azidobutenoate (12.9 mg, 56 µmol, 1.1 eq.) in dimethylformamide (1 mL) was added dropwise to the reaction mixture at 0° C. over 10 minutes. The reaction mixture was agitated 2 hours, quenched with 1 N aqueous HCl till pH=3, and lyophilized.

Purification: AEKTA avant 25 (GE Healthcare), HPLC; column: Kinetex Prep-$C_{18}$ column (5 µm, 250×21.1 mm, Phenomenex, volume 87 mL); wavelength for detection: 280 nm; eluent: (A) water+0.5% acetic acid, (B) 60/40 acetonitrile/water+0.5% acetic acid.

HPLC Gradient:

| start % B | end % B | Flow rate [cm/h] | Flow rate [mL/min] | Column volume |
|---|---|---|---|---|
| 0 | 0 | 80 | 4.7 | 2.0 |
| 0 | 100 | 105 | 6.2 | 14.0 |
| 100 | 100 | 105 | 6.2 | 2.0 |

Yield: 146.5 mg (24.75 µmol, 48%), white powder.

LC/MS (ES-API): m/z=1184.6 [M/5+H]$^+$; calculated: 1184.7; $t_R$ (λ=215 nm): 4.30 min (LC/MS—Method 4).

Step 2: N-[6-[1-(4-(human Insulin-B29Lys-amino)-4-oxo-butyl)triazol-4-yl]hexyl]-3,4,5,6-tetrahydroxy-tetrahydropyran-2-carboxamide Method H To a solution of the alkynes (1.2 eq.) and example 111, step 1 (1 eq.) in dimethylformamide and water was added a mixture of the click reagents premixed in this order: $CuSO_4 \cdot 5H_2O$ (0.5 eq.), THPTA (0.8 eq.), and sodium ascorbate (1 eq.). The reaction mixture was agitated at room temperature for 2 hours. The reaction mixture was lyophilised. Purification was done on reverse phase chromatography.

Example 111, step 2 was obtained from example 111, step 1 and example 110 following the click chemistry procedure described in synthesis method H.

Purification and HPLC gradient like in example 111, step 1.

Yield: 2.9 mg (0.46 µmol, 18%), white powder.

LC/MS (ES-API): m/z=1244.9 [M/5+H]$^+$; calculated: 1245.0; $t_R$ (λ=215 nm): 3.95 min (LC/MS—Method 4).

Example 112

4-[4-[3-Oxo-3-[2-[2-[2-[[(3R,4S,5R)-3,4,5,6-tetrahydroxytetrahydropyran-2-yl]methylamino]ethoxy]ethoxy]ethylamino]propyl]triazol-1-yl]butan-(human Insulin-B29Lys)-amide

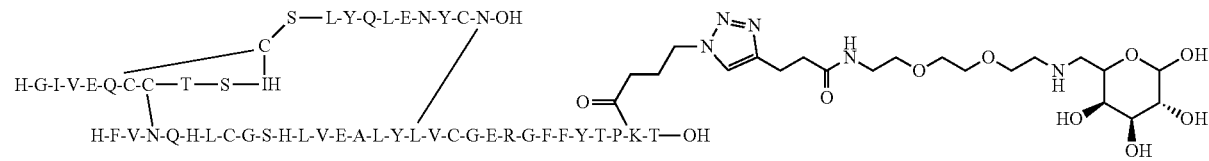

Example 112 was obtained from example 111, step 1 and example 114 following the click chemistry procedure described in synthesis method H.

Purification and HPLC gradient like in example 111, step 1.

Yield: 1.37 mg (0.22 µmol, 11%), white powder.

LC/MS (ES-API): m/z=1262.7 [M/5+H]$^+$; calculated: 1262.8; $t_R$ (λ=215 nm): 3.75 min (LC/MS—Method 4).

Example 113

4-[4-[6-[[(3R,4S,5R)-3,4,5,6-Tetrahydroxytetrahydropyran-2-yl]methylamino]hexyl]triazol-1-yl]butan-(human Insulin-B29Lys)-amide

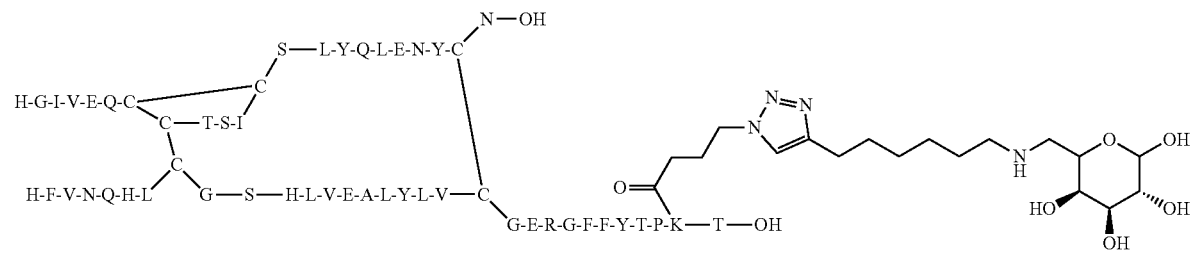

Example 113 was obtained from example 111, step 1 and example 108 following the click chemistry procedure described in synthesis method H.

Purification and HPLC gradient like in example 111, step 1.

Yield: 4.36 mg (0.70 μmol, 35%), white powder.

LC/MS (ES-API): m/z=1242.0 [M/5+H]$^+$; calculated: 1242.2; $t_R$ (λ=215 nm): 3.77 min (LC/MS—Method 4).

Example 114

(3S,4S,5R)—N-[2-[2-[2-[3-[1-(4-(Human insulin-B29Lys)-4-oxo-butyl)triazol-4-yl]propanoylamino]ethoxy]ethoxy]ethyl]-3,4,5,6-tetrahydroxy-tetrahydropyran-2-carboxamide

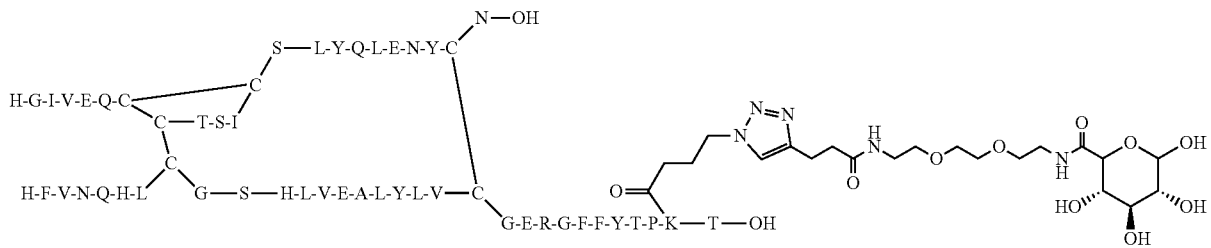

Example 114 was obtained from example 111, step 1 and example 106 following the click chemistry procedure described in synthesis method H.

Purification and HPLC gradient like in example 111, step 1.

Yield: 3.74 mg (0.59 μmol, 29%), white powder.

LC/MS (ES-API): m/z=1265.4[M/5+H]$^+$; calculated: 1265.6; $t_R$ (λ=215 nm): 3.87 min (LC/MS—Method 4).

Example 115

4-[4-[2-[2-[2-[4-[4-[[(3R,4S,5R)-3,4,5,6-Tetrahydroxytetrahydropyran-2-yl]methyl]piperazin-1-yl]phenoxy]ethoxy]ethoxy]ethoxymethyl]triazol-1-yl]butan-(human Insulin-B29Lys)-amide

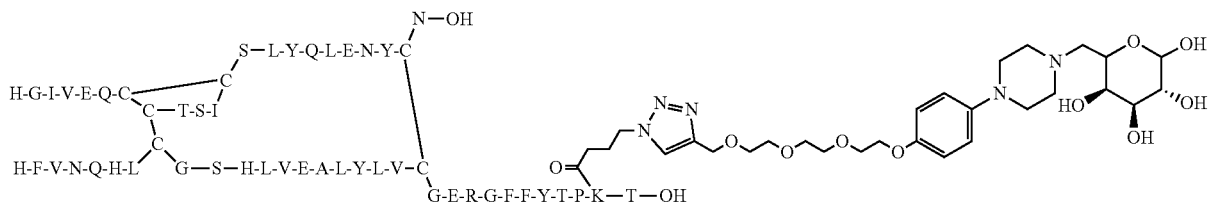

Example 115 was obtained from example 111, step 1 and example 100 following the click chemistry procedure described in synthesis method H.

Purification and HPLC gradient like in example 111, step 1.

Yield: 15.2 mg (2.36 μmol, 28%), white powder.

LC/MS (ES-API): m/z=1072.3 [M/6+H]$^+$; calculated: 1072.5; $t_R$ (λ=215 nm): 3.81 min.

Example 116

Methy-6-O-p-toluylsulfonyl-β-D-glucopyranoside

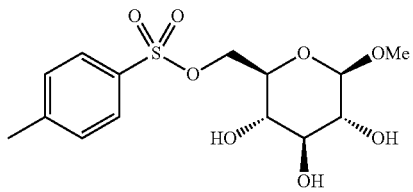 [SMILES: CO[C@@H]1O[C@H](COS(=O)(=O)c2ccc(C)cc2)[C@@H](O)[C@H](O)[C@H]1O]

To a solution of methyl-ß-D-glucopyranoside (15 g, 77.3 mmol) in pyridine (50 mL) a solution of toluenesulfonyl-chloride (19.1 g, 100.5 mmol) in $CH_2Cl_2$ (50 mL) was added dropwise at 0° C. The mixture was then left for 16 h at 8° C. Methanol (200 mL) was added to the reaction and the solvents evaporated under reduced pressure. The residue was purified by column chromatography on silica gel (10:1 $CH_2Cl_2$/MeOH) to give the product as a white solid Yield: 13.1 g (49%).

LC-Mass Method: Mobile phase: A=2.5 mM TFA/H2O, B=2.5 mM TFA/MeCN; Gradient: B=10%-95% in 1 min; Flow rate: 1.5 mL/min; Column: Xbridge-C18, 30×4.6 mm, 2.5 um.). LC purity: 92% (214 nm);

Mass: find peak 370.8 (M+Na)+ at 1.60 min.

$^1$H NMR (400 MHz, DMSO-d6) δ 7.79 (d, J=8.0 Hz, 2H), 7.50 (d, J=8.0 Hz, 2H), 5.23 (d, J=5.6 Hz 1H), 5.13 (d, J=5.2 Hz, 1H), 5.00 (d, J=5.2 Hz, 1H), 4.20 (dd, J=10.4 Hz, 2.0 Hz, 1H), 4.06-4.02 (m, 2H), 3.36-3.34 (m, 1H), 3.30 (s, 3H), 3.12-3.07 (m, 1H), 3.01-2.95 (m, 1H), 2.93-2.87 (m, 1H), 2.43 (s, 3H).

Example 117

Methyl-6-O-(3-phenoxyphenylcarbonyl)-β-glucopyranoside

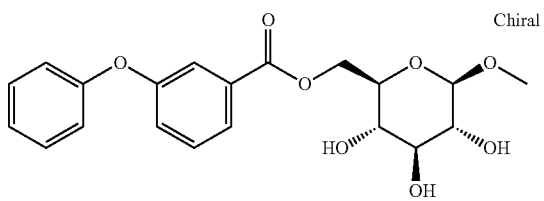 [SMILES: CO[C@@H]1O[C@H](COC(=O)c2cccc(Oc3ccccc3)c2)[C@@H](O)[C@H](O)[C@H]1O]

Sodium hydride (17.22 mg, 430.58 μmol) was added to a solution of 3-phenoxybenzoic acid (92.24 mg, 430.58 μmol) in DMF (4 mL) at 0° C. under argon atmosphere. The reaction mixture was stirred for about 30 min and methyl-6-O-p-toluenesulfonyl-β-D-glucopyranoside 116 (100 mg, 287.05 μmol) was added and the reaction stirred for 16 h at 80° C. The solvent was evaporated under reduced pressure in vacuo and the residue extracted with $CH_2Cl_2$/$H_2O$ (3×). The organic layer was dried, the solvents evaporated and the product purified by HPLC.

Yield: 53 mg (47%)

LC/MS (ES-API): m/z=435.20 [M−H+formic acid]−; calculated: 435.16, tR (λ=220 nm): 1.6 min (LC/MS—Method 2)

$^1$H NMR (400.23 MHz, DMSO-d6) δ ppm 7.72 (d, J=7.48 Hz, 1H), 7.56 (t, J=7.95, 7.95 Hz, 1H), 7.44 (m, 3H), 7.33 (ddd, J=8.19, 2.57, 0.86 Hz, 1H), 7.21 (t, J=7.18, 7.18 Hz, 1H), 7.08 (d, J=7.84 Hz, 2H), 5.15 (br s, 1H), 4.55 (dd, J=11.68, 2.02 Hz, 1H), 4.26 (dd, J=11.74, 6.48 Hz, 1H), 4.08 (d, J=7.82 Hz, 1H), 3.46 (br s, 2H), 3.43 (u), 3.29 (s, 5H), 3.17 (m, 3H), 2.97 (m, 1H).

Example 118

Methyl-6-O-(4-phenoxyphenylcarbonyl)-β-glucopyranoside

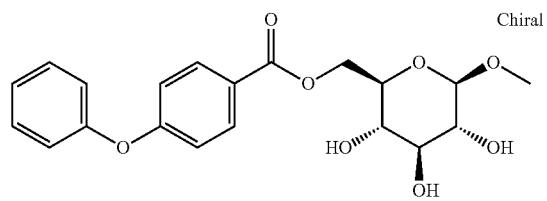 [SMILES: CO[C@@H]1O[C@H](COC(=O)c2ccc(Oc3ccccc3)cc2)[C@@H](O)[C@H](O)[C@H]1O]

Methyl-6-O-(4-phenoxyphenylcarbonyl)-β-D-glucopyranoside was synthesized as described for example 117 from Methyl-6-O-p-toluylsulfonyl-β-D-glucopyranoside (116) (100 mg, 287.05 μmol) and 4-phenoxybenzoic acid (92.24 mg, 430.58 μmol).

Yield: 49 mg (43.7%)

LC/MS (ES-API): m/z=435.22 [M−H+formic acid]−; calculated: 435.16, tR (λ=220 nm): 1.6 min (LC/MS—Method 2)

$^1$H NMR (400.23 MHz, DMSO-d6) δ ppm 7.97 (m(para), 2H), 7.46 (t, J=7.56, 7.56 Hz, 2H), 7.25 (m, 1H), 7.13 (d, J=7.83 Hz, 2H), 7.08 (m(para), 2H), 4.54 (dd, J=11.80, 1.90 Hz, 1H), 4.29 (dd, J=11.80, 6.17 Hz, 1H), 4.11 (d, J=7.82 Hz, 1H), 3.47 (m, 4H), 3.20 (m, 6H), 2.99 (m, 2H), 2.50 (u), 2.33 (m, 1H)

Example 119

Methyl-6-O-(2-Methyl-4-phenoxyphenylcarbonyl)-β-D-glucopyranoside

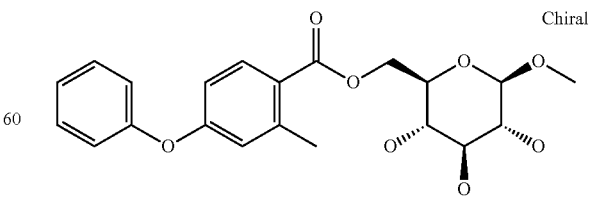

Methyl-6-O-(2-Methyl-4-phenoxyphenylcarbonyl)-β-D-glucopyranoside was synthesized as described for example 117 from Methyl-6-O-p-toluylsulfonyl-β-D-glucopyranoside (116; 100 mg, 287.05 µmol) and 2-Methyl-4-phenoxybenzoic acid (98.28 mg, 430.58 µmol)

Yield: 46 mg (39.6%)

LC/MS (ES-API): m/z=499.17 [M−H+formic acid]⁻; calculated: 449.18, tR (λ=220 nm): 1.63 min (LC/MS—Method 2)

Example 120

Methyl-6-O-(3-chloro-3'-methoxy-4-phenoxyphenylcarbonyl)-β-D-glucopyranoside

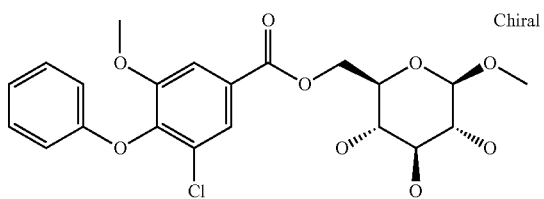 [SMILES: COc1cc(C(=O)OC[C@H]2O[C@@H](OC)[C@H](O)[C@@H](O)[C@@H]2O)cc(Cl)c1Oc1ccccc1]

Methyl-6-O-(3-chloro-3'-methoxy-4-phenoxyphenylcarbonyl)-β-D-glucopyranoside was synthesized as described for example 117 from Methyl-6-O-p-toluylsulfonyl-β-D-glucopyranoside (116; 100 mg, 287.05 µmol) and 3-Chloro-3'-methoxy-4-phenoxybenzoic acid (120 mg, 430.58 µmol).

Yield: 43 mg (32.9%)

LC/MS (ES-API): m/z=499.17 [M−H+formic acid]⁻; calculated: 499.13, tR (λ=220 nm): 1.64 min (LC/MS—Method 2)

Example 121

Methyl-6-O-(3-methoxy-4-phenoxyphenylcarbonyl)-β-D-glucopyranoside

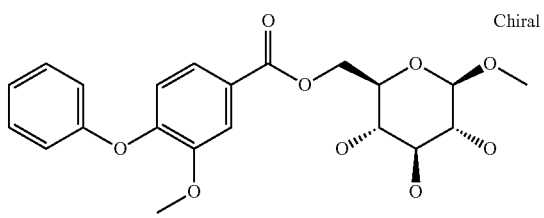 [SMILES: COc1cc(C(=O)OC[C@H]2O[C@@H](OC)[C@H](O)[C@@H](O)[C@@H]2O)ccc1Oc1ccccc1]

Methyl-6-O-(3-methoxy-4-phenoxyphenylcarbonyl)-β-D-glucopyranoside was synthesized as described for example 117 from Methyl-6-O-p-toluylsulfonyl-β-D-glucopyranoside (116; 100 mg, 287.05 µmol) and 3-Methoxy-4-phenoxybenzoic acid (105.17 mg, 430.58 mmol).

Yield: 58 mg (48.1%)

LC/MS (ES-API): m/z=465.14 [M−H+formic acid]⁻; calculated: 465.17, tR (λ=220 nm): 1.53 min (LC/MS—Method 2)

¹H NMR (400.23 MHz, DMSO-d6) δ ppm 7.64 (d, J=1.96 Hz, 1H), 7.59 (dd, J=8.31, 1.96 Hz, 1H), 7.37 (t, J=7.64, 7.64 Hz, 2H), 7.13 (t, J=7.13, 7.13 Hz, 1H), 7.04 (d, J=8.44 Hz, 1H), 6.96 (d, J=7.84 Hz, 2H), 5.24 (d, J=5.01 Hz, 1H), 5.11 (d, J=4.89 Hz, 1H), 5.05 (d, J=4.03 Hz, 1H), 4.59 (dd, J=11.74, 1.96 Hz, 1H), 4.29 (dd, J=11.74, 6.48 Hz, 1H), 4.12 (d, J=7.70 Hz, 1H), 3.83 (s, 3H), 3.47 (u), 3.20 (m, 3H), 3.00 (m, 1H).

Example 122

Methyl-6-O-(1-benzyl-3-bromo-2-oxo-1,2-dihydropyridinyl-4-carbonyl)-β-D-glucopyranoside

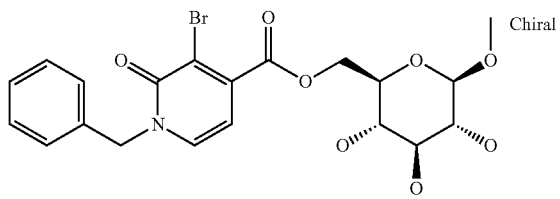 [SMILES: CO[C@@H]1O[C@H](COC(=O)c2ccn(Cc3ccccc3)c(=O)c2Br)[C@@H](O)[C@H](O)[C@H]1O]

Methyl-6-O-(1-benzyl-3-bromo-2-oxo-1,2-dihydropyridinyl-4-carbonyl)-β-D-glucopyranoside was synthesized as described for example 117 from Methyl-6-O-p-toluylsulfonyl-β-D-glucopyranoside (116; 100 mg, 287.05 µmol) and 1-benzyl-3-bromo-2-oxo-1,2-dihydropyridine-4-carboxylate (400 mg, 649.07 µmol).

Yield: 8 mg

LC/MS (ES-API): m/z=484.09 [M+H]⁺; calculated: 484.06, tR (λ=220 nm): 1.33 min (LC/MS—Method 2)

Example 123

Methyl-2-O-(3-methoxy-4-phenoxyphenylcarbonyl)-α-D-glucopyranoside

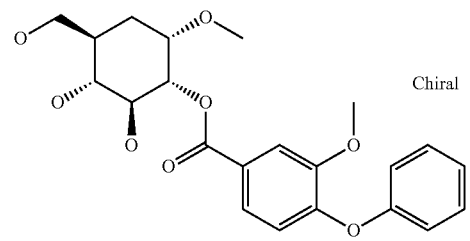 [SMILES: COc1cc(C(=O)O[C@@H]2[C@@H](O)[C@H](O)[C@@H](CO)C[C@@H]2OC)ccc1Oc1ccccc1]

Methyl-2-O-(3-methoxy-4-phenoxyphenylcarbonyl)-α-D-glucopyranoside was synthesized according to a method described by Muramatsu and Takemoto from Methyl-α-D-glucopyranoside and 3-Methoxy-4-phenoxybenzoic acid. 3-Methoxy-4-phenoxybenzoic acid (182.27 mg, 669.47 µmol) is suspended in $CH_2Cl_2$ (3 mL) under Argon atmosphere. 1-Chloro-N,N,2-trimethylpropenylamine (88.57 µl, 669.47 µmol) is added and the reaction mixture stirred for 20 min at 20° C. to yield the corresponding carboxylic acid chloride.

A solution of Methyl-α-D-glucopyranoside (97.05 mg, 257.49 µmol) and Dibutyltinndichloride (16.47 mg, 51.50 µmol) in THF (3 mL) is stirred for 15 min. Tetrabutylammoniumiodide (97.05 mg, 257.49 µmol) and Diisopropylethylamine (DIPEA; 113.85 µl, 669.47 µmol) are added. Subsequently the solution of 3-Methoxy-4-phenoxybenzoic acid chloride in $CH_2Cl_2$ is added, the reaction mixture stirred for 2 h and left for 18 h at 20° C.

The reaction is quenched with NH4Cl-solution and the product extracted with EtOAc (3×5 mL). The product is finally purified by HPLC and freeze dried.

Yield: 55 mg (25.4%)

LC/MS (ES-API): m/z=465.0 [M−H+formic acid]⁻ [M+H tR (λ=220 nm): 1.73 min (LC/MS—Method 2)

¹H NMR (400.23 MHz, DMSO-d6) δ ppm 7.66 (m, 1H), 7.62 (d, J=1.83 Hz, 1H), 7.37 (m, 2H), 7.13 (m, 1H), 7.06 (d, J=8.46 Hz, 1H), 6.95 (d, J=7.82 Hz, 2H), 4.88 (d, J=3.67 Hz, 1H), 4.64 (dd, J=9.96, 3.61 Hz, 1H), 3.84 (s, 3H), 3.78 (m, 1H), 3.69 (br d, J=10.15 Hz, 1H), 3.52 (br dd, J=11.80, 5.56 Hz, 2H), 3.44 (u), 3.28 (s, 5H), 3.25 (m, 1H), 2.50 (u), 2.33 (s, 1H)

Example 124

Methyl-2-O-(3-chloro-3'-methoxy-4-phenoxyphenylcarbonyl)-α-D-glucopyranoside

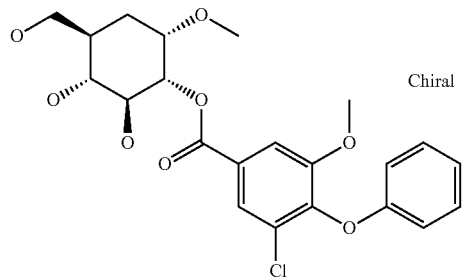 [SMILES: COc1cc(C(=O)O[C@@H]2[C@@H](O)[C@H](O)[C@@H](CO)C[C@@H]2OC)cc(Cl)c1Oc1ccccc1]

Methyl-2-O-(3-chloro-3'-methoxy-4-phenoxyphenylcarbonyl)-α-D-glucopyranoside was synthesized as described for example 123 from Methyl-α-D-glucopyranoside (100 mg, 514.98 μmol) and 3-Chloro-3'-methoxy-4-phenoxybenzoic acid (124.24 mg, 669.47 μmol).

Yield: 124 mg (50%)

LC/MS (ES-API): m/z=499.0 [M−H+formic acid]⁻ tR (λ=220 nm): 1.94 min (LC/MS—Method 2)

¹H NMR (400.23 MHz, DMSO-d6) δ ppm 7.80 (d, J=1.83 Hz, 1H), 7.67 (d, J=1.71 Hz, 1H), 7.31 (t, J=8.01, 8.01 Hz, 2H), 7.05 (t, J=7.40, 7.40 Hz, 1H), 6.82 (d, J=7.95 Hz, 2H), 5.42 (br s, 1H), 5.22 (br s, 1H), 4.91 (d, J=3.55 Hz, 1H), 4.63 (m, 1H), 3.82 (s, 3H), 3.79 (m, 1H), 3.69 (br d, J=10.27 Hz, 1H), 3.53 (dd, J=11.80, 5.56 Hz, 1H), 3.44 (u), 3.29 (s, 5H), 3.27 (m, 1H), 3.20 (br s, 1H), 2.33 (s, 1H)

Synthesis of Allyl-6-O-toluenesulfonyl-β-D-glucopyranoside

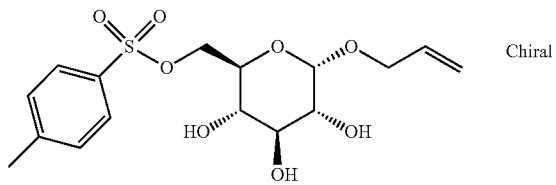 [SMILES: C=CCO[C@H]1O[C@H](COS(=O)(=O)c2ccc(C)cc2)[C@@H](O)[C@H](O)[C@H]1O]

Allyl-6-O-toluenesulfonyl-β-D-glucopyranoside was synthesized according to a published procedure [R. Brisco et al., Carb. Res. 348 (2012), 27-32] starting from commercially available allyl-β-D-glucopyranoside.

To a solution of allyl-β-D-glucopyranoside (1 g, 4.54 mmol) in pyridine (30 mL) was added p-toluenesulfonyl-chloride ((1.47 g, 7.72 mmol) at 0° C. The reaction mixture was stirred for 30 min and then stored at 0° C. for 16 h. The reaction was controlled by TLC (9:1, CH₂Cl₂/MeOH) proving consumption of starting material. The reaction mixture was quenched with MeOH and the solvents were removed under reduced pressure. The Product was purified by flash chromatography (EtOAc/MeOH, 9:1).

Yield: 850 mg (51%)

Example 125

Allyl-6-O-(3-phenoxyphenylcarbonyl)-β-glucopyranoside

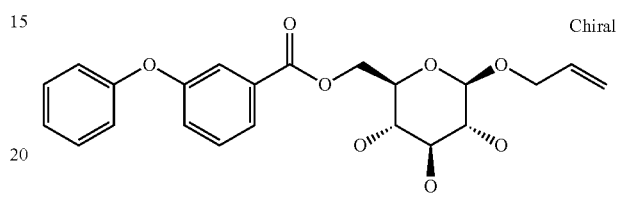

Allyl-6-O-(3-phenoxyphenylcarbonyl)-β-D-glucopyranoside was synthesized from allyl-6-O-toluenesulfonyl-β-D-glucopyranoside (200 mg, 534.18 μmol) and 3-phenoxyphenylcarboxylic acid (171.65 mg, 801.27 μmol) as described for example 117.

Yield: 113 mg (50.8%)

LC/MS (ES-API): m/z=461.25 [M−H+formic acid]⁻; calculated: 461.18 tR (λ=220 nm): 1.69 min (LC/MS—Method 2)

¹H NMR (400.23 MHz, DMSO-d6) δ ppm 7.73 (d, J=7.44 Hz, 1H), 7.57 (t, J=7.95, 7.95 Hz, 1H), 7.48 (s, 1H), 7.43 (t, J=7.27, 7.27 Hz, 2H), 7.33 (ddd, J=8.19, 2.57, 0.98 Hz, 1H), 7.20 (m, 1H), 7.07 (d, J=7.78 Hz, 2H), 5.85 (m, 1H), 5.23 (m, 2H), 5.09 (m, 3H), 4.54 (dd, J=11.74, 1.96 Hz, 1H), 4.28 (dd, J=11.74, 6.60 Hz, 1H), 4.16 (m, 2H), 3.98 (m, 1H), 3.44 (u), 3.17 (m, 2H), 3.01 (td, J=8.34, 8.34, 4.95 Hz, 1H).

Example 126

Allyl-6-O-(4-phenoxyphenylcarbonyl)-β-glucopyranoside

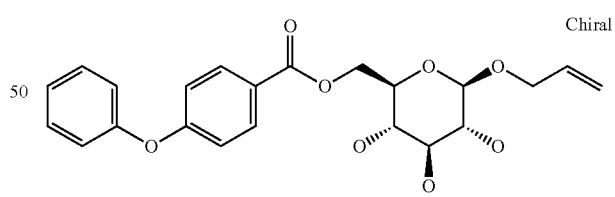

Allyl-6-O-(4-phenoxyphenylcarbonyl)-3-D-glucopyranoside was synthesized from allyl-6-O-toluenesulfonyl-β-D-glucopyranoside (200 mg, 534.18 μmol) and 3-phenoxyphenylcarboxylic acid (171.65 mg, 801.27 μmol) as described for example 117.

Yield: 116 mg (52.1%)

LC/MS (ES-API): m/z=461.20 [M−H+formic acid]⁻; calculated: 461.18 tR (λ=220 nm): 1.70 min (LC/MS—Method 2)

¹H NMR (400.23 MHz, DMSO-d6) δ ppm 7.98 (m(para), 2H), 7.46 (t, J=7.26, 7.26 Hz, 2H), 7.25 (t, J=7.47, 7.47 Hz, 1H), 7.13 (d, J=7.84 Hz, 2H), 7.08 (m(para), 2H), 5.87 (m, 1H), 5.26 (m, 2H), 5.09 (br dd, J=10.39, 1.83 Hz, 2H), 4.53 (dd, J=11.74, 1.96 Hz, 1H), 4.22 (m, 3H), 4.02 (m, 1H), 3.46 (u), 3.20 (m, 4H), 3.03 (m, 1H).

Synthesis of Trimethylsilylethoxy-6-O-tosyl-β-D-glucopyranoside

LCMS Conditions:
LCMS-Condition 01: Method:—LCMS_X-Select (Formic Acid)
Column: X-Select CSH C18 (4.6*50) mm 2.5 u, Mobile Phase: A.0.1% Formic acid in water B. 0.1% Formic acid in Acetonitrile Inj Volume; 5.0 μL, Flow Rate: 1.0 mL/minute, Gradient program: 2% B to 98% B in 2.8 minute, Hold till 4.8 min, At 5.0 min B conc is 2% up to 7.0 min.
ELSD Conditions:
ELSD-Condition 01: Method:—LCMS_X-Bridge (NH$_3$)
Column: X-Bridge C18 (4.6*50) mm 3.5μ; Mobile Phase: A. 0.05% NH3 in water. B: 0.05% NH3 in Acetonitrile Inj Volume; 0.2 μL, Flow Rate: 1.200 mL/minute; Gradient program: 2% B to 100% B in 3.5 minute, Hold till 4.5 min, At 4.7 min B conc is 2% up to 6.0 min.

Step-1: Synthesis of (2R,3R,4S,5R,6R)-6-(acetoxymethyl)tetrahydro-2H-pyran-2,3,4,5-tetrayl tetraacetate (2)

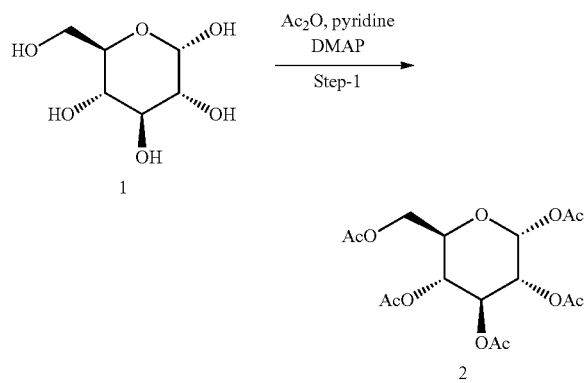

To (2S,3R,4S,5S,6R)-6-(hydroxymethyl)tetrahydro-2H-pyran-2,3,4,5-tetraol 1 (50 g, 277.7 mmol) in pyridine (500 mL) at 0° C. was added DMAP (339 mg, 2.777 mmol) and acetic anhydride (500 mL). The reaction mixture was further stirred at room temperature for 20 h. After completion of the reaction, the pyridine was evaporated under reduced pressure and the residue was diluted with water and extracted with CH$_2$Cl$_2$ (thrice). The combined organic layer was dried over anhydrous Na$_2$SO$_4$, filtered and concentrated under reduced pressure. The crude compound was purified by trituration with n-hexane to afford 100 g (92% yield) of compound 2 as off white solid.
ELSD-Condition-1: [M+H]$^+$=408.00; Rt=2.88 min
$^1$H NMR (400 MHz, CDCl$_3$) δ: 6.33 (d, J=3.91 Hz, 1H), 5.47 (t, J=10.03 Hz, 1H), 5.07-5.17 (m, 2H), 4.24-4.29 (m, 1H), 4.08-4.15 (m, 2H), 2.18 (s, 3H), 2.09 (s, 3H), 2.04 (s, 3H), 2.03 (s, 3H), 2.02 (s, 3H).

Step-2: Synthesis of (2R,3R,4S,5R,6R)-2-(acetoxymethyl)-6-bromotetrahydro-2H-pyran-3,4,5-triyl triacetate (3)

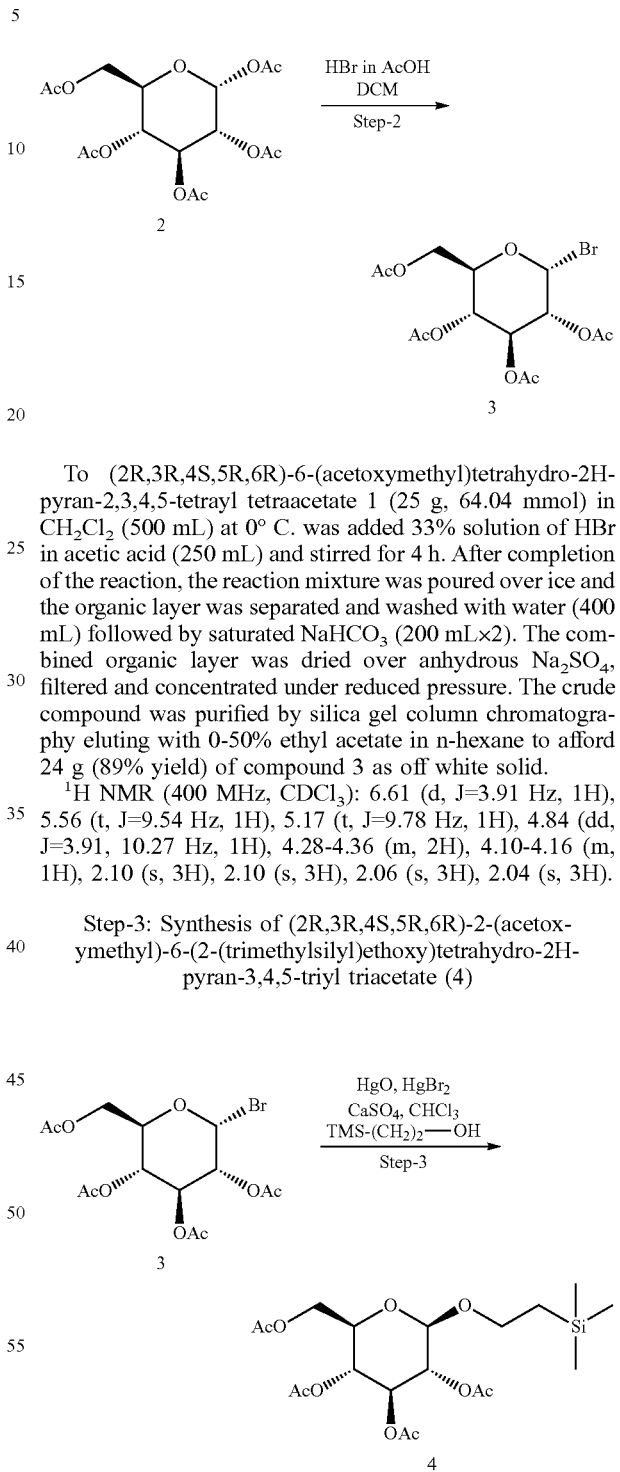

To (2R,3R,4S,5R,6R)-6-(acetoxymethyl)tetrahydro-2H-pyran-2,3,4,5-tetrayl tetraacetate 1 (25 g, 64.04 mmol) in CH$_2$Cl$_2$ (500 mL) at 0° C. was added 33% solution of HBr in acetic acid (250 mL) and stirred for 4 h. After completion of the reaction, the reaction mixture was poured over ice and the organic layer was separated and washed with water (400 mL) followed by saturated NaHCO$_3$ (200 mL×2). The combined organic layer was dried over anhydrous Na$_2$SO$_4$, filtered and concentrated under reduced pressure. The crude compound was purified by silica gel column chromatography eluting with 0-50% ethyl acetate in n-hexane to afford 24 g (89% yield) of compound 3 as off white solid.
$^1$H NMR (400 MHz, CDCl$_3$): 6.61 (d, J=3.91 Hz, 1H), 5.56 (t, J=9.54 Hz, 1H), 5.17 (t, J=9.78 Hz, 1H), 4.84 (dd, J=3.91, 10.27 Hz, 1H), 4.28-4.36 (m, 2H), 4.10-4.16 (m, 1H), 2.10 (s, 3H), 2.10 (s, 3H), 2.06 (s, 3H), 2.04 (s, 3H).

Step-3: Synthesis of (2R,3R,4S,5R,6R)-2-(acetoxymethyl)-6-(2-(trimethylsilyl)ethoxy)tetrahydro-2H-pyran-3,4,5-triyl triacetate (4)

To a stirred solution of HgO (12.1 g, 55.93 mmol), HgBr$_2$ (700 mg catalytic), CaSO$_4$ (15.2 g, 111.86 mmol) and 2-(trimethylsilyl)ethan-1-ol (9.9 g, 83.90 mmol) in CHCl$_3$ (184 mL) was added (2R,3R,4S,5R,6R)-2-(acetoxymethyl)-6-bromotetrahydro-2H-pyran-3,4,5-triyl triacetate 3 (23 g, 55.93 mmol) and stirred at room temperature for 1 h. After completion of the reaction, the reaction mixture was filtered through a pad of Celite and washed with CH$_2$Cl$_2$ and washed with saturated NaHCO$_3$ solution. The combined organic layer was dried over anhydrous Na$_2$SO$_4$, filtered and concentrated under reduced pressure. The crude compound was purified by silica gel column chromatography eluting with 0-30% ethyl acetate in n-hexane to afford 20 g (83% yield) of compound 4 as colorless oil.

$^1$H NMR (400 MHz, CDCl$_3$): 5.19 (dd, J=8.07, 9.54 Hz, 1H), 5.08 (dd, J=8.07, 9.54 Hz, 1H), 4.97 (dd, J=8.07, 9.54 Hz, 1H), 4.51 (d, J=8.31 Hz, 1H), 4.23-4.29 (m, 1H), 4.09-4.16 (m, 2H), 3.97 (dt, J=5.87, 10.03 Hz, 1H), 3.66-3.76 (m, 2H), 3.52-3.60 (m, 1H), 2.08 (s, 3H), 2.03-2.04 (m, 3H), 2.02 (s, 3H), 2.00 (s, 3H), 1.25 (t, J=7.09 Hz, 1H), 0.85-0.98 (m, 3H), 0.02 (s, 3H), 0.00 (s, 6H).

Step-4: Synthesis of (2R,3S,4S,5R,6R)-2-(hydroxymethyl)-6-(2-(trimethylsilyl)ethoxy)tetrahydro-2H-pyran-3,4,5-triol (5)

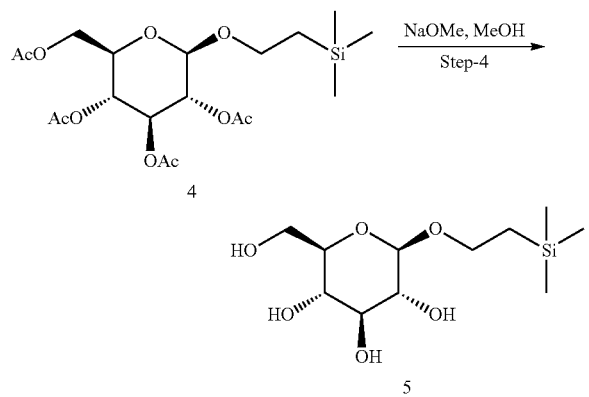

To (2R,3R,4S,5R,6R)-2-(acetoxymethyl)-6-(2-(trimethylsilyl)ethoxy)tetrahydro-2H-pyran-3,4,5-triyl triacetate 4 (10 g, 22.32 mmol) in methanol (100 mL) was added solution of sodium methoxide (100 mg sodium in 7.5 mL methanol) and stirred at room temperature for 12 h. After completion of the reaction, the pyridine was evaporated under reduced pressure and the residue was stirred in diethyl ether. The solid precipitated out was filtered and dried to afford 4.2 g (67% yield) of 5 as off white solid.

$^1$H NMR (400 MHz, D$_2$O) δ: 4.34 (d, J=7.83 Hz, 1H), 3.87-3.96 (m, 1H), 3.78 (d, J=11.74 Hz, 1H), 3.55-3.68 (m, 2H), 3.22-3.38 (m, 4H), 3.11 (t, J=8.56 Hz, 1H), 0.80-1.00 (m, 2H), −0.10 (s, 9H).

Step-5: Synthesis of ((2R,3S,4S,5R,6R)-3,4,5-trihydroxy-6-(2-(trimethylsilyl)ethoxy)tetrahydro-2H-pyran-2-yl)methyl 4-methylbenzenesulfonate (2016-00144)

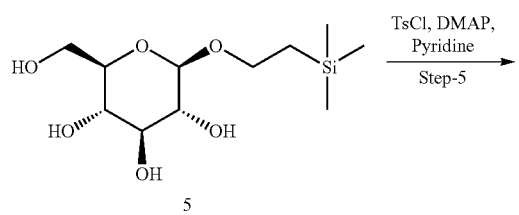

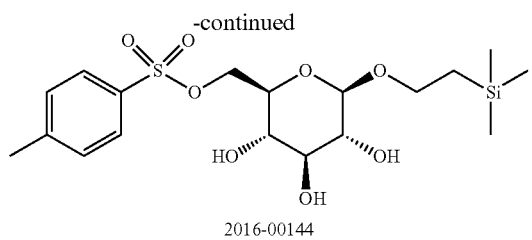

2016-00144

To (2R,3S,4S,5R,6R)-2-(hydroxymethyl)-6-(2-(trimethylsilyl)ethoxy)tetrahydro-2H-pyran-3,4,5-triol 5 (9.5 g, 33.92 mmol) in pyridine (95 mL) was added DMAP (413 mg, 3.392 mmol) and tosyl chloride (7.1 g, 37.32 mmol) stirred at room temperature for 12 h. After completion of the reaction, the pyridine was evaporated under reduced pressure and the residue was diluted with water and extracted with ethyl acetate. The combined organic layer was dried over anhydrous Na$_2$SO$_4$, filtered and concentrated under reduced pressure. The crude compound was purified by silica gel column chromatography eluting with 0-10% methanol in CH$_2$Cl$_2$ to afford 10.2 g (69% yield) of 2016-00144 as off white solid.

LCMS-Condition-1: [M+18]$^+$=452.15; Rt=1.78 min $^1$H NMR (400 MHz, DMSO-d$_6$) δ: 7.76 (d, J=8.31 Hz, 2H), 7.47 (d, J=8.31 Hz, 2H), 5.16 (d, J=5.38 Hz, 1H), 4.99 (dd, J=4.89, 9.29 Hz, 2H), 4.21 (d, J=10.27 Hz, 1H), 4.12 (d, J=7.83 Hz, 1H), 4.02 (dd, J=6.60, 10.03 Hz, 1H), 3.69-3.79 (m, 1H), 3.43-3.52 (m, 1H), 3.35 (br. s, 1H), 3.05-3.13 (m, 1H), 2.95-3.03 (m, 1H), 2.84-2.92 (m, 1H), 2.42 (s, 3H), 0.82-0.95 (m, 2H), 0.00 (s, 9H).

Example 127 trimethylsilylethyl-6-O-(2-methyl-3-phenoxyphenylcarbonyl)-β-D-glucopyranoside

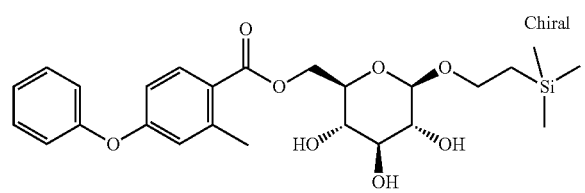 [SMILES: Cc1cc(Oc2ccccc2)ccc1C(=O)OC[C@H]1O[C@@H](OCC[Si](C)(C)C)[C@H](O)[C@@H](O)[C@@H]1O]

Trimethylsilylethyl-6-O-(2-methyl-3-phenoxyphenylcarbonyl)-β-D-glucopyranoside was synthesized as described for example 117 from trimethylsilylethoxy-6-O-tosyl-β-D-glucopyranoside (100 mg, 230.11 μmol) and 2-methyl-3-phenoxybenzoic acid (78.78 mg (345.16 μmol).

Yield: 63 mg (55.8%)

LC/MS (ES-API): m/z=535.23 (M−H+formic acid]$^-$; calculated: 535.23;

tR (λ=220 nm): 1.94 min (LC/MS—Method 2)

$^1$H NMR (400.23 MHz, DMSO-d6) δ ppm 7.95 (d, J=8.68 Hz, 1H), 7.52 (t, J=7.23, 7.23 Hz, 2H), 7.31 (t, J=7.14, 7.14 Hz, 1H), 7.17 (d, J=7.82 Hz, 2H), 7.00 (d, J=2.32 Hz, 1H), 6.89 (dd, J=8.68, 2.45 Hz, 1H), 5.28 (br s, 1H), 5.07 (br s, 2H), 4.60 (dd, J=11.68, 2.02 Hz, 1H), 4.33 (dd, J=11.68, 7.15 Hz, 1H), 4.27 (d, J=7.82 Hz, 1H), 3.84 (ddd, J=11.06, 9.78, 6.05 Hz, 1H), 3.55 (m, 2H), 3.24 (quin, J=8.71, 8.71, 8.71, 8.71 Hz, 2H), 3.05 (t, J=8.19, 8.19 Hz, 1H), 2.58 (m, 10H), 2.50 (u), 0.95 (m, 2H).

Example 128

Trimethylsilylethyl-6-O-(3-chloro-3'-methoxy-4-phenoxyphenylcarbonyl)-β-D-glucopyranoside

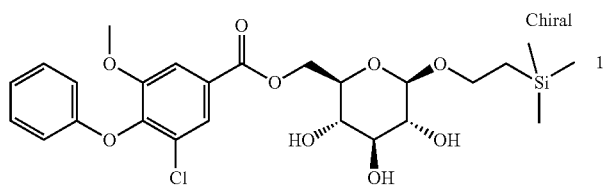

trimethylsilylethyl-6-O-(3-chloro-3'-methoxy-4-phenoxyphenylcarbonyl)-β-D-glucopyranoside was synthesized as described for example 117 from trimethylsilylethoxy-6-O-tosyl-β-D-glucopyranoside (100 mg, 230.11 μmol) and 2-methyl-3-phenoxybenzoic acid (78.78 mg, 345.16 μmol).

Yield: 64 mg (51.4%)

LC/MS (ES-API): m/z=585.15 [M−H+formic acid]⁻; calculated: 585.19 tR (λ=220 nm): 1.92 min (LC/MS—Method 2)

¹H NMR (400.23 MHz, DMSO-d6) δ ppm 7.79 (d, J=1.83 Hz, 1H), 7.72 (d, J=1.83 Hz, 1H), 7.39 (t, J=7.24, 7.24 Hz, 2H), 7.13 (t, J=7.34, 7.34 Hz, 1H), 6.88 (d, J=7.82 Hz, 2H), 5.34 (br s, 1H), 5.10 (br s, 1H), 4.66 (dd, J=11.62, 1.96 Hz, 1H), 4.45 (dd, J=11.68, 7.15 Hz, 1H), 4.30 (d, J=7.82 Hz, 1H), 3.89 (s, 3H), 3.84 (m, 1H), 3.60 (m, 2H), 3.56 (s, 1H), 3.26 (m, 2H), 3.07 (br t, J=8.13, 8.13 Hz, 1H), 2.58 (dt, J=3.61, 1.74, 1.74 Hz, 16H), 2.50 (u), 0.95 (m, 2H), 0.08 (s, 1H)

Example 129

Trimethylsilylethyl-6-O-(3-methoxy-4-phenoxyphenylcarbonyl)-β-D-glucopyranoside

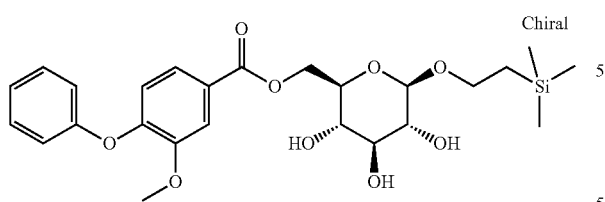

Trimethylsilylethyl-6-O-(3-methoxy-4-phenoxyphenylcarbonyl)-β-D-glucopyranoside was synthesized as described for example 117 from trimethylsilylethoxy-6-O-toluenesulfonyl-β-D-glucopyranoside (100 mg, 230.11 μmol) and 2-methyl-3-phenoxybenzoic acid (84.31 mg, 345.16 μmol).

Yield: 73 mg (52.6%)

LC/MS (ES-API): m/z=551.16 [M−H+formic acid]⁻; calculated: 551.23 tR (λ=220 nm): 1.84 min (LC/MS—Method 2)

Example 130

6-O-(3-phenoxyphenylcarbonyl)-D-glucopyranose

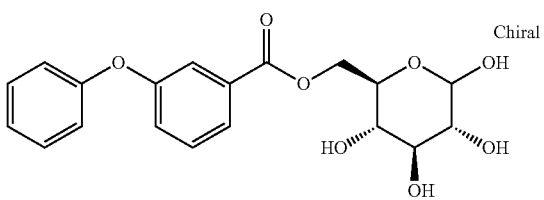 [SMILES: O=C(OC[C@H]1OC(O)[C@H](O)[C@@H](O)[C@@H]1O)c1cccc(Oc2ccccc2)c1]

To a solution of allyl-6-O-(3-phenoxyphenylcarbonyl)-β-D-glucopyranoside (Example 125; 110 mg, 264.15 μmol) in MeOH (2 mL) Pd (II)chloride (9.37 mg, 52.83 μmol) was added. After 3 h at 25° C. the reaction was controlled by LC/MS. A product with the desired mass could be detected. MeOH was added (4 mL) and the product was purified by HPLC.

Yield: 51 mg (53%, mixture of anomers)

LC/MS (ES-API): m/z=375.14 [M−H+formic acid]⁻; calculated: 375.12 tR (λ=220 nm): 1.45/1.43 min (Mixture of anomers, LC/MS—Method 2)

¹H NMR (400.23 MHz, DMSO-d6) δ ppm 7.72 (m, 1H), 7.48 (m, 4H), 7.31 (ddd, J=8.10, 2.54, 0.86 Hz, 1H), 7.21 (m, 1H), 7.08 (m, 2H), 4.91 (d, J=3.55 Hz, 1H), 4.52 (dd, J=11.74, 1.83 Hz, 1H), 4.47 (dd, J=11.68, 1.90 Hz, 1H), 4.31 (m, 2H), 3.88 (m, 1H), 3.48 (br s, 4H), 3.16 (m, 4H).

Example 131

6-O-(4-Phenoxyphenylcarbonyl)-D-glucopyranose

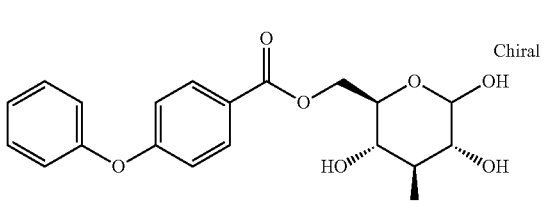

6-O-(4-phenoxyphenylcarbonyl)-D-glucopyranose was synthesized as described for example 129 from Allyl-6-O-(4-phenoxyphenylcarbonyl)-β-D-glucopyranoside (Example 126; 110 mg, 264.15 mg) as described for Example 129.

Yield: 46 mg (46.3%, mixture of anomers)

LC/MS (ES-API): m/z=375.09 [M−H]⁻; calculated: 375.12 tR (λ=220 nm): 1.46/1.44 min (Mixture of anomers, LC/MS—Method 2)

Example 132

6-O-(2-Methyl-4-phenoxyphenylcarbonyl)-D-glucopyranose

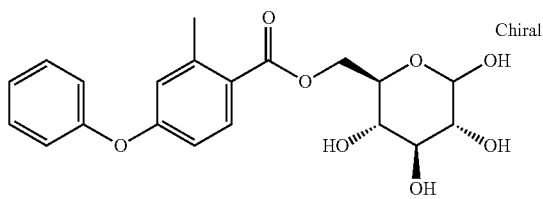 [SMILES: Cc1cc(Oc2ccccc2)ccc1C(=O)OC[C@H]1OC(O)[C@H](O)[C@@H](O)[C@@H]1O]

To a solution of Trimethylsilylethyl-6-O-(2-methyl-3-phenoxyphenylcarbonyl)-β-D-glucopyranoside (Example 127, 60 mg, 122.29 μmol) in CH$_2$Cl$_2$ (1.8 mL) TFA (200 μl, 2.60 mmol) was added under Argon atmosphere wurde. After 5 h LC/MS analysis showed consumption of starting material and one new peak could be detected. The reaction mixture was diluted with Water and freeze dried. The product was purified by HPLC.

Yield: 42 mg (88% mixture of anomers)

LC/MS (ES-API): m/z=389.16 [M−H]$^-$; calculated: 389.13 tR (λ=220 nm): 1.53/1.51 min (Mixture of anomers, LC/MS—Method 2)

Example 133

6-O-(3-Chloro-3'methyloxy-4-phenoxyphenylcarbonyl)-D-glucopyranose

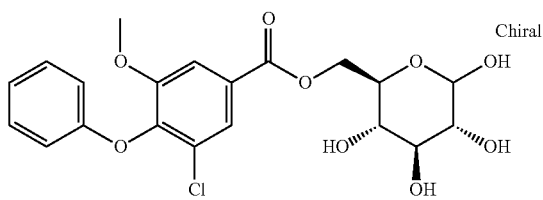 [SMILES: COc1cc(C(=O)OC[C@H]2OC(O)[C@H](O)[C@@H](O)[C@@H]2O)cc(Cl)c1Oc1ccccc1]

6-O-(3-Chloro-3'methyloxy-4-phenoxyphenylcarbonyl)-D-glucopyranose was synthesized from trimethylsilylethyl-6-O-(3-chloro-3'-methoxy-4-phenoxyphenylcarbonyl)-β-D-glucopyranoside (128; 60 mg, 110.89 μmol) as described for example 131

Yield: 42 mg (85.9%, mixture of anomers)

LC/MS (ES-API): m/z=485.1/487.0 [M−H+formic acid]$^-$; calculated: 485.12 tR (λ=220 nm): 1.55/1.53 min (Mixture of anomers, LC/MS—Method 2)

Example 134

6-O-(4-Hydroxy-2-methyl-phenylcarbonyl)-D-glucopyranose

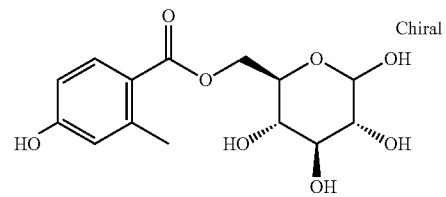 [SMILES: Cc1cc(O)ccc1C(=O)OC[C@H]1OC(O)[C@H](O)[C@@H](O)[C@@H]1O]

6-O-(3-Chloro-3'methyloxy-4-phenoxyphenylcarbonyl)-D-glucopyranose was synthesized from trimethylsilylethyl-6-O-(4-hydroxy-2-methylphenyl)carbonyl-β-D-glucopyranoside (21 mg, 50.66 μmol) as described for example 131

Yield: 16 mg (quantitative, mixture of anomers)

LC/MS (ES-API): m/z=313.06 [M−H]$^-$; calculated: 313.10 tR (λ=220 nm): 0.72/0.64 min (Mixture of anomers, LC/MS—Method 2)

$^1$H NMR (400.23 MHz, DMSO-d6) δ ppm 10.11 (d, J=4.77 Hz, 1H), 7.75 (d, J=7.58 Hz, 1H), 6.67 (m, 2H), 6.32 (brd, J=3.55 Hz, 1H), 5.14 (brs, 1H), 5.08 (brs, 1H), 4.92 (br s, 1H), 4.74 (br s, 1H), 4.50 (br s, 1H), 4.43 (ddd, J=17.76, 11.71, 1.71 Hz, 1H), 4.33 (br s, 1H), 4.20 (m, 1H), 3.87 (m, 1H), 3.48 (u), 3.16 (m, 3H), 2.92 (br t, J=8.19, 8.19 Hz, 1H).

Example 135

6-O-(3-Methyloxy-4-phenoxyphenylcarbonyl)-D-glucopyranose

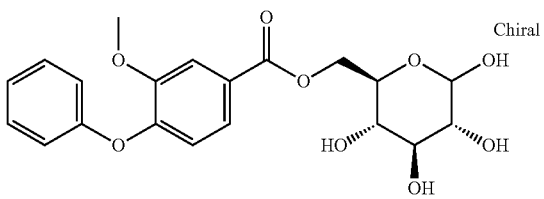 [SMILES: COc1cc(C(=O)OC[C@H]2OC(O)[C@H](O)[C@@H](O)[C@@H]2O)ccc1Oc1ccccc1]

6-O-(3-Methyloxy-4-phenoxyphenylcarbonyl)-D-glucopyranose was synthesized from trimethylsilylethyl-6-O-(3-chloro-3'-methoxy-4-phenoxyphenylcarbonyl)-β-D-glucopyranoside (128; 60 mg, 110.89 μmol) as described for example 131

Yield: 42 mg (85.9%, mixture of anomers)

LC/MS (ES-API): m/z=405.09 [M−H]$^-$; calculated: 405.13 tR (λ=220 nm): 1.43/1.41 min (Mixture of anomers, LC/MS—Method 2)

$^1$H NMR (400.23 MHz, DMSO-d6) δ ppm 7.64 (m, 1H), 7.58 (d, J=8.60 Hz, 1H), 7.37 (t, J=7.64, 7.64 Hz, 2H), 7.13 (t, J=7.04, 7.04 Hz, 1H), 7.06 (d, J=8.58 Hz, 1H), 6.95 (d, J=8.44 Hz, 2H), 4.93 (d, J=3.42 Hz, 1H), 4.51 (m, 1H), 4.32 (m, 1H), 3.91 (br dd, J=9.90, 3.91 Hz, 1H), 3.84 (s, 3H), 3.49 (brs, 2H), 3.46 (brd, J=9.17 Hz, 3H), 3.18 (m, 5H), 2.93 (br t, J=8.19, 8.19 Hz, 1H), 2.50 (u), 2.33 (br s, 1H)

Example 136

1,2:3,4-Diisopropyliden-6-O-(3-Methoxy-4-phenoxy)-phenylcarbonyl-D-glucopyranose

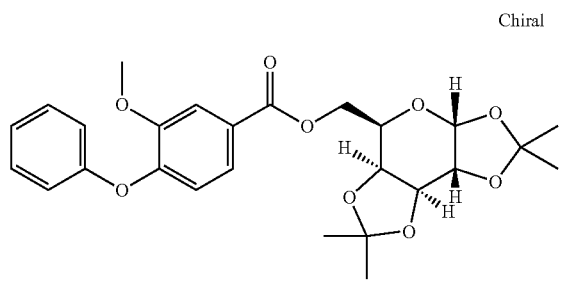 [SMILES: COc1cc(C(=O)OC[C@H]2O[C@@H]3OC(C)(C)O[C@@H]3[C@H]3OC(C)(C)O[C@H]32)ccc1Oc1ccccc1]

Lit: Angew. Chem. Int. Ed. 2008, 47, 8264-8267

A solution of 3-Methoxy-4-phenoxybenzoic acid (93.84 mg, 384.19 µmol) in CH2Cl2 (1.5 ml) was stirred under argon atmosphere at 0° C. Consecutively a solution of 1,2:3,4-Di-O-isopropyliden-D-galactose (100 mg, 384.19 µmol) in DMF (1 mL), DMAP (9.39 mg, 76.84 µmol) and finally DCC (79.27 mg, 384.19 µmol) where added and the reaction was kept at 0° C. for 10 min. The reaction mixture was left at 25° C. for 16 h. The desired mass could be detected by LC/MS. The reaction mixture was diluted with MeOH (2 mL) filtrated and the product finally purified by HPLC, Yield: 154 mg (82.4%)

LC/MS (ES-API): m/z=487.20 [M–H]$^-$; calculated: 487.19 tR (λ=220 nm): 2.72 min (LC/MS—Method 2)

$^1$H NMR (400.23 MHz, DMSO-d6) δ ppm 7.63 (d, J=1.71 Hz, 1H), 7.57 (dd, J=8.38, 0.90 Hz, 1H), 7.38 (t, J=7.95, 7.95 Hz, 2H), 7.14 (t, J=7.16, 7.16 Hz, 1H), 7.00 (m, 3H), 0.48 (d, J=5.01 Hz, 1H), 4.65 (dd, J=7.95, 2.32 Hz, 1H), 4.36 (m, 4H), 4.12 (m, 1H), 3.83 (s, 3H), 3.46 (u), 2.50 (u), 1.44 (s, 3H), 1.39 (s, 3H), 1.31 (s, 3H), 1.28 (s, 3H)

Example 137

6-O-(3-Methoxy-4-phenoxyphenylcarbonyl)-D-glucopyranose

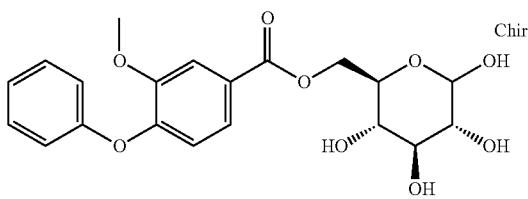

1,2:3,4-Diisopropyliden-6-O-(3-methoxy-4-phenoxyphenylcarbonyl)-D-glucopyranose (154 mg, 316.54 µmol) was dissolved in acetonitril. Under argon atmosphere HCl (2.37 ml, 4.75 mmol) was added and the Reaction mixture was stirred at 40° C. for 16 h. Water was added and the product was freeze dried. The product was finally purified by HPLC.

Yield: 51 mg (39.6%) (Mixture of Anomers)

LC/MS (ES-API): m/z=389.1 [M+H—H$_2$O]$^+$; calculated: 389.11 tR (λ=220 nm): 1.58/1.60 min (LC/MS—Method 2)

Example 138

6-O-(3-Chloro-3'Methoxy-4-phenoxyphenylcarbonyl)-D-glucopyranose

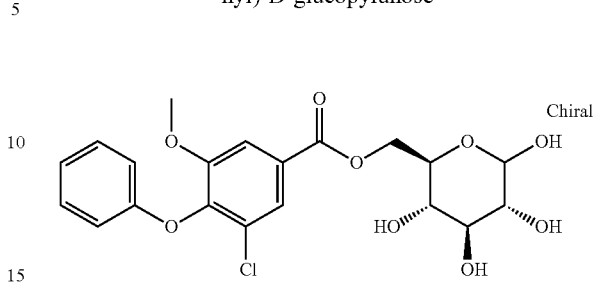

6-O-(3-Chloro-3'Methoxy-4-phenoxyphenylcarbonyl)-D-glucopyranose was synthesized as described for example 136 from 1,2:3,4-Diisopropyliden-6-O-(3-chloro-3'methoxy-4-phenoxy)phenylcarbonyl-D-glucopyranose (150 mg, 287.93 µmol).

Yield: 93 mg (73.3%).

LC/MS (ES-API): m/z=423.1/425.1 [M+H—H$_2$O]$^+$; calculated: 423.07 tR (λ=220 nm): 1.76/1.78 min (LC/MS—Method 2)

Example 139

Step 1: Amide Coupling 4-(2,4-Dichlorophenyl)piperazin-1yl-(1,2:3,4-diisopropyliden)-D-galacturonic acid amide

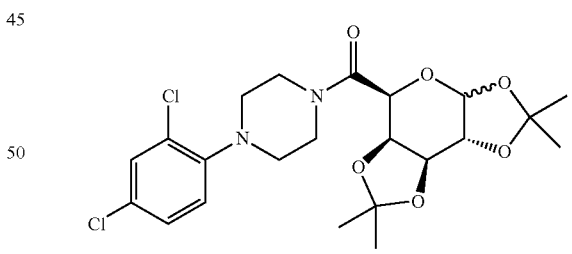

A solution of 1,2:3,4-Diisopropyliden-D-galacturonic acid (150 mg, 546.91 µmol) in DMF (5 ml) under argon atmosphere was treated with HATU (291.14 mg, 765.67 µmol) and the reaction mixture stirred for 5 min. 1-(2,4-dichlorophenyl)piperazine (176.96 mg, 765.67 µmol) was added and the reaction mixture was stirred at 25° C. The reaction was monitored by LCMS. After 24 h starting material could be detected, DIPEA (2.2 equivalents) was added and the reaction mixture left for another 24 h at 25° C. CH2Cl2 (1×10 ml) and water were added and the product extracted. The organic layer was dried, the solvents evaporated and the product purified by HPLC.

Yield: 163 mg (61.2%)

Example 140

Step 2: Deprotection 4-(2,4-Dichlorophenyl)piperazin-1-yl-D-galacturonic acid amide

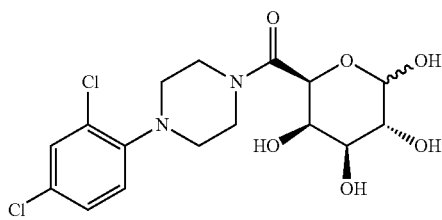 [SMILES: O=C([C@H]1OC(O)[C@H](O)[C@@H](O)[C@H]1O)N1CCN(c2ccc(Cl)cc2Cl)CC1]

A suspension of 4-(2,4-Dichlorophenyl)piperazin-1yl-(1,2:3,4-Diisopropyliden)-D-galacturonic acid amide (163 mg, 334.45 µmol) was treated with aqueous HCl (2.51 ml, 5.02 mmol) under argon atmosphere and left for 16 h at 25° C. The reaction was monitored by LC/MS, starting material could still be detected. The reaction mixture was dissolved in MeOH and again treated with HCl (2.5 mL) and left at 25° C. for 16 h. Methanol was evaporated, the residue diluted with water and freeze dried. The product was purified by HPLC.

Yield: 46 mg (28.3%)

LC/MS (ES-API): m/z=407.1/409.0/411. [M+H]+; calculated: 407.24 tR (λ=220 nm): 1.46/1.48 min (LC/MS—Method 2)

Example 140

Step 1: Preparation of substituted amine (R)-2-((benzyloxy)methyl)-4-chloro-piperazine

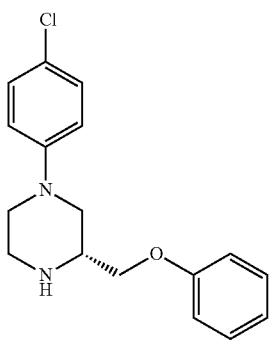 [SMILES: Clc1ccc(N2CCN[C@@H](COc3ccccc3)C2)cc1]

Lit.: ACS Med. Chem. Lett., 2015, 6 (10), pp 1041-1046

A solution of tert-butyl (R)-2-((benzyloxy)methyl)piperazine-1-carboxylate (333.98 mg, 1.09 mmol), 1-bromo-4-chlorobenzene (227.46 mg, 1.19 mmol) and BINAP (40.72 mg, 65.40 µmol) in toluene (5 ml) was treated with Pd(II) acetate (9.79 mg, 43.60 µmol) under argon atmosphere. KoTBu (183.47 mg, 1.64 mmol) was added and the reaction mixture was irradiated in the microwave for 30 min at 130° C.

EtOAc and H2O where added, the reaction mixture filtered, and the filtrate washed with brine. The solvent was evaporated and the residue purified by HPLC.

Yield: 142 mg (41%)

Step 2: Reductive Amination

6-Desoxy-6-((R)-2-((benzyloxy)methyl)-4-chlorophenyl)-piperazin-1-yl-(1,2:3,4-diisopropyliden)-D-galactopyranose

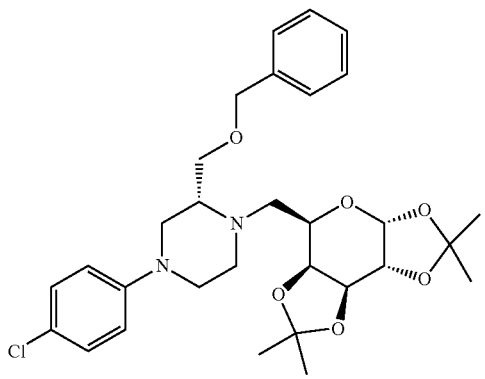 [SMILES: CC1(C)O[C@H]2[C@@H](O1)[C@@H](CN1CCN(c3ccc(Cl)cc3)C[C@@H]1COCc1ccccc1)O[C@@H]1OC(C)(C)O[C@@H]12]

To a solution of (3aR,5S,5aR,8aS,8bR)-2,2,7,7-tetramethyltetrahydro-5H-bis([1,3]dioxolo)[4,5-b:4',5'-d]pyran-5-carbaldehyde (125.54 mg, 486.07 µmol) in methanol (2 ml), (R)-3-((benzyloxy)methyl)-1-(4-chlorophenyl)piperazine (140 mg, 441.88 µmol), acetic acid (50.59 µl, 883.76 µmol) and sodiumcyanoborhydride (58.46 mg, 883.76 µmol) are added. The reaction mixture was left for 16 h at 25° C. LCMS showed consumption of starting material. The reaction mixture was evaporated and the product purified by HPLC.

Yield: 105 mg (40%)

Step 3: Deprotection

Methyl-6-desoxy-6-((R)-2-((benzyloxy)methyl)-4-chlorophenyl)-piperazin-1-yl-D-galactopyranoside

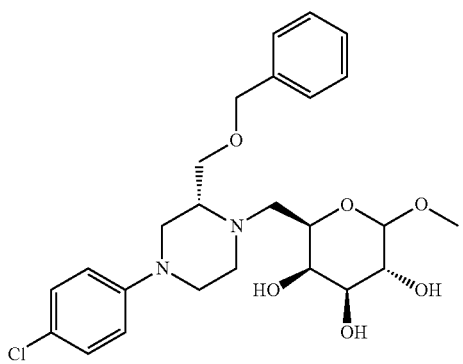 [SMILES: COC1O[C@H](CN2CCN(c3ccc(Cl)cc3)C[C@@H]2COCc2ccccc2)[C@H](O)[C@H](O)[C@H]1O]

A suspension of 6-desoxy-6-(4-chlorophenyl)piperazino-(1,2:3,4-diisopropyliden)-D-galactopyranose (103 mg, 172.95 µmol) in MeOH (2 mL) is treated with mit HCl (1.73 ml, 3.46 mmol) and stirred for 2 h and left for 16 h at 25° C.

Yield: 13 mg (12.4%)

LC/MS (ES-API): m/z=479.3/481.3. [M+H]+; calculated: 478.20 tR (λ=220 nm): 1.37 (LC/MS—Method 2)

1H NMR (400.23 MHz, DMSO-d6) δ ppm 9.62 (br s, 1H), 7.35 (m, 8H), 7.02 (br d, J=8.80 Hz, 2H), 5.05 (br s, 1H), 4.93 (br s, 1H), 4.58 (m, 3H), 4.38 (br d, J=5.50 Hz, 1H), 4.28 (br d, J=10.03 Hz, 1H), 3.95 (br s, 1H), 3.89 (br d, J=10.64 Hz, 2H), 3.77 (m, 4H), 3.64 (brd, J=6.85 Hz, 1H), 3.57 (m, 4H), 3.17 (brs, 1H), 3.01 (m, 2H), 2.50 (u) 1H NMR (250.13 MHz, DMSO-d6) δ ppm 7.29 (m, 6H), 6.92 (m, 2H), 5.02 (m, 1H), 4.55 (s, 2H), 3.80 (m, 4H), 3.63 (m, 1H), 3.52 (brs, 2H), 3.18 (m, 7H), 2.93 (brs, 97H), 2.75 (br s, 4H), 2.50 (u).

Synthesis of Example 141

Step 1: Reductive Amination

6-Desoxy-6-(3-hydroxyphenyl)-piperazin-1-yl-(1,2:3,4-diisopropyliden)-D-galactopyranose

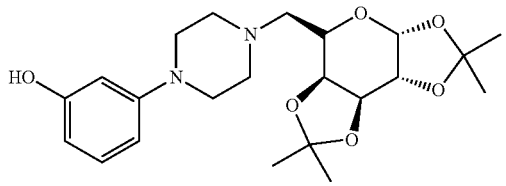

(3aR,5S,5aR,8aS,8bR)-2,2,7,7-tetramethyltetrahydro-5H-bis([1,3]dioxolo)[4,5-b:4',5'-d]pyran-5-carbaldehyde (239.09 mg, 925.74 μmol) was dissolved in MeOH (3 ml). 3-(piperazin-1-yl)phenol (150 mg, 841.59 μmol), acetic acid, (96.36 μl, 1.68 mmol) and NaCNBH3 (111.34 mg, 1.68 mmol) where added and the reaction mixture stirred for 3 h and left for 16 h at 25° C. The reaction was monitored by LCMS. Starting material was consumed. The solvent was evaporated, the residue taken up in EtOAc/H2O and the product extracted with EtOAc and finally purified by HPLC.

Yield: 280 mg (72.8%)

Step 2: Activation of Spacer

Undec-10-yn-1-yl 4-methylbenzenesulfonate

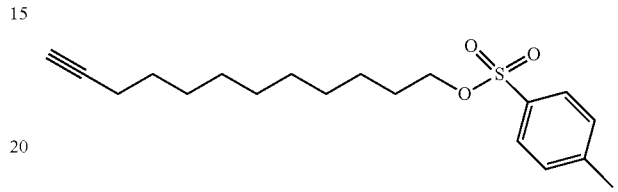

Lit.: Tetrahedron 56 (2000) p 1233-1245

Undec-10-yn-1-ol (343.17 μl, 2.97 mmol) was dissolved in CH2Cl2 (10 ml) under argon atmosphere. 4-Methylbenzenesulfonyl chloride (810.01 mg, 4.25 mmol) was added and the reaction mixture cooled to 0° C. Pyridine (355.67 μl, 4.40 mmol) was added dropwise over 5 min and the reaction mixture was stirred for 3 h at 0° C. The ice bath was removed and the solution was left for 16 h at 25° C. The reaction was monitored by LCMS. 1 N HCl was added and the product extracted with CH2Cl2. The solvent was removed in vacuo and the product purified by HPLC Yield: 1.57 g (29.3%)

Step 3: Ether Coupling

6-Desoxy-6-(3-undecenyloxyphenyl)-4-piperazin-1-yl-(1,2:3,4-diisopropyliden)-D-galactopyranose

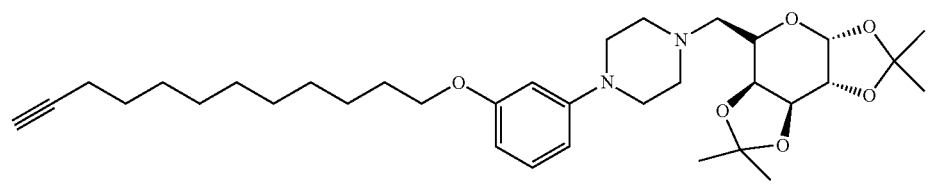

A mixture of 6-desoxy-6-(3-hydroxyphenyl)-piperazin-1-yl-(1,2:3,4-diisopropyliden)-D-galactopyranose Hydrochlorid (275 mg, 601.80 µmol) and undec-10-yn-1-yl 4-methylbenzenesulfonate (445.78 mg, 842.52 µmol) was treated with Cesiumcarbonat (980.39 mg, 3.01 mmol). DMF (2 mL) was added and the reaction mixture was irradiated in the microwave at 80° C. for 1 h. LCMS showed the expected mass. The product was extracted with EtOAc/H$_2$O, the organic layer washed with aqueous NaCL solution (10%) and dried. The solvent was evaporated in vacuo and the product purified by HPLC.

Yield: 105 mg (28.7%)

Step 3: Deprotection

Example 141

6-Desoxy-6-(3-undecenyloxypheny)-4-piperazin-1-yl-D-galactopyranose

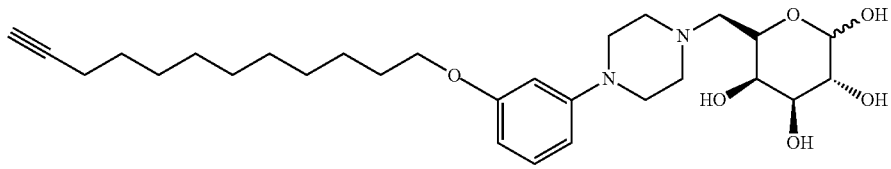

6-Desoxy-6-(3-undecenyloxyphenyl)-4-piperazin-1-yl-(1,2:3,4-diisopropyliden)-D-galactopyranose (101 mg, 166.33 µmol) was treated with 2 n HCl (1.66 ml, 3.33 mmol) and then heated for 2 h at 80° C. LCMS showed consumption of starting material, the reaction mixture was diluted with H$_2$O and freeze dried.

Yield: 18 mg (20.5%)

Synthesis of Example 142

6-Desoxy-6-(1-(4-(2-(2-(2-(prop-2-yn-1-yloxy)ethoxy)ethoxy)ethoxy)phenyl)piperazin-1 yl-D-galactopyranose

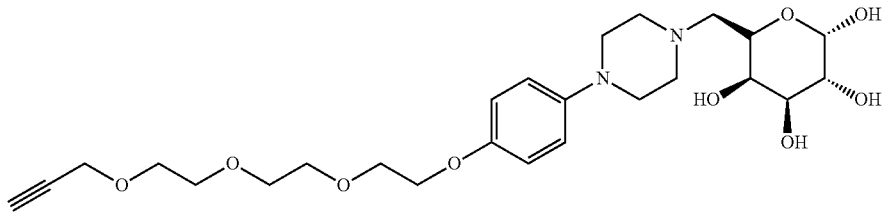

The synthesis of example 142 was following the procedure described for example 141 starting from 2-(2-(2-(prop-2-yn-1-yloxy)ethoxy)ethoxy)ethan-1-ol (500 mg, 2.66 mmol) and 4-methylbenzenesulfonyl chloride (759.63 mg, 3.98 mmol) to yield the activated spacer (2-(2-(2-(prop-2-yn-1-yloxy)ethoxy)ethoxy)ethyl 4-methyl-benzenesulfonate, yield: 420 mg, 46.2%).

In parallel 6-Desoxy-6-(4-hydroxyphenyl)-piperazin-1-yl-(1,2:3,4-diisopropyliden)-D-galactopyranose (269 mg, 639.71 µmol) was prepared and then coupled with (2-(2-(2-(prop-2-yn-1-yloxy)ethoxy)ethoxy)ethyl 4-methyl-benzenesulfonate (262.85 mg, 767.65 µmol) to yield. 6-desoxy-6-(1-(4-(2-(2-(2-(prop-2-yn-1-yloxy)ethoxy)ethoxy)ethoxy)phenyl)piperazin-1 yl-(1,2:3,4-diisopropyliden)-D-galactopyranose (180 mg, 47.6%), which was then deprotected with aqueous HCl.

Yield: 130 mg (69.5%)

LC/MS (ES-API): m/z=511.38 [M+H]+; calculated: 510.25 tR (λ=220 nm): 0.98 (LC/MS—Method 2)

Example 143

Biological Assays
1. HepG2 Assay:
Procedure

For measurement of $^{14}$C 2-deoxy-D-glucose transport into HepG2 cells, cells were seeded in collagen treated 96-well plates (Cytostar-T Plates Perkin Elmer, 40.000 cells/200 μ/well) in medium complete (MEM W/GLUT-I, EARLES (Gibco #41090) /NEAA/PS/10% FCS) and grown for 48 hours. After starvation for 2 hours with MEM W/GLUT-I, EARLES (Gibco #41090)/NEAA/no serum 100 μl/well and washing twice with 200 μL KRB buffer, cells were stimulated in a dose dependent manner by adding 20 μL of test compound dilution 0-750 μM (7.5 times higher concentration than final) or 20 μL of 188 μM Cytochalasin B solution as negative control, to 80 μL KRB buffer and incubated for 30 minutes. After compound stimulation, the transport of $^{14}$C 2-deoxy-D-glucose was started by adding of 50 μL $^{14}$C 2-deoxy-D-glucose solution (250 μM 2-deoxy-D-glucose cold and 15 μM $^{14}$C 2-deoxy-D-glucose 0.13 μCi/well) for 20 minutes. Transport was stopped by adding 50 μL/well 40 μM Cytochalasin B solution. Plates were measured in a 96-well Wallac Microbeta device. The cpm (counts per minute) values were used to determine the % inhibition values for the test compounds within each experiment, which then are averaged over the number of experiments performed.

Table of results:

| Example | % inhibition of $^{14}$C-2-deoxy-glucose transport [100 μM] | SD |
| --- | --- | --- |
| 1 | 6.32 | 6.32 ± 3.81 |
| 2 | 6.50 | 6.50 ± 4.16 |
| 6 | 7.75 | 7.75 ± 3.28 |
| 7 | 6.99 | 6.99 ± 2.52 |
| 8 | 7.67 | 7.67 ± 5.12 |
| 9 | 5.11 | 5.11 ± 3.56 |
| 12 | 5.43 | 5.43 ± 6.31 |
| 14 | 5.67 | 5.67 ± 5.11 |
| 19 | 6.89 | 6.89 ± 6.28 |
| 21 | 7.53 | 7.53 ± 3.59 |
| 22 | 11.40 | 11.40 ± 3.95 |
| 27 | 13.06 | 13.06 ± 1.96 |
| 28 | 9.95 | 9.95 ± 1.83 |
| 29 | 18.44 | 18.44 ± 3.80 |
| 34 | 20.47 | 20.47 ± 3.07 |
| 36 | 20.63 | 20.63 ± 3.24 |
| 37 | 6.88 | 6.88 ± 1.71 |
| 38 | 12.70 | 12.70 ± 1.51 |
| 39 | 10.99 | 10.99 ± 4.75 |
| 40 | 10.08 | 10.08 ± 7.98 |
| 45 | 29.31 | 29.31 ± 4.46 |
| 46 | 8.76 | 8.76 ± 2.67 |
| 47 | 13.82 | 13.82 ± 5.23 |
| 48 | 28.82 | 28.82 ± 4.82 |
| 49 | 19.91 | 19.91 ± 3.87 |
| 50 | 13.84 | 13.84 ± 1.91 |
| 51 | 17.86 | 17.86 ± 6.82 |
| 52 | 14.55 | 14.55 ± 3.95 |
| 53 | 23.89 | 23.89 ± 5.32 |
| 54 | 10.48 | 10.48 ± 8.16 |
| 55 | 12.39 | 12.39 ± 2.89 |
| 56 | 21.08 | 21.08 ± 2.76 |
| 57 | 24.14 | 24.14 ± 5.94 |
| 58 | 19.98 | 19.98 ± 5.00 |
| 59 | 7.56 | 7.56 ± 4.50 |
| 60 | 14.75 | 14.75 ± 4.72 |
| 61 | 9.42 | 9.42 ± 6.75 |
| 63 | 37.62 | 37.62 ± 4.09 |
| 64 | 8.86 | 8.86 ± 3.67 |
| 65 | 7.79 | 7.79 ± 2.92 |
| 66 | 5.12 | 5.12 ± 6.07 |
| 67 | 25.77 | 25.77 ± 3.88 |
| 69 | 6.14 | 6.14 ± 6.61 |
| 75 | 31.19 | 31.19 ± 6.64 |
| 79 | 25.54 | 25.54 ± 3.49 |
| 88 | 31.37 | 31.37 ± 1.75 |
| 92 | 23.10 | 23.10 4.60 |

2. Glucose Displacement Assay (ATP Measurement)

| Reagent | Provider | Catalogue n. |
| --- | --- | --- |
| CellTiter-Glo ® Luminescence Cell Viability Assay | Promega | G-7571 |
| A2780 Human Carcinoma Cell line | ECACC | 93112519 |
| 96-well LIA plate, white | Greiner Bio-one | 655073 |
| RPMI 1640 medium GlutaMAX | Thermo Fisher Scientitic | 61870 |
| RPMI 1640 medium (no glucose) | Thermo Fisher Scientific | 11879 |
| Fetal Bovine Serum | Pan Biotech | P-30-3305 |
| D-(+)-Glucose solution | Sigma Aldrich | G-8644 |
| PBS buffer | Life Technologies | 14190 |
| KRB buffer | PAN | P05-32500* |
| DMSO | Sigma | D-2650 |
| Rotenone | Sigma | R-8875 |

*Customer Formulation, sterile filtered: 1.7 mM CaCl$_2$ x 2H$_2$O; 1.2 mM KH$_2$PO$_4$; 4.8 mM KCl; 1.2 mM MgSO$_4$ x 7H$_2$O; 120 mM NaCl; 26 mM NaHCO$_3$ 30.000 A2780 Human Carcinoma Cells are seeded per well in a Greiner 96-well plate. Cells are expanded and cultured in RPMI 1640 medium+GlutaMAX® with 10% FCS and 11 mM glucose, at 37° C. with 5% CO2. After 44 h, culture media is changed and washed once with PBS to starvation media consisting of RPMI 1640 medium with 1% FCS without glucose for 2 hours. Cells are then washed with KRB buffer, followed incubation for 20 min at 37° C. of the treatment mix consisting of: 60 μL KRB buffer/well with 10 μL of compound or DMSO 10×. 10 μl of rotenone is added to the mix to a final concentration of 0.5 μM. Cell plates are left for 2 min at room temperature. 20 μL of different glucose concentrations are added to the mix—typically 0.1 to 20 mM range -. Cells are incubated for another 15 min at 37° C., before measuring ATP with the CellTiter-Glo® Assay, under manufacturer's guidance, but without the equilibration step at room temperature for 30 min. In brief, 100 μl of Cell-Titer-Glo® Reagent is added to the wells containing already 100 μl of the previous reaction mix. Plates are mixed for 2 min at 800 rpm, followed by incubation at room temperature for 10 min to stabilize the luminescent signal. Luminescence is then recorded with the Tekan Ultra Evolution reader.

Example 140

IC$_{50}$ 67.9 μM

Example 141

IC$_{50}$ 84.8 μM

Example 138

IC$_{50}$ 8.37 μM (>100 μM @ 10 mM Gluc)

Example 124

IC$_{50}$ 33.2 μM (>100 μM @ 10 mM Gluc)

3. Erythrocyte Dialysis Assay

6-NBD Glc (6-(N-(7-Nitrobenz-2-oxa-1,3-diazol-4-yl) amino)-6-Deoxyglucose) is a small fluorescent glucose derivative, which has been shown to bind to GluT-1 in astrocytes (L. F. Barros et al., JOURNAL OF NEUROCHEMISTRY 109 (2009) 94-100). Here 6-NBD-Glc or alternatively 2-NBD-Glc was used in dialysis based competition experiments.

Freshly isolated heparinized rat blood samples were immideately diluted (1:5) in PBS buffer to generate a stable stock solution. This stock solution was further diluted (1:1 or 1:3) for the following dialysis experiments in Rapid Equilibrium Dialysis (RED) devices (Thermo Scientific Pierce).

The aforementioned stock solution was further diluted (1:1 or 1:3 respectively) and added to the dialysis compartiment of a RED device. In parallel stock solution was diluted (1:1) with buffer containing 6 NBD Glc (25 µM).

Dialyses was started by addition of 6 NBD Glc (25 µM) in PBS Buffer ($k^{on}$) or pure PBS buffer ($k^{off}$) respectively into the buffer compartment. Aliquots (20 µl) were taken after defined time intervals from the buffer compartment and fluorescence was measured in a UV plate reader (Thermovarioskan, Thermo).

As a control, free diffusion of 6-NBD-Glc (25 µM) in PBS buffer vs pure buffer was measured.

Data are given in the following table:

| Time (min) | 1:1 Dilution $k^{on}$ | 1:1 Dilution $k^{off}$ | Diffusion (Control) |
|---|---|---|---|
| 0 | 55 | 0 | 0 |
| 30 | 50.6 | 3.4 | 3.7 |
| 60 | 45.1 | 6.5 | 7.5 |
| 90 | 33 | 12 | 9.2 |
| 120 | 34 | 16.1 | 10 |

Graphical evaluation of the different slopes gave a $K_D = 0.68$ for 6-NBD-Glc.
$K^{on} = 0.199$;
$K^{off} = 0.136$;
$K_D = 0.136/0.199$;
$K_D = 0.68$: 68% free.

FIG. 1: Fluorescence intensity [AU] is plotted vs time [min].

Squares: Decreasing fluorescence intensity measured in buffer compartment, due to binding to eyrothrocytes.

Triangles: Increasing fluorescence intensity measured in buffer compartment, due to release from erythrocytes.

$K_D$ was calculated from the slopes: $K_D=0.68$ for 6-NBD-Glc.

Glucose dependency was determined following the protocol described above, comparing the following solutions: 6 NBD-Glc (100 µM), 6 NBD-Glucose (100 µM)+Glucose 20 mM. Data are shown in the next table

| Time (min) | 6-NBD-Glc [50 µM] | NBD-Glc [50 µM] + Glc [10 mM] |
|---|---|---|
| 0 | 0 | 0 |
| 15 | 7.5 | 7.2 |
| 30 | 10.6 | 11.9 |
| 60 | 11.1 | 17 |
| 90 | 14.9 | 18.5 |
| 120 | 15.8 | 20.3 |
| 180 | 16 | 22.5 |

Free concentration of 6-NBD-Glc is increased in presence of Glc [10 mM].

Figure 2:
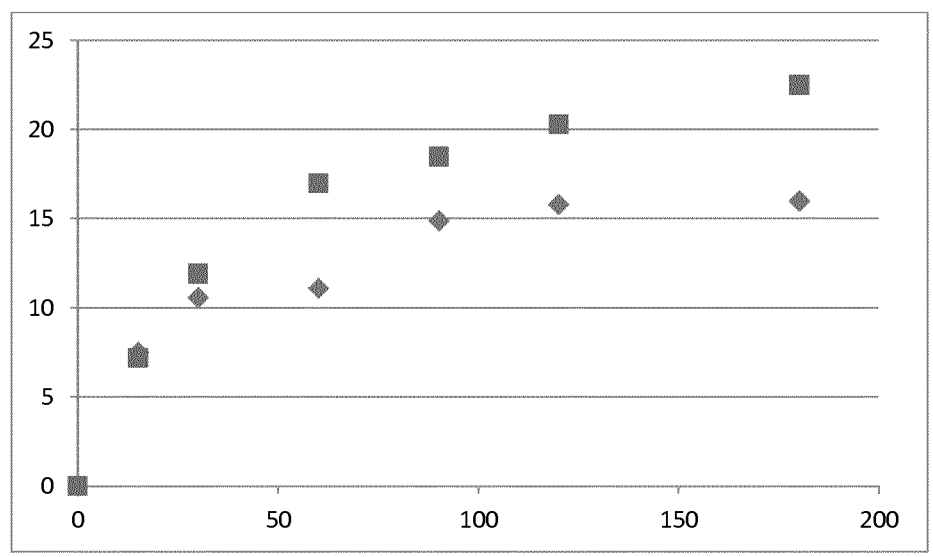

FIG. 2: Fluorescence intensity [AU] is plotted vs time [min].

Increase of fluorescence in buffer compartment in presence (squares) or absence of glucose (rhombus).

Example 102 was investigated in a competition experiment following the same protocol using a 6-NBD-Glc solution (100 µM) in comparison to 6 NBD-Glucose (100 µM)+Example 102 (50 µM). The results are shown in the following table

| Time (min) | Example 102 [25 µM] | Control |
|---|---|---|
| 0 | 0 | 0 |
| 15 | 4.9 | 0.9 |
| 30 | 11.1 | 2.2 |
| 60 | 12.5 | 3.3 |
| 90 | 19.3 | 3.8 |
| 120 | 25.1 | 8 |
| 180 | 32.1 | 10.1 |

Figure 3:
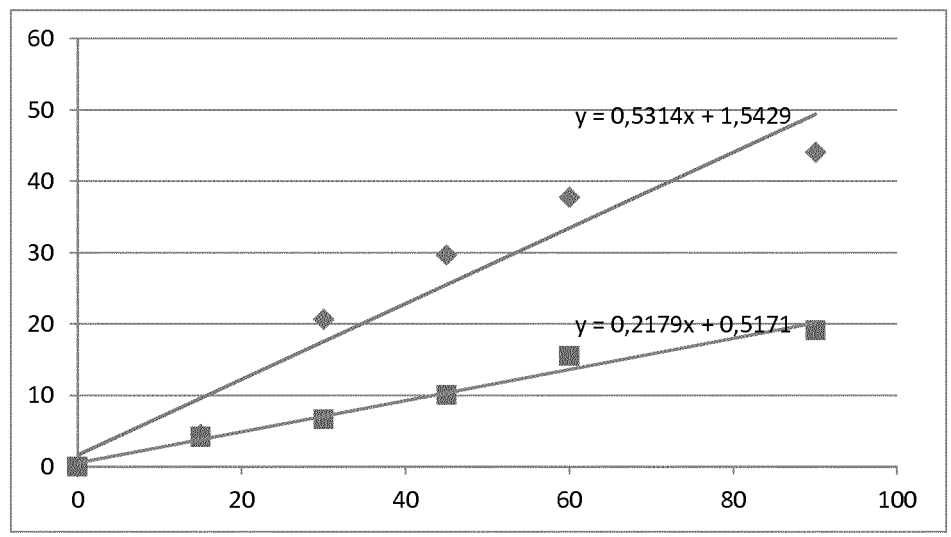

FIG. 3: Fluorescence intensity [AU] is plotted vs time [min].

In presence of the Example 102 a clear increase in the slope (rhombus) is seen in comparison to control (squares) indicating the competition with 6-NBD-Glc.

The invention claimed is:
1. A conjugate consisting of formula (I)

$$P-[L_1]_m-[A_1]_o-[L_2]_p-[A_2]_r-[L_3]_q-S \qquad (I)$$

wherein:
P is an insulin or an insulinotropic peptide;
$L_1$, $L_2$, and $L_3$ are independently a linker having a chain length of 1-20 atoms;
$A_1$ and $A_2$ are independently:
  a 5 to 6 membered monocyclic ring,
  a 9 to 12 membered bicyclic ring,
  two 5 to 6 membered monocyclic rings connected to each other,
  two 9 to 12 membered bicyclic rings connected to each other, or
  a 5 to 6 membered monocyclic ring and a 9 to 12 membered bicyclic ring connected to each other,
  wherein each ring is independently a saturated, unsaturated, or aromatic carbocyclic or heterocyclic ring, and wherein each ring is optionally modified with at least one substituent;
S is a sugar moiety which binds to the insulin independent glucose transporter GluT1, wherein the sugar moiety S comprises a terminal pyranose moiety S1 having a backbone structure of Formula (II)

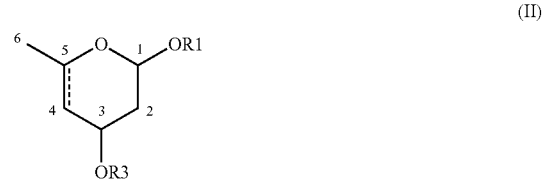

wherein:
1, 2, 3, 4, 5, and 6 denote the positions of the C-atoms in the pyranose moiety;
—— is a single bond and ‑ ‑ ‑ is a single or a double bond; and
R1 and R3 are H or a protecting group,
wherein S is attached via position 2, 4, or 6 to the conjugate of formula (I), and wherein the sugar moiety S comprises a single terminal saccharide moiety;
and
m, o, p, r, and q are independently 0 or 1, wherein at least one of r and o is 1,
or a pharmaceutically acceptable salt or solvate thereof.

2. The conjugate of formula (I) of claim 1, wherein P is an insulin which is attached via the amino side chain of an insulin B29Lys residue or via the amino terminus of an insulin B1Phe residue.

3. The conjugate of formula (I) of claim 1, wherein $L_1$, $L_2$, and $L_3$ are independently $(C_1-C_{20})$ alkylene, $(C_2-C_{20})$ alkenylene, or $(C_2-C_{20})$ alkynylene, wherein one or more C-atoms are optionally replaced by heteroatoms or heteroatom moieties selected from the group consisting of O, NH, $N(C_{1-4})$ alkyl, S, SO, $SO_2$, O—$SO_2$, O—$SO_3$, O—$PHO_2$, and O—$PO_3$, and/or wherein one or more C-atoms is optionally modified with $(C_{1-4})$ alkyl, $(C_{1-4})$ alkyloxy, oxo, carboxyl, halogen, or a phosphorus-containing group.

4. The conjugate of formula (I) of claim 1, wherein:
(i) $L_3$ is $(C_1-C_6)$ alkylene, wherein one or two C-atoms are optionally replaced by heteroatoms or heteroatom moieties selected from the group consisting of O, NH, $N(C_{1-4})$ alkyl, S, SO, $SO_2$, O—$SO_2$, O—$SO_3$, O—$PHO_2$, and O—$PO_3$, and/or wherein one or more C-atoms is optionally modified with $(C_{1-4})$ alkyl, $(C_{1-4})$ alkyloxy, oxo, carboxyl, halogen, or a phosphorus-containing group;
(ii) $L_3$ is C═O; or
(iii) $L_2$ is selected from the group consisting of —CO—$(CH_2)_3$—, —$(CH_2)_6$—NH—, —$(CH_2)_2$—CO—$(CH_2$—$CH_2$—O$)_2$—$(CH_2)_2$—NH— and —$CH_2$—O—$(CH_2$—$CH_2$—O$)_3$—.

5. The conjugate of formula (I) of claim 1, wherein:
(i) $A_1$ and $A_2$ are independently a heterocyclic ring, wherein the ring is optionally modified with at least one substituent;
(ii) $A_1$ and $A_2$ are independently a 5 to 6 membered monocyclic or a 9 to 12 membered bicyclic ring, wherein the ring is heterocyclic with 1 to 4 heteroatom(s) selected from the group consisting of N, O, and S, and wherein the ring is optionally modified with at least one substituent; or
(iii) $A_1$ and $A_2$ are independently a 5 to 6 membered monocyclic ring, wherein the ring is a heteroalkyl ring optionally modified with at least one substituent, or a 9 to 12 membered bicyclic ring wherein the ring is a heterocyclic ring with 1 to 4 heteroatom(s) selected from the group consisting of N, O, and S, and wherein the ring is optionally modified with at least one substituent.

6. The conjugate of formula (I) of claim 1, wherein:
(i) $A_1$ and $A_2$ are independently 1,2,3-triazolyl;
(ii) $A_2$ is 1,2,3-triazolyl; or
(iii) $A_2$ is piperazinyl.

7. The conjugate of formula (I) of claim 1, wherein:
(i) r=1 and $A_2$ is present and o=0 and $A_1$ is absent; or
(ii) r=1 and $A_2$ is present and o=1 and $A_1$ is present.

8. The conjugate of formula (I) of claim 1, wherein:
(i) m=1, o=0, p=0, and q=0 or 1; or
(ii) m=1, o=1, p=1, and q=0 or 1.

9. The conjugate of formula (I) of claim 1, wherein:
(i) $A_2$ is piperazinyl, $L_2$ is absent and $A_1$ is cyclohexanyl;
(ii) $A_2$ is piperazinyl, $L_2$ is —$CH_2$— and $A_1$ is cyclohexanyl;
(iii) $A_2$ is piperazinyl, $L_2$ is absent and $A_1$ is phenyl; or
(iv) $A_2$ is 1,2,3-triazolyl, $L_2$ is absent and $A_1$ is phenyl.

10. The conjugate of formula (I) of claim 1, wherein: $L_3$ is —CO—, $A_1$ is phenyl, $L_2$ is —O— and $A_1$ is phenyl, wherein the phenyl ring is unsubstituted or is modified with at least one substituent selected from the group consisting of halogen, $NO_2$, CN, $(C_{1-4})$ alkyl, $(C_{1-4})$ alkoxy, $(C_{1-4})$alkyl-$(C_{3-7})$cycloalkyl, $(C_{3-7})$ cycloalkyl, OH, benzyl, —O-benzyl, carboxyl, carboxyester, carboxamide, mono $(C_{1-4})$ alkyl carboxamide, and di $(C_{1-4})$ alkyl carboxamide.

11. The conjugate of formula (I) of claim 1, wherein the group -$A_2$-$L_3$- is selected from the group consisting of:

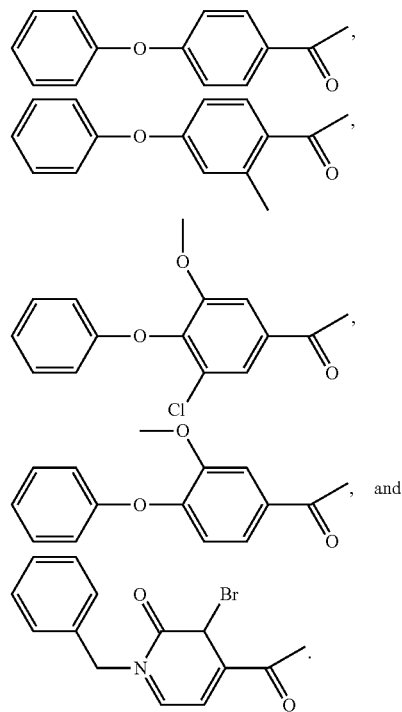

12. The conjugate of formula (I) of claim 1, wherein the terminal pyranose moiety S1 is selected from the group consisting of glucose, galactose, 4-deoxyglucose, and 4,5-dehydroglucose derivatives, attached via position 2, 4, or 6 in the conjugate of formula (I), or selected from mannose attached via position 6.

13. The conjugate of formula (I) of claim 1, wherein the terminal pyranose moiety S1 is of Formula (IIIa) or (IIIb):

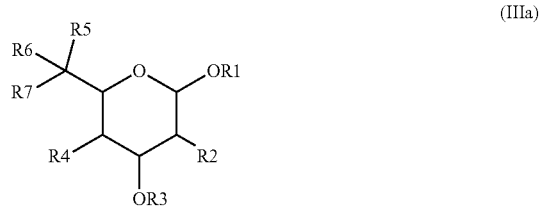

(IIIa)

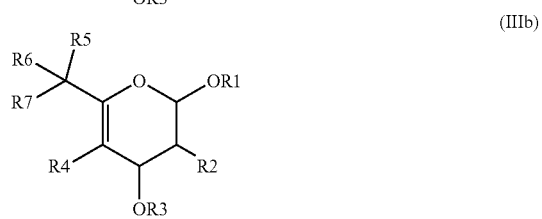

(IIIb)

wherein:
R1 is H or a protecting group;
R2 is OR8, NHR8, or an attachment site in the conjugate of formula (I), wherein R8 is H or a protecting group;
R3 is H or a protecting group;
R4 is H, OR8, NHR8, or an attachment site in the conjugate of formula (I), wherein R8 is H or a protecting group;
R5 and R6 are H or form, together with the carbon atom to which they are bound, a carbonyl group;
R7 is OR8, NHR8, or an attachment site in the conjugate of formula (I), wherein R8 is H or a protecting group, and wherein one of R2, R4, and R7 is the attachment site in the conjugate of formula (I).

14. The conjugate of formula (I) of claim 13, wherein:
(i) R1 and R3 are each H; or
(ii) R2 is OR8 or an attachment site in the conjugate of formula (I);
R4 is H, OR8, or an attachment site in the conjugate of formula (I);
R7 is OR8 or an attachment site in the conjugate of formula (I); and
wherein R8 is H or a protecting group.

15. The conjugate of formula (I) of claim 13, wherein position 6 of the pyranose moiety S1 is the attachment site in the conjugate of formula (I).

16. The conjugate of formula (I) of claim 1, wherein the pyranose moiety S1 is of formula (IVa), (IVb), (IVc), (IVd), or (IVe):

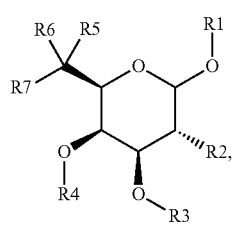
(IVa)

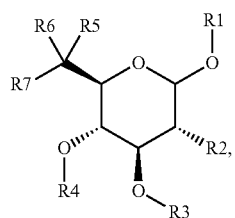
(IVb)

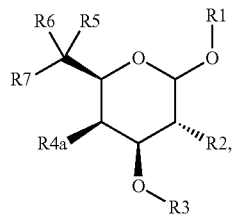
(IVc)

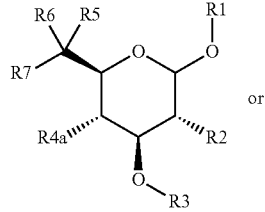
(IVd)
or

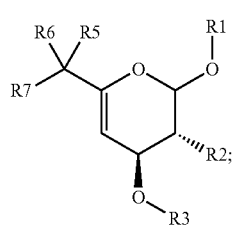
(IVe)

wherein:
R1 is H or a protecting group;
R2 is OR8, NHR8, or an attachment site in the conjugate of formula (I), wherein R8 is H or a protecting group;
R3 is H or a protecting group;
R5 and R6 are H or form, together with the carbon atom to which they are bound, a carbonyl group;
R7 is OR8, NHR8, or an attachment site in the conjugate of formula (I), wherein R8 is H or a protecting group;
R4 is H, a protecting group, or an attachment site in the conjugate of formula (I); and
R4a is H or an attachment site in the conjugate of formula (I).

17. The conjugate of formula (I) of claim 1, wherein the sugar moiety S is of Formula (V):

$$—[X_2—S2]_s\text{-}X_1—S1 \qquad (V)$$

wherein:
$X_1$ is a bond or O;
$X_2$ is a bond, NH or O;
S2 is a mono- or disaccharide moiety;
S1 is a terminal pyranose moiety having a backbone structure of Formula (II)

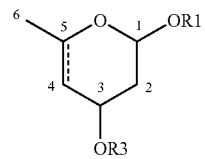
(II)

wherein:
1, 2, 3, 4, 5, and 6 denote the positions of the C-atoms in the pyranose moiety;
——— is a single bond and - - - is a single or a double bond; and
R1 and R3 are independently H or a protecting group, wherein S1 is attached via position 2, 4, or 6 in the conjugate of formula (I); and
s is 0 or 1.

18. The conjugate of formula (I) of claim 17, wherein:
(i) the saccharide moiety S2 is a pyranose moiety, or
(ii) the saccharide moiety S2 is of Formula (VIa), (VIb), (VIc), (VId), or (VIe):

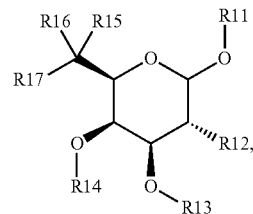
(VIa)

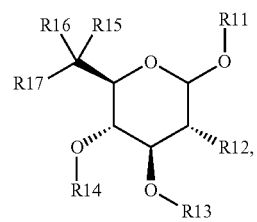
(VIb)

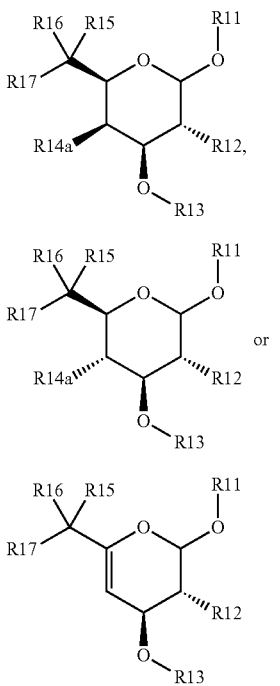

wherein:
R11 is a bond to $X_1$;
R12 is OR8, NHR8, or an attachment site to $X_2$, wherein R8 is H or a protecting group;
R13 is H or a protecting group;
R14 is R8 or an attachment site to $X_2$, wherein R8 is H or a protecting group;

R14a is H or an attachment site to $X_2$;
R15 and R16 are each H or are taken together with the carbon atom to which they are bound to form a carbonyl group;
R17 is OR8 or an attachment site to $X_2$, wherein R8 is H or a protecting group;
wherein one of R12, R14, and R17 is an attachment site to $X_2$.

19. The conjugate of formula (I) of claim 1, wherein the conjugate has an affinity of 10-500 nM to the insulin independent glucose transporter GluT1.

20. The conjugate of formula (I) of claim 1, wherein the conjugate reversibly binds to the insulin independent glucose transporter GluT1 dependent upon the glucose concentration in the surrounding medium.

21. A pharmaceutical composition comprising the conjugate of formula (I) of claim 1 and a pharmaceutically acceptable carrier.

22. A method of treating a disorder caused by and/or accompanied by a dysregulated glucose metabolism that elevates glucose blood level, comprising administering the conjugate of formula (I) of claim 1 to a subject in need thereof.

23. A method of treating diabetes type 2 or diabetes type 1, comprising administering the conjugate of formula (I) of claim 1 to a subject in need thereof.

24. A method of treating a disorder caused by and/or accompanied by a dysregulated glucose metabolism that elevates glucose blood level, comprising administering the composition of claim 21 to a subject in need thereof.

25. A method of treating diabetes type 2 or diabetes type 1, comprising administering the composition of claim 21 to a subject in need thereof.

26. The conjugate of formula (I) of claim 13, wherein R7 is the attachment site in the conjugate of formula (I).

* * * * *

UNITED STATES PATENT AND TRADEMARK OFFICE
CERTIFICATE OF CORRECTION

| | |
|---|---|
| PATENT NO. | : 11,090,364 B2 |
| APPLICATION NO. | : 16/306243 |
| DATED | : August 17, 2021 |
| INVENTOR(S) | : Petry et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 81 days.

Signed and Sealed this
Twenty-fifth Day of October, 2022

Katherine Kelly Vidal
*Director of the United States Patent and Trademark Office*